US012617862B2

(12) United States Patent
Shi et al.

(10) Patent No.: US 12,617,862 B2
(45) Date of Patent: May 5, 2026

(54) ANTI-CD73 ANTIBODY AND APPLICATION THEREOF

(71) Applicant: Harbour BioMed (Shanghai) Co., Ltd, Shanghai (CN)

(72) Inventors: Lei Shi, Shanghai (CN); Xin Gan, Shanghai (CN); Qianqian Shan, Shanghai (CN); Yiping Rong, Shanghai (CN); Yun He, Shanghai (CN)

(73) Assignee: Harbour BioMed (Shanghai) Co., Ltd., Shanghai (CN)

( * ) Notice: Subject to any disclaimer, the term of this patent is extended or adjusted under 35 U.S.C. 154(b) by 1110 days.

(21) Appl. No.: 17/636,848

(22) PCT Filed: Aug. 20, 2020

(86) PCT No.: PCT/CN2020/110340
§ 371 (c)(1),
(2) Date: Feb. 18, 2022

(87) PCT Pub. No.: WO2021/032173
PCT Pub. Date: Feb. 25, 2021

(65) Prior Publication Data
US 2023/0357425 A1      Nov. 9, 2023

(30) Foreign Application Priority Data

Aug. 21, 2019    (WO) ................ PCT/CN2019/101837

(51) Int. Cl.
*C07K 16/28*      (2006.01)
*A61P 35/00*      (2006.01)
*C12N 15/63*      (2006.01)
(52) U.S. Cl.
CPC .......... *C07K 16/2896* (2013.01); *A61P 35/00* (2018.01); *C12N 15/63* (2013.01); *C07K 2317/24* (2013.01); *C07K 2317/565* (2013.01)
(58) Field of Classification Search
None
See application file for complete search history.

(56) References Cited

U.S. PATENT DOCUMENTS

| | | | |
|---|---|---|---|
| 2016/0129108 A1 | 5/2016 | Sachsenmeier et al. | |
| 2018/0009899 A1* | 1/2018 | Griffin .................... | A61P 35/00 |

FOREIGN PATENT DOCUMENTS

| | | |
|---|---|---|
| JP | 2017-534648 A | 11/2017 |
| JP | 2017-537620 A | 12/2017 |
| JP | 2018-501197 A | 1/2018 |
| KR | 10-2017-0080607 A | 7/2017 |
| TW | 201905001 A | 2/2019 |
| WO | WO 2016/075099 A1 | 5/2016 |
| WO | WO 2016/081748 A2 | 5/2016 |
| WO | WO 2016/131950 A1 | 8/2016 |
| WO | WO 2018/137598 A1 | 8/2018 |
| WO | WO 2018/187512 A1 | 10/2018 |
| WO | WO 2018/215535 A1 | 11/2018 |
| WO | WO 2018/237157 A1 | 12/2018 |
| WO | WO 2019/068907 A1 | 4/2019 |

OTHER PUBLICATIONS

U.S. Appl. No. 18/564,598, filed May 24, 2022.*
Rudikoff, 1982, Proceedings of the National Academy of Sciences, 79.6: 1979-1983. (Year: 1982).*
Sela-Culang, Frontiers in Immunology 4: 302 (Year: 2013).*
Hasegawa, mAbs, 9(5), 854-873 (Year: 2017).*
Allard et al., Targeting CD73 enhances the antitumor activity of anti-PD-1 and anti-CTLA-4 mAbs. Clin Cancer Res. Oct. 15, 2013;19(20):5626-35. Epub Aug. 27, 2013.
Beavis et al., CD73: A potential biomarker for anti-PD-1 therapy. Oncoimmunology. May 5, 2015;4(11):e1046675(1-3).
Ohta et al., A2A adenosine receptor protects tumors from antitumor T cells. Proc Natl Acad Sci U S A. Aug. 29, 2006;103(35):13132-7. Epub Aug. 17, 2006.
Qiao et al., A Novel Specific Anti-CD73 Antibody Inhibits Triple-Negative Breast Cancer Cell Motility by Regulating Autophagy. Int J Mol Sci. Feb. 28, 2019;20(5):1057(1-15).
Rust et al., Combining phenotypic and proteomic approaches to identify membrane targets in a 'triple negative' breast cancer cell type. Mol Cancer. Feb. 13, 2013;12:11 pages.
Sachsenmeier et al., Development of a novel ectonucleotidase assay suitable for high-throughput screening. J Biomol Screen. Aug. 2012;17(7):993-8. Epub Apr. 20, 2012.
Stagg et al., Anti-CD73 antibody therapy inhibits breast tumor growth and metastasis. Proc Natl Acad Sci U S A. Jan. 26, 2010;107(4):1547-52. pub Jan. 4, 2010.
Terp et al., Anti-human CD73 monoclonal antibody inhibits metastasis formation in human breast cancer by inducing clustering and internalization of CD73 expressed on the surface of cancer cells. J Immunol. Oct. 15, 2013;191(8):4165-73. Epub Sep. 16, 2013.
Caldas, Cristina, et al. "Humanization of the anti-CD18 antibody 6.7: an unexpected effect of a framework residue in binding to antigen.", Molecular Immunology, vol. 39, No. 15, pp. 941-995, May 1, 2003.
Du, Jiamu, et al. "Molecular Basis of Recognition of Human Osteopontin by 23C3, a Potential Therapeutic Antibody for Treatment of Rheumatoid Arthritis", Journal of Molecular Biology, vol. 382, No. 4, pp. 835-842, Oct. 17, 2008.
Kunik, Vered, et al. "Structural Consensus among Antibodies Defines the Antigen Binding Site", PLoS Computational Biology, vol. 8, No. 2, article e1002388, Feb. 23, 2012.

* cited by examiner

*Primary Examiner* — Julie Wu
(74) *Attorney, Agent, or Firm* — Mintz Levin Cohn Ferris Glovsky and Popeo, P.C.

(57)      ABSTRACT
Provided an isolated antigen binding protein having one or more of the following properties: a. capable of binding to both human CD73 and Cynomolgus monkey CD73; b. capable of inhibiting 5'ectonucleotidase activity of CD73; c. capable of mediating CD73 internalization; d. capable of promoting T cell proliferation; e. with a relatively stable concentration in serum; and f. capable of inhibiting tumor growth and/or tumor cell proliferation. In addition, provided a method for producing the isolated antigen binding protein as well as pharmaceutical uses of the isolated antigen binding protein in preventing, alleviating and/or treating tumor.

20 Claims, 19 Drawing Sheets

Specification includes a Sequence Listing.

| tab2 | PR000497 | PR000506 |
|------|----------|----------|
| 1.294 | 0.4446 | 0.3772 |

| | Tab1 | PR000506 | PR001408 |
|------|------|----------|----------|
| EC50 | 1.408 | 0.9213 | 1.036 |

| tab1 | PR000497 | PR000822 | PR000824 | PR000826 |
|------|----------|----------|----------|----------|
| 0.8419 | 1.333 | 0.8318 | 0.9901 | 0.9329 |

| PR000497 | PR000815 | PR000817 | PR000818 | PR000819 | PR000820 |
|----------|----------|----------|----------|----------|----------|
| 1.016 | 2.063 | 1.971 | 0.9742 | 0.9299 | 1.014 |

A

B

A

B

A

B

A

B

240-254: IVTSDDGRKVPVVQA (#90)

CD73 mutants binding to PR000846

| | |
|---|---|
| R1007_K136A | |
| R1007_V137A | |
| R1007_L138A | |
| R1007-D142A | |
| R1007_E143A | |
| R1007_V144A | |
| R1007_K180A | |
| R1007_N185A | |
| R1007_V186A | |
| R1007_N187A | |
| hCD73 wt | |

| Mutants | Top | EC50 |
|---|---|---|
| R1007_K136A | 1.804 | 0.1543 |
| R1007-V137A | 1.328 | 0.2646 |
| R1007_L138A | 1.725 | 0.1356 |
| R1007-D142A | 1.447 | 0.4515 |
| R1007_E143A | 1.524 | 0.1289 |
| R1007_V144A | 2.073 | 0.145 |
| R1007_K180A | 1.94 | 0.1918 |
| R1007_N185A | 2.387 | 0.1542 |
| R1007_V186A | 1.6 | 0.1426 |
| R1007_N187A | 1.923 | 0.1397 |
| hCD73 wt | 2.537 | 0.173 |

CD73 mutants binding to PR000846

| | |
|---|---|
| R1007_K188A | |
| R1007_Y223A | |
| R1007_P238A | |
| R1007_I240A | |
| R1007_V241A | |
| R1007_D245A | |
| R1007_R247A | |
| V144A+N185A | |
| K180A+N185A | |
| V144A+K180A+N185A | |
| hCD73 wt | |

| Mutants | Top | EC50 |
|---|---|---|
| R1007_K188A | 2.331 | 0.1548 |
| R1007_Y223A | 2.201 | 0.1941 |
| R1007_P238A | 2.366 | 0.2323 |
| R1007_I240A | 2.398 | 0.2107 |
| R1007_V241A | 2.566 | 0.1844 |
| R1007_D245A | 2.626 | 0.2049 |
| R1007_R247A | 2.762 | 0.1815 |
| V144A+N185A | 2.596 | 0.2063 |
| K180A+N185A | 1.864 | 0.4645 |
| V144A+K180A+N185A | 2.348 | 0.1776 |
| hCD73 wt | 2.597 | 0.1573 |

SEQUENCE LISTING

```
<160> NUMBER OF SEQ ID NOS: 169

<210> SEQ ID NO 1
<211> LENGTH: 25
<212> TYPE: PRT
<213> ORGANISM: Artificial Sequence
<220> FEATURE:
<223> OTHER INFORMATION: PR000497 HFWR1 Chothia, PR000815 HFWR1 Chothia,
      PR000816 HFWR1 Chothia

<400> SEQUENCE: 1

Gln Val Gln Val Val Glu Ser Gly Gly Gly Val Val Gln Pro Gly Arg
1               5                   10                  15

Ser Leu Arg Leu Ser Cys Ala Ala Ser
            20                  25

<210> SEQ ID NO 2
<211> LENGTH: 25
<212> TYPE: PRT
<213> ORGANISM: Artificial Sequence
<220> FEATURE:
<223> OTHER INFORMATION: PR000506 HFWR1 Chothia, PR000843 HFWR1 Chothia,
      PR000844 HFWR1 Chothia

<400> SEQUENCE: 2

Gln Val Gln Leu Val Glu Ser Gly Gly Gly Val Ala Gln Pro Gly Arg
1               5                   10                  15

Ser Leu Ser Leu Ser Cys Ala Ala Ser
            20                  25

<210> SEQ ID NO 3
<211> LENGTH: 25
<212> TYPE: PRT
<213> ORGANISM: Artificial Sequence
<220> FEATURE:
<223> OTHER INFORMATION: PR000690 HFWR1 Chothia, PR000817 HFWR1 Chothia,
      PR000818 HFWR1 Chothia

<400> SEQUENCE: 3

Gln Val Gln Leu Val Glu Ser Gly Gly Gly Val Val Gln Pro Gly Arg
1               5                   10                  15

Ser Leu Arg Leu Ser Cys Ala Ala Ser
            20                  25

<210> SEQ ID NO 4
<211> LENGTH: 25
<212> TYPE: PRT
<213> ORGANISM: Artificial Sequence
<220> FEATURE:
<223> OTHER INFORMATION: PR000752 HFWR1 Chothia

<400> SEQUENCE: 4

Glu Ile Gln Leu Gln Gln Ser Gly Pro Glu Leu Val Lys Pro Gly Ala
1               5                   10                  15

Ser Val Lys Val Ser Cys Lys Ala Ser
            20                  25

<210> SEQ ID NO 5
<211> LENGTH: 25
<212> TYPE: PRT
```

<213> ORGANISM: Artificial Sequence
<220> FEATURE:
<223> OTHER INFORMATION: PR002078 HFWR1 Chothia

<400> SEQUENCE: 5

Glu Val Gln Leu Leu Glu Ser Gly Gly Gly Leu Val Gln Pro Gly Gly
1               5                   10                  15

Ser Leu Arg Leu Ser Cys Ala Ala Ser
            20                  25

<210> SEQ ID NO 6
<211> LENGTH: 7
<212> TYPE: PRT
<213> ORGANISM: Artificial Sequence
<220> FEATURE:
<223> OTHER INFORMATION: PR000497 HCDR1 Chothia, PR000815 HCDR1 Chothia,
      PR000816 HCDR1 Chothia

<400> SEQUENCE: 6

Gly Phe Thr Phe Ser Ser Tyr
1               5

<210> SEQ ID NO 7
<211> LENGTH: 7
<212> TYPE: PRT
<213> ORGANISM: Artificial Sequence
<220> FEATURE:
<223> OTHER INFORMATION: PR000506 HCDR1 Chothia, PR000843 HCDR1 Chothia,
      PR000844 HCDR1 Chothia

<400> SEQUENCE: 7

Gly Phe Thr Phe Ser Asp Tyr
1               5

<210> SEQ ID NO 8
<211> LENGTH: 7
<212> TYPE: PRT
<213> ORGANISM: Artificial Sequence
<220> FEATURE:
<223> OTHER INFORMATION: PR000690 HCDR1 Chothia

<400> SEQUENCE: 8

Gly Phe Thr Phe Ser Asn Tyr
1               5

<210> SEQ ID NO 9
<211> LENGTH: 7
<212> TYPE: PRT
<213> ORGANISM: Artificial Sequence
<220> FEATURE:
<223> OTHER INFORMATION: PR000752 HCDR1 Chothia

<400> SEQUENCE: 9

Gly Tyr Ala Phe Thr Ser Tyr
1               5

<210> SEQ ID NO 10
<211> LENGTH: 7
<212> TYPE: PRT
<213> ORGANISM: Artificial Sequence
<220> FEATURE:
<223> OTHER INFORMATION: PR001408 HCDR1 Chothia

<400> SEQUENCE: 10

Gly Phe Thr Phe Tyr Ser Tyr
1               5

```
<210> SEQ ID NO 11
<211> LENGTH: 19
<212> TYPE: PRT
<213> ORGANISM: Artificial Sequence
<220> FEATURE:
<223> OTHER INFORMATION: PR000497 HFWR2 Chothia, PR000815 HFWR2 Chothia,
      PR000816 HFWR2 Chothia

<400> SEQUENCE: 11

Asp Met His Trp Val Arg Gln Ala Pro Gly Lys Gly Leu Glu Trp Val
1               5                   10                  15

Ala Ser Thr

<210> SEQ ID NO 12
<211> LENGTH: 19
<212> TYPE: PRT
<213> ORGANISM: Artificial Sequence
<220> FEATURE:
<223> OTHER INFORMATION: PR000506 HFWR2 Chothia, PR000843 HFWR2 Chothia,
      PR000844 HFWR2 Chothia

<400> SEQUENCE: 12

Gly Met His Trp Val Arg Gln Ala Pro Gly Lys Gly Leu Glu Trp Val
1               5                   10                  15

Ala Leu Ile

<210> SEQ ID NO 13
<211> LENGTH: 19
<212> TYPE: PRT
<213> ORGANISM: Artificial Sequence
<220> FEATURE:
<223> OTHER INFORMATION: PR000690 HFWR2 Chothia

<400> SEQUENCE: 13

Gly Met His Trp Val Arg Gln Ala Pro Gly Lys Gly Leu Glu Trp Val
1               5                   10                  15

Ala Val Ile

<210> SEQ ID NO 14
<211> LENGTH: 19
<212> TYPE: PRT
<213> ORGANISM: Artificial Sequence
<220> FEATURE:
<223> OTHER INFORMATION: PR000752 HFWR2 Chothia

<400> SEQUENCE: 14

Asn Met Tyr Trp Val Lys Gln Ser His Gly Lys Ser Leu Glu Trp Ile
1               5                   10                  15

Gly Tyr Ile

<210> SEQ ID NO 15
<211> LENGTH: 19
<212> TYPE: PRT
<213> ORGANISM: Artificial Sequence
<220> FEATURE:
<223> OTHER INFORMATION: PR001408 HFWR2 Chothia

<400> SEQUENCE: 15

Gly Met His Trp Val Arg Gln Thr Pro Gly Lys Gly Leu Glu Trp Val
1               5                   10                  15

Ala Leu Ile

<210> SEQ ID NO 16
```

```
<211> LENGTH: 19
<212> TYPE: PRT
<213> ORGANISM: Artificial Sequence
<220> FEATURE:
<223> OTHER INFORMATION: PR002078 HFWR2 Chothia

<400> SEQUENCE: 16

Ala Tyr Ser Trp Val Arg Gln Ala Pro Gly Lys Gly Leu Glu Trp Val
1               5                   10                  15

Ser Ala Ile

<210> SEQ ID NO 17
<211> LENGTH: 6
<212> TYPE: PRT
<213> ORGANISM: Artificial Sequence
<220> FEATURE:
<223> OTHER INFORMATION: PR000497 HCDR2 Chothia, PR000819 HCDR2 Chothia,
     PR000820 HCDR2 Chothia

<400> SEQUENCE: 17

Trp Tyr Asp Gly Ser Lys
1               5

<210> SEQ ID NO 18
<211> LENGTH: 6
<212> TYPE: PRT
<213> ORGANISM: Artificial Sequence
<220> FEATURE:
<223> OTHER INFORMATION: PR000506 HCDR2 Chothia, PR000851 HCDR2 Chothia

<400> SEQUENCE: 18

Trp Tyr Asp Gly Ser Phe
1               5

<210> SEQ ID NO 19
<211> LENGTH: 6
<212> TYPE: PRT
<213> ORGANISM: Artificial Sequence
<220> FEATURE:
<223> OTHER INFORMATION: PR000690 HCDR2 Chothia

<400> SEQUENCE: 19

Leu Tyr Asp Gly Ser Asn
1               5

<210> SEQ ID NO 20
<211> LENGTH: 6
<212> TYPE: PRT
<213> ORGANISM: Artificial Sequence
<220> FEATURE:
<223> OTHER INFORMATION: PR000752 HCDR2 Chothia

<400> SEQUENCE: 20

Asp Pro Tyr Asn Gly Gly
1               5

<210> SEQ ID NO 21
<211> LENGTH: 6
<212> TYPE: PRT
<213> ORGANISM: Artificial Sequence
<220> FEATURE:
<223> OTHER INFORMATION: PR000815 HCDR2 Chothia, PR000817 HCDR2 Chothia

<400> SEQUENCE: 21

Trp Tyr Glu Gly Ser Lys
1               5
```

```
<210> SEQ ID NO 22
<211> LENGTH: 6
<212> TYPE: PRT
<213> ORGANISM: Artificial Sequence
<220> FEATURE:
<223> OTHER INFORMATION: PR000816 HCDR2 Chothia, PR000818 HCDR2 Chothia,
      PR000822 HCDR2 Chothia

<400> SEQUENCE: 22

Trp Tyr Asp Ala Ser Lys
1               5

<210> SEQ ID NO 23
<211> LENGTH: 6
<212> TYPE: PRT
<213> ORGANISM: Artificial Sequence
<220> FEATURE:
<223> OTHER INFORMATION: PR000843 HCDR2 Chothia, PR000844 HCDR2 Chothia,
      PR000847 HCDR2 Chothia

<400> SEQUENCE: 23

Trp Tyr Glu Gly Ser Phe
1               5

<210> SEQ ID NO 24
<211> LENGTH: 6
<212> TYPE: PRT
<213> ORGANISM: Artificial Sequence
<220> FEATURE:
<223> OTHER INFORMATION: PR000845 HCDR2 Chothia, PR000846 HCDR2 Chothia,
      PR000849 HCDR2 Chothia

<400> SEQUENCE: 24

Trp Tyr Asp Ala Ser Phe
1               5

<210> SEQ ID NO 25
<211> LENGTH: 6
<212> TYPE: PRT
<213> ORGANISM: Artificial Sequence
<220> FEATURE:
<223> OTHER INFORMATION: PR001408 HCDR2 Chothia

<400> SEQUENCE: 25

Trp Tyr Asp Gly Ser Asn
1               5

<210> SEQ ID NO 26
<211> LENGTH: 6
<212> TYPE: PRT
<213> ORGANISM: Artificial Sequence
<220> FEATURE:
<223> OTHER INFORMATION: PR002078 HCDR2 Chothia

<400> SEQUENCE: 26

Ser Gly Ser Gly Gly Arg
1               5

<210> SEQ ID NO 27
<211> LENGTH: 41
<212> TYPE: PRT
<213> ORGANISM: Artificial Sequence
<220> FEATURE:
<223> OTHER INFORMATION: PR000497 HFWR3 Chothia, PR000815 HFWR3 Chothia,
      PR000816 HFWR3 Chothia

<400> SEQUENCE: 27
```

-continued

```
Lys Tyr Tyr Ala Asp Ser Val Lys Gly Arg Phe Thr Ile Ser Arg Asp
1               5                   10                  15

Asn Ser Lys Asn Thr Leu Tyr Leu Lys Met Asn Ser Leu Arg Gly Asp
            20                  25                  30

Asp Thr Ala Val Tyr Tyr Cys Ala Lys
        35                  40

<210> SEQ ID NO 28
<211> LENGTH: 41
<212> TYPE: PRT
<213> ORGANISM: Artificial Sequence
<220> FEATURE:
<223> OTHER INFORMATION: PR000506 HFWR3 Chothia, PR000843 HFWR3 Chothia,
      PR000844 HFWR3 Chothia

<400> SEQUENCE: 28

Glu Tyr Tyr Ala Asp Ser Val Lys Gly Arg Phe Ser Ile Ser Arg Asp
1               5                   10                  15

Asn Ser Lys Asn Thr Leu Tyr Leu Gln Met Asn Ser Leu Arg Ala Glu
            20                  25                  30

Asp Thr Ala Val Tyr Tyr Cys Val Arg
        35                  40

<210> SEQ ID NO 29
<211> LENGTH: 41
<212> TYPE: PRT
<213> ORGANISM: Artificial Sequence
<220> FEATURE:
<223> OTHER INFORMATION: PR000690 HFWR3 Chothia

<400> SEQUENCE: 29

Lys Tyr Tyr Pro Asp Ser Val Lys Gly Arg Phe Thr Ile Ser Arg Asp
1               5                   10                  15

Asn Ser Lys Asn Thr Leu Tyr Leu Gln Met Asn Ser Leu Arg Ala Glu
            20                  25                  30

Asp Thr Ala Val Tyr Tyr Cys Ala Arg
        35                  40

<210> SEQ ID NO 30
<211> LENGTH: 41
<212> TYPE: PRT
<213> ORGANISM: Artificial Sequence
<220> FEATURE:
<223> OTHER INFORMATION: PR000752 HFWR3 Chothia

<400> SEQUENCE: 30

Thr Ser Tyr Asn Gln Lys Phe Lys Gly Lys Ala Thr Leu Thr Val Asp
1               5                   10                  15

Lys Ser Ser Ser Thr Ala Tyr Met His Leu Asn Ser Leu Thr Ser Glu
            20                  25                  30

Asp Ser Ala Val Tyr Tyr Cys Ala Arg
        35                  40

<210> SEQ ID NO 31
<211> LENGTH: 41
<212> TYPE: PRT
<213> ORGANISM: Artificial Sequence
<220> FEATURE:
<223> OTHER INFORMATION: PR000817 HFWR3 Chothia, PR000818 HFWR3 Chothia,
      PR000819 HFWR3 Chothia

<400> SEQUENCE: 31

Lys Tyr Tyr Ala Asp Ser Val Lys Gly Arg Phe Thr Ile Ser Arg Asp
```

-continued

```
1               5                  10                 15

Asn Ser Lys Asn Thr Leu Tyr Leu Gln Met Asn Ser Leu Arg Ala Glu
            20                 25                 30

Asp Thr Ala Val Tyr Tyr Cys Ala Lys
        35                 40

<210> SEQ ID NO 32
<211> LENGTH: 41
<212> TYPE: PRT
<213> ORGANISM: Artificial Sequence
<220> FEATURE:
<223> OTHER INFORMATION: PR001408 HFWR3 Chothia

<400> SEQUENCE: 32

Asn Tyr Tyr Ala Asp Ser Val Lys Gly Arg Phe Thr Ile Ser Arg Asp
1               5                  10                 15

Asn Ser Lys Asn Thr Leu Tyr Leu Gln Met Asn Ser Leu Arg Ala Glu
            20                 25                 30

Asp Thr Ala Val Tyr Tyr Cys Ala Thr
        35                 40

<210> SEQ ID NO 33
<211> LENGTH: 41
<212> TYPE: PRT
<213> ORGANISM: Artificial Sequence
<220> FEATURE:
<223> OTHER INFORMATION: PR002078 HFWR3 Chothia

<400> SEQUENCE: 33

Thr Tyr Tyr Ala Asp Ser Val Lys Gly Arg Phe Thr Ile Ser Arg Asp
1               5                  10                 15

Asn Ser Lys Asn Thr Leu Tyr Leu Gln Met Asn Ser Leu Arg Ala Glu
            20                 25                 30

Asp Thr Ala Val Tyr Tyr Cys Ala Arg
        35                 40

<210> SEQ ID NO 34
<211> LENGTH: 13
<212> TYPE: PRT
<213> ORGANISM: Artificial Sequence
<220> FEATURE:
<223> OTHER INFORMATION: PR000497 HCDR3 Chothia, PR000815 HCDR3 Chothia,
     PR000816 HCDR3 Chothia

<400> SEQUENCE: 34

Gly Gly Asp Leu Leu Thr Gly Pro Asn Ala Phe Asp Ile
1               5                  10

<210> SEQ ID NO 35
<211> LENGTH: 10
<212> TYPE: PRT
<213> ORGANISM: Artificial Sequence
<220> FEATURE:
<223> OTHER INFORMATION: PR000506 HCDR3 Chothia, PR000851 HCDR3 Chothia

<400> SEQUENCE: 35

Asp Gly Gln Trp Gly Ser Arg Leu Asp Tyr
1               5                  10

<210> SEQ ID NO 36
<211> LENGTH: 12
<212> TYPE: PRT
<213> ORGANISM: Artificial Sequence
<220> FEATURE:
```

<223> OTHER INFORMATION: PR000690 HCDR3 Chothia

<400> SEQUENCE: 36

Gly Gly Ser Ser Trp Tyr Pro Asp Ser Phe Asp Ile
1               5                   10

<210> SEQ ID NO 37
<211> LENGTH: 11
<212> TYPE: PRT
<213> ORGANISM: Artificial Sequence
<220> FEATURE:
<223> OTHER INFORMATION: PR000752 HCDR3 Chothia

<400> SEQUENCE: 37

Gly Tyr Gly Asn Tyr Lys Ala Trp Phe Ala Tyr
1               5                   10

<210> SEQ ID NO 38
<211> LENGTH: 10
<212> TYPE: PRT
<213> ORGANISM: Artificial Sequence
<220> FEATURE:
<223> OTHER INFORMATION: PR000843 HCDR3 Chothia, PR000845 HCDR3 Chothia,
      PR000847 HCDR3 Chothia

<400> SEQUENCE: 38

Glu Gly Gln Trp Gly Ser Arg Leu Asp Tyr
1               5                   10

<210> SEQ ID NO 39
<211> LENGTH: 10
<212> TYPE: PRT
<213> ORGANISM: Artificial Sequence
<220> FEATURE:
<223> OTHER INFORMATION: PR000844 HCDR3 Chothia, PR000846 HCDR3 Chothia,
      PR000848 HCDR3 Chothia

<400> SEQUENCE: 39

Asp Ala Gln Trp Gly Ser Arg Leu Asp Tyr
1               5                   10

<210> SEQ ID NO 40
<211> LENGTH: 14
<212> TYPE: PRT
<213> ORGANISM: Artificial Sequence
<220> FEATURE:
<223> OTHER INFORMATION: PR001408 HCDR3 Chothia

<400> SEQUENCE: 40

Glu Arg Ser Ser Ser Phe Tyr Tyr Tyr Tyr Gly Met Asp Val
1               5                   10

<210> SEQ ID NO 41
<211> LENGTH: 8
<212> TYPE: PRT
<213> ORGANISM: Artificial Sequence
<220> FEATURE:
<223> OTHER INFORMATION: PR002078 HCDR3 Chothia

<400> SEQUENCE: 41

Leu Gly Tyr Gly Arg Val Asp Glu
1               5

<210> SEQ ID NO 42
<211> LENGTH: 11
<212> TYPE: PRT
<213> ORGANISM: Artificial Sequence

```
<220> FEATURE:
<223> OTHER INFORMATION: PR000497 HFWR4 Chothia, PR000690 HFWR4 Chothia,
      PR000815 HFWR4 Chothia

<400> SEQUENCE: 42

Trp Gly Gln Gly Thr Met Val Thr Val Ser Ser
1               5                   10

<210> SEQ ID NO 43
<211> LENGTH: 11
<212> TYPE: PRT
<213> ORGANISM: Artificial Sequence
<220> FEATURE:
<223> OTHER INFORMATION: PR000506 HFWR4 Chothia, PR000843 HFWR4 Chothia,
      PR000844 HFWR4 Chothia

<400> SEQUENCE: 43

Trp Gly Gln Gly Thr Leu Val Thr Val Ser Ser
1               5                   10

<210> SEQ ID NO 44
<211> LENGTH: 11
<212> TYPE: PRT
<213> ORGANISM: Artificial Sequence
<220> FEATURE:
<223> OTHER INFORMATION: PR000752 HFWR4 Chothia

<400> SEQUENCE: 44

Trp Gly Gln Gly Thr Leu Val Thr Val Ser Ala
1               5                   10

<210> SEQ ID NO 45
<211> LENGTH: 11
<212> TYPE: PRT
<213> ORGANISM: Artificial Sequence
<220> FEATURE:
<223> OTHER INFORMATION: PR001408 HFWR4 Chothia

<400> SEQUENCE: 45

Trp Gly Gln Gly Thr Thr Val Thr Val Ser Ser
1               5                   10

<210> SEQ ID NO 46
<211> LENGTH: 11
<212> TYPE: PRT
<213> ORGANISM: Artificial Sequence
<220> FEATURE:
<223> OTHER INFORMATION: PR002078 HFWR4 Chothia

<400> SEQUENCE: 46

Trp Gly Arg Gly Thr Leu Val Thr Val Ser Ser
1               5                   10

<210> SEQ ID NO 47
<211> LENGTH: 23
<212> TYPE: PRT
<213> ORGANISM: Artificial Sequence
<220> FEATURE:
<223> OTHER INFORMATION: PR000497 LFWR1 Chothia, PR000815 LFWR1 Chothia,
      PR000816 LFWR1 Chothia

<400> SEQUENCE: 47

Asp Ile Gln Met Thr Gln Ser Pro Ser Thr Leu Ser Ala Ser Val Gly
1               5                   10                  15

Asp Arg Val Thr Ile Thr Cys
            20
```

<210> SEQ ID NO 48
<211> LENGTH: 23
<212> TYPE: PRT
<213> ORGANISM: Artificial Sequence
<220> FEATURE:
<223> OTHER INFORMATION: PR000506 LFWR1 Chothia, PR000843 LFWR1 Chothia,
      PR000844 LFWR1 Chothia

<400> SEQUENCE: 48

Lys Ile Val Met Thr Gln Ser Pro Ala Thr Leu Ser Leu Ser Pro Gly
1               5                   10                  15

Glu Arg Ala Thr Leu Ser Cys
            20

<210> SEQ ID NO 49
<211> LENGTH: 23
<212> TYPE: PRT
<213> ORGANISM: Artificial Sequence
<220> FEATURE:
<223> OTHER INFORMATION: PR000690 LFWR1 Chothia

<400> SEQUENCE: 49

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 50
<211> LENGTH: 23
<212> TYPE: PRT
<213> ORGANISM: Artificial Sequence
<220> FEATURE:
<223> OTHER INFORMATION: PR000752 LFWR1 Chothia

<400> SEQUENCE: 50

Asp Ala Val Met Thr Gln Thr Pro Lys Phe Leu Leu Val Ser Ala Gly
1               5                   10                  15

Asp Arg Val Thr Ile Thr Cys
            20

<210> SEQ ID NO 51
<211> LENGTH: 23
<212> TYPE: PRT
<213> ORGANISM: Artificial Sequence
<220> FEATURE:
<223> OTHER INFORMATION: PR000847 LFWR1 Chothia, PR000848 LFWR1 Chothia,
      PR000849 LFWR1 Chothia

<400> SEQUENCE: 51

Glu Ile Val Leu Thr Gln Ser Pro Ala Thr Leu Ser Leu Ser Pro Gly
1               5                   10                  15

Glu Arg Ala Thr Leu Ser Cys
            20

<210> SEQ ID NO 52
<211> LENGTH: 23
<212> TYPE: PRT
<213> ORGANISM: Artificial Sequence
<220> FEATURE:
<223> OTHER INFORMATION: PR001408 LFWR1 Chothia

<400> SEQUENCE: 52

Asp Ile Gln Leu Thr Gln Ser Pro Ser Phe Leu Ser Thr Ser Val Gly
1               5                   10                  15

-continued

Asp Arg Val Thr Ile Thr Cys
            20

<210> SEQ ID NO 53
<211> LENGTH: 22
<212> TYPE: PRT
<213> ORGANISM: Artificial Sequence
<220> FEATURE:
<223> OTHER INFORMATION: PR002078 LFWR1 Chothia

<400> SEQUENCE: 53

Gln Ser Val Leu Thr Gln Pro Pro Ser Ala Ser Gly Thr Pro Gly Gln
1               5                   10                  15

Arg Val Thr Ile Ser Cys
            20

<210> SEQ ID NO 54
<211> LENGTH: 11
<212> TYPE: PRT
<213> ORGANISM: Artificial Sequence
<220> FEATURE:
<223> OTHER INFORMATION: PR000497 LCDR1 Chothia, PR000815 LCDR1 Chothia,
      PR000816 LCDR1 Chothia

<400> SEQUENCE: 54

Arg Ala Ser Gln Ser Ile Ser Ser Trp Leu Ala
1               5                   10

<210> SEQ ID NO 55
<211> LENGTH: 11
<212> TYPE: PRT
<213> ORGANISM: Artificial Sequence
<220> FEATURE:
<223> OTHER INFORMATION: PR000506 LCDR1 Chothia, PR000843 LCDR1 Chothia,
      PR000844 LCDR1 Chothia

<400> SEQUENCE: 55

Arg Ala Ser Gln Ser Val Ser Arg Tyr Leu Ala
1               5                   10

<210> SEQ ID NO 56
<211> LENGTH: 11
<212> TYPE: PRT
<213> ORGANISM: Artificial Sequence
<220> FEATURE:
<223> OTHER INFORMATION: PR000690 LCDR1 Chothia

<400> SEQUENCE: 56

Arg Ala Ser Gln Gly Ile Ser Ser Trp Leu Ala
1               5                   10

<210> SEQ ID NO 57
<211> LENGTH: 11
<212> TYPE: PRT
<213> ORGANISM: Artificial Sequence
<220> FEATURE:
<223> OTHER INFORMATION: PR000752 LCDR1 Chothia

<400> SEQUENCE: 57

Lys Ala Ser Gln Ser Val Thr Asn Asp Val Ala
1               5                   10

<210> SEQ ID NO 58
<211> LENGTH: 11
<212> TYPE: PRT
<213> ORGANISM: Artificial Sequence
<220> FEATURE:

<223> OTHER INFORMATION: PR001408 LCDR1 Chothia

<400> SEQUENCE: 58

Arg Ala Ser Gln Gly Ile Ser Ser Tyr Leu Ala
1               5                   10

<210> SEQ ID NO 59
<211> LENGTH: 13
<212> TYPE: PRT
<213> ORGANISM: Artificial Sequence
<220> FEATURE:
<223> OTHER INFORMATION: PR002078 LCDR1 Chothia

<400> SEQUENCE: 59

Ser Gly Ser Leu Ser Asn Ile Gly Arg Asn Pro Val Asn
1               5                   10

<210> SEQ ID NO 60
<211> LENGTH: 15
<212> TYPE: PRT
<213> ORGANISM: Artificial Sequence
<220> FEATURE:
<223> OTHER INFORMATION: PR000497 LFWR2 Chothia, PR000815 LFWR2 Chothia,
      PR000816 LFWR2 Chothia

<400> SEQUENCE: 60

Trp Tyr Gln Gln Lys Pro Gly Lys Ala Pro Lys Leu Leu Ile Tyr
1               5                   10                  15

<210> SEQ ID NO 61
<211> LENGTH: 15
<212> TYPE: PRT
<213> ORGANISM: Artificial Sequence
<220> FEATURE:
<223> OTHER INFORMATION: PR000506 LFWR2 Chothia, PR000843 LFWR2 Chothia,
      PR000844 LFWR2 Chothia

<400> SEQUENCE: 61

Trp Tyr Gln Gln Lys Pro Gly Gln Ala Pro Arg Leu Leu Ile Tyr
1               5                   10                  15

<210> SEQ ID NO 62
<211> LENGTH: 15
<212> TYPE: PRT
<213> ORGANISM: Artificial Sequence
<220> FEATURE:
<223> OTHER INFORMATION: PR000690 LFWR2 Chothia

<400> SEQUENCE: 62

Trp Tyr Gln Gln Lys Pro Glu Lys Ala Pro Lys Ser Leu Ile Tyr
1               5                   10                  15

<210> SEQ ID NO 63
<211> LENGTH: 15
<212> TYPE: PRT
<213> ORGANISM: Artificial Sequence
<220> FEATURE:
<223> OTHER INFORMATION: PR000752 LFWR2 Chothia

<400> SEQUENCE: 63

Trp Tyr Gln Gln Lys Pro Gly Gln Ser Pro Lys Leu Leu Ile Tyr
1               5                   10                  15

<210> SEQ ID NO 64
<211> LENGTH: 15
<212> TYPE: PRT
<213> ORGANISM: Artificial Sequence -continued

```
<220> FEATURE:
<223> OTHER INFORMATION: PR002078 LFWR2 Chothia

<400> SEQUENCE: 64

Trp Tyr Gln Gln Leu Pro Gly Thr Ala Pro Lys Leu Leu Ile Tyr
1               5                   10                  15

<210> SEQ ID NO 65
<211> LENGTH: 7
<212> TYPE: PRT
<213> ORGANISM: Artificial Sequence
<220> FEATURE:
<223> OTHER INFORMATION: PR000497 LCDR2 Chothia, PR000815 LCDR2 Chothia,
      PR000816 LCDR2 Chothia

<400> SEQUENCE: 65

Lys Ala Ser Ser Leu Glu Ser
1               5

<210> SEQ ID NO 66
<211> LENGTH: 7
<212> TYPE: PRT
<213> ORGANISM: Artificial Sequence
<220> FEATURE:
<223> OTHER INFORMATION: PR000506 LCDR2 Chothia, PR000843 LCDR2 Chothia,
      PR000844 LCDR2 Chothia

<400> SEQUENCE: 66

Asp Ala Ser Asn Arg Ala Thr
1               5

<210> SEQ ID NO 67
<211> LENGTH: 7
<212> TYPE: PRT
<213> ORGANISM: Artificial Sequence
<220> FEATURE:
<223> OTHER INFORMATION: PR000690 LCDR2 Chothia

<400> SEQUENCE: 67

Ala Ala Ser Ser Leu Gln Ser
1               5

<210> SEQ ID NO 68
<211> LENGTH: 7
<212> TYPE: PRT
<213> ORGANISM: Artificial Sequence
<220> FEATURE:
<223> OTHER INFORMATION: PR000752 LCDR2 Chothia

<400> SEQUENCE: 68

Tyr Ala Ser Asn Arg Tyr Thr
1               5

<210> SEQ ID NO 69
<211> LENGTH: 7
<212> TYPE: PRT
<213> ORGANISM: Artificial Sequence
<220> FEATURE:
<223> OTHER INFORMATION: PR001408 LCDR2 Chothia

<400> SEQUENCE: 69

Ala Ala Ser Thr Leu Gln Ser
1               5

<210> SEQ ID NO 70
<211> LENGTH: 7
<212> TYPE: PRT
```

-continued

```
<213> ORGANISM: Artificial Sequence
<220> FEATURE:
<223> OTHER INFORMATION: PR002078 LCDR2 Chothia

<400> SEQUENCE: 70

Leu Asp Asn Leu Arg Leu Ser
1               5

<210> SEQ ID NO 71
<211> LENGTH: 32
<212> TYPE: PRT
<213> ORGANISM: Artificial Sequence
<220> FEATURE:
<223> OTHER INFORMATION: PR000497 LFWR3 Chothia, PR000815 LFWR3 Chothia,
     PR000816 LFWR3 Chothia

<400> SEQUENCE: 71

Gly Val Pro Ser Arg Phe Ser Gly Ser Gly Ser Gly Thr Glu Phe Thr
1               5                   10                  15

Leu Thr Ile Ser Ser Leu Gln Pro Asp Asp Phe Ala Thr Tyr Tyr Cys
            20                  25                  30

<210> SEQ ID NO 72
<211> LENGTH: 32
<212> TYPE: PRT
<213> ORGANISM: Artificial Sequence
<220> FEATURE:
<223> OTHER INFORMATION: PR000506 LFWR3 Chothia, PR000843 LFWR3 Chothia,
     PR000844 LFWR3 Chothia

<400> SEQUENCE: 72

Gly Ile Pro Ala Arg Phe Ser Gly Ser Gly Ser Gly Thr Asp Phe Thr
1               5                   10                  15

Leu Thr Ile Ser Ser Leu Glu Pro Glu Asp Phe Ala Val Tyr Tyr Cys
            20                  25                  30

<210> SEQ ID NO 73
<211> LENGTH: 32
<212> TYPE: PRT
<213> ORGANISM: Artificial Sequence
<220> FEATURE:
<223> OTHER INFORMATION: PR000690 LFWR3 Chothia

<400> SEQUENCE: 73

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 74
<211> LENGTH: 32
<212> TYPE: PRT
<213> ORGANISM: Artificial Sequence
<220> FEATURE:
<223> OTHER INFORMATION: PR000752 LFWR3 Chothia

<400> SEQUENCE: 74

Gly Val Pro Asp Arg Phe Thr Gly Ser Gly Tyr Gly Thr Asp Phe Thr
1               5                   10                  15

Phe Thr Ile Ser Thr Val Gln Ala Glu Asp Leu Ala Val Tyr Phe Cys
            20                  25                  30

<210> SEQ ID NO 75
<211> LENGTH: 32
<212> TYPE: PRT
```

-continued

<213> ORGANISM: Artificial Sequence
<220> FEATURE:
<223> OTHER INFORMATION: PR001408 LFWR3 Chothia

<400> SEQUENCE: 75

Gly Val Pro Ser Arg Phe Ser Gly Ser Gly Ser Gly Thr Glu Phe Thr
1               5                   10                  15

Leu Thr Ile Ser Ser Leu Gln Pro Glu Asp Phe Ala Thr Tyr Tyr Cys
            20                  25                  30

<210> SEQ ID NO 76
<211> LENGTH: 32
<212> TYPE: PRT
<213> ORGANISM: Artificial Sequence
<220> FEATURE:
<223> OTHER INFORMATION: PR002078 LFWR3 Chothia

<400> SEQUENCE: 76

Gly Val Pro Asp Arg Phe Ser Gly Ser Lys Ser Gly Thr Ser Ala Ser
1               5                   10                  15

Leu Ala Ile Ser Gly Leu Gln Ser Glu Asp Glu Ala Asp Tyr Tyr Cys
            20                  25                  30

<210> SEQ ID NO 77
<211> LENGTH: 9
<212> TYPE: PRT
<213> ORGANISM: Artificial Sequence
<220> FEATURE:
<223> OTHER INFORMATION: PR000497 LCDR3 Chothia, PR000815 LCDR3 Chothia,
      PR000816 LCDR3 Chothia

<400> SEQUENCE: 77

Gln Gln Tyr Asp Asn Tyr Ser Asn Thr
1               5

<210> SEQ ID NO 78
<211> LENGTH: 9
<212> TYPE: PRT
<213> ORGANISM: Artificial Sequence
<220> FEATURE:
<223> OTHER INFORMATION: PR000506 LCDR3 Chothia, PR000843 LCDR3 Chothia,
      PR000844 LCDR3 Chothia

<400> SEQUENCE: 78

Gln Gln Arg Ser Asn Trp Ile Phe Thr
1               5

<210> SEQ ID NO 79
<211> LENGTH: 9
<212> TYPE: PRT
<213> ORGANISM: Artificial Sequence
<220> FEATURE:
<223> OTHER INFORMATION: PR000690 LCDR3 Chothia

<400> SEQUENCE: 79

Gln Gln Tyr Asn Ser Tyr Pro Leu Thr
1               5

<210> SEQ ID NO 80
<211> LENGTH: 8
<212> TYPE: PRT
<213> ORGANISM: Artificial Sequence
<220> FEATURE:
<223> OTHER INFORMATION: PR000752 LCDR3 Chothia

<400> SEQUENCE: 80

```
Gln Gln Asp Tyr Ser Ser Leu Thr
1               5

<210> SEQ ID NO 81
<211> LENGTH: 9
<212> TYPE: PRT
<213> ORGANISM: Artificial Sequence
<220> FEATURE:
<223> OTHER INFORMATION: PR000820 LCDR3 Chothia, PR000822 LCDR3 Chothia,
      PR000824 LCDR3 Chothia

<400> SEQUENCE: 81

Gln Gln Tyr Asp Gln Tyr Ser Asn Thr
1               5

<210> SEQ ID NO 82
<211> LENGTH: 9
<212> TYPE: PRT
<213> ORGANISM: Artificial Sequence
<220> FEATURE:
<223> OTHER INFORMATION: PR001408 LCDR3 Chothia

<400> SEQUENCE: 82

Gln Gln Leu Asn Ser Tyr Pro Tyr Thr
1               5

<210> SEQ ID NO 83
<211> LENGTH: 11
<212> TYPE: PRT
<213> ORGANISM: Artificial Sequence
<220> FEATURE:
<223> OTHER INFORMATION: PR002078 LCDR3 Chothia

<400> SEQUENCE: 83

Ala Thr Trp Asp Asp Ser His Pro Gly Trp Thr
1               5                   10

<210> SEQ ID NO 84
<211> LENGTH: 9
<212> TYPE: PRT
<213> ORGANISM: Artificial Sequence
<220> FEATURE:
<223> OTHER INFORMATION: PR003832 LCDR3 Chothia

<400> SEQUENCE: 84

Gln Gln Tyr Asp Met Tyr Ser Asn Thr
1               5

<210> SEQ ID NO 85
<211> LENGTH: 9
<212> TYPE: PRT
<213> ORGANISM: Artificial Sequence
<220> FEATURE:
<223> OTHER INFORMATION: PR003833 LCDR3 Chothia

<400> SEQUENCE: 85

Gln Gln Tyr Asp Thr Tyr Ser Asn Thr
1               5

<210> SEQ ID NO 86
<211> LENGTH: 9
<212> TYPE: PRT
<213> ORGANISM: Artificial Sequence
<220> FEATURE:
<223> OTHER INFORMATION: PR003834 LCDR3 Chothia

<400> SEQUENCE: 86
```

```
Gln Gln Tyr Asp Ser Tyr Ser Asn Thr
1               5

<210> SEQ ID NO 87
<211> LENGTH: 9
<212> TYPE: PRT
<213> ORGANISM: Artificial Sequence
<220> FEATURE:
<223> OTHER INFORMATION: PR003835 LCDR3 Chothia

<400> SEQUENCE: 87

Gln Gln Tyr Asp Asn Tyr Lys Asn Thr
1               5

<210> SEQ ID NO 88
<211> LENGTH: 9
<212> TYPE: PRT
<213> ORGANISM: Artificial Sequence
<220> FEATURE:
<223> OTHER INFORMATION: PR003836 LCDR3 Chothia

<400> SEQUENCE: 88

Gln Gln Tyr Asp Asn Tyr Glu Asn Thr
1               5

<210> SEQ ID NO 89
<211> LENGTH: 10
<212> TYPE: PRT
<213> ORGANISM: Artificial Sequence
<220> FEATURE:
<223> OTHER INFORMATION: PR000497 LFWR4 Chothia, PR000815 LFWR4 Chothia,
      PR000816 LFWR4 Chothia

<400> SEQUENCE: 89

Phe Gly Gln Gly Thr Lys Leu Glu Ile Lys
1               5                   10

<210> SEQ ID NO 90
<211> LENGTH: 10
<212> TYPE: PRT
<213> ORGANISM: Artificial Sequence
<220> FEATURE:
<223> OTHER INFORMATION: PR000506 LFWR4 Chothia, PR000843 LFWR4 Chothia,
      PR000844 LFWR4 Chothia

<400> SEQUENCE: 90

Phe Gly Pro Gly Thr Lys Val Asp Ile Lys
1               5                   10

<210> SEQ ID NO 91
<211> LENGTH: 10
<212> TYPE: PRT
<213> ORGANISM: Artificial Sequence
<220> FEATURE:
<223> OTHER INFORMATION: PR000690 LFWR4 Chothia

<400> SEQUENCE: 91

Phe Gly Gly Gly Thr Lys Val Glu Ile Lys
1               5                   10

<210> SEQ ID NO 92
<211> LENGTH: 10
<212> TYPE: PRT
<213> ORGANISM: Artificial Sequence
<220> FEATURE:
<223> OTHER INFORMATION: PR000752 LFWR4 Chothia

<400> SEQUENCE: 92
```

```
Phe Gly Ala Gly Thr Lys Leu Glu Leu Lys
1               5                   10

<210> SEQ ID NO 93
<211> LENGTH: 10
<212> TYPE: PRT
<213> ORGANISM: Artificial Sequence
<220> FEATURE:
<223> OTHER INFORMATION: PR001408 LFWR4 Chothia

<400> SEQUENCE: 93

Phe Gly Gln Gly Thr Glu Leu Glu Ile Lys
1               5                   10

<210> SEQ ID NO 94
<211> LENGTH: 10
<212> TYPE: PRT
<213> ORGANISM: Artificial Sequence
<220> FEATURE:
<223> OTHER INFORMATION: PR002078 LFWR4 Chothia

<400> SEQUENCE: 94

Phe Gly Gly Gly Thr Lys Leu Thr Val Leu
1               5                   10

<210> SEQ ID NO 95
<211> LENGTH: 122
<212> TYPE: PRT
<213> ORGANISM: Artificial Sequence
<220> FEATURE:
<223> OTHER INFORMATION: PR000497 VH, PR000820 VH

<400> SEQUENCE: 95

Gln Val Gln Val Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Pro Gly Lys Gly Leu Glu Trp Val
        35                  40                  45

Ala Ser Thr Trp Tyr Asp Gly Ser Lys Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Lys Met Asn Ser Leu Arg Gly Asp Asp Thr Ala Val Tyr Tyr Cys
                85                  90                  95

Ala Lys Gly Gly Asp Leu Leu Thr Gly Pro Asn Ala Phe Asp Ile Trp
            100                 105                 110

Gly Gln Gly Thr Met Val Thr Val Ser Ser
        115                 120

<210> SEQ ID NO 96
<211> LENGTH: 119
<212> TYPE: PRT
<213> ORGANISM: Artificial Sequence
<220> FEATURE:
<223> OTHER INFORMATION: PR000506 VH, PR000851 VH

<400> SEQUENCE: 96

Gln Val Gln Leu Val Glu Ser Gly Gly Gly Val Ala Gln Pro Gly Arg
1               5                   10                  15

Ser Leu Ser Leu Ser Cys Ala Ala Ser Gly Phe Thr Phe Ser Asp Tyr
            20                  25                  30
```

-continued

```
Gly Met His Trp Val Arg Gln Ala Pro Gly Lys Gly Leu Glu Trp Val
        35                  40                  45

Ala Leu Ile Trp Tyr Asp Gly Ser Phe Glu Tyr Tyr Ala Asp Ser Val
    50                  55                  60

Lys Gly Arg Phe Ser Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Arg Asp Gly Gln Trp Gly Ser Arg Leu Asp Tyr Trp Gly Gln Gly
                100                 105                 110

Thr Leu Val Thr Val Ser Ser
        115
```

<210> SEQ ID NO 97
<211> LENGTH: 121
<212> TYPE: PRT
<213> ORGANISM: Artificial Sequence
<220> FEATURE:
<223> OTHER INFORMATION: PR000690 VH

<400> SEQUENCE: 97

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Val
        35                  40                  45

Ala Val Ile Leu Tyr Asp Gly Ser Asn Lys Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Ser Ser Trp Tyr Pro Asp Ser Phe Asp Ile Trp Gly
                100                 105                 110

Gln Gly Thr Met Val Thr Val Ser Ser
        115                 120
```

<210> SEQ ID NO 98
<211> LENGTH: 120
<212> TYPE: PRT
<213> ORGANISM: Artificial Sequence
<220> FEATURE:
<223> OTHER INFORMATION: PR000752 VH

<400> SEQUENCE: 98

```
Glu Ile Gln Leu Gln Gln Ser Gly Pro Glu Leu Val Lys Pro Gly Ala
1               5                   10                  15

Ser Val Lys Val Ser Cys Lys Ala Ser Gly Tyr Ala Phe Thr Ser Tyr
            20                  25                  30

Asn Met Tyr Trp Val Lys Gln Ser His Gly Lys Ser Leu Glu Trp Ile
        35                  40                  45

Gly Tyr Ile Asp Pro Tyr Asn Gly Gly Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met His Leu Asn Ser Leu Thr Ser Glu Asp Ser Ala Val Tyr Tyr Cys
```

-continued

```
                    85                  90                  95
Ala Arg Gly Tyr Gly Asn Tyr Lys Ala Trp Phe Ala Tyr Trp Gly Gln
            100                 105                 110

Gly Thr Leu Val Thr Val Ser Ala
        115                 120

<210> SEQ ID NO 99
<211> LENGTH: 122
<212> TYPE: PRT
<213> ORGANISM: Artificial Sequence
<220> FEATURE:
<223> OTHER INFORMATION: PR000815 VH

<400> SEQUENCE: 99

Gln Val Gln Val Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Pro Gly Lys Gly Leu Glu Trp Val
        35                  40                  45

Ala Ser Thr Trp Tyr Glu Gly Ser Lys Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Lys Met Asn Ser Leu Arg Gly Asp Asp Thr Ala Val Tyr Tyr Cys
                85                  90                  95

Ala Lys Gly Gly Asp Leu Leu Thr Gly Pro Asn Ala Phe Asp Ile Trp
            100                 105                 110

Gly Gln Gly Thr Met Val Thr Val Ser Ser
        115                 120

<210> SEQ ID NO 100
<211> LENGTH: 122
<212> TYPE: PRT
<213> ORGANISM: Artificial Sequence
<220> FEATURE:
<223> OTHER INFORMATION: PR000816 VH, PR000822 VH

<400> SEQUENCE: 100

Gln Val Gln Val Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Pro Gly Lys Gly Leu Glu Trp Val
        35                  40                  45

Ala Ser Thr Trp Tyr Asp Ala Ser Lys Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Lys Met Asn Ser Leu Arg Gly Asp Asp Thr Ala Val Tyr Tyr Cys
                85                  90                  95

Ala Lys Gly Gly Asp Leu Leu Thr Gly Pro Asn Ala Phe Asp Ile Trp
            100                 105                 110

Gly Gln Gly Thr Met Val Thr Val Ser Ser
        115                 120

<210> SEQ ID NO 101
<211> LENGTH: 122
```

-continued

```
<212> TYPE: PRT
<213> ORGANISM: Artificial Sequence
<220> FEATURE:
<223> OTHER INFORMATION: PR000817 VH

<400> SEQUENCE: 101

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Pro Gly Lys Gly Leu Glu Trp Val
        35                  40                  45

Ala Ser Thr Trp Tyr Glu Gly Ser Lys Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Gly Asp Leu Leu Thr Gly Pro Asn Ala Phe Asp Ile Trp
            100                 105                 110

Gly Gln Gly Thr Met Val Thr Val Ser Ser
        115                 120

<210> SEQ ID NO 102
<211> LENGTH: 122
<212> TYPE: PRT
<213> ORGANISM: Artificial Sequence
<220> FEATURE:
<223> OTHER INFORMATION: PR000818 VH, PR000824 VH, PR003832 VH, PR003833
      VH, PR003834 VH, PR003

<400> SEQUENCE: 102

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Pro Gly Lys Gly Leu Glu Trp Val
        35                  40                  45

Ala Ser Thr Trp Tyr Asp Ala Ser Lys Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Gly Asp Leu Leu Thr Gly Pro Asn Ala Phe Asp Ile Trp
            100                 105                 110

Gly Gln Gly Thr Met Val Thr Val Ser Ser
        115                 120

<210> SEQ ID NO 103
<211> LENGTH: 122
<212> TYPE: PRT
<213> ORGANISM: Artificial Sequence
<220> FEATURE:
<223> OTHER INFORMATION: PR000819 VH, PR000825 VH

<400> SEQUENCE: 103

Gln Val Gln Leu Val Glu Ser Gly Gly Gly Val Val Gln Pro Gly Arg
1               5                   10                  15
```

```
Ser Leu Arg Leu Ser Cys Ala Ala Ser Gly Phe Thr Phe Ser Ser Tyr
        20                  25                  30

Asp Met His Trp Val Arg Gln Ala Pro Gly Lys Gly Leu Glu Trp Val
        35                  40                  45

Ala Ser Thr Trp Tyr Asp Gly Ser Lys Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Gly Asp Leu Leu Thr Gly Pro Asn Ala Phe Asp Ile Trp
            100                 105                 110

Gly Gln Gly Thr Met Val Thr Val Ser Ser
            115                 120

<210> SEQ ID NO 104
<211> LENGTH: 119
<212> TYPE: PRT
<213> ORGANISM: Artificial Sequence
<220> FEATURE:
<223> OTHER INFORMATION: PR000843 VH, PR000847 VH

<400> SEQUENCE: 104

Gln Val Gln Leu Val Glu Ser Gly Gly Gly Val Ala Gln Pro Gly Arg
1               5                   10                  15

Ser Leu Ser Leu Ser Cys Ala Ala Ser Gly Phe Thr Phe Ser Asp Tyr
        20                  25                  30

Gly Met His Trp Val Arg Gln Ala Pro Gly Lys Gly Leu Glu Trp Val
        35                  40                  45

Ala Leu Ile Trp Tyr Glu Gly Ser Phe Glu Tyr Tyr Ala Asp Ser Val
        50                  55                  60

Lys Gly Arg Phe Ser Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Arg Glu Gly Gln Trp Gly Ser Arg Leu Asp Tyr Trp Gly Gln Gly
            100                 105                 110

Thr Leu Val Thr Val Ser Ser
        115

<210> SEQ ID NO 105
<211> LENGTH: 119
<212> TYPE: PRT
<213> ORGANISM: Artificial Sequence
<220> FEATURE:
<223> OTHER INFORMATION: PR000844 VH, PR000848 VH

<400> SEQUENCE: 105

Gln Val Gln Leu Val Glu Ser Gly Gly Gly Val Ala Gln Pro Gly Arg
1               5                   10                  15

Ser Leu Ser Leu Ser Cys Ala Ala Ser Gly Phe Thr Phe Ser Asp Tyr
        20                  25                  30

Gly Met His Trp Val Arg Gln Ala Pro Gly Lys Gly Leu Glu Trp Val
        35                  40                  45

Ala Leu Ile Trp Tyr Glu Gly Ser Phe Glu Tyr Tyr Ala Asp Ser Val
        50                  55                  60

Lys Gly Arg Phe Ser Ile Ser Arg Asp Asn Ser Lys Asn Thr Leu Tyr
65                  70                  75                  80
```

-continued

```
Leu Gln Met Asn Ser Leu Arg Ala Glu Asp Thr Ala Val Tyr Tyr Cys
                85                  90                  95

Val Arg Asp Ala Gln Trp Gly Ser Arg Leu Asp Tyr Trp Gly Gln Gly
            100                 105                 110

Thr Leu Val Thr Val Ser Ser
        115
```

<210> SEQ ID NO 106
<211> LENGTH: 119
<212> TYPE: PRT
<213> ORGANISM: Artificial Sequence
<220> FEATURE:
<223> OTHER INFORMATION: PR000845 VH, PR000849 VH

<400> SEQUENCE: 106

```
Gln Val Gln Leu Val Glu Ser Gly Gly Gly Val Ala Gln Pro Gly Arg
1               5                   10                  15

Ser Leu Ser Leu Ser Cys Ala Ala Ser Gly Phe Thr Phe Ser Asp Tyr
            20                  25                  30

Gly Met His Trp Val Arg Gln Ala Pro Gly Lys Gly Leu Glu Trp Val
        35                  40                  45

Ala Leu Ile Trp Tyr Asp Ala Ser Phe Glu Tyr Tyr Ala Asp Ser Val
    50                  55                  60

Lys Gly Arg Phe Ser Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Arg Glu Gly Gln Trp Gly Ser Arg Leu Asp Tyr Trp Gly Gln Gly
            100                 105                 110

Thr Leu Val Thr Val Ser Ser
        115
```

<210> SEQ ID NO 107
<211> LENGTH: 119
<212> TYPE: PRT
<213> ORGANISM: Artificial Sequence
<220> FEATURE:
<223> OTHER INFORMATION: PR000846 VH, PR000850 VH

<400> SEQUENCE: 107

```
Gln Val Gln Leu Val Glu Ser Gly Gly Gly Val Ala Gln Pro Gly Arg
1               5                   10                  15

Ser Leu Ser Leu Ser Cys Ala Ala Ser Gly Phe Thr Phe Ser Asp Tyr
            20                  25                  30

Gly Met His Trp Val Arg Gln Ala Pro Gly Lys Gly Leu Glu Trp Val
        35                  40                  45

Ala Leu Ile Trp Tyr Asp Ala Ser Phe Glu Tyr Tyr Ala Asp Ser Val
    50                  55                  60

Lys Gly Arg Phe Ser Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Arg Asp Ala Gln Trp Gly Ser Arg Leu Asp Tyr Trp Gly Gln Gly
            100                 105                 110

Thr Leu Val Thr Val Ser Ser
        115
```

-continued

```
<210> SEQ ID NO 108
<211> LENGTH: 123
<212> TYPE: PRT
<213> ORGANISM: Artificial Sequence
<220> FEATURE:
<223> OTHER INFORMATION: PR001408 VH

<400> SEQUENCE: 108

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Tyr Ser Tyr
                20                  25                  30

Gly Met His Trp Val Arg Gln Thr Pro Gly Lys Gly Leu Glu Trp Val
            35                  40                  45

Ala Leu Ile Trp Tyr Asp Gly Ser Asn Asn Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Glu Arg Ser Ser Ser Phe Tyr Tyr Tyr Tyr Gly Met Asp Val
                100                 105                 110

Trp Gly Gln Gly Thr Thr Val Thr Val Ser Ser
            115                 120

<210> SEQ ID NO 109
<211> LENGTH: 117
<212> TYPE: PRT
<213> ORGANISM: Artificial Sequence
<220> FEATURE:
<223> OTHER INFORMATION: PR002078 VH

<400> SEQUENCE: 109

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Tyr Ser Trp Val Arg Gln Ala Pro Gly Lys Gly Leu Glu Trp Val
            35                  40                  45

Ser Ala Ile Ser Gly Ser Gly Gly Arg Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Gly Tyr Gly Arg Val Asp Glu Trp Gly Arg Gly Thr Leu
                100                 105                 110

Val Thr Val Ser Ser
        115

<210> SEQ ID NO 110
<211> LENGTH: 107
<212> TYPE: PRT
<213> ORGANISM: Artificial Sequence
<220> FEATURE:
<223> OTHER INFORMATION: PR000497 VL, PR000815 VL, PR000816 VL, PR000817
      VL, PR000818 VL, PR000

<400> SEQUENCE: 110

Asp Ile Gln Met Thr Gln Ser Pro Ser Thr Leu Ser Ala Ser Val Gly
```

-continued

```
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asp Asn Tyr Ser Asn
                85                  90                  95

Thr Phe Gly Gln Gly Thr Lys Leu Glu Ile Lys
            100                 105

<210> SEQ ID NO 111
<211> LENGTH: 107
<212> TYPE: PRT
<213> ORGANISM: Artificial Sequence
<220> FEATURE:
<223> OTHER INFORMATION: PR000506 VL, PR000843 VL, PR000844 VL, PR000845
      VL, PR000846 VL

<400> SEQUENCE: 111

Lys Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Arg Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Ile Phe
                85                  90                  95

Thr Phe Gly Pro Gly Thr Lys Val Asp Ile Lys
            100                 105

<210> SEQ ID NO 112
<211> LENGTH: 107
<212> TYPE: PRT
<213> ORGANISM: Artificial Sequence
<220> FEATURE:
<223> OTHER INFORMATION: PR000690 VL

<400> SEQUENCE: 112

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95
```

-continued

```
Thr Phe Gly Gly Gly Thr Lys Val Glu Ile Lys
            100                 105

<210> SEQ ID NO 113
<211> LENGTH: 106
<212> TYPE: PRT
<213> ORGANISM: Artificial Sequence
<220> FEATURE:
<223> OTHER INFORMATION: PR000752 VL

<400> SEQUENCE: 113

Asp Ala Val Met Thr Gln Thr Pro Lys Phe Leu Leu Val Ser Ala Gly
1               5                   10                  15

Asp Arg Val Thr Ile Thr Cys Lys Ala Ser Gln Ser Val Thr Asn Asp
                20                  25                  30

Val Ala Trp Tyr Gln Gln Lys Pro Gly Gln Ser Pro Lys Leu Leu Ile
            35                  40                  45

Tyr Tyr Ala Ser Asn Arg Tyr Thr Gly Val Pro Asp Arg Phe Thr Gly
    50                  55                  60

Ser Gly Tyr Gly Thr Asp Phe Thr Phe Thr Ile Ser Thr Val Gln Ala
65                  70                  75                  80

Glu Asp Leu Ala Val Tyr Phe Cys Gln Gln Asp Tyr Ser Ser Leu Thr
                85                  90                  95

Phe Gly Ala Gly Thr Lys Leu Glu Leu Lys
            100                 105

<210> SEQ ID NO 114
<211> LENGTH: 107
<212> TYPE: PRT
<213> ORGANISM: Artificial Sequence
<220> FEATURE:
<223> OTHER INFORMATION: PR000820 VL, PR000822 VL, PR000824 VL, PR000825
      VL

<400> SEQUENCE: 114

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
                20                  25                  30

Leu Ala Trp Tyr Gln Gln Lys Pro Gly Lys Ala Pro Lys Leu Leu Ile
            35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asp Gln Tyr Ser Asn
                85                  90                  95

Thr Phe Gly Gln Gly Thr Lys Leu Glu Ile Lys
            100                 105

<210> SEQ ID NO 115
<211> LENGTH: 107
<212> TYPE: PRT
<213> ORGANISM: Artificial Sequence
<220> FEATURE:
<223> OTHER INFORMATION: PR000847 VL, PR000848 VL, PR000849 VL, PR000850
      VL, PR000851 VL

<400> SEQUENCE: 115

Glu Ile Val Leu Thr Gln Ser Pro Ala Thr Leu Ser Leu Ser Pro Gly
```

-continued

```
1               5               10              15

Glu Arg Ala Thr Leu Ser Cys Arg Ala Ser Gln Ser Val Ser Arg Tyr
            20              25              30

Leu Ala Trp Tyr Gln Gln Lys Pro Gly Gln Ala Pro Arg Leu Leu Ile
        35              40              45

Tyr Asp Ala Ser Asn Arg Ala Thr Gly Ile Pro Ala Arg Phe Ser Gly
    50              55              60

Ser Gly Ser Gly Thr Asp Phe Thr Leu Thr Ile Ser Ser Leu Glu Pro
65              70              75              80

Glu Asp Phe Ala Val Tyr Tyr Cys Gln Gln Arg Ser Asn Trp Ile Phe
            85              90              95

Thr Phe Gly Pro Gly Thr Lys Val Asp Ile Lys
            100             105

<210> SEQ ID NO 116
<211> LENGTH: 107
<212> TYPE: PRT
<213> ORGANISM: Artificial Sequence
<220> FEATURE:
<223> OTHER INFORMATION: PR001408 VL

<400> SEQUENCE: 116

Asp Ile Gln Leu Thr Gln Ser Pro Ser Phe Leu Ser Thr Ser Val Gly
1               5               10              15

Asp Arg Val Thr Ile Thr Cys Arg Ala Ser Gln Gly Ile Ser Ser Tyr
            20              25              30

Leu Ala Trp Tyr Gln Gln Lys Pro Gly Lys Ala Pro Lys Leu Leu Ile
        35              40              45

Tyr Ala Ala Ser Thr Leu Gln Ser Gly Val Pro Ser Arg Phe Ser Gly
    50              55              60

Ser Gly Ser Gly Thr Glu Phe Thr Leu Thr Ile Ser Ser Leu Gln Pro
65              70              75              80

Glu Asp Phe Ala Thr Tyr Tyr Cys Gln Gln Leu Asn Ser Tyr Pro Tyr
            85              90              95

Thr Phe Gly Gln Gly Thr Glu Leu Glu Ile Lys
            100             105

<210> SEQ ID NO 117
<211> LENGTH: 110
<212> TYPE: PRT
<213> ORGANISM: Artificial Sequence
<220> FEATURE:
<223> OTHER INFORMATION: PR002078 VL

<400> SEQUENCE: 117

Gln Ser Val Leu Thr Gln Pro Pro Ser Ala Ser Gly Thr Pro Gly Gln
1               5               10              15

Arg Val Thr Ile Ser Cys Ser Gly Ser Leu Ser Asn Ile Gly Arg Asn
            20              25              30

Pro Val Asn Trp Tyr Gln Gln Leu Pro Gly Thr Ala Pro Lys Leu Leu
        35              40              45

Ile Tyr Leu Asp Asn Leu Arg Leu Ser Gly Val Pro Asp Arg Phe Ser
    50              55              60

Gly Ser Lys Ser Gly Thr Ser Ala Ser Leu Ala Ile Ser Gly Leu Gln
65              70              75              80

Ser Glu Asp Glu Ala Asp Tyr Tyr Cys Ala Thr Trp Asp Asp Ser His
            85              90              95
```

```
Pro Gly Trp Thr Phe Gly Gly Gly Thr Lys Leu Thr Val Leu
        100                 105                 110

<210> SEQ ID NO 118
<211> LENGTH: 107
<212> TYPE: PRT
<213> ORGANISM: Artificial Sequence
<220> FEATURE:
<223> OTHER INFORMATION: PR003832 VL

<400> SEQUENCE: 118

Asp Ile Gln Met Thr Gln Ser Pro Ser Thr Leu Ser Ala Ser Val Gly
1                 5                 10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asp Met Tyr Ser Asn
                85                  90                  95

Thr Phe Gly Gln Gly Thr Lys Leu Glu Ile Lys
            100                 105

<210> SEQ ID NO 119
<211> LENGTH: 107
<212> TYPE: PRT
<213> ORGANISM: Artificial Sequence
<220> FEATURE:
<223> OTHER INFORMATION: PR003833 VL

<400> SEQUENCE: 119

Asp Ile Gln Met Thr Gln Ser Pro Ser Thr Leu Ser Ala Ser Val Gly
1                 5                 10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asp Thr Tyr Ser Asn
                85                  90                  95

Thr Phe Gly Gln Gly Thr Lys Leu Glu Ile Lys
            100                 105

<210> SEQ ID NO 120
<211> LENGTH: 107
<212> TYPE: PRT
<213> ORGANISM: Artificial Sequence
<220> FEATURE:
<223> OTHER INFORMATION: PR003834 VL

<400> SEQUENCE: 120

Asp Ile Gln Met Thr Gln Ser Pro Ser Thr Leu Ser Ala Ser Val Gly
1                 5                 10                  15

Asp Arg Val Thr Ile Thr Cys Arg Ala Ser Gln Ser Ile Ser Ser Trp
```

-continued

```
              20                  25                  30

Leu Ala Trp Tyr Gln Gln Lys Pro Gly Lys Ala Pro Lys Leu Leu Ile
         35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asp Ser Tyr Ser Asn
                   85                  90                  95

Thr Phe Gly Gln Gly Thr Lys Leu Glu Ile Lys
              100                 105
```

<210> SEQ ID NO 121
<211> LENGTH: 107
<212> TYPE: PRT
<213> ORGANISM: Artificial Sequence
<220> FEATURE:
<223> OTHER INFORMATION: PR003835 VL

<400> SEQUENCE: 121

```
Asp Ile Gln Met Thr Gln Ser Pro Ser Thr Leu Ser Ala Ser Val Gly
1                   5                  10                  15

Asp Arg Val Thr Ile Thr Cys Arg Ala Ser Gln Ser Ile Ser Ser Trp
              20                  25                  30

Leu Ala Trp Tyr Gln Gln Lys Pro Gly Lys Ala Pro Lys Leu Leu Ile
         35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asp Asn Tyr Lys Asn
                   85                  90                  95

Thr Phe Gly Gln Gly Thr Lys Leu Glu Ile Lys
              100                 105
```

<210> SEQ ID NO 122
<211> LENGTH: 107
<212> TYPE: PRT
<213> ORGANISM: Artificial Sequence
<220> FEATURE:
<223> OTHER INFORMATION: PR003836 VL

<400> SEQUENCE: 122

```
Asp Ile Gln Met Thr Gln Ser Pro Ser Thr Leu Ser Ala Ser Val Gly
1                   5                  10                  15

Asp Arg Val Thr Ile Thr Cys Arg Ala Ser Gln Ser Ile Ser Ser Trp
              20                  25                  30

Leu Ala Trp Tyr Gln Gln Lys Pro Gly Lys Ala Pro Lys Leu Leu Ile
         35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asp Asn Tyr Glu Asn
                   85                  90                  95

Thr Phe Gly Gln Gly Thr Lys Leu Glu Ile Lys
              100                 105
```

-continued

<210> SEQ ID NO 123
<211> LENGTH: 452
<212> TYPE: PRT
<213> ORGANISM: Artificial Sequence
<220> FEATURE:
<223> OTHER INFORMATION: PR000497 HC, PR000820 HC

<400> SEQUENCE: 123

Gln Val Gln Val Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Pro Gly Lys Gly Leu Glu Trp Val
        35                  40                  45

Ala Ser Thr Trp Tyr Asp Gly Ser Lys Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Lys Met Asn Ser Leu Arg Gly Asp Asp Thr Ala Val Tyr Tyr Cys
                85                  90                  95

Ala Lys Gly Gly Asp Leu Leu Thr Gly Pro Asn Ala Phe Asp Ile Trp
            100                 105                 110

Gly Gln Gly Thr Met Val Thr Val Ser Ser Ala Ser Thr Lys Gly Pro
            115                 120                 125

Ser Val Phe Pro Leu Ala Pro Ser Ser Lys Ser Thr Ser Gly Gly Thr
        130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
            195                 200                 205

His Lys Pro Ser Asn Thr Lys Val Asp Lys Lys Val Glu Pro Lys Ser
        210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
            245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
        290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

-continued

```
Ser Leu Thr Cys Leu Val Lys Gly Phe Tyr Pro Ser Asp Ile Ala Val
    370             375             380

Glu Trp Glu Ser Asn Gly Gln Pro Glu Asn Asn Tyr Lys Thr Thr Pro
385             390             395             400

Pro Val Leu Asp Ser Asp Gly Ser Phe Phe Leu Tyr Ser Lys Leu Thr
                405             410             415

Val Asp Lys Ser Arg Trp Gln Gln Gly Asn Val Phe Ser Cys Ser Val
            420             425             430

Met His Glu Ala Leu His Asn His Tyr Thr Gln Lys Ser Leu Ser Leu
            435             440             445

Ser Pro Gly Lys
    450
```

```
<210> SEQ ID NO 124
<211> LENGTH: 449
<212> TYPE: PRT
<213> ORGANISM: Artificial Sequence
<220> FEATURE:
<223> OTHER INFORMATION: PR000506 HC, PR000851 HC

<400> SEQUENCE: 124
```

```
Gln Val Gln Leu Val Glu Ser Gly Gly Gly Val Ala Gln Pro Gly Arg
1               5               10              15

Ser Leu Ser Leu Ser Cys Ala Ala Ser Gly Phe Thr Phe Ser Asp Tyr
            20              25              30

Gly Met His Trp Val Arg Gln Ala Pro Gly Lys Gly Leu Glu Trp Val
            35              40              45

Ala Leu Ile Trp Tyr Asp Gly Ser Phe Glu Tyr Tyr Ala Asp Ser Val
    50              55              60

Lys Gly Arg Phe Ser Ile Ser Arg Asp Asn Ser Lys Asn Thr Leu Tyr
65              70              75              80

Leu Gln Met Asn Ser Leu Arg Ala Glu Asp Thr Ala Val Tyr Tyr Cys
            85              90              95

Val Arg Asp Gly Gln Trp Gly Ser Arg Leu Asp Tyr Trp Gly Gln Gly
            100             105             110

Thr Leu Val Thr Val Ser Ser Ala Ser Thr Lys Gly Pro Ser Val Phe
            115             120             125

Pro Leu Ala Pro Ser Ser Lys Ser Thr Ser Gly Gly Thr Ala Ala Leu
    130             135             140

Gly Cys Leu Val Lys Asp Tyr Phe Pro Glu Pro Val Thr Val Ser Trp
145             150             155             160

Asn Ser Gly Ala Leu Thr Ser Gly Val His Thr Phe Pro Ala Val Leu
            165             170             175

Gln Ser Ser Gly Leu Tyr Ser Leu Ser Ser Val Val Thr Val Pro Ser
            180             185             190

Ser Ser Leu Gly Thr Gln Thr Tyr Ile Cys Asn Val Asn His Lys Pro
            195             200             205

Ser Asn Thr Lys Val Asp Lys Lys Val Glu Pro Lys Ser Cys Asp Lys
    210             215             220

Thr His Thr Cys Pro Pro Cys Pro Ala Pro Glu Ala Ala Gly Gly Pro
225             230             235             240

Ser Val Phe Leu Phe Pro Pro Lys Pro Lys Asp Thr Leu Met Ile Ser
            245             250             255

Arg Thr Pro Glu Val Thr Cys Val Val Val Asp Val Ser His Glu Asp
            260             265             270
```

```
Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
        435                 440                 445

Lys
```

<210> SEQ ID NO 125
<211> LENGTH: 451
<212> TYPE: PRT
<213> ORGANISM: Artificial Sequence
<220> FEATURE:
<223> OTHER INFORMATION: PR000690 HC

<400> SEQUENCE: 125

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
        20                  25                  30

Gly Met His Trp Val Arg Gln Ala Pro Gly Lys Gly Leu Glu Trp Val
        35                  40                  45

Ala Val Ile Leu Tyr Asp Gly Ser Asn Lys Tyr Tyr Pro Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Ser Ser Trp Tyr Pro Asp Ser Phe Asp Ile Trp Gly
        100                 105                 110

Gln Gly Thr Met Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
```

-continued

```
                   180               185               190
Pro Ser Ser Ser Leu Gly Thr Gln Thr Tyr Ile Cys Asn Val Asn His
        195               200               205
Lys Pro Ser Asn Thr Lys Val Asp Lys Lys Val Glu Pro Lys Ser Cys
    210               215               220
Asp Lys Thr His Thr Cys Pro Pro Cys Pro Ala Pro Glu Ala Glu Gly
225               230               235               240
Ala Pro Ser Val Phe Leu Phe Pro Pro Lys Pro Lys Asp Thr Leu Met
            245               250               255
Ile Ser Arg Thr Pro Glu Val Thr Cys Val Val Val Asp Val Ser His
            260               265               270
Glu Asp Pro Glu Val Lys Phe Asn Trp Tyr Val Asp Gly Val Glu Val
        275               280               285
His Asn Ala Lys Thr Lys Pro Arg Glu Glu Gln Tyr Asn Ser Thr Tyr
        290               295               300
Arg Val Val Ser Val Leu Thr Val Leu His Gln Asp Trp Leu Asn Gly
305               310               315               320
Lys Glu Tyr Lys Cys Lys Val Ser Asn Lys Ala Leu Pro Ser Ser Ile
            325               330               335
Glu Lys Thr Ile Ser Lys Ala Lys Gly Gln Pro Arg Glu Pro Gln Val
            340               345               350
Tyr Thr Leu Pro Pro Ser Arg Glu Glu Met Thr Lys Asn Gln Val Ser
            355               360               365
Leu Thr Cys Leu Val Lys Gly Phe Tyr Pro Ser Asp Ile Ala Val Glu
    370               375               380
Trp Glu Ser Asn Gly Gln Pro Glu Asn Asn Tyr Lys Thr Thr Pro Pro
385               390               395               400
Val Leu Asp Ser Asp Gly Ser Phe Phe Leu Tyr Ser Lys Leu Thr Val
            405               410               415
Asp Lys Ser Arg Trp Gln Gln Gly Asn Val Phe Ser Cys Ser Val Met
            420               425               430
His Glu Ala Leu His Asn His Tyr Thr Gln Lys Ser Leu Ser Leu Ser
        435               440               445
Pro Gly Lys
    450
```

<210> SEQ ID NO 126
<211> LENGTH: 450
<212> TYPE: PRT
<213> ORGANISM: Artificial Sequence
<220> FEATURE:
<223> OTHER INFORMATION: PR000752 HC

<400> SEQUENCE: 126

```
Glu Ile Gln Leu Gln Gln Ser Gly Pro Glu Leu Val Lys Pro Gly Ala
1               5                 10                15
Ser Val Lys Val Ser Cys Lys Ala Ser Gly Tyr Ala Phe Thr Ser Tyr
            20                25                30
Asn Met Tyr Trp Val Lys Gln Ser His Gly Lys Ser Leu Glu Trp Ile
        35                40                45
Gly Tyr Ile Asp Pro Tyr Asn Gly Gly Thr Ser Tyr Asn Gln Lys Phe
    50                55                60
Lys Gly Lys Ala Thr Leu Thr Val Asp Lys Ser Ser Ser Thr Ala Tyr
65                70                75                80
Met His Leu Asn Ser Leu Thr Ser Glu Asp Ser Ala Val Tyr Tyr Cys
```

```
                    85              90              95

Ala Arg Gly Tyr Gly Asn Tyr Lys Ala Trp Phe Ala Tyr Trp Gly Gln
            100             105             110

Gly Thr Leu Val Thr Val Ser Ala Ala Ser Thr Lys Gly Pro Ser Val
            115             120             125

Phe Pro Leu Ala Pro Ser Ser Lys Ser Thr Ser Gly Gly Thr Ala Ala
        130             135             140

Leu Gly Cys Leu Val Lys Asp Tyr Phe Pro Glu Pro Val Thr Val Ser
145             150             155             160

Trp Asn Ser Gly Ala Leu Thr Ser Gly Val His Thr Phe Pro Ala Val
            165             170             175

Leu Gln Ser Ser Gly Leu Tyr Ser Leu Ser Ser Val Val Thr Val Pro
            180             185             190

Ser Ser Ser Leu Gly Thr Gln Thr Tyr Ile Cys Asn Val Asn His Lys
            195             200             205

Pro Ser Asn Thr Lys Val Asp Lys Lys Val Glu Pro Lys Ser Cys Asp
        210             215             220

Lys Thr His Thr Cys Pro Pro Cys Pro Ala Pro Glu Leu Leu Gly Gly
225             230             235             240

Pro Ser Val Phe Leu Phe Pro Pro Lys Pro Lys Asp Thr Leu Met Ile
            245             250             255

Ser Arg Thr Pro Glu Val Thr Cys Val Val Val Asp Val Ser His Glu
            260             265             270

Asp Pro Glu Val Lys Phe Asn Trp Tyr Val Asp Gly Val Glu Val His
            275             280             285

Asn Ala Lys Thr Lys Pro Arg Glu Glu Gln Tyr Gln Ser Thr Tyr Arg
        290             295             300

Val Val Ser Val Leu Thr Val Leu His Gln Asp Trp Leu Asn Gly Lys
305             310             315             320

Glu Tyr Lys Cys Lys Val Ser Asn Lys Ala Leu Pro Ala Pro Ile Glu
            325             330             335

Lys Thr Ile Ser Lys Ala Lys Gly Gln Pro Arg Glu Pro Gln Val Tyr
            340             345             350

Thr Leu Pro Pro Ser Arg Glu Glu Met Thr Lys Asn Gln Val Ser Leu
            355             360             365

Thr Cys Leu Val Lys Gly Phe Tyr Pro Ser Asp Ile Ala Val Glu Trp
        370             375             380

Glu Ser Asn Gly Gln Pro Glu Asn Asn Tyr Lys Thr Thr Pro Pro Val
385             390             395             400

Leu Asp Ser Asp Gly Ser Phe Phe Leu Tyr Ser Lys Leu Thr Val Asp
            405             410             415

Lys Ser Arg Trp Gln Gln Gly Asn Val Phe Ser Cys Ser Val Met His
            420             425             430

Glu Ala Leu His Asn His Tyr Thr Gln Lys Ser Leu Ser Leu Ser Pro
        435             440             445

Gly Lys
    450
```

<210> SEQ ID NO 127
<211> LENGTH: 452
<212> TYPE: PRT
<213> ORGANISM: Artificial Sequence
<220> FEATURE:
<223> OTHER INFORMATION: PR000815 HC

```
<400> SEQUENCE: 127

Gln Val Gln Val Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Pro Gly Lys Gly Leu Glu Trp Val
        35                  40                  45

Ala Ser Thr Trp Tyr Glu Gly Ser Lys Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Lys Met Asn Ser Leu Arg Gly Asp Asp Thr Ala Val Tyr Tyr Cys
                85                  90                  95

Ala Lys Gly Gly Asp Leu Leu Thr Gly Pro Asn Ala Phe Asp Ile Trp
            100                 105                 110

Gly Gln Gly Thr Met Val Thr Val Ser Ser Ala Ser Thr Lys Gly Pro
            115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
            195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
            355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415
```

-continued

```
Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
            435                 440                 445

Ser Pro Gly Lys
    450

<210> SEQ ID NO 128
<211> LENGTH: 452
<212> TYPE: PRT
<213> ORGANISM: Artificial Sequence
<220> FEATURE:
<223> OTHER INFORMATION: PR000816 HC, PR000822 HC

<400> SEQUENCE: 128

Gln Val Gln Val Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Pro Gly Lys Gly Leu Glu Trp Val
            35                  40                  45

Ala Ser Thr Trp Tyr Asp Ala Ser Lys Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Lys Met Asn Ser Leu Arg Gly Asp Asp Thr Ala Val Tyr Tyr Cys
                85                  90                  95

Ala Lys Gly Gly Asp Leu Leu Thr Gly Pro Asn Ala Phe Asp Ile Trp
            100                 105                 110

Gly Gln Gly Thr Met Val Thr Val Ser Ser Ala Ser Thr Lys Gly Pro
            115                 120                 125

Ser Val Phe Pro Leu Ala Pro Ser Ser Lys Ser Thr Ser Gly Gly Thr
            130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
            195                 200                 205

His Lys Pro Ser Asn Thr Lys Val Asp Lys Lys Val Glu Pro Lys Ser
            210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
                260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
            290                 295                 300

Tyr Arg Val Val Ser Val Leu Thr Val Leu His Gln Asp Trp Leu Asn
305                 310                 315                 320
```

-continued

```
Gly Lys Glu Tyr Lys Cys Lys Val Ser Asn Lys Ala Leu Pro Ala Pro
                325             330             335

Ile Glu Lys Thr Ile Ser Lys Ala Lys Gly Gln Pro Arg Glu Pro Gln
            340             345             350

Val Tyr Thr Leu Pro Pro Ser Arg Glu Glu Met Thr Lys Asn Gln Val
        355             360             365

Ser Leu Thr Cys Leu Val Lys Gly Phe Tyr Pro Ser Asp Ile Ala Val
    370             375             380

Glu Trp Glu Ser Asn Gly Gln Pro Glu Asn Asn Tyr Lys Thr Thr Pro
385             390             395             400

Pro Val Leu Asp Ser Asp Gly Ser Phe Phe Leu Tyr Ser Lys Leu Thr
                405             410             415

Val Asp Lys Ser Arg Trp Gln Gln Gly Asn Val Phe Ser Cys Ser Val
            420             425             430

Met His Glu Ala Leu His Asn His Tyr Thr Gln Lys Ser Leu Ser Leu
        435             440             445

Ser Pro Gly Lys
    450

<210> SEQ ID NO 129
<211> LENGTH: 452
<212> TYPE: PRT
<213> ORGANISM: Artificial Sequence
<220> FEATURE:
<223> OTHER INFORMATION: PR000817 HC

<400> SEQUENCE: 129

Gln Val Gln Leu Val Glu Ser Gly Gly Gly Val Val Gln Pro Gly Arg
1               5               10              15

Ser Leu Arg Leu Ser Cys Ala Ala Ser Gly Phe Thr Phe Ser Ser Tyr
            20              25              30

Asp Met His Trp Val Arg Gln Ala Pro Gly Lys Gly Leu Glu Trp Val
        35              40              45

Ala Ser Thr Trp Tyr Glu Gly Ser Lys Lys Tyr Tyr Ala Asp Ser Val
    50              55              60

Lys Gly Arg Phe Thr Ile Ser Arg Asp Asn Ser Lys Asn Thr Leu Tyr
65              70              75              80

Leu Gln Met Asn Ser Leu Arg Ala Glu Asp Thr Ala Val Tyr Tyr Cys
                85              90              95

Ala Lys Gly Gly Asp Leu Leu Thr Gly Pro Asn Ala Phe Asp Ile Trp
            100             105             110

Gly Gln Gly Thr Met Val Thr Val Ser Ser Ala Ser Thr Lys Gly Pro
        115             120             125

Ser Val Phe Pro Leu Ala Pro Ser Ser Lys Ser Thr Ser Gly Gly Thr
    130             135             140

Ala Ala Leu Gly Cys Leu Val Lys Asp Tyr Phe Pro Glu Pro Val Thr
145             150             155             160

Val Ser Trp Asn Ser Gly Ala Leu Thr Ser Gly Val His Thr Phe Pro
                165             170             175

Ala Val Leu Gln Ser Ser Gly Leu Tyr Ser Leu Ser Ser Val Val Thr
            180             185             190

Val Pro Ser Ser Ser Leu Gly Thr Gln Thr Tyr Ile Cys Asn Val Asn
        195             200             205

His Lys Pro Ser Asn Thr Lys Val Asp Lys Lys Val Glu Pro Lys Ser
    210             215             220
```

```
Cys Asp Lys Thr His Thr Cys Pro Pro Cys Pro Ala Pro Glu Ala Ala
225                 230             235             240

Gly Gly Pro Ser Val Phe Leu Phe Pro Pro Lys Pro Lys Asp Thr Leu
                245             250             255

Met Ile Ser Arg Thr Pro Glu Val Thr Cys Val Val Val Asp Val Ser
            260             265             270

His Glu Asp Pro Glu Val Lys Phe Asn Trp Tyr Val Asp Gly Val Glu
        275             280             285

Val His Asn Ala Lys Thr Lys Pro Arg Glu Glu Gln Tyr Asn Ser Thr
    290             295             300

Tyr Arg Val Val Ser Val Leu Thr Val Leu His Gln Asp Trp Leu Asn
305             310             315             320

Gly Lys Glu Tyr Lys Cys Lys Val Ser Asn Lys Ala Leu Pro Ala Pro
                325             330             335

Ile Glu Lys Thr Ile Ser Lys Ala Lys Gly Gln Pro Arg Glu Pro Gln
            340             345             350

Val Tyr Thr Leu Pro Pro Ser Arg Glu Glu Met Thr Lys Asn Gln Val
            355             360             365

Ser Leu Thr Cys Leu Val Lys Gly Phe Tyr Pro Ser Asp Ile Ala Val
    370             375             380

Glu Trp Glu Ser Asn Gly Gln Pro Glu Asn Asn Tyr Lys Thr Thr Pro
385             390             395             400

Pro Val Leu Asp Ser Asp Gly Ser Phe Phe Leu Tyr Ser Lys Leu Thr
                405             410             415

Val Asp Lys Ser Arg Trp Gln Gln Gly Asn Val Phe Ser Cys Ser Val
            420             425             430

Met His Glu Ala Leu His Asn His Tyr Thr Gln Lys Ser Leu Ser Leu
        435             440             445

Ser Pro Gly Lys
    450

<210> SEQ ID NO 130
<211> LENGTH: 452
<212> TYPE: PRT
<213> ORGANISM: Artificial Sequence
<220> FEATURE:
<223> OTHER INFORMATION: PR000818 HC, PR000824 HC, PR003832 HC, PR003833
      HC, PR003834 HC, PR003

<400> SEQUENCE: 130

Gln Val Gln Leu Val Glu Ser Gly Gly Gly Val Val Gln Pro Gly Arg
1               5               10              15

Ser Leu Arg Leu Ser Cys Ala Ala Ser Gly Phe Thr Phe Ser Ser Tyr
            20              25              30

Asp Met His Trp Val Arg Gln Ala Pro Gly Lys Gly Leu Glu Trp Val
        35              40              45

Ala Ser Thr Trp Tyr Asp Ala Ser Lys Lys Tyr Tyr Ala Asp Ser Val
    50              55              60

Lys Gly Arg Phe Thr Ile Ser Arg Asp Asn Ser Lys Asn Thr Leu Tyr
65              70              75              80

Leu Gln Met Asn Ser Leu Arg Ala Glu Asp Thr Ala Val Tyr Tyr Cys
                85              90              95

Ala Lys Gly Gly Asp Leu Leu Thr Gly Pro Asn Ala Phe Asp Ile Trp
            100             105             110

Gly Gln Gly Thr Met Val Thr Val Ser Ser Ala Ser Thr Lys Gly Pro
```

-continued

```
              115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
                180                 185                 190

Val Pro Ser Ser Ser Leu Gly Thr Gln Thr Tyr Ile Cys Asn Val Asn
                195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
                260                 265                 270

His Glu Asp Pro Glu Val Lys Phe Asn Trp Tyr Val Asp Gly Val Glu
    275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
                340                 345                 350

Val Tyr Thr Leu Pro Pro Ser Arg Glu Glu Met Thr Lys Asn Gln Val
                355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
                420                 425                 430

Met His Glu Ala Leu His Asn His Tyr Thr Gln Lys Ser Leu Ser Leu
    435                 440                 445

Ser Pro Gly Lys
    450
```

```
<210> SEQ ID NO 131
<211> LENGTH: 452
<212> TYPE: PRT
<213> ORGANISM: Artificial Sequence
<220> FEATURE:
<223> OTHER INFORMATION: PR000819 HC, PR000825 HC

<400> SEQUENCE: 131

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
```

-continued

```
               20                 25                 30
Asp Met His Trp Val Arg Gln Ala Pro Gly Lys Gly Leu Glu Trp Val
            35                 40                 45

Ala Ser Thr Trp Tyr Asp Gly Ser Lys Lys Tyr Tyr Ala Asp Ser Val
        50                 55                 60

Lys Gly Arg Phe Thr Ile Ser Arg Asp Asn Ser Lys Asn Thr Leu Tyr
65                 70                 75                 80

Leu Gln Met Asn Ser Leu Arg Ala Glu Asp Thr Ala Val Tyr Tyr Cys
                85                 90                 95

Ala Lys Gly Gly Asp Leu Leu Thr Gly Pro Asn Ala Phe Asp Ile Trp
            100                105                110

Gly Gln Gly Thr Met Val Thr Val Ser Ser Ala Ser Thr Lys Gly Pro
        115                120                125

Ser Val Phe Pro Leu Ala Pro Ser Ser Lys Ser Thr Ser Gly Gly Thr
        130                135                140

Ala Ala Leu Gly Cys Leu Val Lys Asp Tyr Phe Pro Glu Pro Val Thr
145                150                155                160

Val Ser Trp Asn Ser Gly Ala Leu Thr Ser Gly Val His Thr Phe Pro
                165                170                175

Ala Val Leu Gln Ser Ser Gly Leu Tyr Ser Leu Ser Ser Val Val Thr
            180                185                190

Val Pro Ser Ser Ser Leu Gly Thr Gln Thr Tyr Ile Cys Asn Val Asn
            195                200                205

His Lys Pro Ser Asn Thr Lys Val Asp Lys Lys Val Glu Pro Lys Ser
        210                215                220

Cys Asp Lys Thr His Thr Cys Pro Pro Cys Pro Ala Pro Glu Ala Ala
225                230                235                240

Gly Gly Pro Ser Val Phe Leu Phe Pro Pro Lys Pro Lys Asp Thr Leu
            245                250                255

Met Ile Ser Arg Thr Pro Glu Val Thr Cys Val Val Val Asp Val Ser
            260                265                270

His Glu Asp Pro Glu Val Lys Phe Asn Trp Tyr Val Asp Gly Val Glu
        275                280                285

Val His Asn Ala Lys Thr Lys Pro Arg Glu Glu Gln Tyr Asn Ser Thr
        290                295                300

Tyr Arg Val Val Ser Val Leu Thr Val Leu His Gln Asp Trp Leu Asn
305                310                315                320

Gly Lys Glu Tyr Lys Cys Lys Val Ser Asn Lys Ala Leu Pro Ala Pro
            325                330                335

Ile Glu Lys Thr Ile Ser Lys Ala Lys Gly Gln Pro Arg Glu Pro Gln
            340                345                350

Val Tyr Thr Leu Pro Pro Ser Arg Glu Glu Met Thr Lys Asn Gln Val
            355                360                365

Ser Leu Thr Cys Leu Val Lys Gly Phe Tyr Pro Ser Asp Ile Ala Val
        370                375                380

Glu Trp Glu Ser Asn Gly Gln Pro Glu Asn Asn Tyr Lys Thr Thr Pro
385                390                395                400

Pro Val Leu Asp Ser Asp Gly Ser Phe Phe Leu Tyr Ser Lys Leu Thr
                405                410                415

Val Asp Lys Ser Arg Trp Gln Gln Gly Asn Val Phe Ser Cys Ser Val
            420                425                430

Met His Glu Ala Leu His Asn His Tyr Thr Gln Lys Ser Leu Ser Leu
            435                440                445
```

-continued

```
Ser Pro Gly Lys
    450

<210> SEQ ID NO 132
<211> LENGTH: 449
<212> TYPE: PRT
<213> ORGANISM: Artificial Sequence
<220> FEATURE:
<223> OTHER INFORMATION: PR000843 HC, PR000847 HC

<400> SEQUENCE: 132

Gln Val Gln Leu Val Glu Ser Gly Gly Gly Val Ala Gln Pro Gly Arg
1               5                   10                  15

Ser Leu Ser Leu Ser Cys Ala Ala Ser Gly Phe Thr Phe Ser Asp Tyr
            20                  25                  30

Gly Met His Trp Val Arg Gln Ala Pro Gly Lys Gly Leu Glu Trp Val
        35                  40                  45

Ala Leu Ile Trp Tyr Glu Gly Ser Phe Glu Tyr Tyr Ala Asp Ser Val
    50                  55                  60

Lys Gly Arg Phe Ser Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Arg Glu Gly Gln Trp Gly Ser Arg Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350
```

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
        435                 440                 445

Lys

<210> SEQ ID NO 133
<211> LENGTH: 449
<212> TYPE: PRT
<213> ORGANISM: Artificial Sequence
<220> FEATURE:
<223> OTHER INFORMATION: PR000844 HC, PR000848 HC

<400> SEQUENCE: 133

Gln Val Gln Leu Val Glu Ser Gly Gly Gly Val Ala Gln Pro Gly Arg
1               5                   10                  15

Ser Leu Ser Leu Ser Cys Ala Ala Ser Gly Phe Thr Phe Ser Asp Tyr
            20                  25                  30

Gly Met His Trp Val Arg Gln Ala Pro Gly Lys Gly Leu Glu Trp Val
        35                  40                  45

Ala Leu Ile Trp Tyr Glu Gly Ser Phe Glu Tyr Tyr Ala Asp Ser Val
    50                  55                  60

Lys Gly Arg Phe Ser Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Arg Asp Ala Gln Trp Gly Ser Arg Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 134
<211> LENGTH: 449
<212> TYPE: PRT
<213> ORGANISM: Artificial Sequence
<220> FEATURE:
<223> OTHER INFORMATION: PR000845 HC, PR000849 HC

<400> SEQUENCE: 134

Gln Val Gln Leu Val Glu Ser Gly Gly Gly Val Ala Gln Pro Gly Arg
1               5                   10                  15

Ser Leu Ser Leu Ser Cys Ala Ala Ser Gly Phe Thr Phe Ser Asp Tyr
            20                  25                  30

Gly Met His Trp Val Arg Gln Ala Pro Gly Lys Gly Leu Glu Trp Val
        35                  40                  45

Ala Leu Ile Trp Tyr Asp Ala Ser Phe Glu Tyr Ala Asp Ser Val
    50                  55                  60

Lys Gly Arg Phe Ser Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Val Arg Glu Gly Gln Trp Gly Ser Arg Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu

-continued

```
                165                170                175
Gln Ser Ser Gly Leu Tyr Ser Leu Ser Ser Val Val Thr Val Pro Ser
            180                185                190

Ser Ser Leu Gly Thr Gln Thr Tyr Ile Cys Asn Val Asn His Lys Pro
            195                200                205

Ser Asn Thr Lys Val Asp Lys Lys Val Glu Pro Lys Ser Cys Asp Lys
    210                215                220

Thr His Thr Cys Pro Pro Cys Pro Ala Pro Glu Ala Ala Gly Gly Pro
225                230                235                240

Ser Val Phe Leu Phe Pro Pro Lys Pro Lys Asp Thr Leu Met Ile Ser
            245                250                255

Arg Thr Pro Glu Val Thr Cys Val Val Val Asp Val Ser His Glu Asp
            260                265                270

Pro Glu Val Lys Phe Asn Trp Tyr Val Asp Gly Val Glu Val His Asn
            275                280                285

Ala Lys Thr Lys Pro Arg Glu Glu Gln Tyr Asn Ser Thr Tyr Arg Val
            290                295                300

Val Ser Val Leu Thr Val Leu His Gln Asp Trp Leu Asn Gly Lys Glu
305                310                315                320

Tyr Lys Cys Lys Val Ser Asn Lys Ala Leu Pro Ala Pro Ile Glu Lys
            325                330                335

Thr Ile Ser Lys Ala Lys Gly Gln Pro Arg Glu Pro Gln Val Tyr Thr
            340                345                350

Leu Pro Pro Ser Arg Glu Glu Met Thr Lys Asn Gln Val Ser Leu Thr
            355                360                365

Cys Leu Val Lys Gly Phe Tyr Pro Ser Asp Ile Ala Val Glu Trp Glu
    370                375                380

Ser Asn Gly Gln Pro Glu Asn Asn Tyr Lys Thr Thr Pro Pro Val Leu
385                390                395                400

Asp Ser Asp Gly Ser Phe Phe Leu Tyr Ser Lys Leu Thr Val Asp Lys
            405                410                415

Ser Arg Trp Gln Gln Gly Asn Val Phe Ser Cys Ser Val Met His Glu
            420                425                430

Ala Leu His Asn His Tyr Thr Gln Lys Ser Leu Ser Leu Ser Pro Gly
            435                440                445

Lys
```

```
<210> SEQ ID NO 135
<211> LENGTH: 449
<212> TYPE: PRT
<213> ORGANISM: Artificial Sequence
<220> FEATURE:
<223> OTHER INFORMATION: PR000846 HC, PR000850 HC

<400> SEQUENCE: 135

Gln Val Gln Leu Val Glu Ser Gly Gly Gly Val Ala Gln Pro Gly Arg
1               5                10                15

Ser Leu Ser Leu Ser Cys Ala Ala Ser Gly Phe Thr Phe Ser Asp Tyr
            20                25                30

Gly Met His Trp Val Arg Gln Ala Pro Gly Lys Gly Leu Glu Trp Val
            35                40                45

Ala Leu Ile Trp Tyr Asp Ala Ser Phe Glu Tyr Tyr Ala Asp Ser Val
    50                55                60

Lys Gly Arg Phe Ser Ile Ser Arg Asp Asn Ser Lys Asn Thr Leu Tyr
65                70                75                80
```

-continued

```
Leu Gln Met Asn Ser Leu Arg Ala Glu Asp Thr Ala Val Tyr Tyr Cys
            85                  90                  95

Val Arg Asp Ala Gln Trp Gly Ser Arg Leu Asp Tyr Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys
```

```
<210> SEQ ID NO 136
<211> LENGTH: 453
<212> TYPE: PRT
<213> ORGANISM: Artificial Sequence
<220> FEATURE:
<223> OTHER INFORMATION: PR001408 HC
```

<400> SEQUENCE: 136

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Tyr Ser Tyr
                20                  25                  30

Gly Met His Trp Val Arg Gln Thr Pro Gly Lys Gly Leu Glu Trp Val
            35                  40                  45

Ala Leu Ile Trp Tyr Asp Gly Ser Asn Asn Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Glu Arg Ser Ser Ser Phe Tyr Tyr Tyr Gly Met Asp Val
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Ser Ser Lys Ser Thr Ser Gly Gly
        130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
        210                 215                 220

Ser Cys Asp Lys Thr His Thr Cys Pro Pro Cys Pro Ala Pro Glu Ala
225                 230                 235                 240

Ala Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
        290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
            355                 360                 365

Val Ser Leu Thr Cys Leu Val Lys Gly Phe Tyr Pro Ser Asp Ile Ala
        370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu

-continued

```
                    405                 410                 415

Thr Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
            435                 440                 445

Leu Ser Pro Gly Lys
        450

<210> SEQ ID NO 137
<211> LENGTH: 447
<212> TYPE: PRT
<213> ORGANISM: Artificial Sequence
<220> FEATURE:
<223> OTHER INFORMATION: PR002078 HC

<400> SEQUENCE: 137

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Tyr Ser Trp Val Arg Gln Ala Pro Gly Lys Gly Leu Glu Trp Val
        35                  40                  45

Ser Ala Ile Ser Gly Ser Gly Gly Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Gly Tyr Gly Arg Val Asp Glu Trp Gly Arg Gly Thr Leu
            100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
            195                 200                 205

Thr Lys Val Asp Lys Lys Val Glu Pro Lys Ser Cys Asp Lys Thr His
        210                 215                 220

Thr Cys Pro Pro Cys Pro Ala Pro Glu Phe Glu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
        290                 295                 300

Val Leu Thr Val Leu His Gln Asp Trp Leu Asn Gly Lys Glu Tyr Lys
```

-continued

```
305                310                315                320

Cys Lys Val Ser Asn Lys Ala Leu Pro Ala Ser Ile Glu Lys Thr Ile
             325                330                335

Ser Lys Ala Lys Gly Gln Pro Arg Glu Pro Gln Val Tyr Thr Leu Pro
             340                345                350

Pro Ser Arg Glu Glu Met Thr Lys Asn Gln Val Ser Leu Thr Cys Leu
             355                360                365

Val Lys Gly Phe Tyr Pro Ser Asp Ile Ala Val Glu Trp Glu Ser Asn
     370                375                380

Gly Gln Pro Glu Asn Asn Tyr Lys Thr Thr Pro Pro Val Leu Asp Ser
385                390                395                400

Asp Gly Ser Phe Phe Leu Tyr Ser Lys Leu Thr Val Asp Lys Ser Arg
             405                410                415

Trp Gln Gln Gly Asn Val Phe Ser Cys Ser Val Met His Glu Ala Leu
             420                425                430

His Asn His Tyr Thr Gln Lys Ser Leu Ser Leu Ser Pro Gly Lys
             435                440                445

<210> SEQ ID NO 138
<211> LENGTH: 214
<212> TYPE: PRT
<213> ORGANISM: Artificial Sequence
<220> FEATURE:
<223> OTHER INFORMATION: PR000497 LC, PR000815 LC, PR000816 LC, PR000817
      LC, PR000818 LC, PR000

<400> SEQUENCE: 138

Asp Ile Gln Met Thr Gln Ser Pro Ser Thr Leu Ser Ala Ser Val Gly
1                5                10                15

Asp Arg Val Thr Ile Thr Cys Arg Ala Ser Gln Ser Ile Ser Ser Trp
             20                25                30

Leu Ala Trp Tyr Gln Gln Lys Pro Gly Lys Ala Pro Lys Leu Leu Ile
         35                40                45

Tyr Lys Ala Ser Ser Leu Glu Ser Gly Val Pro Ser Arg Phe Ser Gly
     50                55                60

Ser Gly Ser Gly Thr Glu Phe Thr Leu Thr Ile Ser Ser Leu Gln Pro
65                70                75                80

Asp Asp Phe Ala Thr Tyr Tyr Cys Gln Gln Tyr Asp Asn Tyr Ser Asn
             85                90                95

Thr Phe Gly Gln Gly Thr Lys Leu Glu Ile Lys Arg Thr Val Ala Ala
             100                105                110

Pro Ser Val Phe Ile Phe Pro Pro Ser Asp Glu Gln Leu Lys Ser Gly
         115                120                125

Thr Ala Ser Val Val Cys Leu Leu Asn Asn Phe Tyr Pro Arg Glu Ala
     130                135                140

Lys Val Gln Trp Lys Val Asp Asn Ala Leu Gln Ser Gly Asn Ser Gln
145                150                155                160

Glu Ser Val Thr Glu Gln Asp Ser Lys Asp Ser Thr Tyr Ser Leu Ser
             165                170                175

Ser Thr Leu Thr Leu Ser Lys Ala Asp Tyr Glu Lys His Lys Val Tyr
             180                185                190

Ala Cys Glu Val Thr His Gln Gly Leu Ser Ser Pro Val Thr Lys Ser
         195                200                205

Phe Asn Arg Gly Glu Cys
     210
```

```
<210> SEQ ID NO 139
<211> LENGTH: 214
<212> TYPE: PRT
<213> ORGANISM: Artificial Sequence
<220> FEATURE:
<223> OTHER INFORMATION: PR000506 LC, PR000843 LC, PR000844 LC, PR000845
      LC, PR000846 LC

<400> SEQUENCE: 139

Lys Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Arg Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Ile Phe
                85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 140
<211> LENGTH: 214
<212> TYPE: PRT
<213> ORGANISM: Artificial Sequence
<220> FEATURE:
<223> OTHER INFORMATION: PR000690 LC

<400> SEQUENCE: 140

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
```

```
                85                      90                       95
Thr Phe Gly Gly Gly Thr Lys Val Glu Ile Lys Arg Thr Val Ala Ala
            100                     105                      110
Pro Ser Val Phe Ile Phe Pro Pro Ser Asp Glu Gln Leu Lys Ser Gly
            115                     120                      125
Thr Ala Ser Val Val Cys Leu Leu Asn Asn Phe Tyr Pro Arg Glu Ala
        130                     135                      140
Lys Val Gln Trp Lys Val Asp Asn Ala Leu Gln Ser Gly Asn Ser Gln
145                     150                     155                 160
Glu Ser Val Thr Glu Gln Asp Ser Lys Asp Ser Thr Tyr Ser Leu Ser
                165                     170                      175
Ser Thr Leu Thr Leu Ser Lys Ala Asp Tyr Glu Lys His Lys Val Tyr
            180                     185                      190
Ala Cys Glu Val Thr His Gln Gly Leu Ser Ser Pro Val Thr Lys Ser
            195                     200                      205
Phe Asn Arg Gly Glu Cys
    210
```

```
<210> SEQ ID NO 141
<211> LENGTH: 213
<212> TYPE: PRT
<213> ORGANISM: Artificial Sequence
<220> FEATURE:
<223> OTHER INFORMATION: PR000752 LC

<400> SEQUENCE: 141

Asp Ala Val Met Thr Gln Thr Pro Lys Phe Leu Leu Val Ser Ala Gly
1               5                   10                      15
Asp Arg Val Thr Ile Thr Cys Lys Ala Ser Gln Ser Val Thr Asn Asp
            20                  25                  30
Val Ala Trp Tyr Gln Gln Lys Pro Gly Gln Ser Pro Lys Leu Leu Ile
            35                  40                  45
Tyr Tyr Ala Ser Asn Arg Tyr Thr Gly Val Pro Asp Arg Phe Thr Gly
    50                  55                  60
Ser Gly Tyr Gly Thr Asp Phe Thr Phe Thr Ile Ser Thr Val Gln Ala
65                  70                  75                      80
Glu Asp Leu Ala Val Tyr Phe Cys Gln Gln Asp Tyr Ser Ser Leu Thr
                85                  90                      95
Phe Gly Ala Gly Thr Lys Leu Glu Leu Lys Arg Thr Val Ala Ala Pro
            100                     105                      110
Ser Val Phe Ile Phe Pro Pro Ser Asp Glu Gln Leu Lys Ser Gly Thr
            115                     120                      125
Ala Ser Val Val Cys Leu Leu Asn Asn Phe Tyr Pro Arg Glu Ala Lys
        130                     135                      140
Val Gln Trp Lys Val Asp Asn Ala Leu Gln Ser Gly Asn Ser Gln Glu
145                     150                     155                 160
Ser Val Thr Glu Gln Asp Ser Lys Asp Ser Thr Tyr Ser Leu Ser Ser
                165                     170                      175
Thr Leu Thr Leu Ser Lys Ala Asp Tyr Glu Lys His Lys Val Tyr Ala
            180                     185                      190
Cys Glu Val Thr His Gln Gly Leu Ser Ser Pro Val Thr Lys Ser Phe
            195                     200                      205
Asn Arg Gly Glu Cys
    210
```

-continued

```
<210> SEQ ID NO 142
<211> LENGTH: 214
<212> TYPE: PRT
<213> ORGANISM: Artificial Sequence
<220> FEATURE:
<223> OTHER INFORMATION: PR000820 LC, PR000822 LC, PR000824 LC, PR000825
      LC

<400> SEQUENCE: 142

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asp Gln Tyr Ser Asn
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 143
<211> LENGTH: 214
<212> TYPE: PRT
<213> ORGANISM: Artificial Sequence
<220> FEATURE:
<223> OTHER INFORMATION: PR000847 LC, PR000848 LC, PR000849 LC, PR000850
      LC, PR000851 LC

<400> SEQUENCE: 143

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Arg Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Ile Phe
```

-continued

```
                 85                  90                  95
Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 144
<211> LENGTH: 214
<212> TYPE: PRT
<213> ORGANISM: Artificial Sequence
<220> FEATURE:
<223> OTHER INFORMATION: PR001408 LC

<400> SEQUENCE: 144

Asp Ile Gln Leu Thr Gln Ser Pro Ser Phe Leu Ser Thr Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
            35                  40                  45

Tyr Ala Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro Tyr
                85                  90                  95

Thr Phe Gly Gln Gly Thr Glu Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210
```

```
<210> SEQ ID NO 145
<211> LENGTH: 216
<212> TYPE: PRT
<213> ORGANISM: Artificial Sequence
<220> FEATURE:
<223> OTHER INFORMATION: PR002078 LC

<400> SEQUENCE: 145

Gln Ser Val Leu Thr Gln Pro Pro Ser Ala Ser Gly Thr Pro Gly Gln
1               5                   10                  15

Arg Val Thr Ile Ser Cys Ser Gly Ser Leu Ser Asn Ile Gly Arg Asn
            20                  25                  30

Pro Val Asn Trp Tyr Gln Gln Leu Pro Gly Thr Ala Pro Lys Leu Leu
        35                  40                  45

Ile Tyr Leu Asp Asn Leu Arg Leu Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Thr Trp Asp Asp Ser His
                85                  90                  95

Pro Gly Trp Thr Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 146
<211> LENGTH: 214
<212> TYPE: PRT
<213> ORGANISM: Artificial Sequence
<220> FEATURE:
<223> OTHER INFORMATION: PR003832 LC

<400> SEQUENCE: 146

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asp Met Tyr Ser Asn
                85                  90                  95
```

-continued

```
Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
    210
```

```
<210> SEQ ID NO 147
<211> LENGTH: 214
<212> TYPE: PRT
<213> ORGANISM: Artificial Sequence
<220> FEATURE:
<223> OTHER INFORMATION: PR003833 LC

<400> SEQUENCE: 147
```

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
            35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asp Thr Tyr Ser Asn
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
    210
```

```
<210> SEQ ID NO 148
<211> LENGTH: 214
```

-continued

```
<212> TYPE: PRT
<213> ORGANISM: Artificial Sequence
<220> FEATURE:
<223> OTHER INFORMATION: PR003834 LC

<400> SEQUENCE: 148

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
                20                  25                  30

Leu Ala Trp Tyr Gln Gln Lys Pro Gly Lys Ala Pro Lys Leu Leu Ile
            35                  40                  45

Tyr Lys Ala Ser Ser Leu Glu Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asp Ser Tyr Ser Asn
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 149
<211> LENGTH: 214
<212> TYPE: PRT
<213> ORGANISM: Artificial Sequence
<220> FEATURE:
<223> OTHER INFORMATION: PR003835 LC

<400> SEQUENCE: 149

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
                20                  25                  30

Leu Ala Trp Tyr Gln Gln Lys Pro Gly Lys Ala Pro Lys Leu Leu Ile
            35                  40                  45

Tyr Lys Ala Ser Ser Leu Glu Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asp Asn Tyr Lys Asn
                85                  90                  95

Thr Phe Gly Gln Gly Thr Lys Leu Glu Ile Lys Arg Thr Val Ala Ala
            100                 105                 110
```

-continued

```
Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 150
<211> LENGTH: 214
<212> TYPE: PRT
<213> ORGANISM: Artificial Sequence
<220> FEATURE:
<223> OTHER INFORMATION: PR003836 LC

<400> SEQUENCE: 150

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
                20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asp Asn Tyr Glu Asn
                85                  90                  95

Thr Phe Gly Gln Gly Thr Lys Leu Glu Ile Lys Arg Thr Val Ala Ala
        100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 151
<211> LENGTH: 107
<212> TYPE: PRT
<213> ORGANISM: Artificial Sequence
```

```
<220> FEATURE:
<223> OTHER INFORMATION: PR000506; PR000843; PR000844; PR000845;
      PR000846; PR000847; PR000848; PR000849; PR000850; PR000851
<220> FEATURE:
<221> NAME/KEY: misc_feature
<222> LOCATION: (1)..(1)
<223> OTHER INFORMATION: Xaa = Glu or Lys
<220> FEATURE:
<221> NAME/KEY: misc_feature
<222> LOCATION: (4)..(4)
<223> OTHER INFORMATION: Xaa = Leu or Met

<400> SEQUENCE: 151

Xaa Ile Val Xaa Thr Gln Ser Pro Ala Thr Leu Ser Leu Ser Pro Gly
1               5                   10                  15

Glu Arg Ala Thr Leu Ser Cys Arg Ala Ser Gln Ser Val Ser Arg Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Ile Phe
                85                  90                  95

Thr Phe Gly Pro Gly Thr Lys Val Asp Ile Lys
            100                 105

<210> SEQ ID NO 152
<211> LENGTH: 119
<212> TYPE: PRT
<213> ORGANISM: Artificial Sequence
<220> FEATURE:
<223> OTHER INFORMATION: PR000506; PR000851; PR000843; PR000847;
      PR000844; PR000848; PR000845; PR000849; PR000846; PR000850
<220> FEATURE:
<221> NAME/KEY: misc_feature
<222> LOCATION: (54)..(54)
<223> OTHER INFORMATION: Xaa = Asp or Glu
<220> FEATURE:
<221> NAME/KEY: misc_feature
<222> LOCATION: (55)..(55)
<223> OTHER INFORMATION: Xaa = Ala or Gly
<220> FEATURE:
<221> NAME/KEY: misc_feature
<222> LOCATION: (99)..(99)
<223> OTHER INFORMATION: Xaa = Asp or Glu
<220> FEATURE:
<221> NAME/KEY: misc_feature
<222> LOCATION: (100)..(100)
<223> OTHER INFORMATION: Xaa = Ala or Gly

<400> SEQUENCE: 152

Gln Val Gln Leu Val Glu Ser Gly Gly Gly Val Ala Gln Pro Gly Arg
1               5                   10                  15

Ser Leu Ser Leu Ser Cys Ala Ala Ser Gly Phe Thr Phe Ser Asp Tyr
            20                  25                  30

Gly Met His Trp Val Arg Gln Ala Pro Gly Lys Gly Leu Glu Trp Val
        35                  40                  45

Ala Leu Ile Trp Tyr Xaa Xaa Ser Phe Glu Tyr Tyr Ala Asp Ser Val
    50                  55                  60

Lys Gly Arg Phe Ser Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

```
Val Arg Xaa Xaa Gln Trp Gly Ser Arg Leu Asp Tyr Trp Gly Gln Gly
            100                 105                 110

Thr Leu Val Thr Val Ser Ser
        115

<210> SEQ ID NO 153
<211> LENGTH: 6
<212> TYPE: PRT
<213> ORGANISM: Artificial Sequence
<220> FEATURE:
<223> OTHER INFORMATION: PR000506; PR000851; PR000843; PR000844;
      PR000847; PR000848; PR000845; PR000846; PR000849; PR000850
<220> FEATURE:
<221> NAME/KEY: misc_feature
<222> LOCATION: (3)..(3)
<223> OTHER INFORMATION: Xaa = Asp or Glu
<220> FEATURE:
<221> NAME/KEY: misc_feature
<222> LOCATION: (4)..(4)
<223> OTHER INFORMATION: Xaa = Ala or Gly

<400> SEQUENCE: 153

Trp Tyr Xaa Xaa Ser Phe
1               5

<210> SEQ ID NO 154
<211> LENGTH: 10
<212> TYPE: PRT
<213> ORGANISM: Artificial Sequence
<220> FEATURE:
<223> OTHER INFORMATION: PR000506; PR000851; PR000843; PR000845;
      PR000847; PR000849; PR000844; PR000846; PR000848; PR000850
<220> FEATURE:
<221> NAME/KEY: misc_feature
<222> LOCATION: (1)..(1)
<223> OTHER INFORMATION: Xaa = Asp or Glu
<220> FEATURE:
<221> NAME/KEY: misc_feature
<222> LOCATION: (2)..(2)
<223> OTHER INFORMATION: Xaa = Ala or Gly

<400> SEQUENCE: 154

Xaa Xaa Gln Trp Gly Ser Arg Leu Asp Tyr
1               5                   10

<210> SEQ ID NO 155
<211> LENGTH: 107
<212> TYPE: PRT
<213> ORGANISM: Artificial Sequence
<220> FEATURE:
<223> OTHER INFORMATION: PR000497; PR000815; PR000816; PR000817;
      PR000818; PR000819; PR000820; PR000822; PR000824; PR000825;
      PR003832; PR003833; PR003834; PR003835; PR003836
<220> FEATURE:
<221> NAME/KEY: misc_feature
<222> LOCATION: (93)..(93)
<223> OTHER INFORMATION: Xaa = Met, Asn, Gln, Ser or Thr
<220> FEATURE:
<221> NAME/KEY: misc_feature
<222> LOCATION: (95)..(95)
<223> OTHER INFORMATION: Xaa = Glu, Lys or Ser

<400> SEQUENCE: 155

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45
```

-continued

```
Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asp Xaa Tyr Xaa Asn
                85                  90                  95

Thr Phe Gly Gln Gly Thr Lys Leu Glu Ile Lys
            100                 105

<210> SEQ ID NO 156
<211> LENGTH: 122
<212> TYPE: PRT
<213> ORGANISM: Artificial Sequence
<220> FEATURE:
<223> OTHER INFORMATION: PR000819; PR000825; PR000818; PR000824;
      PR003832; PR003833; PR003834; PR003835; PR003836; PR000817;
      PR000816; PR000822; PR000815; PR000497; PR000820
<220> FEATURE:
<221> NAME/KEY: misc_feature
<222> LOCATION: (4)..(4)
<223> OTHER INFORMATION: Xaa = Leu or Val
<220> FEATURE:
<221> NAME/KEY: misc_feature
<222> LOCATION: (54)..(54)
<223> OTHER INFORMATION: Xaa = Asp or Glu
<220> FEATURE:
<221> NAME/KEY: misc_feature
<222> LOCATION: (55)..(55)
<223> OTHER INFORMATION: Xaa = Ala or Gly
<220> FEATURE:
<221> NAME/KEY: misc_feature
<222> LOCATION: (82)..(82)
<223> OTHER INFORMATION: Xaa = Lys or Gln
<220> FEATURE:
<221> NAME/KEY: misc_feature
<222> LOCATION: (88)..(88)
<223> OTHER INFORMATION: Xaa = Ala or Gly
<220> FEATURE:
<221> NAME/KEY: misc_feature
<222> LOCATION: (89)..(89)
<223> OTHER INFORMATION: Xaa = Asp or Glu

<400> SEQUENCE: 156

Gln Val Gln Xaa Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Asp Met His Trp Val Arg Gln Ala Pro Gly Lys Gly Leu Glu Trp Val
            35                  40                  45

Ala Ser Thr Trp Tyr Xaa Xaa Ser Lys Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Xaa Met Asn Ser Leu Arg Xaa Xaa Asp Thr Ala Val Tyr Tyr Cys
                85                  90                  95

Ala Lys Gly Gly Asp Leu Leu Thr Gly Pro Asn Ala Phe Asp Ile Trp
            100                 105                 110

Gly Gln Gly Thr Met Val Thr Val Ser Ser
        115                 120

<210> SEQ ID NO 157
<211> LENGTH: 9
<212> TYPE: PRT
<213> ORGANISM: Artificial Sequence
<220> FEATURE:
```

-continued

```
<223> OTHER INFORMATION: PR000497; PR000815; PR000816; PR000817;
      PR000818; PR000819; PR000820; PR000822; PR000824; PR000825;
      PR003832; PR003833; PR003834; PR003835; PR003836
<220> FEATURE:
<221> NAME/KEY: misc_feature
<222> LOCATION: (5)..(5)
<223> OTHER INFORMATION: Xaa = Met, Asn, Gln, Ser or Thr
<220> FEATURE:
<221> NAME/KEY: misc_feature
<222> LOCATION: (7)..(7)
<223> OTHER INFORMATION: Xaa = Glu, Lys or Ser

<400> SEQUENCE: 157

Gln Gln Tyr Asp Xaa Tyr Xaa Asn Thr
1               5

<210> SEQ ID NO 158
<211> LENGTH: 6
<212> TYPE: PRT
<213> ORGANISM: Artificial Sequence
<220> FEATURE:
<223> OTHER INFORMATION: PR000497; PR000819; PR000820; PR000825;
      PR000815; PR000817; PR000816; PR000818; PR000822; PR000824;
      PR003832; PR003833; PR003834; PR003835; PR003836
<220> FEATURE:
<221> NAME/KEY: misc_feature
<222> LOCATION: (3)..(3)
<223> OTHER INFORMATION: Xaa = Asp or Glu
<220> FEATURE:
<221> NAME/KEY: misc_feature
<222> LOCATION: (4)..(4)
<223> OTHER INFORMATION: Xaa = Ala or Gly

<400> SEQUENCE: 158

Trp Tyr Xaa Xaa Ser Lys
1               5

<210> SEQ ID NO 159
<211> LENGTH: 214
<212> TYPE: PRT
<213> ORGANISM: Artificial Sequence
<220> FEATURE:
<223> OTHER INFORMATION: PR000847; PR000848; PR000849; PR000850;
      PR000851; PR000506; PR000843; PR000844; PR000845; PR000846
<220> FEATURE:
<221> NAME/KEY: misc_feature
<222> LOCATION: (1)..(1)
<223> OTHER INFORMATION: Xaa = Glu or Lys
<220> FEATURE:
<221> NAME/KEY: misc_feature
<222> LOCATION: (4)..(4)
<223> OTHER INFORMATION: Xaa = Leu or Met

<400> SEQUENCE: 159

Xaa Ile Val Xaa Thr Gln Ser Pro Ala Thr Leu Ser Leu Ser Pro Gly
1               5                   10                  15

Glu Arg Ala Thr Leu Ser Cys Arg Ala Ser Gln Ser Val Ser Arg Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Ile Phe
                85                  90                  95

Thr Phe Gly Pro Gly Thr Lys Val Asp Ile Lys Arg Thr Val Ala Ala
            100                 105                 110
```

-continued

```
Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

```
<210> SEQ ID NO 160
<211> LENGTH: 214
<212> TYPE: PRT
<213> ORGANISM: Artificial Sequence
<220> FEATURE:
<223> OTHER INFORMATION: PR000497; PR000815; PR000816; PR000817;
      PR000818; PR000819; PR000820; PR000822; PR000824; PR000825;
      PR003832; PR003833; PR003834; PR003835; PR003836
<220> FEATURE:
<221> NAME/KEY: misc_feature
<222> LOCATION: (93)..(93)
<223> OTHER INFORMATION: Xaa = Met, Asn, Gln, Ser or Thr
<220> FEATURE:
<221> NAME/KEY: misc_feature
<222> LOCATION: (95)..(95)
<223> OTHER INFORMATION: Xaa = Glu, Lys or Ser

<400> SEQUENCE: 160
```

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asp Xaa Tyr Xaa Asn
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
```

-continued

```
                195                 200                 205

Phe Asn Arg Gly Glu Cys
    210

<210> SEQ ID NO 161
<211> LENGTH: 452
<212> TYPE: PRT
<213> ORGANISM: Artificial Sequence
<220> FEATURE:
<223> OTHER INFORMATION: PR000497; PR000820; PR000815; PR000816;
      PR000822; PR000817; PR000818; PR000824; PR003832; PR003833;
      PR003834; PR003835; PR003836; PR000819; PR000825
<220> FEATURE:
<221> NAME/KEY: misc_feature
<222> LOCATION: (4)..(4)
<223> OTHER INFORMATION: Xaa = Leu or Val
<220> FEATURE:
<221> NAME/KEY: misc_feature
<222> LOCATION: (54)..(54)
<223> OTHER INFORMATION: Xaa = Asp or Glu
<220> FEATURE:
<221> NAME/KEY: misc_feature
<222> LOCATION: (55)..(55)
<223> OTHER INFORMATION: Xaa = Ala or Gly
<220> FEATURE:
<221> NAME/KEY: misc_feature
<222> LOCATION: (82)..(82)
<223> OTHER INFORMATION: Xaa = Lys or Gln
<220> FEATURE:
<221> NAME/KEY: misc_feature
<222> LOCATION: (88)..(88)
<223> OTHER INFORMATION: Xaa = Ala or Gly
<220> FEATURE:
<221> NAME/KEY: misc_feature
<222> LOCATION: (89)..(89)
<223> OTHER INFORMATION: Xaa = Asp or Glu

<400> SEQUENCE: 161

Gln Val Gln Xaa Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Pro Gly Lys Gly Leu Glu Trp Val
        35                  40                  45

Ala Ser Thr Trp Tyr Xaa Xaa Ser Lys Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Xaa Met Asn Ser Leu Arg Xaa Xaa Asp Thr Ala Val Tyr Tyr Cys
            85                  90                  95

Ala Lys Gly Gly Asp Leu Leu Thr Gly Pro Asn Ala Phe Asp Ile Trp
            100                 105                 110

Gly Gln Gly Thr Met Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205
```

```
His Lys Pro Ser Asn Thr Lys Val Asp Lys Lys Val Glu Pro Lys Ser
    210             215             220
```

```
Cys Asp Lys Thr His Thr Cys Pro Pro Cys Pro Ala Pro Glu Ala Ala
225             230             235             240
```

```
Gly Gly Pro Ser Val Phe Leu Phe Pro Pro Lys Pro Lys Asp Thr Leu
            245             250             255
```

```
Met Ile Ser Arg Thr Pro Glu Val Thr Cys Val Val Val Asp Val Ser
            260             265             270
```

```
His Glu Asp Pro Glu Val Lys Phe Asn Trp Tyr Val Asp Gly Val Glu
        275             280             285
```

```
Val His Asn Ala Lys Thr Lys Pro Arg Glu Glu Gln Tyr Asn Ser Thr
    290             295             300
```

```
Tyr Arg Val Val Ser Val Leu Thr Val Leu His Gln Asp Trp Leu Asn
305             310             315             320
```

```
Gly Lys Glu Tyr Lys Cys Lys Val Ser Asn Lys Ala Leu Pro Ala Pro
            325             330             335
```

```
Ile Glu Lys Thr Ile Ser Lys Ala Lys Gly Gln Pro Arg Glu Pro Gln
            340             345             350
```

```
Val Tyr Thr Leu Pro Pro Ser Arg Glu Glu Met Thr Lys Asn Gln Val
            355             360             365
```

```
Ser Leu Thr Cys Leu Val Lys Gly Phe Tyr Pro Ser Asp Ile Ala Val
    370             375             380
```

```
Glu Trp Glu Ser Asn Gly Gln Pro Glu Asn Asn Tyr Lys Thr Thr Pro
385             390             395             400
```

```
Pro Val Leu Asp Ser Asp Gly Ser Phe Phe Leu Tyr Ser Lys Leu Thr
            405             410             415
```

```
Val Asp Lys Ser Arg Trp Gln Gln Gly Asn Val Phe Ser Cys Ser Val
            420             425             430
```

```
Met His Glu Ala Leu His Asn His Tyr Thr Gln Lys Ser Leu Ser Leu
            435             440             445
```

```
Ser Pro Gly Lys
    450
```

```
<210> SEQ ID NO 162
<211> LENGTH: 449
<212> TYPE: PRT
<213> ORGANISM: Artificial Sequence
<220> FEATURE:
<223> OTHER INFORMATION: PR000497; PR000825; PR000815; PR000819;
      PR000816; PR000820; PR000817; PR000822; PR000818; PR000824
<220> FEATURE:
<221> NAME/KEY: misc_feature
<222> LOCATION: (54)..(54)
<223> OTHER INFORMATION: Xaa = Asp or Glu
<220> FEATURE:
<221> NAME/KEY: misc_feature
<222> LOCATION: (55)..(55)
<223> OTHER INFORMATION: Xaa = Ala or Gly
<220> FEATURE:
<221> NAME/KEY: misc_feature
<222> LOCATION: (99)..(99)
<223> OTHER INFORMATION: Xaa = Asp or Glu
<220> FEATURE:
<221> NAME/KEY: misc_feature
<222> LOCATION: (100)..(100)
<223> OTHER INFORMATION: Xaa = Ala or Gly

<400> SEQUENCE: 162

Gln Val Gln Leu Val Glu Ser Gly Gly Gly Val Ala Gln Pro Gly Arg
1               5               10              15
```

-continued

```
Ser Leu Ser Leu Ser Cys Ala Ala Ser Gly Phe Thr Phe Ser Asp Tyr
        20                      25                      30

Gly Met His Trp Val Arg Gln Ala Pro Gly Lys Gly Leu Glu Trp Val
        35                      40                      45

Ala Leu Ile Trp Tyr Xaa Xaa Ser Phe Glu Tyr Tyr Ala Asp Ser Val
        50                      55                      60

Lys Gly Arg Phe Ser Ile Ser Arg Asp Asn Ser Lys Asn Thr Leu Tyr
65                      70                      75                      80

Leu Gln Met Asn Ser Leu Arg Ala Glu Asp Thr Ala Val Tyr Tyr Cys
                85                      90                      95

Val Arg Xaa Xaa Gln Trp Gly Ser Arg Leu Asp Tyr Trp Gly Gln Gly
                100                     105                     110

Thr Leu Val Thr Val Ser Ser Ala Ser Thr Lys Gly Pro Ser Val Phe
                115                     120                     125

Pro Leu Ala Pro Ser Ser Lys Ser Thr Ser Gly Gly Thr Ala Ala Leu
        130                     135                     140

Gly Cys Leu Val Lys Asp Tyr Phe Pro Glu Pro Val Thr Val Ser Trp
145                     150                     155                     160

Asn Ser Gly Ala Leu Thr Ser Gly Val His Thr Phe Pro Ala Val Leu
                165                     170                     175

Gln Ser Ser Gly Leu Tyr Ser Leu Ser Ser Val Val Thr Val Pro Ser
                180                     185                     190

Ser Ser Leu Gly Thr Gln Thr Tyr Ile Cys Asn Val Asn His Lys Pro
                195                     200                     205

Ser Asn Thr Lys Val Asp Lys Lys Val Glu Pro Lys Ser Cys Asp Lys
        210                     215                     220

Thr His Thr Cys Pro Pro Cys Pro Ala Pro Glu Ala Ala Gly Gly Pro
225                     230                     235                     240

Ser Val Phe Leu Phe Pro Pro Lys Pro Lys Asp Thr Leu Met Ile Ser
                245                     250                     255

Arg Thr Pro Glu Val Thr Cys Val Val Val Asp Val Ser His Glu Asp
                260                     265                     270

Pro Glu Val Lys Phe Asn Trp Tyr Val Asp Gly Val Glu Val His Asn
                275                     280                     285

Ala Lys Thr Lys Pro Arg Glu Glu Gln Tyr Asn Ser Thr Tyr Arg Val
        290                     295                     300

Val Ser Val Leu Thr Val Leu His Gln Asp Trp Leu Asn Gly Lys Glu
305                     310                     315                     320

Tyr Lys Cys Lys Val Ser Asn Lys Ala Leu Pro Ala Pro Ile Glu Lys
                325                     330                     335

Thr Ile Ser Lys Ala Lys Gly Gln Pro Arg Glu Pro Gln Val Tyr Thr
                340                     345                     350

Leu Pro Pro Ser Arg Glu Glu Met Thr Lys Asn Gln Val Ser Leu Thr
                355                     360                     365

Cys Leu Val Lys Gly Phe Tyr Pro Ser Asp Ile Ala Val Glu Trp Glu
        370                     375                     380

Ser Asn Gly Gln Pro Glu Asn Asn Tyr Lys Thr Thr Pro Pro Val Leu
385                     390                     395                     400

Asp Ser Asp Gly Ser Phe Phe Leu Tyr Ser Lys Leu Thr Val Asp Lys
                405                     410                     415

Ser Arg Trp Gln Gln Gly Asn Val Phe Ser Cys Ser Val Met His Glu
                420                     425                     430

Ala Leu His Asn His Tyr Thr Gln Lys Ser Leu Ser Leu Ser Pro Gly
```

-continued

```
              435                 440                 445
Lys

<210> SEQ ID NO 163
<211> LENGTH: 23
<212> TYPE: PRT
<213> ORGANISM: Artificial Sequence
<220> FEATURE:
<223> OTHER INFORMATION: PR000847; PR000848; PR000849; PR000850;
      PR000851; PR000506; PR000843; PR000844; PR000845; PR000846
<220> FEATURE:
<221> NAME/KEY: misc_feature
<222> LOCATION: (1)..(1)
<223> OTHER INFORMATION: Xaa = Glu or Lys
<220> FEATURE:
<221> NAME/KEY: misc_feature
<222> LOCATION: (4)..(4)
<223> OTHER INFORMATION: Xaa = Leu or Met

<400> SEQUENCE: 163

Xaa Ile Val Xaa Thr Gln Ser Pro Ala Thr Leu Ser Leu Ser Pro Gly
1               5                   10                  15

Glu Arg Ala Thr Leu Ser Cys
            20

<210> SEQ ID NO 164
<211> LENGTH: 25
<212> TYPE: PRT
<213> ORGANISM: Artificial Sequence
<220> FEATURE:
<223> OTHER INFORMATION: PR000497; PR000820; PR000815; PR000816;
      PR000822; PR000817; PR000818; PR000824; PR003832; PR003833;
      PR003834; PR003835; PR003836; PR000819; PR000825
<220> FEATURE:
<221> NAME/KEY: misc_feature
<222> LOCATION: (4)..(4)
<223> OTHER INFORMATION: Xaa = Leu or Val

<400> SEQUENCE: 164

Gln Val Gln Xaa Val Glu Ser Gly Gly Gly Val Val Gln Pro Gly Arg
1               5                   10                  15

Ser Leu Arg Leu Ser Cys Ala Ala Ser
            20                  25

<210> SEQ ID NO 165
<211> LENGTH: 41
<212> TYPE: PRT
<213> ORGANISM: Artificial Sequence
<220> FEATURE:
<223> OTHER INFORMATION: PR000497; PR000820; PR000815; PR000816;
      PR000822; PR000817; PR000818; PR000824; PR003832; PR003833;
      PR003834; PR003835; PR003836; PR000819; PR000825
<220> FEATURE:
<221> NAME/KEY: misc_feature
<222> LOCATION: (25)..(25)
<223> OTHER INFORMATION: Xaa = Lys or Gln
<220> FEATURE:
<221> NAME/KEY: misc_feature
<222> LOCATION: (31)..(31)
<223> OTHER INFORMATION: Xaa = Ala or Gly
<220> FEATURE:
<221> NAME/KEY: misc_feature
<222> LOCATION: (32)..(32)
<223> OTHER INFORMATION: Xaa = Asp or Glu

<400> SEQUENCE: 165

Lys Tyr Tyr Ala Asp Ser Val Lys Gly Arg Phe Thr Ile Ser Arg Asp
1               5                   10                  15

Asn Ser Lys Asn Thr Leu Tyr Leu Xaa Met Asn Ser Leu Arg Xaa Xaa
```

-continued

```
            20              25              30

Asp Thr Ala Val Tyr Tyr Cys Ala Lys
        35              40

<210> SEQ ID NO 166
<211> LENGTH: 107
<212> TYPE: PRT
<213> ORGANISM: Artificial Sequence
<220> FEATURE:
<223> OTHER INFORMATION: light chain constant region

<400> SEQUENCE: 166

Arg Thr Val Ala Ala Pro Ser Val Phe Ile Phe Pro Pro Ser Asp Glu
1               5              10              15

Gln Leu Lys Ser Gly Thr Ala Ser Val Val Cys Leu Leu Asn Asn Phe
            20              25              30

Tyr Pro Arg Glu Ala Lys Val Gln Trp Lys Val Asp Asn Ala Leu Gln
        35              40              45

Ser Gly Asn Ser Gln Glu Ser Val Thr Glu Gln Asp Ser Lys Asp Ser
    50              55              60

Thr Tyr Ser Leu Ser Ser Thr Leu Thr Leu Ser Lys Ala Asp Tyr Glu
65              70              75              80

Lys His Lys Val Tyr Ala Cys Glu Val Thr His Gln Gly Leu Ser Ser
                85              90              95

Pro Val Thr Lys Ser Phe Asn Arg Gly Glu Cys
        100             105

<210> SEQ ID NO 167
<211> LENGTH: 330
<212> TYPE: PRT
<213> ORGANISM: Artificial Sequence
<220> FEATURE:
<223> OTHER INFORMATION: heavy chain constant region

<400> SEQUENCE: 167

Ala Ser Thr Lys Gly Pro Ser Val Phe Pro Leu Ala Pro Ser Ser Lys
1               5              10              15

Ser Thr Ser Gly Gly Thr Ala Ala Leu Gly Cys Leu Val Lys Asp Tyr
            20              25              30

Phe Pro Glu Pro Val Thr Val Ser Trp Asn Ser Gly Ala Leu Thr Ser
        35              40              45

Gly Val His Thr Phe Pro Ala Val Leu Gln Ser Ser Gly Leu Tyr Ser
    50              55              60

Leu Ser Ser Val Val Thr Val Pro Ser Ser Ser Leu Gly Thr Gln Thr
65              70              75              80

Tyr Ile Cys Asn Val Asn His Lys Pro Ser Asn Thr Lys Val Asp Lys
                85              90              95

Lys Val Glu Pro Lys Ser Cys Asp Lys Thr His Thr Cys Pro Pro Cys
            100             105             110

Pro Ala Pro Glu Ala Ala Gly Gly Pro Ser Val Phe Leu Phe Pro Pro
        115             120             125

Lys Pro Lys Asp Thr Leu Met Ile Ser Arg Thr Pro Glu Val Thr Cys
    130             135             140

Val Val Val Asp Val Ser His Glu Asp Pro Glu Val Lys Phe Asn Trp
145             150             155             160

Tyr Val Asp Gly Val Glu Val His Asn Ala Lys Thr Lys Pro Arg Glu
                165             170             175
```

-continued

```
Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

```
<210> SEQ ID NO 168
<211> LENGTH: 123
<212> TYPE: PRT
<213> ORGANISM: Artificial Sequence
<220> FEATURE:
<223> OTHER INFORMATION: VH
<220> FEATURE:
<221> NAME/KEY: misc_feature
<222> LOCATION: (4)..(4)
<223> OTHER INFORMATION: Xaa = Leu or Val
<220> FEATURE:
<221> NAME/KEY: misc_feature
<222> LOCATION: (12)..(12)
<223> OTHER INFORMATION: Xaa = Ala or Val
<220> FEATURE:
<221> NAME/KEY: misc_feature
<222> LOCATION: (19)..(19)
<223> OTHER INFORMATION: Xaa = Arg or Ser
<220> FEATURE:
<221> NAME/KEY: misc_feature
<222> LOCATION: (30)..(30)
<223> OTHER INFORMATION: Xaa = Ser or Tyr
<220> FEATURE:
<221> NAME/KEY: misc_feature
<222> LOCATION: (31)..(31)
<223> OTHER INFORMATION: Xaa = Asp or Ser
<220> FEATURE:
<221> NAME/KEY: misc_feature
<222> LOCATION: (33)..(33)
<223> OTHER INFORMATION: Xaa = Asp or Gly
<220> FEATURE:
<221> NAME/KEY: misc_feature
<222> LOCATION: (40)..(40)
<223> OTHER INFORMATION: Xaa = Ala or Thr
<220> FEATURE:
<221> NAME/KEY: misc_feature
<222> LOCATION: (50)..(50)
<223> OTHER INFORMATION: Xaa = Leu or Ser
<220> FEATURE:
<221> NAME/KEY: misc_feature
<222> LOCATION: (51)..(51)
<223> OTHER INFORMATION: Xaa = Ile or Thr
<220> FEATURE:
<221> NAME/KEY: misc_feature
<222> LOCATION: (54)..(54)
<223> OTHER INFORMATION: Xaa = Asp or Glu
<220> FEATURE:
<221> NAME/KEY: misc_feature
```

```
<222> LOCATION: (55)..(55)
<223> OTHER INFORMATION: Xaa = Ala or Gly
<220> FEATURE:
<221> NAME/KEY: misc_feature
<222> LOCATION: (57)..(57)
<223> OTHER INFORMATION: Xaa = Phe, Lys or Asn
<220> FEATURE:
<221> NAME/KEY: misc_feature
<222> LOCATION: (58)..(58)
<223> OTHER INFORMATION: Xaa = Glu, Lys or Asn
<220> FEATURE:
<221> NAME/KEY: misc_feature
<222> LOCATION: (69)..(69)
<223> OTHER INFORMATION: Xaa = Ser or Thr
<220> FEATURE:
<221> NAME/KEY: misc_feature
<222> LOCATION: (82)..(82)
<223> OTHER INFORMATION: Xaa = Lys or Gln
<220> FEATURE:
<221> NAME/KEY: misc_feature
<222> LOCATION: (88)..(88)
<223> OTHER INFORMATION: Xaa = Ala or Gly
<220> FEATURE:
<221> NAME/KEY: misc_feature
<222> LOCATION: (89)..(89)
<223> OTHER INFORMATION: Xaa = Asp or Glu
<220> FEATURE:
<221> NAME/KEY: misc_feature
<222> LOCATION: (97)..(97)
<223> OTHER INFORMATION: Xaa = Ala or Val
<220> FEATURE:
<221> NAME/KEY: misc_feature
<222> LOCATION: (98)..(98)
<223> OTHER INFORMATION: Xaa = Lys, Arg or Thr
<220> FEATURE:
<221> NAME/KEY: misc_feature
<222> LOCATION: (99)..(99)
<223> OTHER INFORMATION: Xaa = Asp, Glu or Gly
<220> FEATURE:
<221> NAME/KEY: misc_feature
<222> LOCATION: (100)..(100)
<223> OTHER INFORMATION: Xaa = Ala, Gly or Arg
<220> FEATURE:
<221> NAME/KEY: misc_feature
<222> LOCATION: (101)..(101)
<223> OTHER INFORMATION: Xaa = Asp, Gln or Ser
<220> FEATURE:
<221> NAME/KEY: misc_feature
<222> LOCATION: (102)..(102)
<223> OTHER INFORMATION: Xaa = Leu, Ser or Trp
<220> FEATURE:
<221> NAME/KEY: misc_feature
<222> LOCATION: (103)..(103)
<223> OTHER INFORMATION: Xaa = Gly, Leu or Ser
<220> FEATURE:
<221> NAME/KEY: misc_feature
<222> LOCATION: (104)..(104)
<223> OTHER INFORMATION: Xaa = Phe, Ser or Thr
<220> FEATURE:
<221> NAME/KEY: misc_feature
<222> LOCATION: (105)..(105)
<223> OTHER INFORMATION: Xaa = Gly, Arg or Tyr
<220> FEATURE:
<221> NAME/KEY: misc_feature
<222> LOCATION: (106)..(106)
<223> OTHER INFORMATION: Xaa = Leu, Pro or Tyr
<220> FEATURE:
<221> NAME/KEY: misc_feature
<222> LOCATION: (107)..(107)
<223> OTHER INFORMATION: Xaa = Asp, Asn or Tyr
<220> FEATURE:
<221> NAME/KEY: misc_feature
<222> LOCATION: (108)..(108)
<223> OTHER INFORMATION: Xaa = Ala or Tyr
<220> FEATURE:
<221> NAME/KEY: misc_feature
<222> LOCATION: (109)..(109)
<223> OTHER INFORMATION: Xaa = Phe, Gly or Trp
<220> FEATURE:
```

```
<221> NAME/KEY: misc_feature
<222> LOCATION: (110)..(110)
<223> OTHER INFORMATION: Xaa = Asp, Gly or Met
<220> FEATURE:
<221> NAME/KEY: misc_feature
<222> LOCATION: (111)..(111)
<223> OTHER INFORMATION: Xaa = Asp, Ile or Gln
<220> FEATURE:
<221> NAME/KEY: misc_feature
<222> LOCATION: (112)..(112)
<223> OTHER INFORMATION: Xaa = Gly, Val or Trp
<220> FEATURE:
<221> NAME/KEY: misc_feature
<222> LOCATION: (113)..(113)
<223> OTHER INFORMATION: Xaa = Gly, Thr or Trp
<220> FEATURE:
<221> NAME/KEY: misc_feature
<222> LOCATION: (114)..(114)
<223> OTHER INFORMATION: Xaa = Gly, Leu or Gln
<220> FEATURE:
<221> NAME/KEY: misc_feature
<222> LOCATION: (115)..(115)
<223> OTHER INFORMATION: Xaa = Gly, Gln or Val
<220> FEATURE:
<221> NAME/KEY: misc_feature
<222> LOCATION: (116)..(116)
<223> OTHER INFORMATION: Xaa = Gly or Thr
<220> FEATURE:
<221> NAME/KEY: misc_feature
<222> LOCATION: (117)..(117)
<223> OTHER INFORMATION: Xaa = Met, Thr or Val
<220> FEATURE:
<221> NAME/KEY: misc_feature
<222> LOCATION: (118)..(118)
<223> OTHER INFORMATION: Xaa = Ser, Thr or Val
<220> FEATURE:
<221> NAME/KEY: misc_feature
<222> LOCATION: (119)..(119)
<223> OTHER INFORMATION: Xaa = Ser, Thr or Val
<220> FEATURE:
<221> NAME/KEY: misc_feature
<222> LOCATION: (120)..(120)
<223> OTHER INFORMATION: Xaa = Thr, Val or missing
<220> FEATURE:
<221> NAME/KEY: misc_feature
<222> LOCATION: (121)..(121)
<223> OTHER INFORMATION: Xaa = Ser, Val or missing
<220> FEATURE:
<221> NAME/KEY: misc_feature
<222> LOCATION: (122)..(122)
<223> OTHER INFORMATION: Xaa = Ser or missing
<220> FEATURE:
<221> NAME/KEY: misc_feature
<222> LOCATION: (123)..(123)
<223> OTHER INFORMATION: Xaa = Ser or missing

<400> SEQUENCE: 168

Gln Val Gln Xaa Val Glu Ser Gly Gly Gly Val Xaa Gln Pro Gly Arg
1               5                   10                  15

Ser Leu Xaa Leu Ser Cys Ala Ala Ser Gly Phe Thr Phe Xaa Xaa Tyr
            20                  25                  30

Xaa Met His Trp Val Arg Gln Xaa Pro Gly Lys Gly Leu Glu Trp Val
        35                  40                  45

Ala Xaa Xaa Trp Tyr Xaa Xaa Ser Xaa Xaa Tyr Tyr Ala Asp Ser Val
    50                  55                  60

Lys Gly Arg Phe Xaa Ile Ser Arg Asp Asn Ser Lys Asn Thr Leu Tyr
65                  70                  75                  80

Leu Xaa Met Asn Ser Leu Arg Xaa Xaa Asp Thr Ala Val Tyr Tyr Cys
            85                  90                  95

Xaa Xaa Xaa Xaa Xaa Xaa Xaa Xaa Xaa Xaa Xaa Xaa Xaa Xaa Xaa Xaa
            100                 105                 110
```

-continued

```
Xaa Xaa Xaa Xaa Xaa Xaa Xaa Xaa Xaa Xaa Xaa
        115                 120

<210> SEQ ID NO 169
<211> LENGTH: 107
<212> TYPE: PRT
<213> ORGANISM: Artificial Sequence
<220> FEATURE:
<223> OTHER INFORMATION: VL
<220> FEATURE:
<221> NAME/KEY: misc_feature
<222> LOCATION: (1)..(1)
<223> OTHER INFORMATION: Xaa = Asp, Glu or Lys
<220> FEATURE:
<221> NAME/KEY: misc_feature
<222> LOCATION: (3)..(3)
<223> OTHER INFORMATION: Xaa = Gln or Val
<220> FEATURE:
<221> NAME/KEY: misc_feature
<222> LOCATION: (4)..(4)
<223> OTHER INFORMATION: Xaa = Leu or Met
<220> FEATURE:
<221> NAME/KEY: misc_feature
<222> LOCATION: (9)..(9)
<223> OTHER INFORMATION: Xaa = Ala or Ser
<220> FEATURE:
<221> NAME/KEY: misc_feature
<222> LOCATION: (10)..(10)
<223> OTHER INFORMATION: Xaa = Phe or Thr
<220> FEATURE:
<221> NAME/KEY: misc_feature
<222> LOCATION: (13)..(13)
<223> OTHER INFORMATION: Xaa = Ala, Leu or Thr
<220> FEATURE:
<221> NAME/KEY: misc_feature
<222> LOCATION: (15)..(15)
<223> OTHER INFORMATION: Xaa = Pro or Val
<220> FEATURE:
<221> NAME/KEY: misc_feature
<222> LOCATION: (17)..(17)
<223> OTHER INFORMATION: Xaa = Asp or Glu
<220> FEATURE:
<221> NAME/KEY: misc_feature
<222> LOCATION: (19)..(19)
<223> OTHER INFORMATION: Xaa = Ala or Val
<220> FEATURE:
<221> NAME/KEY: misc_feature
<222> LOCATION: (21)..(21)
<223> OTHER INFORMATION: Xaa = Ile or Leu
<220> FEATURE:
<221> NAME/KEY: misc_feature
<222> LOCATION: (22)..(22)
<223> OTHER INFORMATION: Xaa = Ser or Thr
<220> FEATURE:
<221> NAME/KEY: misc_feature
<222> LOCATION: (28)..(28)
<223> OTHER INFORMATION: Xaa = Gly or Ser
<220> FEATURE:
<221> NAME/KEY: misc_feature
<222> LOCATION: (29)..(29)
<223> OTHER INFORMATION: Xaa = Ile or Val
<220> FEATURE:
<221> NAME/KEY: misc_feature
<222> LOCATION: (31)..(31)
<223> OTHER INFORMATION: Xaa = Arg or Ser
<220> FEATURE:
<221> NAME/KEY: misc_feature
<222> LOCATION: (32)..(32)
<223> OTHER INFORMATION: Xaa = Trp or Tyr
<220> FEATURE:
<221> NAME/KEY: misc_feature
<222> LOCATION: (42)..(42)
<223> OTHER INFORMATION: Xaa = Lys or Gln
<220> FEATURE:
<221> NAME/KEY: misc_feature
<222> LOCATION: (45)..(45)
<223> OTHER INFORMATION: Xaa = Lys or Arg
<220> FEATURE:
```

-continued

```
<221> NAME/KEY: misc_feature
<222> LOCATION: (50)..(50)
<223> OTHER INFORMATION: Xaa = Ala, Asp or Lys
<220> FEATURE:
<221> NAME/KEY: misc_feature
<222> LOCATION: (53)..(53)
<223> OTHER INFORMATION: Xaa = Asn, Ser or Thr
<220> FEATURE:
<221> NAME/KEY: misc_feature
<222> LOCATION: (54)..(54)
<223> OTHER INFORMATION: Xaa = Leu or Arg
<220> FEATURE:
<221> NAME/KEY: misc_feature
<222> LOCATION: (55)..(55)
<223> OTHER INFORMATION: Xaa = Ala, Glu or Gln
<220> FEATURE:
<221> NAME/KEY: misc_feature
<222> LOCATION: (56)..(56)
<223> OTHER INFORMATION: Xaa = Ser or Thr
<220> FEATURE:
<221> NAME/KEY: misc_feature
<222> LOCATION: (58)..(58)
<223> OTHER INFORMATION: Xaa = Ile or Val
<220> FEATURE:
<221> NAME/KEY: misc_feature
<222> LOCATION: (60)..(60)
<223> OTHER INFORMATION: Xaa = Ala or Ser
<220> FEATURE:
<221> NAME/KEY: misc_feature
<222> LOCATION: (70)..(70)
<223> OTHER INFORMATION: Xaa = Asp or Glu
<220> FEATURE:
<221> NAME/KEY: misc_feature
<222> LOCATION: (79)..(79)
<223> OTHER INFORMATION: Xaa = Glu or Gln
<220> FEATURE:
<221> NAME/KEY: misc_feature
<222> LOCATION: (81)..(81)
<223> OTHER INFORMATION: Xaa = Asp or Glu
<220> FEATURE:
<221> NAME/KEY: misc_feature
<222> LOCATION: (85)..(85)
<223> OTHER INFORMATION: Xaa = Thr or Val
<220> FEATURE:
<221> NAME/KEY: misc_feature
<222> LOCATION: (91)..(91)
<223> OTHER INFORMATION: Xaa = Leu, Arg or Tyr
<220> FEATURE:
<221> NAME/KEY: misc_feature
<222> LOCATION: (92)..(92)
<223> OTHER INFORMATION: Xaa = Asp, Asn or Ser
<220> FEATURE:
<221> NAME/KEY: misc_feature
<222> LOCATION: (93)..(93)
<223> OTHER INFORMATION: Xaa = Met, Asn, Gln, Ser or Thr
<220> FEATURE:
<221> NAME/KEY: misc_feature
<222> LOCATION: (94)..(94)
<223> OTHER INFORMATION: Xaa = Trp or Tyr
<220> FEATURE:
<221> NAME/KEY: misc_feature
<222> LOCATION: (95)..(95)
<223> OTHER INFORMATION: Xaa = Ile, Lys, Pro or Ser
<220> FEATURE:
<221> NAME/KEY: misc_feature
<222> LOCATION: (96)..(96)
<223> OTHER INFORMATION: Xaa = Phe, Asn or Tyr
<220> FEATURE:
<221> NAME/KEY: misc_feature
<222> LOCATION: (100)..(100)
<223> OTHER INFORMATION: Xaa = Pro or Gln
<220> FEATURE:
<221> NAME/KEY: misc_feature
<222> LOCATION: (103)..(103)
<223> OTHER INFORMATION: Xaa = Glu or Lys
<220> FEATURE:
<221> NAME/KEY: misc_feature
<222> LOCATION: (104)..(104)
<223> OTHER INFORMATION: Xaa = Leu or Val
```

-continued

```
<220> FEATURE:
<221> NAME/KEY: misc_feature
<222> LOCATION: (105)..(105)
<223> OTHER INFORMATION: Xaa = Asp or Glu

<400> SEQUENCE: 169

Xaa Ile Xaa Xaa Thr Gln Ser Pro Xaa Xaa Leu Ser Xaa Ser Xaa Gly
1               5                   10                  15

Xaa Arg Xaa Thr Xaa Xaa Cys Arg Ala Ser Gln Xaa Xaa Ser Xaa Xaa
            20                  25                  30

Leu Ala Trp Tyr Gln Gln Lys Pro Gly Xaa Ala Pro Xaa Leu Leu Ile
        35                  40                  45

Tyr Xaa Ala Ser Xaa Xaa Xaa Gly Xaa Pro Xaa Arg Phe Ser Gly
    50                  55                  60

Ser Gly Ser Gly Thr Xaa Phe Thr Leu Thr Ile Ser Ser Leu Xaa Pro
65                  70                  75                  80

Xaa Asp Phe Ala Xaa Tyr Tyr Cys Gln Gln Xaa Xaa Xaa Xaa Xaa Xaa
                85                  90                  95

Thr Phe Gly Xaa Gly Thr Xaa Xaa Xaa Ile Lys
            100                 105
```

ANTI-CD73 ANTIBODY AND APPLICATION THEREOF

The present application is a United States National Phase under 35 U.S.C. § 371 of International Application No. PCT/CN2020/110340, filed Aug. 20, 2020, which claims priority to International Application No. PCT/CN2019/101837, filed on Aug. 21, 2019, the contents of each which are incorporated by reference in their entirety.

BACKGROUND OF THE INVENTION

Cluster of differentiation 73, CD73, also known as 5'-nucleotidase, is an enzyme that in humans is encoded by the NTSE gene. CD73 consists of a dimer of 2 identical 70-kD subunits bound by a glycosyl phosphatidyl inositol linkage to the external face of the plasma membrane.

CD73 is known to catalyze the dephosphorylation of extracellular nucleoside monophosphates into nucleosides, such as adenosine. Extracellular adenosine accumulates in cancerous tissues and constitutes an important mechanism of tumor immune escape. Among other effects, tumor-derived adenosine profoundly inhibits infiltrating effector T cells through adenylyl cyclase-activating A2A receptors (Ohta, et al., (2006) Proc Natl Acad Sci USA 103:13132-13137). CD73 expression has been reported in a range of tumor cells, including leukemia, bladder cancer, glioma, glioblastoma, ovarian cancer, melanoma, prostate cancer, thyroid cancer, esophageal cancer and breast cancer (Jin et al., Cancer Res 2010; 70:2245-55 and Stagg et al., PNAS 2010; 107:1547-52).

While CD73 has been shown to regulate cell-cell and cell-matrix interactions on tumor cells, CD73 expression and activity has also been linked to reduced T-cell responses and implicated in drug resistance. Another problem is that antibodies generically referred to as CD73 inhibitors may not act by modulating the ecto-5' nucleotidase activity of CD73. One antibody, 7G2 (mIgG2 isotype, Life Technologies), has been reported to inhibit CD73, however this antibody does not bind cell surface CD73 in flow cytometry, or at best only with very low affinity. Another antibody that binds CD73, clone AD2 (mouse IgG1 isotype), has been reported to cause receptor clustering and internalization but have minimal effect on enzymatic activity. Yet another agent, 1E9 (mouse IgG3 isotype, Santa Cruz Biotechnology, Inc.), is reported to promote T cell signaling independently of enzymatic inhibition. A further mAb, 4G4 (IgG1 isotype, Novus Biologicals), is reported to induce CD73 shedding from the T cell surface. Only one agent, although not further characterized, was reported to have partial ability to block enzymatic in an assay using recombinant CD73 (Sachsenmeier et al. ((2012) J. Biomed. Screening 17:993-998), and was later described as an antibody that induces intracellular internalization (Rust et al. (2013) Mol. Cancer 12:11). Additionally, one further complicating factor is that the antibodies described in the literature have generally been of murine isotypes that are capable of being bound by Fcγ receptors, making it difficult to separate any potential blocking effect from Fc-mediated effects. Anti-CD73 antibodies that are bound by Fcγ receptors can for example mediate depletion (e.g. by ADCC) of CD73-expressing tumor cells (and possibly CD73-expressing immune suppressor cells), and/or may elicit the production of pro-inflammatory cytokines rather than any true blocking effect. Thus, despite the interest in targeting CD73, the characteristics of the most effective anti-CD73 antibodies remains to be determined.

New assays and antibodies for CD73 are needed for its potential as a novel therapeutic target.

SUMMARY OF THE INVENTION

The present disclosure provides an isolated antigen binding protein having one or more of the following properties: a. capable of binding to both human CD73 and Cynomolgus monkey CD73; b. capable of inhibiting 5'ectonucleotidase activity of CD73; c. capable of mediating CD73 internalization; d. capable of promoting T cell proliferation; e. with a relatively stable concentration in serum for at least 15 days; and f. capable of inhibiting tumor growth and/or tumor cell proliferation. In addition, the present disclosure also provides a method for producing the isolated antigen binding protein as well as pharmaceutical uses of the isolated antigen binding protein in preventing, alleviating and/or treating tumor.

In one aspect, the present disclosure provides an isolated antigen binding protein, having one or more of the following properties: a. capable of binding to both human CD73 and Cynomolgus monkey CD73, with comparable binding affinity; b. capable of inhibiting 5' ectonucleotidase activity of CD73; c. capable of mediating CD73 internalization; d. capable of promoting T cell proliferation; e. with a relatively stable concentration in serum for at least 15 days; and f. capable of inhibiting tumor growth and/or tumor cell proliferation.

In some embodiments, said isolated antigen binding protein comprises any one of HCDR1, HCDR2 and/or HCDR3 regions from the heavy chain variable region VH of SEQ ID NO: 168.

In some embodiments, said isolated antigen binding protein comprises any one of LCDR1, LCDR2 and/or LCDR3 regions from the light chain variable region VL of SEQ ID NO: 169.

In some embodiments, said isolated antigen binding protein comprises an antibody or an antigen binding fragment thereof.

In some embodiments, said antigen binding fragment comprises Fab, Fab', F(ab)2, Fv fragment, F(ab')2, scFv, di-scFv and/or dAb.

In some embodiments, said antibody is selected from a monoclonal antibody, a chimeric antibody, a humanized antibody, and a fully human antibody.

In some embodiments, said isolated antigen binding protein comprises any one of HCDR1, HCDR2 and/or HCDR3 regions from the heavy chain variable region VH of SEQ ID NO: 152.

In some embodiments, said VH comprises an amino acid sequence as set forth in any one of SEQ ID NO: 96, 104, 105, 106 and 107.

In some embodiments, said isolated antigen binding protein comprises any one of LCDR1, LCDR2 and/or LCDR3 regions from the light chain variable region VL of SEQ ID NO: 151.

In some embodiments, said VL comprises an amino acid sequence as set forth in any one of SEQ ID NO: 111 and 115.

In some embodiments, said HCDR3 comprises an amino acid sequence as set forth in SEQ ID NO: 154.

In some embodiments, said HCDR3 comprises an amino acid sequence as set forth in any one of SEQ ID NO: 35, 38 and 39.

In some embodiments, said HCDR2 comprises an amino acid sequence as set forth in SEQ ID NO: 153.

In some embodiments, said HCDR2 comprises an amino acid sequence as set forth in any one of SEQ ID NO: 18, 23 and 24.

In some embodiments, said HCDR1 comprises an amino acid sequence as set forth in SEQ ID NO: 7.

In some embodiments, said isolated antigen binding protein comprises a heavy chain variable region VH, and said VH comprises an amino acid sequence as set forth in SEQ ID NO: 152.

In some embodiments, said VH comprises an amino acid sequence as set forth in any of SEQ ID 96, 104, 105, 106 and 107.

In some embodiments, said isolated antigen binding protein comprises an antibody heavy chain HC, and said HC comprises an amino acid sequence as set in forth in any one of SEQ ID NO: 124, 132, 133, 134, and 135.

In some embodiments, said LCDR3 comprises an amino acid sequence as set forth in SEQ ID NO: 78.

In some embodiments, said LCDR2 comprises an amino acid sequence as set forth in SEQ ID NO:66.

In some embodiments, said LCDR1 comprises an amino acid sequence as set forth in SEQ ID NO: 55.

In some embodiments, said isolated antigen binding protein comprises a light chain variable region VL, wherein said VL comprises an amino acid sequence as set forth in SEQ ID NO: 151.

In some embodiments, said VL comprises an amino acid sequence as set forth in any one of SEQ ID NO: 111 and 115.

In some embodiments, said isolated antigen binding protein comprises an antibody light chain LC, and said LC comprises an amino acid sequence as set forth in any one of SEQ ID NO: 139 and 143.

In some embodiments, said isolated antigen binding protein comprises any one of HCDR1, HCDR2 and/or HCDR3 regions from the heavy chain variable region VH of SEQ ID NO: 156.

In some embodiments, said VH comprises an amino acid sequence as set forth in any one of SEQ ID NO: 95, 99, 100, 101, 102, and 103.

In some embodiments, said isolated antigen binding protein comprises any one of LCDR1, LCDR2 and/or LCDR3 regions from the light chain variable region VL of SEQ ID NO: 155.

In some embodiments, said VL comprises an amino acid sequence as set forth in any one of SEQ ID NO: 110, 114, 118, 119, 120, 121, and 122.

In some embodiments, said HCDR3 comprises an amino acid sequence as set forth in SEQ ID NO: 34.

In some embodiments, said HCDR2 comprises an amino acid sequence as set forth in SEQ ID NO: 158.

In some embodiments, said HCDR2 comprises an amino acid sequence as set forth in any one of SEQ ID NO: 17, 21 and 22.

In some embodiments, said HCDR1 comprises an amino acid sequence as set forth in SEQ ID NO: 6.

In some embodiments, said isolated antigen binding protein comprises a heavy chain variable region VH, wherein the VH comprises an amino acid sequence as set forth in SEQ ID NO:156.

In some embodiments, said VH comprises an amino acid sequence as set forth in any of SEQ ID NO: 95, 99, 100, 101, 102 and 103.

In some embodiments, said isolated antigen binding protein comprises an antibody heavy chain HC, and said HC comprises an amino acid sequence as set forth in any of SEQ ID NO: 123, 127, 128, 129, 130 and 131.

In some embodiments, said LCDR3 comprises an amino acid sequence as set forth in SEQ ID NO: 157.

In some embodiments, said LCDR3 comprises an amino acid sequence as set forth in any of SEQ ID NO:77, 81, 84, 85, 86, 87 and 88.

In some embodiments, said LCDR2 comprises an amino acid sequence as set forth in SEQ ID NO:65.

In some embodiments, said LCDR1 comprises an amino acid sequence as set forth in SEQ ID NO: 54.

In some embodiments, said isolated antigen binding protein comprises a light chain variable region VL, wherein said VL comprises an amino acid sequence as set forth in SEQ ID NO: 155.

In some embodiments, said VL comprises an amino acid sequence as set forth in any of SEQ ID Nos: 110, 114, 118, 119, 120, 121 and 122.

In some embodiments, said isolated antigen binding protein comprises an antibody light chain LC, and said LC comprises an amino acid sequence as set forth in any one of SEQ ID NO: 138, 142, 146, 147, 148, 149 and 150.

In some embodiments, said isolated antigen binding protein comprises any one of HCDR1, HCDR2 and/or HCDR3 regions from the heavy chain variable region VH of SEQ ID NO: 108.

In some embodiments, said isolated antigen binding protein comprises any one of LCDR1, LCDR2 and/or LCDR3 regions from the heavy chain variable region VL of SEQ ID NO: 116.

In some embodiments, said HCDR3 comprises an amino acid sequence as set forth in SEQ ID NO: 40.

In some embodiments, said HCDR2 comprises an amino acid sequence as set forth in SEQ ID NO: 25.

In some embodiments, said HCDR1 comprises an amino acid sequence as set forth in SEQ ID NO: 10.

In some embodiments, said isolated antigen binding protein comprises a heavy chain variable region VH, and said VH comprises an amino acid sequence as set forth in any of SEQ ID:108.

In some embodiments, said isolated antigen binding protein comprises an antibody heavy chain HC, and said HC comprises an amino acid sequence as set in forth in SEQ ID NO: 136.

In some embodiments, said LCDR3 comprises an amino acid sequence as set forth in SEQ ID NO: 82.

In some embodiments, said LCDR2 comprises an amino acid sequence as set forth in SEQ ID NO:69.

In some embodiments, said LCDR1 comprises an amino acid sequence as set forth in SEQ ID NO: 58.

In some embodiments, said isolated antigen binding protein comprises a light chain variable region VL, and said VL comprises an amino acid sequence as set forth in any of SEQ ID No: 116.

In some embodiments, said isolated antigen binding protein comprises an antibody light chain LC, and said LC comprises an amino acid sequence as set forth in SEQ ID NO: 144.

In another aspect, the present disclosure provided an isolated nucleic acid molecule or molecules, encoding for said isolated antigen binding protein.

In another aspect, the present disclosure provided a vector or vectors, comprising said isolated nucleic acid molecule or molecules.

In another aspect, the present disclosure provided a cell, comprising said isolated nucleic acid molecule or molecules, or said vector or vectors.

In another aspect, the present disclosure provided a method for producing an isolated antigen binding protein, comprising culturing the cell under conditions enabling expression of the isolated antigen binding protein.

In another aspect, the present disclosure provided a pharmaceutical composition, comprising the isolated antigen binding protein, the nucleic acid molecule or molecules, the vector or vectors, and/or the cell, and optionally a pharmaceutically acceptable carrier.

In another aspect, the present disclosure provided use of said isolated antigen binding protein of the present disclosure, said nucleic acid molecule and molecules, said vector and vectors said cell and/or said pharmaceutical composition in the manufacture of a medicant for preventing, alleviating and/or treating tumor.

In some embodiments, said tumor comprises a solid tumor and/or a blood tumor.

In another aspect, the present disclosure provided a method for preventing, alleviating and/or treating tumor, comprising administrating to a subject in need thereof an isolated antigen binding protein of the present disclosure.

In some embodiments, said tumor comprises a solid tumor and/or a blood tumor.

In another aspect, the present disclosure provided a method of inhibiting 5' ectonucleotidase activity of CD73, comprising administrating an isolated antigen binding protein of the present disclosure.

In another aspect, the present disclosure provided a method of mediating CD73 internalization, comprising administrating an isolated antigen binding protein of the present disclosure.

In another aspect, the present disclosure provides use of said isolated antigen binding protein, said nucleic acid molecule and molecules, said vector and vectors, said cell and/or said pharmaceutical composition in the manufacture of a medicant for preventing, alleviating and/or treating tumor.

In some embodiments, the tumor comprises a solid tumor and/or a blood tumor.

In another aspect, the present disclosure provides a method for preventing, alleviating and/or treating tumor, comprising administrating to a subject in need thereof an isolated antigen binding protein of the present disclosure.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are employed, and the accompanying drawings (also "figure" and "FIG." herein), of which:

DETAILED DESCRIPTION

Figure 1A:
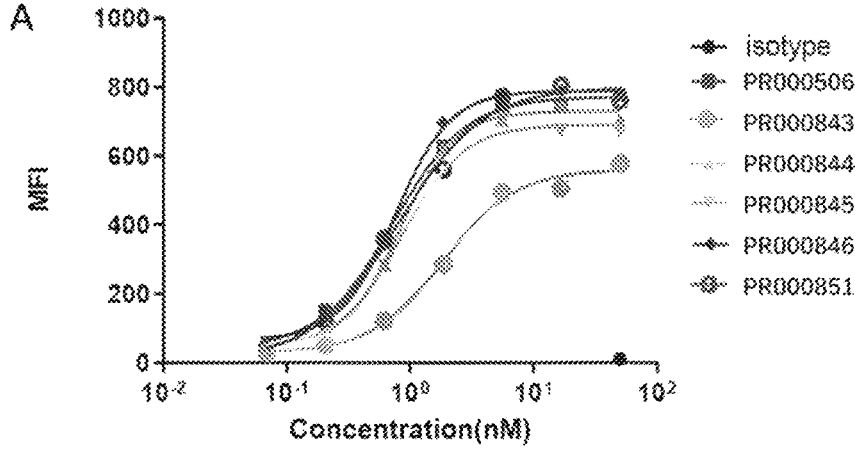
FIGS. 1A and 1B illustrate the antibodies binding to CHO-K1-hCD73 cell line analyzed by FACS.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The singular form "a," "an" and "the," as used herein, generally include plural references unless the context clearly dictates otherwise.

The term "CD73", also known as 5' ectonucleotidase, as used herein, generally refers to an enzyme (nucleotidase) capable of converting extracellular nucleoside 5' monophosphates to nucleosides, namely adenosine monophosphate (AMP) to adenosine. The primary function of CD73 is its conversion of extracellular nucleotides (e.g., 5'-AMP) to adenosine, a highly immunosuppressive molecule. The term "CD73" includes any variants or isoforms of CD73 which are naturally expressed by cells. CD73 or any variants and isoforms thereof, may either be isolated from cells or tissues which naturally express them or be recombinantly produced using well-known techniques in the art and/or those described herein. Accordingly, antigen binding protein described herein may cross-react with from species other than human (e.g., cynomolgus CD73). Alternatively, the antibodies may be specific for human CD73 and may not exhibit any cross-reactivity with other species. The amino acid sequence of human CD73 is shown in GenBank under accession number AAH65937.1(5'-nucleotidase, ecto) NP 002517(isoform 1 preproprotein) or NP 001191742(isoform 2 preproprotein).

The term "Tab1" or PR002078, as used herein, generally refers to an anti-CD73 antibody. The amino acid sequence of heavy chain of Tab1 was set forth in SEQ ID NO.137, and the amino acid sequence of light chain of Tab1 was set forth in SEQ ID NO.145.

The term "Tab2" or PR000752, as used herein, generally refers to an anti-CD73 antibody. The amino acid sequence of heavy chain of Tab2 was set forth in SEQ ID NO.126, and the amino acid sequence of light chain of Tab3 was set forth in SEQ ID NO.141.

The term "Tab3" or PR000690, as used herein, generally refers to an anti-CD73 antibody. The amino acid sequence of heavy chain of Tab3 was set forth in SEQ ID NO.125, and the amino acid sequence of light chain of Tab3 was set forth in SEQ ID NO.140.

The term "internalization", as used herein, refers to the molecular, biochemical and cellular events associated with the process of translocating a molecule from the extracellular surface of a cell to the intracellular surface of a cell. The processes can involve, inter alia, the internalization of extracellular molecules (such as hormones, antibodies, and small organic molecules); membrane-associated molecules (such as cell-surface receptors); and complexes of membrane-associated molecules bound to extracellular molecules (for example, a ligand bound to a transmembrane receptor or an antibody bound to a membrane-associated molecule).

The term "antigen binding protein" as used herein, generally refers to a protein comprising a portion that binds to an antigen and, optionally, a scaffold or framework portion that allows the antigen binding portion to adopt a conformation that promotes binding of the antigen binding protein to the antigen. Examples of antigen binding proteins include antibodies, antibody fragments (e.g., an antigen binding portion of an antibody), antibody derivatives, and antibody analogs. An antigen binding protein can have, for example, the structure of a naturally occurring immunoglobulin. An "immunoglobulin" is a tetrameric molecule. In a naturally occurring immunoglobulin, each tetramer is composed of two identical pairs of polypeptide chains, each pair having one light chain (LC) and one heavy chain (HC). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as κ or λ light chains. Heavy chains are classified as μ, γ, α, or Σ, and define the antibody's isotype as IgM, IgD, IgG, IgA, and IgE, respectively. The variable regions of naturally occurring immunoglobulin chains exhibit the same general structure of relatively conserved framework regions (FR) joined by three hypervariable regions, also called complementarity determining regions or CDRs. From N-terminus to C-terminus, both light and heavy chains comprise the domains FR1, CDR1, FR2, CDR2, FR3, CDR3 and FR4

The term "CDR" as used herein, generally refers to the complementarity determining region amino acid sequences of an antigen binding protein. These are the hypervariable regions of immunoglobulin heavy and light chains. There are three heavy chain and three light chain CDRs (or CDR regions) in the variable portion of an immunoglobulin. It will be apparent to those skilled in the art that there are various numbering systems for CDR sequences, e.g., Chothia (Chothia et al. (1989) Nature 342: 877-883), Kabat (Kabat et al., Sequences of Proteins of Immunological Interest, National Institutes of Health, Bethesda, Md. (1987 and 1991)). The Chothia numbering system is used for numbering the residues in an antibody of the present disclosure.

TABLE 1

| Numbering systems for the amino acids to each region (reference to http://bioinf.org.uk/abs/) | | | |
|---|---|---|---|
| | Kabat | Chothia | Combined |
| LCDR1 | L24-L34 | L24-L34 | L24-L34 |
| LCDR2 | L50-L56 | L50-L56 | L50-L56 |
| LCDR3 | L89-L97 | L89-L97 | L89-L97 |
| HCDR1 | H31-H35 | H26-H32 | H26-H35 |
| HCDR2 | H50-H65 | H52-H56 | H50-H65 |
| HCDR3 | H95-H102 | H95-H102 | H95-H102 |

Wherein, Laa-Lbb may refer to, from N-terminal, the amino acids sequence from NO.aa to NO.bb. For example, L24-L34 refers to the amino acid sequence from NO.24 to NO.34 of light chain.

The term "isolated" when applied to a nucleic acid or protein, denotes that the nucleic acid or protein is substantially free of other cellular components with which it is associated in the natural state.

The term "$K_D$" or "$K_D$", as used herein, generally refers to the dissociation constant, a specific type of equilibrium constant that measures the propensity of a larger object to separate (dissociate) reversibly into smaller components, as when a complex falls apart into its component molecules. The dissociation constant is the inverse of the association constant. In the specific case of antibodies binding to antigen, usually the term affinity constant refers to the association constant.

The term "antigen-binding fragment", as used herein, generally refers to a portion of an immunoglobulin molecule. An antigen-binding fragment may comprise one light chain and part of a heavy chain with a single antigen-binding site. An antigen-binding fragment may be obtained by papain digestion of an immunoglobulin molecule. For example, an antigen-binding may be composed of one constant and one variable domain of each of the heavy and the light chain. The variable domain may contain the paratope (the antigen-binding site), comprising a set of the complementarity determining regions, at the amino-terminal end of the immunoglobulin molecule. The enzyme papain may be used to cleave an immunoglobulin molecule into two Fab fragments and one Fc fragment. The enzyme pepsin cleaves below the hinge region, so a F(ab')2 fragment and a pFc' fragment is formed. Divalent $F(ab)_2$ or $F(ab')_2$ fragments have two antigen binding regions that are linked by disulfide bonds. Reduction of $F(ab)_2$ or $F(ab')_2$ fragments produces 2 monovalent Fab or Fab' fragments, which have a free sulfhydryl group that is useful for conjugation to other molecules.

The term "Fv fragment", as used herein, generally refers to the smallest fragment made from enzymatic cleavage of IgG and IgM class antibodies.

The term "ScFv", as used herein, generally refers to a single-chain antibody fragment. An ScFv may be a recombinant single chain polypeptide molecule in which light and heavy chain variable regions of an antibody are connected, either directly or via a peptide linker.

The term "fully human antibody", as used herein, generally refers to an antibody with fully human amino acid sequence derived antibody region therapeutics where antigen specificity has been selected either in vivo by the use of genetically modified mice or by antibody engineering processes combined with screening.

The term "isolated nucleic acid molecule or molecules" as used herein, generally refers to a polymeric form of nucleotides of any length, either deoxyribonucleotides or ribonucleotides, or analogs thereof, isolated from its native environment, or that is artificially synthesized.

The term "vector or vectors" as used herein, generally refers to a nucleic acid vehicle into which a polynucleotide encoding a protein can be inserted and expressed. The genetic material elements carried in the vector can be expressed in a host cell by transforming, transducing, or transfecting the host cell with the vector. Embodiments of vectors include: plasmids; phagemids; cosmid; artificial chromosomes such as yeast artificial chromosomes (YACs), bacterial artificial chromosomes (BACs) or P1-derived artificial chromosomes (PACs); phages such as λ phage or M13 phage and animal viruses. A vector may contain a variety of elements that control expression, including promoter sequences, transcriptional initiation sequences, enhancer sequences, selection elements, and reporter genes. In addition, the vector may also contain an origin of replication. It is also possible that the vector may include components that assist its entry into the cell, such as viral particles, liposomes or protein shells, but not only these substances.

The term "cell" as used herein, generally refers to a cell that may be used to carry the vector or vectors of the present disclosure, or be used to express or produce the antibody, the antigen binding fragment or variant of the present disclosure. A cell of the present disclosure may be a host cell. The cell may be a prokaryotic cell such as *Escherichia coli* and *Bacillus subtilis*, a fungal cell such as yeast cell or *Aspergillus* cell, an insect cell such as S2 *Drosophila* cell or Sf9, or another cell such as a CHO cell, a COS cell, an NSO cell, or other cells suitable for antibody expression.

The term "conditions enabling expression", as used herein, generally refers to conditions enabling the expression of the isolated antigen binding protein of the present disclosure. In some embodiments, such conditions may include but not limited to incubation time, temperature, and culture medium, and may depend on cell type and may be readily determined by a skilled arctician.

Isolated Antigen Binding Protein

In one aspect, the present disclosure provides an isolated antigen binding protein which may be capable of binding to both human CD73 and Cynomolgus monkey CD73, with comparable binding affinity. The term "comparable binding affinity", as used herein, generally refers to the ratio of two binding affinities of antibodies were from about 0.01 nM to about 100 nM, such as, from about 0.02 nM to about 50 nM, from about 0.05 nM to about 30 nM, from about 0.1 nM to about 20 nM, from about 0.1 nM to about 10 nM, from about 0.2 nM to about 10 nM, from about 0.5 nM to about 3 nM. A binding affinity of antibody and CD73 can be evaluated using a CD73 stable cell line (e.g., a CHO-K1 cell line), for example, in FACS analysis.

The isolated antigen binding protein may be capable of inhibiting 5' ectonucleotidase activity of CD73. The isolated antigen binding protein may inhibit CD73-mediated generation of adenosine, i.e. the inhibition of CD73-mediated catabolism of AMP to adenosine. This can be evaluated by the capacity of a test antibody to block the conversion of AMP to adenosine, either directly or indirectly. In some cases, the isolated antigen binding protein may inhibit activity of cell based CD73. This can be measured by constructing cell line expressing CD73 stably, e.g., CHO-K1 cell line. For example, the isolated antigen binding protein may inhibit 50% of 5' ectonucleotidase activity of cell based CD73 at a concentration from about 0.01 nM to about 100 nM, such as, from about 0.02 nM to about 50 nM, from about 0.001 nM to about 10 nM, from about 0.001 nM to about 1 nM, from about 0.01 nM to about 0.5 nM, from about 0.01 nM to about 0.3 nM, from about 0.05 nM to about 0.25 nM, as describe in examples. In another cases, the isolated antigen binding protein may inhibit activity of soluble recombination CD73. For example, by quantifying the enzymatic product inorganic phosphate, the isolated antigen binding protein can causes at least a 40% decrease in the conversion of AMP to adenosine, at least a 50% decrease in the conversion of AMP to adenosine, at least a 60% decrease in the conversion of AMP to adenosine, at least a 70% decrease in the conversion of AMP to adenosine, or at least a 90% decrease in the conversion of AMP to adenosine.

The isolated antigen binding protein may be capable of mediating CD73 internalization. In some cases, the percent of internalization can be evaluated by remaining of CD73 on cell surface, e.g., NCI-H292, as measured by flow cytometry. For example, after incubated with antibodies for 4 hours, about 40% to about 99% (e.g., about 40% to about 90%, about 40% to about 80%, about 40% to about 70%, about 40% to about 60%, about 40% to about 55%, or about 50%) of CD73 were internalized intracellularly. In another cases, the internalization can be measured by internalization kit as described in examples. After incubating with antibodies for 3 days, the CD73 on CHO-K1 surface were internalized and the maximal level of antibody mediated internalization of CD73 may be at least 50%, at least 60%, at least 70%, at least 80%, at least 90% or more, depending on the concentration of antibodies.

The activity of the isolated antigen binding protein can also be measured in an indirect assay for its ability to modulate the activity of lymphocytes, for example to relieve the AMP-mediated suppression of lymphocyte activity, or to cause the proliferation of lymphocyte. In some cases, the isolated antigen binding protein can be evaluated in an indirect assay for its ability to modulate the proliferation of lymphocytes. The lymphocyte may be a T cell, including helper T cells (e.g., CD4+ T cells). This can be addressed, for example, using a FACS analysis.

The isolated antigen binding protein may have a relatively stable concentration in serum for at least 15 days. "relatively stable", as used herein, generally refers to a concentration of an antibody in serum changes by no more than 50%, compared with a reference concentration, e.g., the initial concentration in serum of an antibody. The stability in serum of an antibody can be determined by pharmacokinetics analysis. For example, the $t_{1/2}$ of isolated antigen binding protein of the present disclosure is about 15 days, as described in PK analysis.

In the present disclosure, the antigen binding protein may comprise at least one HCDR from the VH of SEQ ID NO: 152.

In the present disclosure, the antigen binding protein may comprise a HCDR3 from the heavy chain variable region VH of SEQ ID NO: 152, and the HCDR3 may comprises an amino acid sequence as set forth in SEQ ID NO.154: $X_1X_2$QWGSRLDY (SEQ ID NO.154); wherein, $X_1$=D or E; $X_2$=G or A. For example, the sequence may be determined according to the Chothia definition.

In some cases, compared to the HCDR3 of the antigen binding protein as DGQWGSRLDY, the HCDR3 may comprise at least an amino acid substitution selected from as following: the amino acid substitution at $X_1$ and $X_2$, wherein the amino acid at $X_1$ may be substituted to E, the amino acid at $X_2$ may be substituted to A.

For example, the HCDR3 may comprise amino acid sequence as set forth in any of SEQ ID NO: 35, 38 and 39.

In the present disclosure, the antigen binding protein may comprise a HCDR2 from the heavy chain variable region VH of SEQ ID NO: 152, and the HCDR2 may comprises an amino acid sequence as set forth in SEQ ID NO.153: WYX$_3$X$_4$SF (SEQ ID NO.153); wherein, $X_3$=D or E; $X_4$=G or A. For example, the sequence may be determined according to the Chothia definition.

For example, the HCDR2 may comprise amino acid sequence as set forth in any of SEQ ID NO: 18, 23 and 24.

In the present disclosure, the antigen binding protein may comprise a HCDR1 from the heavy chain variable region VH of SEQ ID NO: 152, and the HCDR1 may comprises an amino acid sequence as set forth in SEQ ID NO.7: GFTFSDY (SEQ ID NO.7). For example, the sequence may be determined according to the Chothia definition.

In the present disclosure, the antigen binding protein may comprise a H-FR1, C-terminus of the H-FR1 is directly or indirectly linked to N-terminus of said HCDR1, and the H-FR1 may comprises an amino acid sequence as set forth in SEQ ID NO.2: QVQLVESGGGVAQPGRSLSLSCAAS (SEQ ID NO.2). For example, the sequence may be determined according to the Chothia definition.

In the present disclosure, the antigen binding protein may comprise a H-FR2, the H-FR2 is located between said HCDR1 and said HCDR2, and the H-FR2 may comprises an amino acid sequence as set forth in SEQ ID NO.12: GMHWVRQAPGKGLEWVALIWVRQAPGKGLEWVA (SEQ ID NO.12). For example, the sequence may be determined according to the Chothia definition.

In the present disclosure, the antigen binding protein may comprise a H-FR3, the H-FR3 is located between said HCDR2 and said HCDR3, and the H-FR3 may comprises an amino acid sequence as set forth in SEQ ID NO.28: EYYADSVKGRFSISRDNSKNTLYLQMNSLRAED-TAVYYCVR (SEQ ID NO.28). For example, the sequence may be determined according to the Chothia definition.

In the present disclosure, the antigen binding protein may comprise a H-FR4, N-terminus of said H-FR4 is linked directly or indirectly to C-terminus of said HCDR3, and the H-FR4 may comprises an amino acid sequence as set forth in SEQ ID NO.43: WGQGTLVTVSS (SEQ ID NO.43). For example, the sequence may be determined according to the Chothia definition.

In the present disclosure, the antigen binding protein may comprise a VH, and the VH may comprises an amino acid sequence as set forth in SEQ ID NO.152: QVQLVES-GGGVAQPGRSLSLSCAASGFTFSDYGMH WVRQAPGKGLEWVALIWYX$_{54}$X$_{55}$SF EYY-ADSVKGRFSISRDNSKNTLYLQMNSLRAEDTAV YYCVRX$_{99}$X$_{100}$QWGSRLDYWGQGTL VTVSS (SEQ ID NO.152); wherein, $X_{54}$=D or E; $X_{55}$=G or A; $X_{99}$=D or E; and $X_{100}$=G or A. For example, the sequence may be determined according to the Chothia definition.

For example, the VH may comprise amino acid sequence as set forth in any of SEQ ID NO: 96, 104, 105, 106 and 107.

In the present disclosure, the antigen binding protein may comprise an antibody heavy chain constant region, and the antibody heavy chain constant region comprises a human IgG constant region. In some cases, the human IgG constant region may be derived from a human IgG1 constant region. For example, the antibody heavy chain constant region may comprise amino acid sequence as set forth in SEQ ID NO.167:

```
                              (SEQ ID NO. 167)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPEAAGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSREEMTKNQVSLTC

LVKGFYPSDIAVEWESNGQPENNYKTTPPVLDSDGSFFLYSKLTVDKSRW

QQGNVFSCSVMHEALHNHYTQKSLSLSPGK.
```

In the present disclosure, the antigen binding protein may comprise an antibody heavy chain (HC), and the HC comprises an amino acid sequence as set in forth in SEQ ID NO. 162. For example, the HC may comprise amino acid sequence as set forth in any of SEQ ID NO: 124, 132, 133, 134 and 135.

In the present disclosure, the antigen binding protein may comprise at least one LCDR from the VL of SEQ ID NO: 151.

In the present disclosure, the antigen binding protein may comprise a LCDR3 from the heavy chain variable region VH of SEQ ID NO: 152, and the LCDR3 may comprises an amino acid sequence as set forth in SEQ ID NO.78: QQRSNWIFT (SEQ ID NO.78). For example, the sequence may be determined according to the Chothia definition.

In the present disclosure, the antigen binding protein may comprise a LCDR2 from the heavy chain variable region VH of SEQ ID NO: 152, and the LCDR2 may comprises an amino acid sequence as set forth in SEQ ID NO. 66: DASNRAT (SEQ ID NO. 66) For example, the sequence may be determined according to the Chothia definition.

In the present disclosure, the antigen binding protein may comprise a LCDR1 from the heavy chain variable region VH of SEQ ID NO: 152, and the LCDR1 may comprises an amino acid sequence as set forth in SEQ ID NO.55: RASQSVSRYLA (SEQ ID NO.55). For example, the sequence may be determined according to the Chothia definition.

In the present disclosure, the antigen binding protein may comprise a L-FR1, C-terminus of the L-FR1 is directly or indirectly linked to N-terminus of said LCDR1, and the L-FR1 may comprises an amino acid sequence as set forth in SEQ ID NO.48: $X_1$IVX$_4$TQSPATLSLSPGERATLSC (SEQ ID NO.48); wherein, $X_1$=K or E; and $X_4$=M or L. For example, the sequence may be determined according to the Chothia definition.

In some cases, compared to the L-FR1 of the antigen binding protein as set forth in SEQ ID NO.47, the L-FR1 may comprise at least an amino acid substitution selected from as following: the amino acid substitution at $X_1$ and/or $X_4$, wherein the amino acid at $X_1$ may be substituted to E, and the amino acid at $X_4$ may be substituted to L.

For example, the L-FR1 may comprise amino acid sequence as set forth in any of SEQ ID NO: 48 and 51.

In the present disclosure, the antigen binding protein may comprise a L-FR2, the L-FR2 is located between said LCDR1 and said LCDR2, and the L-FR2 may comprises an amino acid sequence as set forth in SEQ ID NO.61:

WYQQKPGQAPRLLIY (SEQ ID NO.61). For example, the sequence may be determined according to the Chothia definition.

In the present disclosure, the antigen binding protein may comprise a L-FR3, the L-FR3 is located between said LCDR2 and said LCDR3, and the L-FR3 may comprises an amino acid sequence as set forth in SEQ ID NO.72: GIPARFSGSGSGTDFTLTISSLEPEDFAVYYC (SEQ ID NO.72). For example, the sequence may be determined according to the Chothia definition.

In the present disclosure, the antigen binding protein may comprise a L-FR4, N-terminus of said L-FR4 is linked directly or indirectly to C-terminus of said LCDR3, and the L-FR4 may comprises an amino acid sequence as set forth in SEQ ID NO.90: FGPGTKVDIK (SEQ ID NO.90). For example, the sequence may be determined according to the Chothia definition.

In the present disclosure, the antigen binding protein may comprise a VL, and the VL may comprise an amino acid sequence as set forth in SEQ ID NO.151: $X_1$IVX$_4$TQSPATLSLSPGERATLSCRASQSVSRYLAWY QQKPGQAPRLLIYDASNRATGIPAR FSGSGSGTDFTLTISSLEPEDFAVYYCQQRSNV-VIFTFGPGTKVDIK (SEQ ID NO.151); wherein, $X_1$=K or E; $X_4$=M or L. For example, the sequence may be determined according to the Chothia definition.

For example, the VL may comprise amino acid sequence as set forth in any of SEQ ID NO: 111 and 115.

In the present disclosure, the antigen binding protein may comprise an antibody light chain constant region, and the antibody light chain constant region comprises a human Igκ constant region. For example, the antibody light chain constant region may comprise amino acid sequence as set forth in SEQ ID NO.166:

(SEQ ID NO: 166)
RTVAAPSVFIFPPSDEQLKSGTASVVCLLNNFYPREAKVQWKVDNALQSG

NSQESVTEQDSKDSTYSLSSTLTLSKADYEKHKVYACEVTHQGLSSPVTK

SFNRGEC.

In the present disclosure, the antigen binding protein may comprise an antibody light chain (LC), and the LC comprises an amino acid sequence as set in forth in SEQ ID NO. 159. For example, the LC may comprise amino acid sequence as set forth in any of SEQ ID NO: 139 and 143.

In the present disclosure, the antigen binding protein may comprise HCDR1-3. The HCDR1 may comprise an amino acid sequence as set forth in SEQ ID NO. 7, the HCDR2 may comprise an amino acid sequence as set forth in SEQ ID NO. 153, and the HCDR3 may comprise an amino acid sequence as set forth in SEQ ID NO. 154.

In some cases, the antigen binding protein may comprise HCDR1-3. The HCDR1 may comprise an amino acid sequence as set forth in any of SEQ ID NO.7, the HCDR2 may comprise an amino acid sequence as set forth in any of SEQ ID NO.18, 23, 24, and the HCDR3 may comprise an amino acid sequence as set forth in any of SEQ ID NO.35, 38 and 39.

For example, the HCDR1 of the antigen binding protein may comprise an amino acid sequence as set forth in SEQ ID NO.7, the HCDR2 may comprise an amino acid sequence as set forth in SEQ ID NO. 18, and the HCDR3 may comprise an amino acid sequence as set forth in SEQ ID NO.35.

For another example, the HCDR1 of the antigen binding protein may comprise an amino acid sequence as set forth in SEQ ID NO.7, the HCDR2 may comprise an amino acid sequence as set forth in SEQ ID NO. 23, and the HCDR3 may comprise an amino acid sequence as set forth in SEQ ID NO.38.

For another example, the HCDR1 of the antigen binding protein may comprise an amino acid sequence as set forth in SEQ ID NO.7, the HCDR2 may comprise an amino acid sequence as set forth in SEQ ID NO.23, and the HCDR3 may comprise an amino acid sequence as set forth in SEQ ID NO.39.

For another example, the HCDR1 of the antigen binding protein may comprise an amino acid sequence as set forth in SEQ ID NO.7, the HCDR2 may comprise an amino acid sequence as set forth in SEQ ID NO.24, and the HCDR3 may comprise an amino acid sequence as set forth in SEQ ID NO.38.

For another example, the HCDR1 of the antigen binding protein may comprise an amino acid sequence as set forth in SEQ ID NO.7, the HCDR2 may comprise an amino acid sequence as set forth in SEQ ID NO.24, and the HCDR3 may comprise an amino acid sequence as set forth in SEQ ID NO.39.

In the present disclosure, the antigen binding protein may comprise LCDR1-3. The LCDR1 may comprise an amino acid sequence as set forth in SEQ ID NO. 55, the LCDR2 may comprise an amino acid sequence as set forth in SEQ ID NO. 66, and the LCDR3 may comprise an amino acid sequence as set forth in SEQ ID NO. 78.

In the present disclosure, the antigen binding protein may comprise a H-FR1-4. The H-FR1 may comprises an amino acid sequence as set forth in SEQ ID NO.2, the H-FR2 may comprises an amino acid sequence as set forth in SEQ ID NO.12, the H-FR3 may comprises an amino acid sequence as set forth in SEQ ID NO.28, and the H-FR4 may comprises an amino acid sequence as set forth in SEQ ID NO.43.

In the present disclosure, the antigen binding protein may comprise a L-FR1-4. The L-FR1 may comprises an amino acid sequence as set forth in SEQ ID NO.48, the L-FR2 may comprises an amino acid sequence as set forth in SEQ ID NO.61, the L-FR3 may comprises an amino acid sequence as set forth in SEQ ID NO.72, and the L-FR4 may comprises an amino acid sequence as set forth in SEQ ID NO.90.

In some cases, the L-FR1 may comprises an amino acid sequence as set forth in any one of SEQ ID NO: 51, the L-FR2 may comprises an amino acid sequence as set forth in any one of SEQ ID NO: 61, the L-FR3 may comprises an amino acid sequence as set forth in any one of SEQ ID NO: 72, and the L-FR4 may comprises an amino acid sequence as set forth in any one of SEQ ID NO.90.

In the present disclosure, the antigen binding protein may comprise HCDR1-3 and LCDR1-3 and. The HCDR1 may comprise an amino acid sequence as set forth in SEQ ID NO. 7, the HCDR2 may comprise an amino acid sequence as set forth in SEQ ID NO. 153, and the HCDR3 may comprise an amino acid sequence as set forth in SEQ ID NO. 154; the LCDR1 may comprise an amino acid sequence as set forth in SEQ ID NO. 55, the LCDR2 may comprise an amino acid sequence as set forth in SEQ ID NO. 66, the LCDR3 may comprise an amino acid sequence as set forth in SEQ ID NO. 78.

In some cases, the HCDR1 of the antigen binding protein may comprise an amino acid sequence as set forth in any of SEQ ID NO.7, the HCDR2 may comprise an amino acid sequence as set forth in any of SEQ ID NO.18, 23 and 24, and the HCDR3 may comprise an amino acid sequence as set forth in any of SEQ ID NO.35, 38 and 39; the LCDR1 may comprise an amino acid sequence as set forth in any of SEQ ID NO.55, the LCDR2 may comprise an amino acid sequence as set forth in any of SEQ ID NO.66, and the LCDR3 may comprise an amino acid sequence as set forth in SEQ ID NO.78.

For example, the HCDR1 of the antigen binding protein may comprise an amino acid sequence as set forth in SEQ ID NO.7, the HCDR2 may comprise an amino acid sequence as set forth in SEQ ID NO. 18, and the HCDR3 may comprise an amino acid sequence as set forth in SEQ ID NO.35; the LCDR1 of the antigen binding protein may comprise an amino acid sequence as set forth in SEQ ID NO.55, the LCDR2 may comprise an amino acid sequence as set forth in SEQ ID NO. 66, and the LCDR3 may comprise an amino acid sequence as set forth in SEQ ID NO.78.

For another example, the HCDR1 of the antigen binding protein may comprise an amino acid sequence as set forth in SEQ ID NO.7, the HCDR2 may comprise an amino acid sequence as set forth in SEQ ID NO. 23, and the HCDR3 may comprise an amino acid sequence as set forth in SEQ ID NO.38; the LCDR1 of the antigen binding protein may comprise an amino acid sequence as set forth in SEQ ID NO.55, the LCDR2 may comprise an amino acid sequence as set forth in SEQ ID NO. 66, and the LCDR3 may comprise an amino acid sequence as set forth in SEQ ID NO.78.

In the present disclosure, the antigen binding protein may comprise a H-FR1-4 and L-FR1-4. The H-FR1 may comprises an amino acid sequence as set forth in SEQ ID NO.2, the H-FR2 may comprises an amino acid sequence as set forth in SEQ ID NO.12, the H-FR3 may comprises an amino acid sequence as set forth in SEQ ID NO.28, and the H-FR4 may comprises an amino acid sequence as set forth in SEQ ID NO.43; the L-FR1 may comprises an amino acid sequence as set forth in SEQ ID NO.48, the L-FR2 may comprises an amino acid sequence as set forth in SEQ ID NO.61, the L-FR3 may comprises an amino acid sequence as set forth in SEQ ID NO.72, and the L-FR4 may comprises an amino acid sequence as set forth in SEQ ID NO.90.

In some cases, the H-FR1 may comprises an amino acid sequence as set forth in any one of SEQ ID NO:2, the H-FR2 may comprises an amino acid sequence as set forth in any one of SEQ ID NO: 12, the H-FR3 may comprises an amino acid sequence as set forth in any one of SEQ ID NO: 28, and the H-FR4 may comprises an amino acid sequence as set forth in SEQ ID NO.43; the L-FR1 may comprises an amino acid sequence as set forth in any one of SEQ ID NO: 51, the L-FR2 may comprises an amino acid sequence as set forth in any one of SEQ ID NO: 61, the L-FR3 may comprises an amino acid sequence as set forth in any one of SEQ ID NO: 72, and the L-FR4 may comprises an amino acid sequence as set forth in any one of SEQ ID NO: 90.

In the present disclosure, the antigen binding protein may comprise a VH and a VL. The VH may comprise an amino acid sequence as set forth in SEQ ID NO: 152, and the VL may comprise an amino acid sequence as set forth in SEQ ID NO:151.

In some cases, the VH may comprise an amino acid sequence as set forth in any of SEQ ID NO:96, 104, 105, 106 and 107, and the VL may comprise an amino acid sequence as set forth in any of SEQ ID NO: 111 and 115.

In some cases, the VH may comprise an amino acid sequence as set forth in SEQ ID NO:96, and the VL may comprise an amino acid sequence as set forth in SEQ ID NO: 111.

In some cases, the VH may comprise an amino acid sequence as set forth in SEQ ID NO:104, and the VL may comprise an amino acid sequence as set forth in SEQ ID NO: 111.

In some cases, the VH may comprise an amino acid sequence as set forth in SEQ ID NO:105, and the VL may comprise an amino acid sequence as set forth in SEQ ID NO: 111.

In some cases, the VH may comprise an amino acid sequence as set forth in SEQ ID NO:106, and the VL may comprise an amino acid sequence as set forth in SEQ ID NO: 111.

In some cases, the VH may comprise an amino acid sequence as set forth in SEQ ID NO:107, and the VL may comprise an amino acid sequence as set forth in SEQ ID NO: 111.

In some cases, the VH may comprise an amino acid sequence as set forth in SEQ ID NO:96, and the VL may comprise an amino acid sequence as set forth in SEQ ID NO: 115.

In some cases, the VH may comprise an amino acid sequence as set forth in SEQ ID NO:104, and the VL may comprise an amino acid sequence as set forth in SEQ ID NO: 115.

In some cases, the VH may comprise an amino acid sequence as set forth in SEQ ID NO:105, and the VL may comprise an amino acid sequence as set forth in SEQ ID NO: 115.

In some cases, the VH may comprise an amino acid sequence as set forth in SEQ ID NO:106, and the VL may comprise an amino acid sequence as set forth in SEQ ID NO: 115.

In some cases, the VH may comprise an amino acid sequence as set forth in SEQ ID NO:107, and the VL may comprise an amino acid sequence as set forth in SEQ ID NO: 115.

In the present disclosure, the antigen binding protein may comprise a heavy chain constant region and a light chain constant region. The heavy chain constant region may comprise an amino acid sequence as set forth in SEQ ID NO: 167, and the light chain constant region may comprise an amino acid sequence as set forth in SEQ ID NO:166.

In the present disclosure, the antigen binding protein may comprise a heavy chain (HC) and a light chain (LC). The HC may comprise an amino acid sequence as set forth in SEQ ID NO: 162, and the LC may comprise an amino acid sequence as set forth in SEQ ID NO.159.

In some cases, the HC comprise an amino acid sequence as set forth in any one of SEQ ID NO: 124, 132, 133, 134 and 135, and the LC constant region may comprise an amino acid sequence as set forth in any one of SEQ ID NO: 139 and 143.

In the present disclosure, the antigen binding protein may comprise a HC and a LC. The HC may comprise a VH and a heavy chain constant. The VH may comprise HCDR1-3 and H-FR1-4, the HCDR1 may comprise an amino acid sequence as set forth in SEQ ID NO. 7, the HCDR2 may comprise an amino acid sequence as set forth in SEQ ID NO. 153, and the HCDR3 may comprise an amino acid sequence as set forth in SEQ ID NO. 154; the H-FR1 may comprises an amino acid sequence as set forth in SEQ ID NO.2, the H-FR2 may comprises an amino acid sequence as set forth in SEQ ID NO.12, the H-FR3 may comprises an amino acid sequence as set forth in SEQ ID NO.28, and the H-FR4 may comprises an amino acid sequence as set forth in SEQ ID NO.33; the VH may comprise an amino sequence as set forth in SEQ ID NO.152; the heavy chain constant region may comprise an amino acid sequence as set forth in SEQ ID NO. 167; the HC may comprise an amino acid sequence as set forth in SEQ ID NO. 162. And the VL may comprise LCDR1-3 and L-FR1-4, the LCDR1 may comprise an amino acid sequence as set forth in SEQ ID NO. 55, the LCDR2 may comprise an amino acid sequence as set forth in SEQ ID NO. 66, and the LCDR3 may comprise an amino acid sequence as set forth in SEQ ID NO. 78; the L-FR1 may comprises an amino acid sequence as set forth in SEQ ID NO.48, the L-FR2 may comprises an amino acid sequence as set forth in SEQ ID NO.61, the L-FR3 may comprises an amino acid sequence as set forth in SEQ ID NO.72 and the L-FR4 may comprises an amino acid sequence as set forth in SEQ ID NO.90; the VL may comprise an amino acid sequence as set forth in SEQ ID NO.151; the light chain constant region may comprise an amino acid sequence as set forth in SEQ ID NO.166; the LC may comprise an amino acid sequence as set forth in SEQ ID NO. 159.

In some cases, the antigen binding protein may comprise a HC and a LC. The HC may comprise a VH and a heavy chain constant. The VH may comprise HCDR1-3 and H-FR1-4, the HCDR1 may comprise an amino acid sequence as set forth in any one of SEQ ID NO.7, the HCDR2 may comprise an amino acid sequence as set forth in any of SEQ ID NO: 18, 23 and 24, and the HCDR3 may comprise an amino acid sequence as set forth in any one of SEQ ID NO. 35,38 and 39; the H-FR1 may comprises an amino acid sequence as set forth in any one of SEQ ID NO.2, the H-FR2 may comprises an amino acid sequence as set forth in any one of SEQ ID NO.12, the H-FR3 may comprises an amino acid sequence as set forth in any one of SEQ ID NO.28, and the H-FR4 may comprises an amino acid sequence as set forth in SEQ ID NO.43; the VH may comprise an amino sequence as set forth in SEQ ID NO. 96, 104, 105, 106 and 107; the heavy chain constant region may comprise an amino acid sequence as set forth in SEQ ID NO. 167; the HC may comprise an amino acid sequence as set forth in SEQ ID NO. 124, 132, 133, 134 and 135. And the VL may comprise LCDR1-3 and L-FR1-4, the LCDR1 may comprise an amino acid sequence as set forth in SEQ ID NO. 55, the LCDR2 may comprise an amino acid sequence as set forth in SEQ ID NO.66, and the LCDR3 may comprise an amino acid sequence as set forth in SEQ ID NO. 78; the L-FR1 may comprises an amino acid sequence as set forth in SEQ ID NO.48 and 51, the L-FR2 may comprises an amino acid sequence as set forth in SEQ ID NO.61, the L-FR3 may comprises an amino acid sequence as set forth in SEQ ID NO.72, and the L-FR4 may comprises an amino acid sequence as set forth in SEQ ID NO.90; the VL may comprise an amino acid sequence as set forth in SEQ ID NO. 111 and 115; the light chain constant region may comprise an amino acid sequence as set forth in SEQ ID NO.166; the LC may comprise an amino acid sequence as set forth in SEQ ID NO. 139 and 143.

For example, the antigen binding protein may comprise a HC and a LC that are the same as those of the antibody PR000506. The HC may comprise a VH and a heavy chain constant. The VH may comprise HCDR1-3 and H-FR1-4, the HCDR1 may comprise an amino acid sequence as set forth in SEQ ID NO. 7, the HCDR2 may comprise an amino acid sequence as set forth in SEQ ID NO. 18, and the HCDR3 may comprise an amino acid sequence as set forth in SEQ ID NO. 35; the H-FR1 may comprises an amino acid sequence as set forth in SEQ ID NO.2, the H-FR2 may comprises an amino acid sequence as set forth in SEQ ID NO.12, the H-FR3 may comprises an amino acid sequence as set forth in SEQ ID NO.28, and the H-FR4 may comprises an amino acid sequence as set forth in SEQ ID NO.43; the VH may comprise an amino sequence as set forth in SEQ ID NO.96; the heavy chain constant region may comprise an amino acid sequence as set forth in SEQ ID NO. 167; the HC may comprise an amino acid sequence as set forth in SEQ ID NO. 124. And the VL may comprise LCDR1-3 and L-FR1-4, the LCDR1 may comprise an amino acid sequence as set forth in SEQ ID NO. 55, the LCDR2 may comprise an amino acid sequence as set forth in SEQ ID NO. 66, and the LCDR3 may comprise an amino acid sequence as set forth in SEQ ID NO. 78; the L-FR1 may comprises an amino acid sequence as set forth in SEQ ID NO.47, the L-FR2 may comprises an amino acid sequence as set forth in SEQ ID NO.61, the L-FR3 may comprises an amino acid sequence as set forth in SEQ ID NO.72, and the L-FR4 may comprises an amino acid sequence as set forth in SEQ ID NO.90; the VL may comprise an amino acid sequence as set forth in SEQ ID NO.111; the light chain constant region may comprise an amino acid sequence as set forth in SEQ ID NO.166; the LC may comprise an amino acid sequence as set forth in SEQ ID NO. 139.

For another example, the antigen binding protein may comprise a HC and a LC that are the same as those of the antibody PR000843. The HC may comprise a VH and a heavy chain constant. The VH may comprise HCDR1-3 and H-FR1-4, the HCDR1 may comprise an amino acid sequence as set forth in SEQ ID NO. 7, the HCDR2 may comprise an amino acid sequence as set forth in SEQ ID NO. 23, and the HCDR3 may comprise an amino acid sequence as set forth in SEQ ID NO. 38; the H-FR1 may comprises an amino acid sequence as set forth in SEQ ID NO.2, the H-FR2 may comprises an amino acid sequence as set forth in SEQ ID NO.12, the H-FR3 may comprises an amino acid sequence as set forth in SEQ ID NO.28, and the H-FR4 may comprises an amino acid sequence as set forth in SEQ ID NO.43; the VH may comprise an amino sequence as set forth in SEQ ID NO.104; the heavy chain constant region may comprise an amino acid sequence as set forth in SEQ ID NO. 167; the HC may comprise an amino acid sequence as set forth in SEQ ID NO. 132. And the VL may comprise LCDR1-3 and L-FR1-4, the LCDR1 may comprise an amino acid sequence as set forth in SEQ ID NO. 55, the LCDR2 may comprise an amino acid sequence as set forth in SEQ ID NO. 66, and the LCDR3 may comprise an amino acid sequence as set forth in SEQ ID NO. 78; the L-FR1 may comprises an amino acid sequence as set forth in SEQ ID NO.47, the L-FR2 may comprises an amino acid sequence as set forth in SEQ ID NO.61, the L-FR3 may comprises an amino acid sequence as set forth in SEQ ID NO.72, and the L-FR4 may comprises an amino acid sequence as set forth in SEQ ID NO.90; the VL may comprise an amino acid sequence as set forth in SEQ ID NO.111; the light chain constant region may comprise an amino acid sequence as set forth in SEQ ID NO.166; the LC may comprise an amino acid sequence as set forth in SEQ ID NO. 139.

For another example, the antigen binding protein may comprise a HC and a LC that are the same as those of the antibody PR000844. The HC may comprise a VH and a heavy chain constant. The VH may comprise HCDR1-3 and H-FR1-4, the HCDR1 may comprise an amino acid sequence as set forth in SEQ ID NO. 7, the HCDR2 may comprise an amino acid sequence as set forth in SEQ ID NO. 23, and the HCDR3 may comprise an amino acid sequence as set forth in SEQ ID NO. 39; the H-FR1 may comprises an amino acid sequence as set forth in SEQ ID NO.2, the H-FR2 may comprises an amino acid sequence as set forth in SEQ ID NO.12, the H-FR3 may comprises an amino acid sequence as set forth in SEQ ID NO.28, and the H-FR4 may comprises an amino acid sequence as set forth in SEQ ID NO.43; the VH may comprise an amino sequence as set forth in SEQ ID NO.105; the heavy chain constant region may comprise an amino acid sequence as set forth in SEQ ID NO. 167; the HC may comprise an amino acid sequence as set forth in SEQ ID NO. 133. And the VL may comprise LCDR1-3 and L-FR1-4, the LCDR1 may comprise an amino acid sequence as set forth in SEQ ID NO. 55, the LCDR2 may comprise an amino acid sequence as set forth in SEQ ID NO.66, and the LCDR3 may comprise an amino acid sequence as set forth in SEQ ID NO. 78; the L-FR1 may comprises an amino acid sequence as set forth in SEQ ID NO.48, the L-FR2 may comprises an amino acid sequence as set forth in SEQ ID NO.61, the L-FR3 may comprises an amino acid sequence as set forth in SEQ ID NO.72, and the L-FR4 may comprises an amino acid sequence as set forth in SEQ ID NO.90; the VL may comprise an amino acid sequence as set forth in SEQ ID NO.111; the light chain constant region may comprise an amino acid sequence as set forth in SEQ ID NO.166; the LC may comprise an amino acid sequence as set forth in SEQ ID NO. 139.

For another example, the antigen binding protein may comprise a HC and a LC that are the same as those of the antibody PR000845. The HC may comprise a VH and a heavy chain constant. The VH may comprise HCDR1-3 and H-FR1-4, the HCDR1 may comprise an amino acid sequence as set forth in SEQ ID NO. 7, the HCDR2 may comprise an amino acid sequence as set forth in SEQ ID NO. 24, and the HCDR3 may comprise an amino acid sequence as set forth in SEQ ID NO.38; the H-FR1 may comprises an amino acid sequence as set forth in SEQ ID NO.2, the H-FR2 may comprises an amino acid sequence as set forth in SEQ ID NO.12, the H-FR3 may comprises an amino acid sequence as set forth in SEQ ID NO.28, and the H-FR4 may comprises an amino acid sequence as set forth in SEQ ID NO.43; the VH may comprise an amino sequence as set forth in SEQ ID NO.106; the heavy chain constant region may comprise an amino acid sequence as set forth in SEQ ID NO. 167; the HC may comprise an amino acid sequence as set forth in SEQ ID NO. 134. And the VL may comprise LCDR1-3 and L-FR1-4, the LCDR1 may comprise an amino acid sequence as set forth in SEQ ID NO. 55, the LCDR2 may comprise an amino acid sequence as set forth in SEQ ID NO. 66, and the LCDR3 may comprise an amino acid sequence as set forth in SEQ ID NO. 78; the L-FR1 may comprises an amino acid sequence as set forth in SEQ ID NO.48, the L-FR2 may comprises an amino acid sequence as set forth in SEQ ID NO.61, the L-FR3 may comprises an amino acid sequence as set forth in SEQ ID NO.72, and the L-FR4 may comprises an amino acid sequence as set forth in SEQ ID NO.90; the VL may comprise an amino acid sequence as set forth in SEQ ID NO.111; the light chain constant region may comprise an amino acid sequence as set forth in SEQ ID NO.166; the LC may comprise an amino acid sequence as set forth in SEQ ID NO. 139.

For another example, the antigen binding protein may comprise a HC and a LC that are the same as those of the antibody PR000846. The HC may comprise a VH and a heavy chain constant. The VH may comprise HCDR1-3 and H-FR1-4, the HCDR1 may comprise an amino acid sequence as set forth in SEQ ID NO. 7, the HCDR2 may comprise an amino acid sequence as set forth in SEQ ID NO. 24, and the HCDR3 may comprise an amino acid sequence as set forth in SEQ ID NO.39; the H-FR1 may comprises an amino acid sequence as set forth in SEQ ID NO.2, the H-FR2 may comprises an amino acid sequence as set forth in SEQ ID NO.12, the H-FR3 may comprises an amino acid sequence as set forth in SEQ ID NO.28, and the H-FR4 may comprises an amino acid sequence as set forth in SEQ ID NO.43; the VH may comprise an amino sequence as set forth in SEQ ID NO.107; the heavy chain constant region may comprise an amino acid sequence as set forth in SEQ ID NO. 167; the HC may comprise an amino acid sequence as set forth in SEQ ID NO. 135. And the VL may comprise LCDR1-3 and L-FR1-4, the LCDR1 may comprise an amino acid sequence as set forth in SEQ ID NO. 55, the LCDR2 may comprise an amino acid sequence as set forth in SEQ ID NO. 66, and the LCDR3 may comprise an amino acid sequence as set forth in SEQ ID NO. 78; the L-FR1 may comprises an amino acid sequence as set forth in SEQ ID NO.48, the L-FR2 may comprises an amino acid sequence as set forth in SEQ ID NO.61, the L-FR3 may comprises an amino acid sequence as set forth in SEQ ID NO.72, and the L-FR4 may comprises an amino acid sequence as set forth in SEQ ID NO.90; the VL may comprise an amino acid sequence as set forth in SEQ ID NO.111; the light chain constant region may comprise an amino acid sequence as set forth in SEQ ID NO.166; the LC may comprise an amino acid sequence as set forth in SEQ ID NO. 139.

For another example, the antigen binding protein may comprise a HC and a LC that are the same as those of the antibody PR000847. The HC may comprise a VH and a heavy chain constant. The VH may comprise HCDR1-3 and H-FR1-4, the HCDR1 may comprise an amino acid sequence as set forth in SEQ ID NO. 7, the HCDR2 may comprise an amino acid sequence as set forth in SEQ ID NO. 23, and the HCDR3 may comprise an amino acid sequence as set forth in SEQ ID NO. 38; the H-FR1 may comprises an amino acid sequence as set forth in SEQ ID NO.2, the H-FR2 may comprises an amino acid sequence as set forth in SEQ ID NO.12, the H-FR3 may comprises an amino acid sequence as set forth in SEQ ID NO.28, and the H-FR4 may comprises an amino acid sequence as set forth in SEQ ID NO.43; the VH may comprise an amino sequence as set forth in SEQ ID NO.104; the heavy chain constant region may comprise an amino acid sequence as set forth in SEQ ID NO. 167; the HC may comprise an amino acid sequence as set forth in SEQ ID NO. 132. And the VL may comprise LCDR1-3 and L-FR1-4, the LCDR1 may comprise an amino acid sequence as set forth in SEQ ID NO. 55, the LCDR2 may comprise an amino acid sequence as set forth in SEQ ID NO. 66, and the LCDR3 may comprise an amino acid sequence as set forth in SEQ ID NO. 78; the L-FR1 may comprises an amino acid sequence as set forth in SEQ ID NO.51, the L-FR2 may comprises an amino acid sequence as set forth in SEQ ID NO.61, the L-FR3 may comprises an amino acid sequence as set forth in SEQ ID NO.72, and the L-FR4 may comprises an amino acid sequence as set forth in SEQ ID NO.90; the VL may comprise an amino acid sequence as set forth in SEQ ID NO.115; the light chain constant region may comprise an amino acid sequence as set forth in SEQ ID NO.166; the LC may comprise an amino acid sequence as set forth in SEQ ID NO. 143.

For another example, the antigen binding protein may comprise a HC and a LC that are the same as those of the antibody PR000848. The HC may comprise a VH and a heavy chain constant. The VH may comprise HCDR1-3 and H-FR1-4, the HCDR1 may comprise an amino acid sequence as set forth in SEQ ID NO. 7, the HCDR2 may comprise an amino acid sequence as set forth in SEQ ID NO. 23, and the HCDR3 may comprise an amino acid sequence as set forth in SEQ ID NO. 39; the H-FR1 may comprises an amino acid sequence as set forth in SEQ ID NO.2, the H-FR2 may comprises an amino acid sequence as set forth in SEQ ID NO.2, the H-FR2 may comprises an amino acid sequence as set forth in SEQ ID NO.12, the H-FR3 may comprises an amino acid sequence as set forth in SEQ ID NO.28, and the H-FR4 may comprises an amino acid sequence as set forth in SEQ ID NO.43; the VH may comprise an amino sequence as set forth in SEQ ID NO.105; the heavy chain constant region may comprise an amino acid sequence as set forth in SEQ ID NO. 167; the HC may comprise an amino acid sequence as set forth in SEQ ID NO. 133. And the VL may comprise LCDR1-3 and L-FR1-4, the LCDR1 may comprise an amino acid sequence as set forth in SEQ ID NO. 55, the LCDR2 may comprise an amino acid sequence as set forth in SEQ ID NO. 66, and the LCDR3 may comprise an amino acid sequence as set forth in SEQ ID NO. 78; the L-FR1 may comprises an amino acid sequence as set forth in SEQ ID NO.51, the L-FR2 may comprises an amino acid sequence as set forth in SEQ ID NO.61, the L-FR3 may comprises an amino acid sequence as set forth in SEQ ID NO.72, and the L-FR4 may comprises an amino acid sequence as set forth in SEQ ID NO.90; the VL may comprise an amino acid sequence as set forth in SEQ ID NO.115; the light chain constant region may comprise an amino acid sequence as set forth in SEQ ID NO.166; the LC may comprise an amino acid sequence as set forth in SEQ ID NO. 143.

For another example, the antigen binding protein may comprise a HC and a LC that are the same as those of the antibody PR000849. The HC may comprise a VH and a heavy chain constant. The VH may comprise HCDR1-3 and H-FR1-4, the HCDR1 may comprise an amino acid sequence as set forth in SEQ ID NO. 7, the HCDR2 may comprise an amino acid sequence as set forth in SEQ ID NO. 24, and the HCDR3 may comprise an amino acid sequence as set forth in SEQ ID NO.38; the H-FR1 may comprises an amino acid sequence as set forth in SEQ ID NO.2, the H-FR2 may comprises an amino acid sequence as set forth in SEQ ID NO.12, the H-FR3 may comprises an amino acid sequence as set forth in SEQ ID NO.28, and the H-FR4 may comprises an amino acid sequence as set forth in SEQ ID NO.43; the VH may comprise an amino sequence as set forth in SEQ ID NO.106; the heavy chain constant region may comprise an amino acid sequence as set forth in SEQ ID NO. 167; the HC may comprise an amino acid sequence as set forth in SEQ ID NO. 134. And the VL may comprise LCDR1-3 and L-FR1-4, the LCDR1 may comprise an amino acid sequence as set forth in SEQ ID NO. 55, the LCDR2 may comprise an amino acid sequence as set forth in SEQ ID NO. 66, and the LCDR3 may comprise an amino acid sequence as set forth in SEQ ID NO. 78; the L-FR1 may comprises an amino acid sequence as set forth in SEQ ID NO.51, the L-FR2 may comprises an amino acid sequence as set forth in SEQ ID NO.61, the L-FR3 may comprises an amino acid sequence as set forth in SEQ ID NO.72, and the L-FR4 may comprises an amino acid sequence as set forth in SEQ ID NO.90; the VL may comprise an amino acid sequence as set forth in SEQ ID NO.115; the light chain constant region may comprise an amino acid sequence as set forth in SEQ ID NO.166; the LC may comprise an amino acid sequence as set forth in SEQ ID NO. 143.

For another example, the antigen binding protein may comprise a HC and a LC that are the same as those of the antibody PR000850. The HC may comprise a VH and a heavy chain constant. The VH may comprise HCDR1-3 and H-FR1-4, the HCDR1 may comprise an amino acid sequence as set forth in SEQ ID NO. 7, the HCDR2 may comprise an amino acid sequence as set forth in SEQ ID NO. 24, and the HCDR3 may comprise an amino acid sequence as set forth in SEQ ID NO. 39; the H-FR1 may comprises an amino acid sequence as set forth in SEQ ID NO.2, the H-FR2 may comprises an amino acid sequence as set forth in SEQ ID NO.12, the H-FR3 may comprises an amino acid sequence as set forth in SEQ ID NO.28, and the H-FR4 may comprises an amino acid sequence as set forth in SEQ ID NO.43; the VH may comprise an amino sequence as set forth in SEQ ID NO.107; the heavy chain constant region may comprise an amino acid sequence as set forth in SEQ ID NO. 167; the HC may comprise an amino acid sequence as set forth in SEQ ID NO. 135. And the VL may comprise LCDR1-3 and L-FR1-4, the LCDR1 may comprise an amino acid sequence as set forth in SEQ ID NO. 55, the LCDR2 may comprise an amino acid sequence as set forth in SEQ ID NO. 66, and the LCDR3 may comprise an amino acid sequence as set forth in SEQ ID NO. 78; the L-FR1 may comprises an amino acid sequence as set forth in SEQ ID NO.51, the L-FR2 may comprises an amino acid sequence as set forth in SEQ ID NO.61, the L-FR3 may comprises an amino acid sequence as set forth in SEQ ID NO.72, and the L-FR4 may comprises an amino acid sequence as set forth in SEQ ID NO.90; the VL may comprise an amino acid sequence as set forth in SEQ ID NO.115; the light chain constant region may comprise an amino acid sequence as set forth in SEQ ID NO.166; the LC may comprise an amino acid sequence as set forth in SEQ ID NO. 143.

For another example, the antigen binding protein may comprise a HC and a LC that are the same as those of the antibody PR000851. The HC may comprise a VH and a heavy chain constant. The VH may comprise HCDR1-3 and H-FR1-4, the HCDR1 may comprise an amino acid sequence as set forth in SEQ ID NO. 7, the HCDR2 may comprise an amino acid sequence as set forth in SEQ ID NO. 18, and the HCDR3 may comprise an amino acid sequence as set forth in SEQ ID NO. 35; the H-FR1 may comprises an amino acid sequence as set forth in SEQ ID NO.2, the H-FR2 may comprises an amino acid sequence as set forth in SEQ ID NO.12, the H-FR3 may comprises an amino acid sequence as set forth in SEQ ID NO.28, and the H-FR4 may comprises an amino acid sequence as set forth in SEQ ID NO.43; the VH may comprise an amino sequence as set forth in SEQ ID NO.96; the heavy chain constant region may comprise an amino acid sequence as set forth in SEQ ID NO. 167; the HC may comprise an amino acid sequence as set forth in SEQ ID NO. 124. And the VL may comprise LCDR1-3 and L-FR1-4, the LCDR1 may comprise an amino acid sequence as set forth in SEQ ID NO. 55, the LCDR2 may comprise an amino acid sequence as set forth in SEQ ID NO. 66, and the LCDR3 may comprise an amino acid sequence as set forth in SEQ ID NO. 78; the L-FR1 may comprises an amino acid sequence as set forth in SEQ ID NO.48, the L-FR2 may comprises an amino acid sequence as set forth in SEQ ID NO.61, the L-FR3 may comprises an amino acid sequence as set forth in SEQ ID NO.72, and the L-FR4 may comprises an amino acid sequence as set forth in SEQ ID NO.90; the VL may comprise an amino acid sequence as set forth in SEQ ID NO.115; the light chain constant region may comprise an amino acid sequence as set forth in SEQ ID NO.166; the LC may comprise an amino acid sequence as set forth in SEQ ID NO. 143.

In the present disclosure, the antigen binding protein may comprise at least one HCDR from the VH of SEQ ID NO: 156.

In the present disclosure, the antigen binding protein may comprise a HCDR3 from the heavy chain variable region VH of SEQ ID NO: 156, and the HCDR3 may comprises an amino acid sequence as set forth in SEQ ID NO.34:

GGDLLTGPNAFDI (SEQ ID NO.34). For example, the sequence may be determined according to the Chothia definition.

In the present disclosure, the antigen binding protein may comprise a HCDR2 from the heavy chain variable region VH of SEQ ID NO: 156, and the HCDR2 may comprises an amino acid sequence as set forth in SEQ ID NO.158: WYX$_3$X$_4$SK (SEQ ID NO.158); wherein, X$_3$=D or E; X$_4$=G or A. For example, the sequence may be determined according to the Chothia definition.

For example, the HCDR2 may comprise amino acid sequence as set forth in any of SEQ ID NO: 17, 21 and 22.

In the present disclosure, the antigen binding protein may comprise a HCDR1 from the heavy chain variable region VH of SEQ ID NO: 156, and the HCDR1 may comprises an amino acid sequence as set forth in SEQ ID NO.6: GFTFSSY (SEQ ID NO.6). For example, the sequence may be determined according to the Chothia definition.

In the present disclosure, the antigen binding protein may comprise a H-FR1, C-terminus of the H-FR1 is directly or indirectly linked to N-terminus of said HCDR1, and the H-FR1 may comprises an amino acid sequence as set forth in SEQ ID NO.1: QVQVVESGGGVVQPGRSLRLSCAAS (SEQ ID NO.1). For example, the sequence may be determined according to the Chothia definition.

In the present disclosure, the antigen binding protein may comprise a H-FR2, the H-FR2 is located between said HCDR1 and said HCDR2, and the H-FR2 may comprises an amino acid sequence as set forth in SEQ ID NO.11: DMHWVRQAPGKGLEWVAST (SEQ ID NO.11). For example, the sequence may be determined according to the Chothia definition.

In the present disclosure, the antigen binding protein may comprise a H-FR3, the H-FR3 is located between said HCDR2 and said HCDR3, and the H-FR3 may comprises an amino acid sequence as set forth in SEQ ID NO.27: KYYADSVKGRFTISRDNSKNTLYLKMNSLRGDDTAVYYCAK (SEQ ID NO.27). For example, the sequence may be determined according to the Chothia definition.

In the present disclosure, the antigen binding protein may comprise a H-FR4, N-terminus of said H-FR4 is linked directly or indirectly to C-terminus of said HCDR3, and the H-FR4 may comprises an amino acid sequence as set forth in SEQ ID NO.42: WGQGTMVTVSS (SEQ ID NO.42). For example, the sequence may be determined according to the Chothia definition.

In the present disclosure, the antigen binding protein may comprise a VH, and the VH may comprises an amino acid sequence as set forth in SEQ ID NO.156: QVQX$_4$VESGGGVVQPGRSLRLSCAASGFTFSSYDM HWVRQAPGKGLEWVASTWYX$_5$X$_6$SK KYYADSVKGRFTISRDNSKNTLYLX$_7$MNSLRX$_8$X$_9$DT AVYYCAKGGDLLTGPNAFDIWGQG TMVTVSS (SEQ ID NO.156); wherein, X$_4$=L or V, X$_5$=D or E; X$_6$=G or A; X$_7$=K or Q; X$_8$=G or A; and X$_9$=D or E. For example, the sequence may be determined according to the Chothia definition.

For example, the VH may comprise amino acid sequence as set forth in any of SEQ ID NO: 95, 99, 100, 101, 102 and 103.

In the present disclosure, the antigen binding protein may comprise an antibody heavy chain constant region, and the antibody heavy chain constant region comprises a human IgG constant region. In some cases, the human IgG constant region may be derived from a human IgG1 constant region.

For example, the antibody heavy chain constant region may comprise amino acid sequence as set forth in SEQ ID NO.167:

(SEQ ID NO. 167)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPEAAGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSREEMTKNQVSLTC

LVKGFYPSDIAVEWESNGQPENNYKTTPPVLDSDGSFFLYSKLTVDKSRW

QQGNVFSCSVMHEALHNHYTQKSLSLSPGK.

In the present disclosure, the antigen binding protein may comprise an antibody heavy chain (HC), and the HC comprises an amino acid sequence as set in forth in SEQ ID NO. 161. For example, the HC may comprise amino acid sequence as set forth in any of SEQ ID NO: 123, 127, 128, 129, 130 and 131.

In the present disclosure, the antigen binding protein may comprise at least one LCDR from the VL of SEQ ID NO: 155.

In the present disclosure, the antigen binding protein may comprise a LCDR3 from the heavy chain variable region VH of SEQ ID NO: 156, and the LCDR3 may comprises an amino acid sequence as set forth in SEQ ID NO.157: QQYDX$_5$YX$_6$NT (SEQ ID NO.157), wherein, X5=M, N, Q, S or T; and X$_6$=E, K, S. For example, the sequence may be determined according to the Chothia definition.

In the present disclosure, the antigen binding protein may comprise a LCDR2 from the heavy chain variable region VH of SEQ ID NO: 156, and the LCDR2 may comprises an amino acid sequence as set forth in SEQ ID NO. 65: KASSLES (SEQ ID NO. 65) For example, the sequence may be determined according to the Chothia definition.

In the present disclosure, the antigen binding protein may comprise a LCDR1 from the heavy chain variable region VH of SEQ ID NO: 156, and the LCDR1 may comprises an amino acid sequence as set forth in SEQ ID NO.54: RASQSISSWLA (SEQ ID NO.54). For example, the sequence may be determined according to the Chothia definition.

In the present disclosure, the antigen binding protein may comprise a L-FR1, C-terminus of the L-FR1 is directly or indirectly linked to N-terminus of said LCDR1, and the L-FR1 may comprises an amino acid sequence as set forth in SEQ ID NO.47: DIQMTQSPSTLSASVGDRVTITC (SEQ ID NO.47). For example, the sequence may be determined according to the Chothia definition.

In the present disclosure, the antigen binding protein may comprise a L-FR2, the L-FR2 is located between said LCDR1 and said LCDR2, and the L-FR2 may comprises an amino acid sequence as set forth in SEQ ID NO.60: WYQQKPGKAPKLLIY (SEQ ID NO.60). For example, the sequence may be determined according to the Chothia definition.

In the present disclosure, the antigen binding protein may comprise a L-FR3, the L-FR3 is located between said LCDR2 and said LCDR3, and the L-FR3 may comprises an amino acid sequence as set forth in SEQ ID NO.71: GVPSRFSGSGSGTEFTLTISSLQPDDFATYYC (SEQ ID NO.71). For example, the sequence may be determined according to the Chothia definition.

In the present disclosure, the antigen binding protein may comprise a L-FR4, N-terminus of said L-FR4 is linked directly or indirectly to C-terminus of said LCDR3, and the L-FR4 may comprises an amino acid sequence as set forth in SEQ ID NO.89: FGQGTKLEIK (SEQ ID NO.89). For example, the sequence may be determined according to the Chothia definition.

In the present disclosure, the antigen binding protein may comprise a VL, and the VL may comprise an amino acid sequence as set forth in SEQ ID NO.155: DIQMTQSPSTL-SASVGDRVTITCRASQSISS-WLAWYQQKPGKAPKLLIYKASSLESGVPSRFS GSGSGIEFTLTISSLQPDDFATYYCQQYDX$_1$YX$_4$NTFG QGTKLEIK (SEQ ID NO.155); wherein, X$_1$=M, N, Q, S or T; X$_4$=E, K or S. For example, the sequence may be determined according to the Chothia definition.

For example, the VL may comprise amino acid sequence as set forth in any of SEQ ID NO: 110, 114, 118, 119, 120, 121 and 122.

In the present disclosure, the antigen binding protein may comprise an antibody light chain constant region, and the antibody light chain constant region comprises a human Igκ constant region. For example, the antibody light chain constant region may comprise amino acid sequence as set forth in SEQ ID NO.166:

```
                                    (SEQ ID NO: 166)
RTVAAPSVFIFPPSDEQLKSGTASVVCLLNNFYPREAKVQWKVDNALQSG

NSQESVTEQDSKDSTYSLSSTLTLSKADYEKHKVYACEVTHQGLSSPVTK

SFNRGEC.
```

In the present disclosure, the antigen binding protein may comprise an antibody light chain (LC), and the LC comprises an amino acid sequence as set in forth in SEQ ID NO. 160. For example, the LC may comprise amino acid sequence as set forth in any of SEQ ID NO: 138, 142, 146, 147, 148, 149 and 150.

In the present disclosure, the antigen binding protein may comprise HCDR1-3. The HCDR1 may comprise an amino acid sequence as set forth in SEQ ID NO. 6, the HCDR2 may comprise an amino acid sequence as set forth in SEQ ID NO. 158, and the HCDR3 may comprise an amino acid sequence as set forth in SEQ ID NO. 34.

In some cases, the antigen binding protein may comprise HCDR1-3. The HCDR1 may comprise an amino acid sequence as set forth in any of SEQ ID NO.6, the HCDR2 may comprise an amino acid sequence as set forth in any of SEQ ID NO.17, 21, 22, and the HCDR3 may comprise an amino acid sequence as set forth in any of SEQ ID NO.34.

For example, the HCDR1 of the antigen binding protein may comprise an amino acid sequence as set forth in SEQ ID NO.6, the HCDR2 may comprise an amino acid sequence as set forth in SEQ ID NO. 17, and the HCDR3 may comprise an amino acid sequence as set forth in SEQ ID NO.34.

For another example, the HCDR1 of the antigen binding protein may comprise an amino acid sequence as set forth in SEQ ID NO.6, the HCDR2 may comprise an amino acid sequence as set forth in SEQ ID NO.21, and the HCDR3 may comprise an amino acid sequence as set forth in SEQ ID NO.34.

For another example, the HCDR1 of the antigen binding protein may comprise an amino acid sequence as set forth in SEQ ID NO.6, the HCDR2 may comprise an amino acid sequence as set forth in SEQ ID NO.22, and the HCDR3 may comprise an amino acid sequence as set forth in SEQ ID NO.34.

In the present disclosure, the antigen binding protein may comprise LCDR1-3. The LCDR1 may comprise an amino acid sequence as set forth in SEQ ID NO. 54, the LCDR2 may comprise an amino acid sequence as set forth in SEQ ID NO. 65, and the LCDR3 may comprise an amino acid sequence as set forth in SEQ ID NO. 157.

For example, the LCDR1 of the antigen binding protein may comprise an amino acid sequence as set forth in SEQ ID NO.54, the LCDR2 may comprise an amino acid sequence as set forth in SEQ ID NO. 65, and the LCDR3 may comprise an amino acid sequence as set forth in SEQ ID NO.77.

For example, the LCDR1 of the antigen binding protein may comprise an amino acid sequence as set forth in SEQ ID NO.54, the LCDR2 may comprise an amino acid sequence as set forth in SEQ ID NO. 65, and the LCDR3 may comprise an amino acid sequence as set forth in SEQ ID NO.81.

For example, the LCDR1 of the antigen binding protein may comprise an amino acid sequence as set forth in SEQ ID NO.54, the LCDR2 may comprise an amino acid sequence as set forth in SEQ ID NO. 65, and the LCDR3 may comprise an amino acid sequence as set forth in SEQ ID NO.84.

For example, the LCDR1 of the antigen binding protein may comprise an amino acid sequence as set forth in SEQ ID NO.54, the LCDR2 may comprise an amino acid sequence as set forth in SEQ ID NO. 65, and the LCDR3 may comprise an amino acid sequence as set forth in SEQ ID NO.85.

For example, the LCDR1 of the antigen binding protein may comprise an amino acid sequence as set forth in SEQ ID NO.54, the LCDR2 may comprise an amino acid sequence as set forth in SEQ ID NO. 65, and the LCDR3 may comprise an amino acid sequence as set forth in SEQ ID NO.86.

For example, the LCDR1 of the antigen binding protein may comprise an amino acid sequence as set forth in SEQ ID NO.54, the LCDR2 may comprise an amino acid sequence as set forth in SEQ ID NO. 65, and the LCDR3 may comprise an amino acid sequence as set forth in SEQ ID NO.87.

For example, the LCDR1 of the antigen binding protein may comprise an amino acid sequence as set forth in SEQ ID NO.54, the LCDR2 may comprise an amino acid sequence as set forth in SEQ ID NO. 65, and the LCDR3 may comprise an amino acid sequence as set forth in SEQ ID NO. 88.

In the present disclosure, the antigen binding protein may comprise a H-FR1-4. The H-FR1 may comprises an amino acid sequence as set forth in SEQ ID NO.164, the H-FR2 may comprises an amino acid sequence as set forth in SEQ ID NO.11, the H-FR3 may comprises an amino acid sequence as set forth in SEQ ID NO.165, and the H-FR4 may comprises an amino acid sequence as set forth in SEQ ID NO.42.

For example, the H-FR1 may comprises an amino acid sequence as set forth in SEQ ID NO:1, the H-FR2 may comprises an amino acid sequence as set forth in any one of SEQ ID NO: 11, the H-FR3 may comprises an amino acid sequence as set forth in any one of SEQ ID NO: 27, and the H-FR4 may comprises an amino acid sequence as set forth in SEQ ID NO.42.

For example, the H-FR1 may comprises an amino acid sequence as set forth in SEQ ID NO:3, the H-FR2 may comprises an amino acid sequence as set forth in any one of SEQ ID NO: 11, the H-FR3 may comprises an amino acid sequence as set forth in any one of SEQ ID NO: 31, and the H-FR4 may comprises an amino acid sequence as set forth in SEQ ID NO.42.

In the present disclosure, the antigen binding protein may comprise a L-FR1-4. The L-FR1 may comprises an amino acid sequence as set forth in SEQ ID NO.47, the L-FR2 may comprises an amino acid sequence as set forth in SEQ ID NO.60, the L-FR3 may comprises an amino acid sequence as set forth in SEQ ID NO.71, and the L-FR4 may comprises an amino acid sequence as set forth in SEQ ID NO.89.

In the present disclosure, the antigen binding protein may comprise HCDR1-3 and LCDR1-3 and. The HCDR1 may comprise an amino acid sequence as set forth in SEQ ID NO. 6, the HCDR2 may comprise an amino acid sequence as set forth in SEQ ID NO. 158, and the HCDR3 may comprise an amino acid sequence as set forth in SEQ ID NO. 34; the LCDR1 may comprise an amino acid sequence as set forth in SEQ ID NO. 54, the LCDR2 may comprise an amino acid sequence as set forth in SEQ ID NO. 65, the LCDR3 may comprise an amino acid sequence as set forth in SEQ ID NO. 157.

In some cases, the HCDR1 of the antigen binding protein may comprise an amino acid sequence as set forth in any of SEQ ID NO.6, the HCDR2 may comprise an amino acid sequence as set forth in any of SEQ ID NO.17, 21 and 22, and the HCDR3 may comprise an amino acid sequence as set forth in SEQ ID NO.34; the LCDR1 may comprise an amino acid sequence as set forth in any of SEQ ID NO.54, the LCDR2 may comprise an amino acid sequence as set forth in any of SEQ ID NO.65, and the LCDR3 may comprise an amino acid sequence as set forth in any of SEQ ID NO:77, 81, 84, 85, 86, 87 and 88.

For example, the HCDR1 of the antigen binding protein may comprise an amino acid sequence as set forth in SEQ ID NO.6, the HCDR2 may comprise an amino acid sequence as set forth in SEQ ID NO. 17, and the HCDR3 may comprise an amino acid sequence as set forth in SEQ ID NO.34; the LCDR1 of the antigen binding protein may comprise an amino acid sequence as set forth in SEQ ID NO.54, the LCDR2 may comprise an amino acid sequence as set forth in SEQ ID NO. 65, and the LCDR3 may comprise an amino acid sequence as set forth in SEQ ID NO.77.

For another example, the HCDR1 of the antigen binding protein may comprise an amino acid sequence as set forth in SEQ ID NO.6, the HCDR2 may comprise an amino acid sequence as set forth in SEQ ID NO. 17, and the HCDR3 may comprise an amino acid sequence as set forth in SEQ ID NO.34; the LCDR1 of the antigen binding protein may comprise an amino acid sequence as set forth in SEQ ID NO.54, the LCDR2 may comprise an amino acid sequence as set forth in SEQ ID NO. 65, and the LCDR3 may comprise an amino acid sequence as set forth in SEQ ID NO.81.

For another example, the HCDR1 of the antigen binding protein may comprise an amino acid sequence as set forth in SEQ ID NO.6, the HCDR2 may comprise an amino acid sequence as set forth in SEQ ID NO. 21, and the HCDR3 may comprise an amino acid sequence as set forth in SEQ ID NO.34; the LCDR1 of the antigen binding protein may comprise an amino acid sequence as set forth in SEQ ID NO.54, the LCDR2 may comprise an amino acid sequence as set forth in SEQ ID NO. 65, and the LCDR3 may comprise an amino acid sequence as set forth in SEQ ID NO.77.

For another example, the HCDR1 of the antigen binding protein may comprise an amino acid sequence as set forth in SEQ ID NO.6, the HCDR2 may comprise an amino acid sequence as set forth in SEQ ID NO. 22, and the HCDR3 may comprise an amino acid sequence as set forth in SEQ ID NO.34; the LCDR1 of the antigen binding protein may comprise an amino acid sequence as set forth in SEQ ID NO.54, the LCDR2 may comprise an amino acid sequence as set forth in SEQ ID NO. 65, and the LCDR3 may comprise an amino acid sequence as set forth in SEQ ID NO.77.

For another example, the HCDR1 of the antigen binding protein may comprise an amino acid sequence as set forth in SEQ ID NO.6, the HCDR2 may comprise an amino acid sequence as set forth in SEQ ID NO. 22, and the HCDR3 may comprise an amino acid sequence as set forth in SEQ ID NO.34; the LCDR1 of the antigen binding protein may comprise an amino acid sequence as set forth in SEQ ID NO.54, the LCDR2 may comprise an amino acid sequence as set forth in SEQ ID NO. 65, and the LCDR3 may comprise an amino acid sequence as set forth in SEQ ID NO.81.

For another example, the HCDR1 of the antigen binding protein may comprise an amino acid sequence as set forth in SEQ ID NO.6, the HCDR2 may comprise an amino acid sequence as set forth in SEQ ID NO. 22, and the HCDR3 may comprise an amino acid sequence as set forth in SEQ ID NO.34; the LCDR1 of the antigen binding protein may comprise an amino acid sequence as set forth in SEQ ID NO.54, the LCDR2 may comprise an amino acid sequence as set forth in SEQ ID NO. 65, and the LCDR3 may comprise an amino acid sequence as set forth in SEQ ID NO.84.

For another example, the HCDR1 of the antigen binding protein may comprise an amino acid sequence as set forth in SEQ ID NO.6, the HCDR2 may comprise an amino acid sequence as set forth in SEQ ID NO. 22, and the HCDR3 may comprise an amino acid sequence as set forth in SEQ ID NO.34; the LCDR1 of the antigen binding protein may comprise an amino acid sequence as set forth in SEQ ID NO.54, the LCDR2 may comprise an amino acid sequence as set forth in SEQ ID NO. 65, and the LCDR3 may comprise an amino acid sequence as set forth in SEQ ID NO.85.

For another example, the HCDR1 of the antigen binding protein may comprise an amino acid sequence as set forth in SEQ ID NO.6, the HCDR2 may comprise an amino acid sequence as set forth in SEQ ID NO. 22, and the HCDR3 may comprise an amino acid sequence as set forth in SEQ ID NO.34; the LCDR1 of the antigen binding protein may comprise an amino acid sequence as set forth in SEQ ID NO.54, the LCDR2 may comprise an amino acid sequence as set forth in SEQ ID NO. 65, and the LCDR3 may comprise an amino acid sequence as set forth in SEQ ID NO.86.

For another example, the HCDR1 of the antigen binding protein may comprise an amino acid sequence as set forth in SEQ ID NO.6, the HCDR2 may comprise an amino acid sequence as set forth in SEQ ID NO. 22, and the HCDR3 may comprise an amino acid sequence as set forth in SEQ ID NO.34; the LCDR1 of the antigen binding protein may comprise an amino acid sequence as set forth in SEQ ID NO.54, the LCDR2 may comprise an amino acid sequence as set forth in SEQ ID NO. 65, and the LCDR3 may comprise an amino acid sequence as set forth in SEQ ID NO.87.

For another example, the HCDR1 of the antigen binding protein may comprise an amino acid sequence as set forth in SEQ ID NO.6, the HCDR2 may comprise an amino acid sequence as set forth in SEQ ID NO. 22, and the HCDR3 may comprise an amino acid sequence as set forth in SEQ ID NO.34; the LCDR1 of the antigen binding protein may comprise an amino acid sequence as set forth in SEQ ID NO.54, the LCDR2 may comprise an amino acid sequence as set forth in SEQ ID NO. 65, and the LCDR3 may comprise an amino acid sequence as set forth in SEQ ID NO.88.

In the present disclosure, the antigen binding protein may comprise a H-FR1-4 and L-FR1-4. The H-FR1 may comprises an amino acid sequence as set forth in SEQ ID NO.164, the H-FR2 may comprises an amino acid sequence as set forth in SEQ ID NO.11, the H-FR3 may comprises an amino acid sequence as set forth in SEQ ID NO.165, and the H-FR4 may comprises an amino acid sequence as set forth in SEQ ID NO.42; the L-FR1 may comprises an amino acid sequence as set forth in SEQ ID NO.47, the L-FR2 may comprises an amino acid sequence as set forth in SEQ ID NO.60, the L-FR3 may comprises an amino acid sequence as set forth in SEQ ID NO.71, and the L-FR4 may comprises an amino acid sequence as set forth in SEQ ID NO.89.

In some cases, the H-FR1 may comprises an amino acid sequence as set forth in any one of SEQ ID NO:1 and 3, the H-FR2 may comprises an amino acid sequence as set forth in any one of SEQ ID NO: 11, the H-FR3 may comprises an amino acid sequence as set forth in any one of SEQ ID NO: 27 and 31, and the H-FR4 may comprises an amino acid sequence as set forth in SEQ ID NO.42; the L-FR1 may comprises an amino acid sequence as set forth in SEQ ID NO: 47, the L-FR2 may comprises an amino acid sequence as set forth in any one of SEQ ID NO: 60, the L-FR3 may comprises an amino acid sequence as set forth in any one of SEQ ID NO: 71, and the L-FR4 may comprises an amino acid sequence as set forth in any one of SEQ ID NO: 89.

In the present disclosure, the antigen binding protein may comprise a VH and a VL. The VH may comprise an amino acid sequence as set forth in SEQ ID NO: 156, and the VL may comprise an amino acid sequence as set forth in SEQ ID NO:155.

In some cases, the VH may comprise an amino acid sequence as set forth in any of SEQ ID NO: 95, 99, 100, 101, 102 and 103, and the VL may comprise an amino acid sequence as set forth in any of SEQ ID NO: 110, 114, 118, 119, 120, 121 and 122.

In some cases, the VH may comprise an amino acid sequence as set forth in SEQ ID NO:95, and the VL may comprise an amino acid sequence as set forth in SEQ ID NO:110.

In some cases, the VH may comprise an amino acid sequence as set forth in SEQ ID NO:99, and the VL may comprise an amino acid sequence as set forth in SEQ ID NO:110.

In some cases, the VH may comprise an amino acid sequence as set forth in SEQ ID NO:100, and the VL may comprise an amino acid sequence as set forth in SEQ ID NO:110.

In some cases, the VH may comprise an amino acid sequence as set forth in SEQ ID NO:101, and the VL may comprise an amino acid sequence as set forth in SEQ ID NO:110.

In some cases, the VH may comprise an amino acid sequence as set forth in SEQ ID NO:102, and the VL may comprise an amino acid sequence as set forth in SEQ ID NO:110.

In some cases, the VH may comprise an amino acid sequence as set forth in SEQ ID NO:103, and the VL may comprise an amino acid sequence as set forth in SEQ ID NO:110.

In some cases, the VH may comprise an amino acid sequence as set forth in SEQ ID NO:95, and the VL may comprise an amino acid sequence as set forth in SEQ ID NO:114.

In some cases, the VH may comprise an amino acid sequence as set forth in SEQ ID NO:100, and the VL may comprise an amino acid sequence as set forth in SEQ ID NO:114.

In some cases, the VH may comprise an amino acid sequence as set forth in SEQ ID NO:102, and the VL may comprise an amino acid sequence as set forth in SEQ ID NO:114.

In some cases, the VH may comprise an amino acid sequence as set forth in SEQ ID NO:103, and the VL may comprise an amino acid sequence as set forth in SEQ ID NO:114.

In some cases, the VH may comprise an amino acid sequence as set forth in SEQ ID NO:102, and the VL may comprise an amino acid sequence as set forth in SEQ ID NO:118.

In some cases, the VH may comprise an amino acid sequence as set forth in SEQ ID NO:102, and the VL may comprise an amino acid sequence as set forth in SEQ ID NO:119.

In some cases, the VH may comprise an amino acid sequence as set forth in SEQ ID NO:102, and the VL may comprise an amino acid sequence as set forth in SEQ ID NO:120.

In some cases, the VH may comprise an amino acid sequence as set forth in SEQ ID NO:102, and the VL may comprise an amino acid sequence as set forth in SEQ ID NO:121.

In some cases, the VH may comprise an amino acid sequence as set forth in SEQ ID NO:102, and the VL may comprise an amino acid sequence as set forth in SEQ ID NO:122.

In the present disclosure, the antigen binding protein may comprise a heavy chain constant region and a light chain constant region. The heavy chain constant region may comprise an amino acid sequence as set forth in SEQ ID NO: 167, and the light chain constant region may comprise an amino acid sequence as set forth in SEQ ID NO:47.

In the present disclosure, the antigen binding protein may comprise a heavy chain (HC) and a light chain (LC). The HC may comprise an amino acid sequence as set forth in SEQ ID NO: 161, and the LC may comprise an amino acid sequence as set forth in SEQ ID NO.160.

In some cases, the HC comprise an amino acid sequence as set forth in any one of SEQ ID NO: 123, 127, 128, 129, 130 and 131, and the LC constant region may comprise an amino acid sequence as set forth in any one of SEQ ID NO: 138, 142, 146,147,148,149 and 150.

In the present disclosure, the antigen binding protein may comprise a HC and a LC. The HC may comprise a VH and a heavy chain constant. The VH may comprise HCDR1-3 and H-FR1-4, the HCDR1 may comprise an amino acid sequence as set forth in SEQ ID NO. 6, the HCDR2 may comprise an amino acid sequence as set forth in SEQ ID NO. 158, and the HCDR3 may comprise an amino acid sequence as set forth in SEQ ID NO. 34; the H-FR1 may comprises an amino acid sequence as set forth in SEQ ID NO.164, the H-FR2 may comprises an amino acid sequence as set forth in SEQ ID NO.11, the H-FR3 may comprises an amino acid sequence as set forth in SEQ ID NO.27, and the H-FR4 may comprises an amino acid sequence as set forth in SEQ ID NO.42; the VH may comprise an amino sequence as set forth in SEQ ID NO.156; the heavy chain constant region may comprise an amino acid sequence as set forth in SEQ ID NO. 167; the HC may comprise an amino acid sequence as set forth in SEQ ID NO. 161. And the VL may comprise LCDR1-3 and L-FR1-4, the LCDR1 may comprise an amino acid sequence as set forth in SEQ ID NO. 54, the LCDR2 may comprise an amino acid sequence as set forth in SEQ ID NO. 65, and the LCDR3 may comprise an amino acid sequence as set forth in SEQ ID NO. 77; the L-FR1 may comprises an amino acid sequence as set forth in SEQ ID NO.47, the L-FR2 may comprises an amino acid sequence as set forth in SEQ ID NO.60, the L-FR3 may comprises an amino acid sequence as set forth in SEQ ID NO.71 and the L-FR4 may comprises an amino acid sequence as set forth in SEQ ID NO.89; the VL may comprise an amino acid sequence as set forth in SEQ ID NO.155; the light chain constant region may comprise an amino acid sequence as set forth in SEQ ID NO.166; the LC may comprise an amino acid sequence as set forth in SEQ ID NO. 160.

In some cases, the antigen binding protein may comprise a HC and a LC. The HC may comprise a VH and a heavy chain constant. The VH may comprise HCDR1-3 and H-FR1-4, the HCDR1 may comprise an amino acid sequence as set forth in any one of SEQ ID NO.6, the HCDR2 may comprise an amino acid sequence as set forth in any of SEQ ID NO. 17, 21, 22, and the HCDR3 may comprise an amino acid sequence as set forth in any one of SEQ ID NO. 34; the H-FR1 may comprises an amino acid sequence as set forth in any one of SEQ ID NO.1 and 3 the H-FR2 may comprises an amino acid sequence as set forth in any one of SEQ ID NO.11, the H-FR3 may comprises an amino acid sequence as set forth in any one of SEQ ID NO.27, and the H-FR4 may comprises an amino acid sequence as set forth in SEQ ID NO.42; the VH may comprise an amino sequence as set forth in SEQ ID NO: 95, 99, 100, 101, 102,103; the heavy chain constant region may comprise an amino acid sequence as set forth in SEQ ID NO. 167; the HC may comprise an amino acid sequence as set forth in SEQ ID NO. 123, 127, 128, 129, 130 and 131. And the VL may comprise LCDR1-3 and L-FR1-4, the LCDR1 may comprise an amino acid sequence as set forth in SEQ ID NO. 54, the LCDR2 may comprise an amino acid sequence as set forth in SEQ ID NO.65, and the LCDR3 may comprise an amino acid sequence as set forth in SEQ ID NO. 77; the L-FR1 may comprises an amino acid sequence as set forth in SEQ ID NO.47, the L-FR2 may comprises an amino acid sequence as set forth in SEQ ID NO.60, the L-FR3 may comprises an amino acid sequence as set forth in SEQ ID NO.71, and the L-FR4 may comprises an amino acid sequence as set forth in SEQ ID NO.89; the VL may comprise an amino acid sequence as set forth in SEQ ID NO. 10, 114, 118, 119, 120, 121 and 122; the light chain constant region may comprise an amino acid sequence as set forth in SEQ ID NO.47; the LC may comprise an amino acid sequence as set forth in SEQ ID NO. 138, 142, 146, 147, 148, 149 and 150.

For example, the antigen binding protein may comprise a HC and a LC that are the same as those of the antibody PR000497. The HC may comprise a VH and a heavy chain constant. The VH may comprise HCDR1-3 and H-FR1-4, the HCDR1 may comprise an amino acid sequence as set forth in SEQ ID NO. 6, the HCDR2 may comprise an amino acid sequence as set forth in SEQ ID NO. 17, and the HCDR3 may comprise an amino acid sequence as set forth in SEQ ID NO. 34; the H-FR1 may comprises an amino acid sequence as set forth in SEQ ID NO.1, the H-FR2 may comprises an amino acid sequence as set forth in SEQ ID NO.11, the H-FR3 may comprises an amino acid sequence as set forth in SEQ ID NO.27, and the H-FR4 may comprises an amino acid sequence as set forth in SEQ ID NO.42; the VH may comprise an amino sequence as set forth in SEQ ID NO.95; the heavy chain constant region may comprise an amino acid sequence as set forth in SEQ ID NO. 167; the HC may comprise an amino acid sequence as set forth in SEQ ID NO. 123. And the VL may comprise LCDR1-3 and L-FR1-4, the LCDR1 may comprise an amino acid sequence as set forth in SEQ ID NO. 54, the LCDR2 may comprise an amino acid sequence as set forth in SEQ ID NO. 65, and the LCDR3 may comprise an amino acid sequence as set forth in SEQ ID NO. 77; the L-FR1 may comprises an amino acid sequence as set forth in SEQ ID NO.47, the L-FR2 may comprises an amino acid sequence as set forth in SEQ ID NO.60, the L-FR3 may comprises an amino acid sequence as set forth in SEQ ID NO.71, and the L-FR4 may comprises an amino acid sequence as set forth in SEQ ID NO.89; the VL may comprise an amino acid sequence as set forth in SEQ ID NO.110; the light chain constant region may comprise an amino acid sequence as set forth in SEQ ID NO.166; the LC may comprise an amino acid sequence as set forth in SEQ ID NO. 138.

For another example, the antigen binding protein may comprise a HC and a LC that are the same as those of the antibody PR000815. The HC may comprise a VH and a heavy chain constant. The VH may comprise HCDR1-3 and H-FR1-4, the HCDR1 may comprise an amino acid sequence as set forth in SEQ ID NO. 6, the HCDR2 may comprise an amino acid sequence as set forth in SEQ ID NO. 21, and the HCDR3 may comprise an amino acid sequence as set forth in SEQ ID NO. 34; the H-FR1 may comprises an amino acid sequence as set forth in SEQ ID NO.1, the H-FR2 may comprises an amino acid sequence as set forth in SEQ ID NO.11, the H-FR3 may comprises an amino acid sequence as set forth in SEQ ID NO.27, and the H-FR4 may comprises an amino acid sequence as set forth in SEQ ID NO.42; the VH may comprise an amino sequence as set forth in SEQ ID NO.99; the heavy chain constant region may comprise an amino acid sequence as set forth in SEQ ID NO. 167; the HC may comprise an amino acid sequence as set forth in SEQ ID NO. 127. And the VL may comprise LCDR1-3 and L-FR1-4, the LCDR1 may comprise an amino acid sequence as set forth in SEQ ID NO. 54, the LCDR2 may comprise an amino acid sequence as set forth in SEQ ID NO. 65, and the LCDR3 may comprise an amino acid sequence as set forth in SEQ ID NO. 77; the L-FR1 may comprises an amino acid sequence as set forth in SEQ ID NO.47, the L-FR2 may comprises an amino acid sequence as set forth in SEQ ID NO.60, the L-FR3 may comprises an amino acid sequence as set forth in SEQ ID NO.71, and the L-FR4 may comprises an amino acid sequence as set forth in SEQ ID NO.89; the VL may comprise an amino acid sequence as set forth in SEQ ID NO.110; the light chain constant region may comprise an amino acid sequence as set forth in SEQ ID NO.166; the LC may comprise an amino acid sequence as set forth in SEQ ID NO. 138.

For another example, the antigen binding protein may comprise a HC and a LC that are the same as those of the antibody PR000816. The HC may comprise a VH and a heavy chain constant. The VH may comprise HCDR1-3 and H-FR1-4, the HCDR1 may comprise an amino acid sequence as set forth in SEQ ID NO. 6, the HCDR2 may comprise an amino acid sequence as set forth in SEQ ID NO.

22, and the HCDR3 may comprise an amino acid sequence as set forth in SEQ ID NO. 34; the H-FR1 may comprises an amino acid sequence as set forth in SEQ ID NO.1; the H-FR2 may comprises an amino acid sequence as set forth in SEQ ID NO.11, the H-FR3 may comprises an amino acid sequence as set forth in SEQ ID NO.27, and the H-FR4 may comprises an amino acid sequence as set forth in SEQ ID NO.42; the VH may comprise an amino sequence as set forth in SEQ ID NO.100; the heavy chain constant region may comprise an amino acid sequence as set forth in SEQ ID NO. 167; the HC may comprise an amino acid sequence as set forth in SEQ ID NO. 128. And the VL may comprise LCDR1-3 and L-FR1-4, the LCDR1 may comprise an amino acid sequence as set forth in SEQ ID NO. 54, the LCDR2 may comprise an amino acid sequence as set forth in SEQ ID NO. 65, and the LCDR3 may comprise an amino acid sequence as set forth in SEQ ID NO. 77; the L-FR1 may comprises an amino acid sequence as set forth in SEQ ID NO.47, the L-FR2 may comprises an amino acid sequence as set forth in SEQ ID NO.60, the L-FR3 may comprises an amino acid sequence as set forth in SEQ ID NO.71, and the L-FR4 may comprises an amino acid sequence as set forth in SEQ ID NO.89; the VL may comprise an amino acid sequence as set forth in SEQ ID NO.110; the light chain constant region may comprise an amino acid sequence as set forth in SEQ ID NO.166; the LC may comprise an amino acid sequence as set forth in SEQ ID NO. 138.

For another example, the antigen binding protein may comprise a HC and a LC that are the same as those of the antibody PR000817. The HC may comprise a VH and a heavy chain constant. The VH may comprise HCDR1-3 and H-FR1-4, the HCDR1 may comprise an amino acid sequence as set forth in SEQ ID NO. 6, the HCDR2 may comprise an amino acid sequence as set forth in SEQ ID NO. 21, and the HCDR3 may comprise an amino acid sequence as set forth in SEQ ID NO.34; the H-FR1 may comprises an amino acid sequence as set forth in SEQ ID NO.3, the H-FR2 may comprises an amino acid sequence as set forth in SEQ ID NO.11, the H-FR3 may comprises an amino acid sequence as set forth in SEQ ID NO.31, and the H-FR4 may comprises an amino acid sequence as set forth in SEQ ID NO.42; the VH may comprise an amino sequence as set forth in SEQ ID NO.101; the heavy chain constant region may comprise an amino acid sequence as set forth in SEQ ID NO. 167; the HC may comprise an amino acid sequence as set forth in SEQ ID NO. 129. And the VL may comprise LCDR1-3 and L-FR1-4, the LCDR1 may comprise an amino acid sequence as set forth in SEQ ID NO. 54, the LCDR2 may comprise an amino acid sequence as set forth in SEQ ID NO. 65, and the LCDR3 may comprise an amino acid sequence as set forth in SEQ ID NO. 77; the L-FR1 may comprises an amino acid sequence as set forth in SEQ ID NO.47, the L-FR2 may comprises an amino acid sequence as set forth in SEQ ID NO.60, the L-FR3 may comprises an amino acid sequence as set forth in SEQ ID NO.71, and the L-FR4 may comprises an amino acid sequence as set forth in SEQ ID NO.89; the VL may comprise an amino acid sequence as set forth in SEQ ID NO.110; the light chain constant region may comprise an amino acid sequence as set forth in SEQ ID NO.166; the LC may comprise an amino acid sequence as set forth in SEQ ID NO. 138.

For another example, the antigen binding protein may comprise a HC and a LC that are the same as those of the antibody PR000818. The HC may comprise a VH and a heavy chain constant. The VH may comprise HCDR1-3 and H-FR1-4, the HCDR1 may comprise an amino acid sequence as set forth in SEQ ID NO.6, the HCDR2 may comprise an amino acid sequence as set forth in SEQ ID NO. 22, and the HCDR3 may comprise an amino acid sequence as set forth in SEQ ID NO. 34; the H-FR1 may comprises an amino acid sequence as set forth in SEQ ID NO.3, the H-FR2 may comprises an amino acid sequence as set forth in SEQ ID NO.11, the H-FR3 may comprises an amino acid sequence as set forth in SEQ ID NO.31, and the H-FR4 may comprises an amino acid sequence as set forth in SEQ ID NO.42; the VH may comprise an amino sequence as set forth in SEQ ID NO.102; the heavy chain constant region may comprise an amino acid sequence as set forth in SEQ ID NO. 167; the HC may comprise an amino acid sequence as set forth in SEQ ID NO. 130. And the VL may comprise LCDR1-3 and L-FR1-4, the LCDR1 may comprise an amino acid sequence as set forth in SEQ ID NO. 54, the LCDR2 may comprise an amino acid sequence as set forth in SEQ ID NO. 65, and the LCDR3 may comprise an amino acid sequence as set forth in SEQ ID NO. 77; the L-FR1 may comprises an amino acid sequence as set forth in SEQ ID NO.47, the L-FR2 may comprises an amino acid sequence as set forth in SEQ ID NO.60, the L-FR3 may comprises an amino acid sequence as set forth in SEQ ID NO.71, and the L-FR4 may comprises an amino acid sequence as set forth in SEQ ID NO.89; the VL may comprise an amino acid sequence as set forth in SEQ ID NO.110; the light chain constant region may comprise an amino acid sequence as set forth in SEQ ID NO.166; the LC may comprise an amino acid sequence as set forth in SEQ ID NO. 138.

For another example, the antigen binding protein may comprise a HC and a LC that are the same as those of the antibody PR000819. The HC may comprise a VH and a heavy chain constant. The VH may comprise HCDR1-3 and H-FR1-4, the HCDR1 may comprise an amino acid sequence as set forth in SEQ ID NO. 6, the HCDR2 may comprise an amino acid sequence as set forth in SEQ ID NO. 17, and the HCDR3 may comprise an amino acid sequence as set forth in SEQ ID NO. 34; the H-FR1 may comprises an amino acid sequence as set forth in SEQ ID NO.3, the H-FR2 may comprises an amino acid sequence as set forth in SEQ ID NO.11, the H-FR3 may comprises an amino acid sequence as set forth in SEQ ID NO.31, and the H-FR4 may comprises an amino acid sequence as set forth in SEQ ID NO.42; the VH may comprise an amino sequence as set forth in SEQ ID NO.103; the heavy chain constant region may comprise an amino acid sequence as set forth in SEQ ID NO. 167; the HC may comprise an amino acid sequence as set forth in SEQ ID NO.131. And the VL may comprise LCDR1-3 and L-FR1-4, the LCDR1 may comprise an amino acid sequence as set forth in SEQ ID NO. 54, the LCDR2 may comprise an amino acid sequence as set forth in SEQ ID NO. 65, and the LCDR3 may comprise an amino acid sequence as set forth in SEQ ID NO. 77; the L-FR1 may comprises an amino acid sequence as set forth in SEQ ID NO.47, the L-FR2 may comprises an amino acid sequence as set forth in SEQ ID NO.60, the L-FR3 may comprises an amino acid sequence as set forth in SEQ ID NO.71, and the L-FR4 may comprises an amino acid sequence as set forth in SEQ ID NO.89; the VL may comprise an amino acid sequence as set forth in SEQ ID NO.110; the light chain constant region may comprise an amino acid sequence as set forth in SEQ ID NO.166; the LC may comprise an amino acid sequence as set forth in SEQ ID NO. 138.

For another example, the antigen binding protein may comprise a HC and a LC that are the same as those of the antibody PR000820. The HC may comprise a VH and a heavy chain constant. The VH may comprise HCDR1-3 and H-FR1-4, the HCDR1 may comprise an amino acid sequence as set forth in SEQ ID NO. 6, the HCDR2 may comprise an amino acid sequence as set forth in SEQ ID NO. 17, and the HCDR3 may comprise an amino acid sequence as set forth in SEQ ID NO. 34; the H-FR1 may comprises an amino acid sequence as set forth in SEQ ID NO.1, the H-FR2 may comprises an amino acid sequence as set forth in SEQ ID NO.11, the H-FR3 may comprises an amino acid sequence as set forth in SEQ ID NO.27, and the H-FR4 may comprises an amino acid sequence as set forth in SEQ ID NO.42; the VH may comprise an amino sequence as set forth in SEQ ID NO.95; the heavy chain constant region may comprise an amino acid sequence as set forth in SEQ ID NO. 167; the HC may comprise an amino acid sequence as set forth in SEQ ID NO. 123. And the VL may comprise LCDR1-3 and L-FR1-4, the LCDR1 may comprise an amino acid sequence as set forth in SEQ ID NO. 54, the LCDR2 may comprise an amino acid sequence as set forth in SEQ ID NO. 65, and the LCDR3 may comprise an amino acid sequence as set forth in SEQ ID NO. 81; the L-FR1 may comprises an amino acid sequence as set forth in SEQ ID NO.47, the L-FR2 may comprises an amino acid sequence as set forth in SEQ ID NO.60, the L-FR3 may comprises an amino acid sequence as set forth in SEQ ID NO.71, and the L-FR4 may comprises an amino acid sequence as set forth in SEQ ID NO.89; the VL may comprise an amino acid sequence as set forth in SEQ ID NO.114; the light chain constant region may comprise an amino acid sequence as set forth in SEQ ID NO.166; the LC may comprise an amino acid sequence as set forth in SEQ ID NO. 142.

For another example, the antigen binding protein may comprise a HC and a LC that are the same as those of the antibody PR000822. The HC may comprise a VH and a heavy chain constant. The VH may comprise HCDR1-3 and H-FR1-4, the HCDR1 may comprise an amino acid sequence as set forth in SEQ ID NO. 6, the HCDR2 may comprise an amino acid sequence as set forth in SEQ ID NO. 22, and the HCDR3 may comprise an amino acid sequence as set forth in SEQ ID NO. 34; the H-FR1 may comprises an amino acid sequence as set forth in SEQ ID NO.1, the H-FR2 may comprises an amino acid sequence as set forth in SEQ ID NO.11, the H-FR3 may comprises an amino acid sequence as set forth in SEQ ID NO.27, and the H-FR4 may comprises an amino acid sequence as set forth in SEQ ID NO.42; the VH may comprise an amino sequence as set forth in SEQ ID NO.100; the heavy chain constant region may comprise an amino acid sequence as set forth in SEQ ID NO. 167; the HC may comprise an amino acid sequence as set forth in SEQ ID NO. 128. And the VL may comprise LCDR1-3 and L-FR1-4, the LCDR1 may comprise an amino acid sequence as set forth in SEQ ID NO. 54, the LCDR2 may comprise an amino acid sequence as set forth in SEQ ID NO. 65, and the LCDR3 may comprise an amino acid sequence as set forth in SEQ ID NO. 81; the L-FR1 may comprises an amino acid sequence as set forth in SEQ ID NO.47, the L-FR2 may comprises an amino acid sequence as set forth in SEQ ID NO.60, the L-FR3 may comprises an amino acid sequence as set forth in SEQ ID NO.71, and the L-FR4 may comprises an amino acid sequence as set forth in SEQ ID NO.89; the VL may comprise an amino acid sequence as set forth in SEQ ID NO.114; the light chain constant region may comprise an amino acid sequence as set forth in SEQ ID NO.166; the LC may comprise an amino acid sequence as set forth in SEQ ID NO. 142.

For another example, the antigen binding protein may comprise a HC and a LC that are the same as those of the antibody PR000824. The HC may comprise a VH and a heavy chain constant. The VH may comprise HCDR1-3 and H-FR1-4, the HCDR1 may comprise an amino acid sequence as set forth in SEQ ID NO. 6, the HCDR2 may comprise an amino acid sequence as set forth in SEQ ID NO. 22, and the HCDR3 may comprise an amino acid sequence as set forth in SEQ ID NO. 34; the H-FR1 may comprises an amino acid sequence as set forth in SEQ ID NO.3, the H-FR2 may comprises an amino acid sequence as set forth in SEQ ID NO.11, the H-FR3 may comprises an amino acid sequence as set forth in SEQ ID NO.31, and the H-FR4 may comprises an amino acid sequence as set forth in SEQ ID NO.42; the VH may comprise an amino sequence as set forth in SEQ ID NO.102; the heavy chain constant region may comprise an amino acid sequence as set forth in SEQ ID NO. 167; the HC may comprise an amino acid sequence as set forth in SEQ ID NO. 130. And the VL may comprise LCDR1-3 and L-FR1-4, the LCDR1 may comprise an amino acid sequence as set forth in SEQ ID NO. 54, the LCDR2 may comprise an amino acid sequence as set forth in SEQ ID NO. 65, and the LCDR3 may comprise an amino acid sequence as set forth in SEQ ID NO. 81; the L-FR1 may comprises an amino acid sequence as set forth in SEQ ID NO.47, the L-FR2 may comprises an amino acid sequence as set forth in SEQ ID NO.60, the L-FR3 may comprises an amino acid sequence as set forth in SEQ ID NO.71, and the L-FR4 may comprises an amino acid sequence as set forth in SEQ ID NO.89; the VL may comprise an amino acid sequence as set forth in SEQ ID NO.114; the light chain constant region may comprise an amino acid sequence as set forth in SEQ ID NO.166; the LC may comprise an amino acid sequence as set forth in SEQ ID NO. 142.

For another example, the antigen binding protein may comprise a HC and a LC that are the same as those of the antibody PR000825. The HC may comprise a VH and a heavy chain constant. The VH may comprise HCDR1-3 and H-FR1-4, the HCDR1 may comprise an amino acid sequence as set forth in SEQ ID NO. 6, the HCDR2 may comprise an amino acid sequence as set forth in SEQ ID NO. 17, and the HCDR3 may comprise an amino acid sequence as set forth in SEQ ID NO. 34; the H-FR1 may comprises an amino acid sequence as set forth in SEQ ID NO.3, the H-FR2 may comprises an amino acid sequence as set forth in SEQ ID NO.11, the H-FR3 may comprises an amino acid sequence as set forth in SEQ ID NO.31, and the H-FR4 may comprises an amino acid sequence as set forth in SEQ ID NO.42; the VH may comprise an amino sequence as set forth in SEQ ID NO.103; the heavy chain constant region may comprise an amino acid sequence as set forth in SEQ ID NO. 167; the HC may comprise an amino acid sequence as set forth in SEQ ID NO. 131. And the VL may comprise LCDR1-3 and L-FR1-4, the LCDR1 may comprise an amino acid sequence as set forth in SEQ ID NO. 54, the LCDR2 may comprise an amino acid sequence as set forth in SEQ ID NO. 65, and the LCDR3 may comprise an amino acid sequence as set forth in SEQ ID NO. 81; the L-FR1 may comprises an amino acid sequence as set forth in SEQ ID NO.47, the L-FR2 may comprises an amino acid sequence as set forth in SEQ ID NO.60, the L-FR3 may comprises an amino acid sequence as set forth in SEQ ID NO.71, and the L-FR4 may comprises an amino acid sequence as set forth in SEQ ID NO.89; the VL may comprise an amino acid sequence as set forth in SEQ ID NO.114; the light chain constant region may comprise an amino acid sequence as set forth in SEQ ID NO.166; the LC may comprise an amino acid sequence as set forth in SEQ ID NO. 142.

For another example, the antigen binding protein may comprise a HC and a LC that are the same as those of the antibody PR000832. The HC may comprise a VH and a heavy chain constant. The VH may comprise HCDR1-3 and H-FR1-4, the HCDR1 may comprise an amino acid sequence as set forth in SEQ ID NO. 6, the HCDR2 may comprise an amino acid sequence as set forth in SEQ ID NO. 22, and the HCDR3 may comprise an amino acid sequence as set forth in SEQ ID NO. 34; the H-FR1 may comprises an amino acid sequence as set forth in SEQ ID NO.3, the H-FR2 may comprises an amino acid sequence as set forth in SEQ ID NO.11, the H-FR3 may comprises an amino acid sequence as set forth in SEQ ID NO.31, and the H-FR4 may comprises an amino acid sequence as set forth in SEQ ID NO.42; the VH may comprise an amino sequence as set forth in SEQ ID NO.102; the heavy chain constant region may comprise an amino acid sequence as set forth in SEQ ID NO. 167; the HC may comprise an amino acid sequence as set forth in SEQ ID NO. 130. And the VL may comprise LCDR1-3 and L-FR1-4, the LCDR1 may comprise an amino acid sequence as set forth in SEQ ID NO. 54, the LCDR2 may comprise an amino acid sequence as set forth in SEQ ID NO. 65, and the LCDR3 may comprise an amino acid sequence as set forth in SEQ ID NO. 84; the L-FR1 may comprises an amino acid sequence as set forth in SEQ ID NO.47, the L-FR2 may comprises an amino acid sequence as set forth in SEQ ID NO.60, the L-FR3 may comprises an amino acid sequence as set forth in SEQ ID NO.71, and the L-FR4 may comprises an amino acid sequence as set forth in SEQ ID NO.89; the VL may comprise an amino acid sequence as set forth in SEQ ID NO.118; the light chain constant region may comprise an amino acid sequence as set forth in SEQ ID NO.166; the LC may comprise an amino acid sequence as set forth in SEQ ID NO. 146.

For another example, the antigen binding protein may comprise a HC and a LC that are the same as those of the antibody PR003833. The HC may comprise a VH and a heavy chain constant. The VH may comprise HCDR1-3 and H-FR1-4, the HCDR1 may comprise an amino acid sequence as set forth in SEQ ID NO. 6, the HCDR2 may comprise an amino acid sequence as set forth in SEQ ID NO. 22, and the HCDR3 may comprise an amino acid sequence as set forth in SEQ ID NO. 34; the H-FR1 may comprises an amino acid sequence as set forth in SEQ ID NO.3, the H-FR2 may comprises an amino acid sequence as set forth in SEQ ID NO.11, the H-FR3 may comprises an amino acid sequence as set forth in SEQ ID NO.31, and the H-FR4 may comprises an amino acid sequence as set forth in SEQ ID NO.42; the VH may comprise an amino sequence as set forth in SEQ ID NO.102; the heavy chain constant region may comprise an amino acid sequence as set forth in SEQ ID NO. 167; the HC may comprise an amino acid sequence as set forth in SEQ ID NO. 130. And the VL may comprise LCDR1-3 and L-FR1-4, the LCDR1 may comprise an amino acid sequence as set forth in SEQ ID NO. 54, the LCDR2 may comprise an amino acid sequence as set forth in SEQ ID NO. 65, and the LCDR3 may comprise an amino acid sequence as set forth in SEQ ID NO. 85; the L-FR1 may comprises an amino acid sequence as set forth in SEQ ID NO.47, the L-FR2 may comprises an amino acid sequence as set forth in SEQ ID NO.60, the L-FR3 may comprises an amino acid sequence as set forth in SEQ ID NO.71, and the L-FR4 may comprises an amino acid sequence as set forth in SEQ ID NO.89; the VL may comprise an amino acid sequence as set forth in SEQ ID NO.119; the light chain constant region may comprise an amino acid sequence as set forth in SEQ ID NO.166; the LC may comprise an amino acid sequence as set forth in SEQ ID NO. 147.

For another example, the antigen binding protein may comprise a HC and a LC that are the same as those of the antibody PR003834. The HC may comprise a VH and a heavy chain constant. The VH may comprise HCDR1-3 and H-FR1-4, the HCDR1 may comprise an amino acid sequence as set forth in SEQ ID NO. 6, the HCDR2 may comprise an amino acid sequence as set forth in SEQ ID NO. 22, and the HCDR3 may comprise an amino acid sequence as set forth in SEQ ID NO. 34; the H-FR1 may comprises an amino acid sequence as set forth in SEQ ID NO.3, the H-FR2 may comprises an amino acid sequence as set forth in SEQ ID NO.11, the H-FR3 may comprises an amino acid sequence as set forth in SEQ ID NO.31, and the H-FR4 may comprises an amino acid sequence as set forth in SEQ ID NO.42; the VH may comprise an amino sequence as set forth in SEQ ID NO.102; the heavy chain constant region may comprise an amino acid sequence as set forth in SEQ ID NO. 167; the HC may comprise an amino acid sequence as set forth in SEQ ID NO. 130. And the VL may comprise LCDR1-3 and L-FR1-4, the LCDR1 may comprise an amino acid sequence as set forth in SEQ ID NO. 54, the LCDR2 may comprise an amino acid sequence as set forth in SEQ ID NO. 65, and the LCDR3 may comprise an amino acid sequence as set forth in SEQ ID NO. 86; the L-FR1 may comprises an amino acid sequence as set forth in SEQ ID NO.47, the L-FR2 may comprises an amino acid sequence as set forth in SEQ ID NO.60, the L-FR3 may comprises an amino acid sequence as set forth in SEQ ID NO.71, and the L-FR4 may comprises an amino acid sequence as set forth in SEQ ID NO.89; the VL may comprise an amino acid sequence as set forth in SEQ ID NO.120; the light chain constant region may comprise an amino acid sequence as set forth in SEQ ID NO.166; the LC may comprise an amino acid sequence as set forth in SEQ ID NO. 148.

For another example, the antigen binding protein may comprise a HC and a LC that are the same as those of the antibody PR003835. The HC may comprise a VH and a heavy chain constant. The VH may comprise HCDR1-3 and H-FR1-4, the HCDR1 may comprise an amino acid sequence as set forth in SEQ ID NO. 6, the HCDR2 may comprise an amino acid sequence as set forth in SEQ ID NO. 22, and the HCDR3 may comprise an amino acid sequence as set forth in SEQ ID NO. 34; the H-FR1 may comprises an amino acid sequence as set forth in SEQ ID NO.3, the H-FR2 may comprises an amino acid sequence as set forth in SEQ ID NO.11, the H-FR3 may comprises an amino acid sequence as set forth in SEQ ID NO.31, and the H-FR4 may comprises an amino acid sequence as set forth in SEQ ID NO.42; the VH may comprise an amino sequence as set forth in SEQ ID NO.102; the heavy chain constant region may comprise an amino acid sequence as set forth in SEQ ID NO. 167; the HC may comprise an amino acid sequence as set forth in SEQ ID NO. 130. And the VL may comprise LCDR1-3 and L-FR1-4, the LCDR1 may comprise an amino acid sequence as set forth in SEQ ID NO. 54, the LCDR2 may comprise an amino acid sequence as set forth in SEQ ID NO. 65, and the LCDR3 may comprise an amino acid sequence as set forth in SEQ ID NO. 87; the L-FR1 may comprises an amino acid sequence as set forth in SEQ ID NO.47, the L-FR2 may comprises an amino acid sequence as set forth in SEQ ID NO.60, the L-FR3 may comprises an amino acid sequence as set forth in SEQ ID NO.71, and the L-FR4 may comprises an amino acid sequence as set forth in SEQ ID NO.89; the VL may comprise an amino acid sequence as set forth in SEQ ID NO.121; the light chain constant region may comprise an amino acid sequence as set forth in SEQ ID NO.166; the LC may comprise an amino acid sequence as set forth in SEQ ID NO. 149.

For another example, the antigen binding protein may comprise a HC and a LC that are the same as those of the antibody PR003836. The HC may comprise a VH and a heavy chain constant. The VH may comprise HCDR1-3 and H-FR1-4, the HCDR1 may comprise an amino acid sequence as set forth in SEQ ID NO. 6, the HCDR2 may comprise an amino acid sequence as set forth in SEQ ID NO. 22, and the HCDR3 may comprise an amino acid sequence as set forth in SEQ ID NO. 34; the H-FR1 may comprises an amino acid sequence as set forth in SEQ ID NO.3, the H-FR2 may comprises an amino acid sequence as set forth in SEQ ID NO.11, the H-FR3 may comprises an amino acid sequence as set forth in SEQ ID NO.31, and the H-FR4 may comprises an amino acid sequence as set forth in SEQ ID NO.42; the VH may comprise an amino sequence as set forth in SEQ ID NO.102; the heavy chain constant region may comprise an amino acid sequence as set forth in SEQ ID NO. 167; the HC may comprise an amino acid sequence as set forth in SEQ ID NO. 130. And the VL may comprise LCDR1-3 and L-FR1-4, the LCDR1 may comprise an amino acid sequence as set forth in SEQ ID NO. 54, the LCDR2 may comprise an amino acid sequence as set forth in SEQ ID NO. 65, and the LCDR3 may comprise an amino acid sequence as set forth in SEQ ID NO. 88; the L-FR1 may comprises an amino acid sequence as set forth in SEQ ID NO.47, the L-FR2 may comprises an amino acid sequence as set forth in SEQ ID NO.60, the L-FR3 may comprises an amino acid sequence as set forth in SEQ ID NO.71, and the L-FR4 may comprises an amino acid sequence as set forth in SEQ ID NO.89; the VL may comprise an amino acid sequence as set forth in SEQ ID NO.122; the light chain constant region may comprise an amino acid sequence as set forth in SEQ ID NO.166; the LC may comprise an amino acid sequence as set forth in SEQ ID NO. 150.

In the present disclosure, the antigen binding protein may comprise at least one HCDR from the VH of SEQ ID NO: 108.

In the present disclosure, the antigen binding protein may comprise a HCDR3 from the heavy chain variable region VH of SEQ ID NO: 108, and the HCDR3 may comprises an amino acid sequence as set forth in SEQ ID NO.40: ERSSSFYYYYGMDV (SEQ ID NO.40). For example, the sequence may be determined according to the Chothia definition.

In the present disclosure, the antigen binding protein may comprise a HCDR2 from the heavy chain variable region VH of SEQ ID NO: 108, and the HCDR2 may comprises an amino acid sequence as set forth in SEQ ID NO.25: WYDGSN (SEQ ID NO.25).

In the present disclosure, the antigen binding protein may comprise a HCDR1 from the heavy chain variable region VH of SEQ ID NO: 108, and the HCDR1 may comprises an amino acid sequence as set forth in SEQ ID NO.10: GFTFYSY (SEQ ID NO.10). For example, the sequence may be determined according to the Chothia definition.

In the present disclosure, the antigen binding protein may comprise a H-FR1, C-terminus of the H-FR1 is directly or indirectly linked to N-terminus of said HCDR1, and the H-FR1 may comprises an amino acid sequence as set forth in SEQ ID NO.3: QVQLVESGGGVVQPGRSLRLSCAAS (SEQ ID NO.3). For example, the sequence may be determined according to the Chothia definition.

In the present disclosure, the antigen binding protein may comprise a H-FR2, the H-FR2 is located between said HCDR1 and said HCDR2, and the H-FR2 may comprises an amino acid sequence as set forth in SEQ ID NO.15:

GMHWVRQTPGKGLEWVALI (SEQ ID NO.15). For example, the sequence may be determined according to the Chothia definition.

In the present disclosure, the antigen binding protein may comprise a H-FR3, the H-FR3 is located between said HCDR2 and said HCDR3, and the H-FR3 may comprises an amino acid sequence as set forth in SEQ ID NO.32: NYYADSVKGRFTISRDNSKNTLYLQMNSLRAEDTAVYYCAT (SEQ ID NO.32). For example, the sequence may be determined according to the Chothia definition.

In the present disclosure, the antigen binding protein may comprise a H-FR4, N-terminus of said H-FR4 is linked directly or indirectly to C-terminus of said HCDR3, and the H-FR4 may comprises an amino acid sequence as set forth in SEQ ID NO.45: WGQGTTVTVSS (SEQ ID NO.45). For example, the sequence may be determined according to the Chothia definition.

In the present disclosure, the antigen binding protein may comprise a VH, and the VH may comprises an amino acid sequence as set forth in SEQ ID NO.108: QVQLVESGGGVVQPGRSLRLSCAASGFTFYSYGMHWVRQTPGKGLEWVALIWYDGSNNYYADSVKGRFTISRDNSKNTLYLQMNSLRAEDTAVYYCATERSSSFYYYYGMDVWGQGTT VTVSS (SEQ ID NO.108). For example, the sequence may be determined according to the Chothia definition.

In the present disclosure, the antigen binding protein may comprise an antibody heavy chain constant region, and the antibody heavy chain constant region comprises a human IgG constant region. In some cases, the human IgG constant region may be derived from a human IgG1 constant region. For example, the antibody heavy chain constant region may comprise amino acid sequence as set forth in SEQ ID NO.167:

```
                                    (SEQ ID NO. 167)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPEAAGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSREEMTKNQVSLTC

LVKGFYPSDIAVEWESNGQPENNYKTTPPVLDSDGSFFLYSKLTVDKSRW

QQGNVFSCSVMHEALHNHYTQKSLSLSPGK.
```

In the present disclosure, the antigen binding protein may comprise an antibody heavy chain (HC), and the HC comprises an amino acid sequence as set in forth in SEQ ID NO. 136.

In the present disclosure, the antigen binding protein may comprise at least one LCDR from the VL of SEQ ID NO: 116.

In the present disclosure, the antigen binding protein may comprise a LCDR3 from the heavy chain variable region VH of SEQ ID NO: 108, and the LCDR3 may comprises an amino acid sequence as set forth in SEQ ID NO.82: QQLNSYPYT (SEQ ID NO.82). For example, the sequence may be determined according to the Chothia definition.

In the present disclosure, the antigen binding protein may comprise a LCDR2 from the heavy chain variable region VH of SEQ ID NO: 108, and the LCDR2 may comprises an amino acid sequence as set forth in SEQ ID NO. 69:

AASTLQS (SEQ ID NO. 69) For example, the sequence may be determined according to the Chothia definition.

In the present disclosure, the antigen binding protein may comprise a LCDR1 from the heavy chain variable region VH of SEQ ID NO: 108, and the LCDR1 may comprises an amino acid sequence as set forth in SEQ ID NO.58: RASQ-GISSYLA (SEQ ID NO.58). For example, the sequence may be determined according to the Chothia definition.

In the present disclosure, the antigen binding protein may comprise a L-FR1, C-terminus of the L-FR1 is directly or indirectly linked to N-terminus of said LCDR1, and the L-FR1 may comprises an amino acid sequence as set forth in SEQ ID NO.52: DIQLTQSPSFLSTSVGDRVTITC (SEQ ID NO.52). For example, the sequence may be determined according to the Chothia definition.

In the present disclosure, the antigen binding protein may comprise a L-FR2, the L-FR2 is located between said LCDR1 and said LCDR2, and the L-FR2 may comprises an amino acid sequence as set forth in SEQ ID NO.60: WYQQKPGKAPKLLIY (SEQ ID NO.60). For example, the sequence may be determined according to the Chothia definition.

In the present disclosure, the antigen binding protein may comprise a L-FR3, the L-FR3 is located between said LCDR2 and said LCDR3, and the L-FR3 may comprises an amino acid sequence as set forth in SEQ ID NO.75: GVPSRFSGSGSGTEFTLTISSLQPEDFATYYC (SEQ ID NO.75). For example, the sequence may be determined according to the Chothia definition.

In the present disclosure, the antigen binding protein may comprise a L-FR4, N-terminus of said L-FR4 is linked directly or indirectly to C-terminus of said LCDR3, and the L-FR4 may comprises an amino acid sequence as set forth in SEQ ID NO.93: FGQGTELEIK (SEQ ID NO.93). For example, the sequence may be determined according to the Chothia definition.

In the present disclosure, the antigen binding protein may comprise a VL, and the VL may comprise an amino acid sequence as set forth in SEQ ID NO.116: DIQLTQSPSFLSTSVGDRVTITCRASQGISSY-LAWYQQKPGKAPKLLIYAASTLQSGVPSRFS GSGSGTEFTLTISSLQPEDFATYYCQQLNSYPYTFGQ-GLELEIK (SEQ ID NO.116). For example, the sequence may be determined according to the Chothia definition.

In the present disclosure, the antigen binding protein may comprise an antibody light chain constant region, and the antibody light chain constant region comprises a human Igic constant region. For example, the antibody light chain constant region may comprise amino acid sequence as set forth in SEQ ID NO.166:

```
                                    (SEQ ID NO: 166)
RTVAAPSVFIFPPSDEQLKSGTASVVCLLNNFYPREAKVQWKVDNALQSG

NSQESVTEQDSKDSTYSLSSTLTLSKADYEKHKVYACEVTHQGLSSPVTK

SFNRGEC.
```

In the present disclosure, the antigen binding protein may comprise an antibody light chain (LC), and the LC comprises an amino acid sequence as set in forth in SEQ ID NO. 144.

In the present disclosure, the antigen binding protein may comprise HCDR1-3. The HCDR1 may comprise an amino acid sequence as set forth in SEQ ID NO. 10, the HCDR2 may comprise an amino acid sequence as set forth in SEQ ID NO. 25, and the HCDR3 may comprise an amino acid sequence as set forth in SEQ ID NO. 40.

In the present disclosure, the antigen binding protein may comprise LCDR1-3. The LCDR1 may comprise an amino acid sequence as set forth in SEQ ID NO. 58, the LCDR2 may comprise an amino acid sequence as set forth in SEQ ID NO. 69, and the LCDR3 may comprise an amino acid sequence as set forth in SEQ ID NO. 82.

In the present disclosure, the antigen binding protein may comprise a H-FR1-4. The H-FR1 may comprises an amino acid sequence as set forth in SEQ ID NO.3, the H-FR2 may comprises an amino acid sequence as set forth in SEQ ID NO.15, the H-FR3 may comprises an amino acid sequence as set forth in SEQ ID NO.32, and the H-FR4 may comprises an amino acid sequence as set forth in SEQ ID NO.45.

In the present disclosure, the antigen binding protein may comprise a L-FR1-4. The L-FR1 may comprises an amino acid sequence as set forth in SEQ ID NO.52, the L-FR2 may comprises an amino acid sequence as set forth in SEQ ID NO.60, the L-FR3 may comprises an amino acid sequence as set forth in SEQ ID NO.75, and the L-FR4 may comprises an amino acid sequence as set forth in SEQ ID NO.93.

In the present disclosure, the antigen binding protein may comprise HCDR1-3 and LCDR1-3 and. The HCDR1 may comprise an amino acid sequence as set forth in SEQ ID NO. 10, the HCDR2 may comprise an amino acid sequence as set forth in SEQ ID NO. 25, and the HCDR3 may comprise an amino acid sequence as set forth in SEQ ID NO. 40; the LCDR1 may comprise an amino acid sequence as set forth in SEQ ID NO. 58, the LCDR2 may comprise an amino acid sequence as set forth in SEQ ID NO. 69, the LCDR3 may comprise an amino acid sequence as set forth in SEQ ID NO. 82.

In the present disclosure, the antigen binding protein may comprise a H-FR1-4 and L-FR1-4. The H-FR1 may comprises an amino acid sequence as set forth in SEQ ID NO.3, the H-FR2 may comprises an amino acid sequence as set forth in SEQ ID NO.15, the H-FR3 may comprises an amino acid sequence as set forth in SEQ ID NO.32, and the H-FR4 may comprises an amino acid sequence as set forth in SEQ ID NO.45; the L-FR1 may comprises an amino acid sequence as set forth in SEQ ID NO.52, the L-FR2 may comprises an amino acid sequence as set forth in SEQ ID NO.60, the L-FR3 may comprises an amino acid sequence as set forth in SEQ ID NO.75, and the L-FR4 may comprises an amino acid sequence as set forth in SEQ ID NO.93.

In the present disclosure, the antigen binding protein may comprise a VH and a VL. The VH may comprise an amino acid sequence as set forth in SEQ ID NO: 108, and the VL may comprise an amino acid sequence as set forth in SEQ ID NO:116.

In the present disclosure, the antigen binding protein may comprise a heavy chain constant region and a light chain constant region. The heavy chain constant region may comprise an amino acid sequence as set forth in SEQ ID NO: 167, and the light chain constant region may comprise an amino acid sequence as set forth in SEQ ID NO:166.

In the present disclosure, the antigen binding protein may comprise a heavy chain (HC) and a light chain (LC). The HC may comprise an amino acid sequence as set forth in SEQ ID NO: 136, and the LC may comprise an amino acid sequence as set forth in SEQ ID NO.144.

In the present disclosure, the antigen binding protein may comprise a HC and a LC. The HC may comprise a VH and a heavy chain constant. The VH may comprise HCDR1-3 and H-FR1-4, the HCDR1 may comprise an amino acid sequence as set forth in SEQ ID NO.10, the HCDR2 may comprise an amino acid sequence as set forth in SEQ ID NO. 25, and the HCDR3 may comprise an amino acid sequence as set forth in SEQ ID NO. 40; the H-FR1 may comprises an amino acid sequence as set forth in SEQ ID NO.3, the H-FR2 may comprises an amino acid sequence as set forth in SEQ ID NO.15, the H-FR3 may comprises an amino acid sequence as set forth in SEQ ID NO.32, and the H-FR4 may comprises an amino acid sequence as set forth in SEQ ID NO.45; the VH may comprise an amino sequence as set forth in SEQ ID NO.108; the heavy chain constant region may comprise an amino acid sequence as set forth in SEQ ID NO. 167; the HC may comprise an amino acid sequence as set forth in SEQ ID NO. 136. And the VL may comprise LCDR1-3 and L-FR1-4, the LCDR1 may comprise an amino acid sequence as set forth in SEQ ID NO. 58, the LCDR2 may comprise an amino acid sequence as set forth in SEQ ID NO. 69, and the LCDR3 may comprise an amino acid sequence as set forth in SEQ ID NO. 82; the L-FR1 may comprises an amino acid sequence as set forth in SEQ ID NO.52, the L-FR2 may comprises an amino acid sequence as set forth in SEQ ID NO.60, the L-FR3 may comprises an amino acid sequence as set forth in SEQ ID NO.75 and the L-FR4 may comprises an amino acid sequence as set forth in SEQ ID NO.93; the VL may comprise an amino acid sequence as set forth in SEQ ID NO.116; the light chain constant region may comprise an amino acid sequence as set forth in SEQ ID NO.166; the LC may comprise an amino acid sequence as set forth in SEQ ID NO. 144.

For example, the antigen binding protein may comprise a HC and a LC that are the same as those of the antibody PR001408. The HC may comprise a VH and a heavy chain constant. The VH may comprise HCDR1-3 and H-FR1-4, the HCDR1 may comprise an amino acid sequence as set forth in SEQ ID NO. 10, the HCDR2 may comprise an amino acid sequence as set forth in SEQ ID NO. 25, and the HCDR3 may comprise an amino acid sequence as set forth in SEQ ID NO. 40; the H-FR1 may comprises an amino acid sequence as set forth in SEQ ID NO.3, the H-FR2 may comprises an amino acid sequence as set forth in SEQ ID NO.15, the H-FR3 may comprises an amino acid sequence as set forth in SEQ ID NO.32, and the H-FR4 may comprises an amino acid sequence as set forth in SEQ ID NO.45; the VH may comprise an amino sequence as set forth in SEQ ID NO.108; the heavy chain constant region may comprise an amino acid sequence as set forth in SEQ ID NO. 167; the HC may comprise an amino acid sequence as set forth in SEQ ID NO. 136. And the VL may comprise LCDR1-3 and L-FR1-4, the LCDR1 may comprise an amino acid sequence as set forth in SEQ ID NO. 58, the LCDR2 may comprise an amino acid sequence as set forth in SEQ ID NO. 69, and the LCDR3 may comprise an amino acid sequence as set forth in SEQ ID NO. 82; the L-FR1 may comprises an amino acid sequence as set forth in SEQ ID NO.52, the L-FR2 may comprises an amino acid sequence as set forth in SEQ ID NO.60, the L-FR3 may comprises an amino acid sequence as set forth in SEQ ID NO.75, and the L-FR4 may comprises an amino acid sequence as set forth in SEQ ID NO.93; the VL may comprise an amino acid sequence as set forth in SEQ ID NO.116; the light chain constant region may comprise an amino acid sequence as set forth in SEQ ID NO.166; the LC may comprise an amino acid sequence as set forth in SEQ ID NO. 144.

Certain Anti-CD73 Antibody

In the present disclosure, the antigen binding protein may compete with a certain anti-CD73 antibody for binding to CD73. In some embodiments, the antigen binding protein of the present disclosure may comprise a antibody comprising the same amino acid sequence as the certain anti-CD73 antibody.

In some cases, the certain anti-CD73 antibody may comprise at least one HCDR region from the heavy chain variable region VH of SEQ ID NO: 152 and at least one LCDR region from the light chain variable region VL of SEQ ID NO: 151.

In the present disclosure, the certain anti-CD73 antibody may comprise HCDR1-3. The HCDR1 may comprise an amino acid sequence as set forth in SEQ ID NO. 7, the HCDR2 may comprise an amino acid sequence as set forth in SEQ ID NO. 153, and the HCDR3 may comprise an amino acid sequence as set forth in SEQ ID NO. 154. In some cases, the certain anti-CD73 antibody may comprise LCDR1-3. The LCDR1 may comprise an amino acid sequence as set forth in SEQ ID NO. 55, the LCDR2 may comprise an amino acid sequence as set forth in SEQ ID NO. 66, and the LCDR3 may comprise an amino acid sequence as set forth in SEQ ID NO. 78.

In the present disclosure, the certain anti-CD73 antibody may comprise a VH and a VL. The VH may comprise an amino acid sequence as set forth in SEQ ID NO: 152, and the VL may comprise an amino acid sequence as set forth in SEQ ID NO:151.

In the present disclosure, the certain anti-CD73 antibody may comprise a heavy chain constant region and a light chain constant region. The heavy chain constant region may comprise an amino acid sequence as set forth in SEQ ID NO: 167, and the light chain constant region may comprise an amino acid sequence as set forth in SEQ ID NO:166.

In the present disclosure, the certain anti-CD73 antibody may comprise a heavy chain (HC) and a light chain (LC). The HC may comprise an amino acid sequence as set forth in SEQ ID NO: 162, and the LC constant region may comprise an amino acid sequence as set forth in SEQ ID NO:159.

In some cases, the certain anti-CD73 antibody may comprise at least one HCDR region from the heavy chain variable region VH of SEQ ID NO: 156 and at least one LCDR region from the light chain variable region VL of SEQ ID NO: 155.

In the present disclosure, the certain anti-CD73 antibody may comprise HCDR1-3. The HCDR1 may comprise an amino acid sequence as set forth in SEQ ID NO.6, the HCDR2 may comprise an amino acid sequence as set forth in SEQ ID NO. 158, and the HCDR3 may comprise an amino acid sequence as set forth in SEQ ID NO. 34. In some cases, the certain anti-CD73 antibody may comprise LCDR1-3. The LCDR1 may comprise an amino acid sequence as set forth in SEQ ID NO. 54, the LCDR2 may comprise an amino acid sequence as set forth in SEQ ID NO. 65, and the LCDR3 may comprise an amino acid sequence as set forth in SEQ ID NO. 157.

In the present disclosure, the certain anti-CD73 antibody may comprise a VH and a VL. The VH may comprise an amino acid sequence as set forth in SEQ ID NO: 156, and the VL may comprise an amino acid sequence as set forth in SEQ ID NO:155.

In the present disclosure, the certain anti-CD73 antibody may comprise a heavy chain constant region and a light chain constant region. The heavy chain constant region may comprise an amino acid sequence as set forth in SEQ ID NO: 167, and the light chain constant region may comprise an amino acid sequence as set forth in SEQ ID NO:166.

In the present disclosure, the certain anti-CD73 antibody may comprise a heavy chain (HC) and a light chain (LC).

The HC may comprise an amino acid sequence as set forth in SEQ ID NO: 161, and the LC constant region may comprise an amino acid sequence as set forth in SEQ ID NO:160.

In some cases, the certain anti-CD73 antibody may comprise at least one HCDR region from the heavy chain variable region VH of SEQ ID NO: 108 and at least one LCDR region from the light chain variable region VL of SEQ ID NO: 116.

In the present disclosure, the certain anti-CD73 antibody may comprise HCDR1-3. The HCDR1 may comprise an amino acid sequence as set forth in SEQ ID NO. 10, the HCDR2 may comprise an amino acid sequence as set forth in SEQ ID NO. 25, and the HCDR3 may comprise an amino acid sequence as set forth in SEQ ID NO. 40. In some cases, the certain anti-CD73 antibody may comprise LCDR1-3. The LCDR1 may comprise an amino acid sequence as set forth in SEQ ID NO. 58, the LCDR2 may comprise an amino acid sequence as set forth in SEQ ID NO. 69, and the LCDR3 may comprise an amino acid sequence as set forth in SEQ ID NO. 82.

In the present disclosure, the certain anti-CD73 antibody may comprise a VH and a VL. The VH may comprise an amino acid sequence as set forth in SEQ ID NO: 108, and the VL may comprise an amino acid sequence as set forth in SEQ ID NO:116.

In the present disclosure, the certain anti-CD73 antibody may comprise a heavy chain constant region and a light chain constant region. The heavy chain constant region may comprise an amino acid sequence as set forth in SEQ ID NO: 167, and the light chain constant region may comprise an amino acid sequence as set forth in SEQ ID NO:166.

In the present disclosure, the certain anti-CD73 antibody may comprise a heavy chain (HC) and a light chain (LC). The HC may comprise an amino acid sequence as set forth in SEQ ID NO: 136, and the LC constant region may comprise an amino acid sequence as set forth in SEQ ID NO:144.

The antigen binding protein of the present disclosure may also encompass a homology or a variant thereof having substantially the same function/property thereto. In some cases, the homology or variant may be a polypeptide different from the antigen binding protein at least one amino acid. For example, the homology or variant may be a polypeptide different from the antigen binding protein by an addition, deletion or substitution of one or more amino acid, such as 1-50, 1-40, 1-30, 1-20, 1-15, 1-14, 1-13, 1-12, 1-11, 1-10, 1-9, 1-8, 1-7, 1-6, 1-5, 1-4, 1-3, or 1-2 amino acids.

In some cases, the antigen binding protein may be further optimized by germlining and PTM removal procedure. The term "germlining" refers to a procedure of reversing hypersomatic mutations of antibodies to corresponding germline sequences. The term "PTM removal" refers to a procedure of mutating PTM motifs to reduce the risk of sequence liability.

Post Translational Modification (PTM) is widely observed in proteins expressed in mammalian cells, which may make the molecules unstable and heterogenous. To reduce the sequence liability, the PTM motifs could be removed by mutations. PTM removal site may be isomerization motifs, e.g., DG in CDR. In some cases, the PTM removal site may comprise one or more sites selected from D54, G55, D99 and/or G100 in HCDR. In some cases, the PTM removal in D54 may be D54E. In some cases, the PTM removal in G55 may be G55A. In some cases, the PTM removal in D99 may be D99E. In some cases, the PTM removal in G100 may be G100A.

The antibody after PTM removal may have similar or higher chemical stability or bioactivity. In some cases, the antibody after PTM removal may have similar or higher binding affinity, enzymic activity, T cell activated activity tumor inhibition activity, and/or serum stability. For example, the PTM removal antibody (e.g., PR000844, PR000846) has comparative binding affinity with PTM antibody (e.g., PR000506).

In some cases, the homology or variant may be a polypeptide having a sequence identity of at least 80% with the antigen binding protein. For example, the homology or variant may be a polypeptide having a sequence identity of 80% (e.g., at least 85%, at least 90%, at least 91%, at least 92%, at least 93%, at least 94%, at least 95%, at least 96%, at least 97%, at least 98%, at least 99% or higher) to the antibody or antigen binding fragment thereof.

The term "percent (%) sequence identity," as used in the context of polypeptide sequences identified herein, generally refers to the percentage of amino acid residues or nucleotides in a query sequence that are identical with the amino acid residues or nucleotides of a second, reference polypeptide sequence or a portion thereof, after aligning the sequences and introducing gaps, if necessary, to achieve the maximum percent sequence identity, and not considering any conservative substitutions as part of the sequence identity. Alignment for purposes of determining percent amino acid/nucleotide sequence identity can be achieved in various ways that are within the skill in the art, for instance, using publicly available computer software such as BLAST, BLAST-2, ALIGN, NEEDLE or Megalign (DNASTAR) software. Those skilled in the art can determine appropriate parameters for measuring alignment, including any algorithms needed to achieve maximal alignment over the full length of the sequences being compared. Percent identity may be measured over the length of an entire defined polypeptide/polynucleotide sequence, or may be measured over a shorter length, for example, over the length of a fragment taken from a larger, defined polypeptide/polynucleotide sequence. It is understood that any fragment length supported by the sequences shown herein, in the tables, figures or Sequence Listing, may be used to describe a length over which percentage identity may be measured.

Nucleic Acid, Vector and Cell

In other aspect, the present disclosure provides isolated nucleic acid molecular or molecules, encoding for the isolated antigen binding protein.

The isolated nucleic acids may comprise one or more nucleic acid molecules, with each encoding the antigen binding protein. For example, the isolated nucleic acids may comprise at least two nucleic acid molecules, with one encoding the antibody heavy chain or a fragment thereof, and one encoding the antibody light chain or a fragment thereof.

The isolated nucleic acid or isolated nucleic acids may be synthesized using recombinant techniques well known in the art. For example, the isolated nucleic acid or isolated nucleic acids may be synthesized with an automated DNA synthesizer. Standard recombinant DNA and molecular cloning techniques include those described by Sambrook, J., Fritsch, E. F. and Maniatis, T. Molecular Cloning: A Laboratory Manual; Cold Spring Harbor Laboratory Press: Cold Spring Harbor, (1989) (Maniatis) and by T. J. Silhavy, M. L. Bennan, and L. W. Enquist, Experiments with Gene Fusions, Cold Spring Harbor Laboratory, Cold Spring Harbor, N.Y. (1984) and by Ausubel, F. M. et al., Current Protocols in Molecular Biology, pub. by Greene Publishing Assoc. and Wiley-Interscience (1987). Briefly, the subject nucleic acids may be prepared from genomic DNA fragments, cDNAs, and RNAs, all of which may be extracted directly from a cell or recombinantly produced by various amplification processes including but not limited to PCR and RT-PCR.

Direct chemical synthesis of nucleic acids typically involves sequential addition of 3'-blocked and 5'-blocked nucleotide monomers to the terminal 5'-hydroxyl group of a growing nucleotide polymer chain, wherein each addition is effected by nucleophilic attack of the terminal 5'-hydroxyl group of the growing chain on the 3'-position of the added monomer, which is typically a phosphorus derivative, such as a phosphotriester, phosphoramidite, or the like. See for example, Matteuci et al., *Tet. Lett.* 521:719 (1980); U.S. Pat. No. 4,500,707 to Caruthers et al.; and U.S. Pat. Nos. 5,436,327 and 5,700,637 to Southern et al.

In other aspect, the present disclosure provides vector or vectors, comprising the isolated nucleic acid molecule or molecules.

The vector may be any linear nucleic acids, plasmids, phagemids, cosmids, RNA vectors, viral vectors and the like. Non-limiting examples of a viral vector may include a retrovirus, an adenovirus and an adeno-associated virus. In some embodiments, the vector is an expression vector, e.g., a plasmid.

An expression vector may be suitable for use in particular types of host cells and not suitable for use in others. For example, the expression vector can be introduced into the host organism, which is then monitored for viability and expression of any genes/polynucleotides contained in the vector.

The expression vector may also contain one or more selectable marker genes that, upon expression, confer one or more phenotypic traits useful for selecting or otherwise identifying host cells that carry the expression vector. Non-limiting examples of suitable selectable markers for eukaryotic cells include dihydrofolate reductase and neomycin resistance.

The subject vectors can be introduced into a host cell stably or transiently by a variety of established techniques. For example, one method involves a calcium chloride treatment wherein the expression vector is introduced via a calcium precipitate. Other salts, for example calcium phosphate, may also be used following a similar procedure. In addition, electroporation (that is, the application of current to increase the permeability of cells to nucleic acids) may be used. Other examples of transformation methods include microinjection, DEAE dextran mediated transformation, and heat shock in the presence of lithium acetate. Lipid complexes, liposomes, and dendrimers may also be employed to transfect the host cells.

In another aspect, the present disclosure provides a cell (e.g., an isolated cell, such as a host cell), comprising the isolated nucleic acid molecule or molecules of the present disclosure or the vector or vectors of the present disclosure. The cell may express the antigen binding protein of the present disclosure. The cell may be a eukaryotic cell or a prokaryotic cell. An appropriate cell may be transformed or transfected with the nucleic acid(s) or vector(s) of the present disclosure and utilized for the expression and/or secretion of the antigen binding protein. For example, the cell may be HEK293 cells, other bacterial host cells, yeast cells, or various higher eukaryotic cells.

In another aspect, the present disclosure provides a method for producing the antigen binding protein of the present disclosure, comprising culturing the cell of the present disclosure under conditions enabling expression of the antigen binding protein. The method optionally may further comprise harvesting the anrigen binding protein of the present disclosure.

Pharmaceutical Compositions, Use and Method

In another aspect, the present disclosure provides a pharmaceutical composition, comprising the isolated antigen binding protein, the nucleic acid molecule or molecules, the vector or vectors, and/or the cell of, and optionally a pharmaceutically acceptable carrier.

As used herein, "pharmaceutically acceptable carrier" includes any and all preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutical compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

The pharmaceutical composition disclosed herein can include other compounds, drugs, and/or agents used for the treatment of cancer. Such compounds, drugs, and/or agents can include, for example, chemotherapy drugs, small molecule drugs or antibodies that stimulate the immune response to a given cancer. In some instances, pharmaceutical compositions can include, for example, one or more of the agents listed in the section on combination therapies. For example, the combination therapy can include an anti-CD73 antibody described herein combined with at least one other anti-cancer and/or T-cell stimulating (e.g., activating) agent. Examples of therapeutic agents that can be used in combination therapy are described in greater detail below in the section on uses of the antibodies described herein.

The isolated antigen binding protein and/or the pharmaceutical composition can be used for preventing, alleviating and/or treating tumor. The tumor solid tumor and/or a blood tumor.

In another aspect, the present disclosure further provides a method for tumor comprises a preventing, alleviating and/or treating tumor, comprising administrating to a subject in need thereof an isolated antigen binding protein, such that the subject is treated, e.g., such that growth of tumors is inhibited or reduced and/or that the tumors regress. An isolated antigen binding protein can be used alone to inhibit the growth of cancerous tumors. Alternatively, an isolated antigen binding protein can be used in conjunction with another agent, e.g., other immunogenic agents, standard cancer treatments, or other antibodies, as known in the art. Accordingly, the present disclosure provides a method for preventing, alleviating and/or treating tumor, e.g., by inhibiting growth of tumor cells, in a subject, comprising administering to the subject a therapeutically effective amount of the antigen binding protein described herein, or antigen-binding portion thereof.

The present disclosure also discloses embodiments as follows:

1. An isolated antigen binding protein, having one or more of the following properties:

a. capable of binding to both human CD73 and Cyno-molgus monkey CD73, with comparable binding affinity;

b. capable of inhibiting 5'ectonucleotidase activity of CD73;

c. capable of mediating CD73 internalization;

d. capable of promoting T cell proliferation;

e. with a relatively stable concentration in serum for at least 15 days; and f. capable of inhibiting tumor growth and/or tumor cell proliferation.

2. The isolated antigen binding protein of embodiment 1, comprising at least one HCDR region from the heavy chain variable region VH of SEQ ID NO: 152.

3. The isolated antigen binding protein of any one of embodiments 1-2, comprising the HCDR3 from the heavy chain variable region VH of SEQ ID NO: 152.

4. The isolated antigen binding protein of any one of embodiments 1-3, comprising the HCDR2 from the heavy chain variable region VH of SEQ ID NO: 152.

5. The isolated antigen binding protein of any one of embodiments 1-4, comprising the HCDR1 from the heavy chain variable region VH of SEQ ID NO: 152.

6. The isolated antigen binding protein of any one of embodiments 1-5, wherein said VH comprises an amino acid sequence as set forth in any of SEQ ID NO: 96, 104, 105, 106 and 107.

7. The isolated antigen binding protein of any one of embodiments 1-6, comprising at least one LCDR region from the light chain variable region VL of SEQ ID NO: 151.

8. The isolated antigen binding protein of any one of embodiments 1-7, comprising the LCDR3 from the light chain variable region VL of SEQ ID NO: 151.

9. The isolated antigen binding protein of any one of embodiments 1-8, comprising the LCDR2 from the light chain variable region VL of SEQ ID NO: 151.

10. The isolated antigen binding protein of any one of embodiments 1-9, comprising the LCDR1 from the light chain variable region VL of SEQ ID NO: 151.

11. The isolated antigen binding protein of any one of embodiments 1-10, wherein said VL comprises an amino acid sequence as set forth in any of SEQ ID NO: 111 and 115.

12. The isolated antigen binding protein of any of embodiments 1-11, comprising an antibody or an antigen binding fragment thereof.

13. The isolated antigen binding protein of embodiment 12, wherein said antigen binding fragment comprises Fab, Fab', F(ab)2, Fv fragment, F(ab')₂, scFv, di-scFv and/or dAb.

14. The isolated antigen binding protein of any of embodiments 1-13, wherein said antibody is selected from a monoclonal antibody, a chimeric antibody, a humanized antibody, and a fully human antibody.

15. The isolated antigen binding protein of any of embodiments 3-14, wherein said HCDR3 comprises an amino acid sequence as set forth in any one of SEQ ID NO: 35, 38 and 39.

16. The isolated antigen binding protein of any of embodiments 4-15, wherein said HCDR2 comprises an amino acid sequence as set forth in any one of SEQ ID NO: 18, 23 and 24.

17. The isolated antigen binding protein of any of embodiments 1-16, comprising a light chain variable region VL, wherein said VL of the antigen binding protein comprises framework regions L-FR1, L-FR2, L-FR3, and L-FR4.

18. The isolated antigen binding protein of embodiment 17, wherein C-terminus of said L-FR1 is directly or indirectly linked to N-terminus of said LCDR1, and said L-FR1 comprises an amino acid sequence as set forth in SEQ ID NO: 163.

19. The isolated antigen binding protein of any of embodiments 17-18, wherein said L-FR1 comprises an amino acid sequence as set forth in any one of SEQ ID NO: 48 and 51.

20. The isolated antigen binding protein of any of embodiments 17-19, wherein said L-FR2 is located between said LCDR1 and said LCDR2, and said L-FR2 comprises an amino acid sequence as set forth in SEQ ID NO: 61.

21. The isolated antigen binding protein of any of embodiments 17-20, wherein said L-FR3 is located between said LCDR2 and said LCDR3, and said L-FR3 comprises an amino acid sequence as set forth in SEQ ID NO: 72.

22. The isolated antigen binding protein of any of embodiments 17-21, wherein N-terminus of said L-FR4 is linked directly or indirectly to C-terminus of said LCDR3, and said L-FR4 comprises an amino acid sequence as set forth in SEQ ID NO:90.

23. The isolated antigen binding protein of any of embodiments 1-22, wherein said VL of the antigen binding protein comprises an amino acid sequence as set forth in SEQ ID NO: 151.

24. The isolated antigen binding protein of any of embodiments 1-23, wherein said VL of the antigen binding protein comprises an amino acid sequence as set forth in any one of SEQ ID NO: 111 and 115.

25. The isolated antigen binding protein of any of embodiments 1-24, comprising an antibody light chain constant region, and said antibody light chain constant region comprises a human Igκ constant region.

26. The isolated antigen binding protein of embodiment 25, wherein said antibody light chain constant region comprises an amino acid sequence as set forth in SEQ ID NO: 166.

27. The isolated antigen binding protein of any of embodiments 1-26, comprising an antibody light chain LC, and said LC comprises an amino acid sequence as set forth in SEQ ID NO: 159.

28. The isolated antigen binding protein of any of embodiments 1-27, comprising an antibody light chain LC, and said LC comprises an amino acid sequence as set forth in any one of SEQ ID NO: 139 and 143.

29. The isolated antigen binding protein of any of embodiments 1-28, wherein comprising a heavy chain variable region VH, wherein said VH of the antigen binding protein comprises framework regions H-FR1, H-FR2, H-FR3, and H-FR4.

30. The isolated antigen binding protein of embodiment 29, wherein C-terminus of said H-FR1 is directly or indirectly linked to N-terminus of said HCDR1, and said H-FR1 comprises an amino acid sequence as set forth in SEQ ID NO: 2.

31. The isolated antigen binding protein of any of embodiments 29-30, wherein said H-FR2 is located between said HCDR1 and said HCDR2, and said H-FR2 comprises an amino acid sequence as set forth in SEQ ID NO: 12.

32. The isolated antigen binding protein of any of embodiments 29-31, wherein said H-FR3 is located between said HCDR2 and said HCDR3, and said H-FR3 comprises an amino acid sequence as set forth in SEQ ID NO:28.

33. The isolated antigen binding protein of any of embodiments 29-32, wherein N-terminus of said H-FR4 is linked directly or indirectly to C-terminus of said HCDR3, and said H-FR4 comprises an amino acid sequence as set forth in SEQ ID NO: 43.

34. The isolated antigen binding protein of any of embodiments 1-33, wherein said VH of the antigen binding protein comprises an amino acid sequence as set forth in SEQ ID NO: 152.

35. The isolated antigen binding protein of any of embodiments 1-34, wherein said VH of the antigen binding protein comprises an amino acid sequence as set forth in any one of SEQ ID NO: 96, 104, 105, 106 and 107.

36. The isolated antigen binding protein of any of embodiments 1-35, comprising an antibody heavy chain constant region, and said antibody heavy chain constant region comprises a human IgG constant region.

37. The isolated antigen binding protein of any of embodiments 1-36, comprising an antibody heavy chain constant region, and said antibody heavy chain constant region comprises a human IgG1 constant region.

38. The isolated antigen binding protein of embodiment 37, wherein said antibody heavy chain constant region comprises an amino acid sequence as set forth in SEQ ID NO: 167.

39. The isolated antigen binding protein of any of embodiments 1-38, comprising an antibody heavy chain HC, and said HC comprises an amino acid sequence as set in forth in SEQ ID NO: 162.

40. The isolated antigen binding protein of any of embodiments 1-39, comprising an antibody heavy chain HC, and said HC comprises an amino acid sequence as set in forth in any one of SEQ ID NO: 124, 132, 133, 134 and 135.

41. Isolated nucleic acid molecule or molecules, encoding for said isolated antigen binding protein of any of embodiments of 1-40.

42. Vector or vectors, comprising said isolated nucleic acid molecule or molecules of embodiment 41.

43. A cell, comprising said isolated nucleic acid molecule or molecules of embodiment 41, or said vector or vectors of embodiment 42.

44. A method for producing an isolated antigen binding protein of any of embodiments 1-40, comprising culturing the cell of embodiment 43 under conditions enabling expression of the isolated antigen binding protein of any of embodiments 1-40.

45. A pharmaceutical composition, comprising the isolated antigen binding protein of any of embodiments 1-40, the nucleic acid molecule or molecules of embodiment 41, the vector or vectors of embodiment 42, and/or the cell of embodiment 43, and optionally a pharmaceutically acceptable adjuvant.

46. Use of said isolated antigen binding protein of any of embodiments 1-40, said nucleic acid molecule and molecules of embodiment 41, said vector and vectors of embodiment 42, said cell of embodiment 43 and/or said pharmaceutical composition of embodiment 45 in the manufacture of a medicant for preventing, alleviating and/or treating tumor.

47. The use of embodiment 46, wherein said tumor comprises a solid tumor and/or a blood tumor.

48. A method for preventing, alleviating and/or treating tumor, comprising administrating to a subject in need thereof an isolated antigen binding protein of any of embodiments 1-40.

EXAMPLES

The following examples are set forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); nt, nucleotide(s); i.m., intramuscular(ly); i.p., intraperitoneal(ly); s.c., subcutaneous(ly); and the like.

Example 1 Generation of Anti-CD73 Antibodies

Immunization

CD73 protein was used as immunogens to generate anti-CD73 antibodies in immunization using Harbour H2L2 mice. Each mouse was administrated with 50 μg of the protein for the first boost and 25 μg for following boosts via s.c. and i.p. together with adjuvant (Sigma, S6322). Such immunization was conducted bi-weekly for 6 times. Final immunization was conducted with immunogen diluted in PBS via i.p. Serum titers were tested against human CD73 using ELISA and FACS. At designated time points, mouse serum was sampled and titrated for ELISA and FACS analysis to test binding against CD73 or CD73 stable cell lines. Good serum titers were observed in protein immunization cohort.

Hybridoma

The mouse splenocytes, isolated from immunized mice, were fused by electric field based electroporator using a cell fusion generator (BEX-LF301) to a mouse myeloma cell line SP2/0 (ATCC, CRL-1581) to obtain hybridomas. Usually 9-14 days post fusion, individual wells were then screened for human anti-CD73 antibodies. After hybridoma sub-cloning, the single clones 38H6 showing good binding activities to CD73 was selected for sequencing. Identified and obtained the heavy chain variable region and the light chain variable region. Then the heavy chain variable region and the light chain variable region were synthesized and cloned into plasmids encoding human IgG1 constant region and plasmids encoding human Igκ region, respectively.

Example 2 Antibody Production and Purification

The recombinant plasmids encoding target antibodies were transiently co-transfected into HEK293-6E or 293-F cell cultures using PEI (Polyscience, 24885). 30 μg of plasmids was mixed and incubated with 120 μL of PEI at room temperature for 15 min. Next, the mixture was added dropwise to 30 mL of 293 cells suspended in Opti-MEM at $1\times10^6$ cells/mL. After transfection, the cells were incubated at 37° C. with 5% $CO_2$ and shaking at 120 rpm. The cell culture supernatants collected on day 6-7 days were used for purification.

Supernatant containing target antibodies were harvested 6-7 days post transfection by centrifugation and filtration. Monoclonal antibodies were purified by passing them through settled rProtein A (GE, 17-1279-02) columns (Bio-Rad, 7311550). Protein A columns were prepared by packing 0.2 mL of rProtein A resin in one column then rinsed with 10 column volumes of $ddH_2O$ and 10 column volumes of PBS. The cell culture supernatants were applied to the columns followed by washing with 10 column volumes of PBS. Then the protein was eluted with 8 column volumes of elution buffer (Thermo, 21004) and mixed immediately after elution with 640 μL of neutralization buffer (1 M Tris-HCl, pH 9.0; Teknova, T1090). Buffer was exchanged by centrifugation at 3800 rpm at 4° C. (Eppendorf, 5810R) in concentrators (Millipore, UFC903024) with DPBS for more than 500-fold exchange and finally concentrated to an appropriate volume. The concentrations of purified anti-LAG3 antibodies were determined by UV absorbance at 280 nm (NanoDrop). Antibody purity was examined by SEC-HPLC and SDS-PAGE. One recombinant antibody PR000506 was successfully expressed and purified for characterization.

Example 3 Antibody Engineering

The VH and VL sequences of anti-CD73 antibody PR000506 were further optimized by germlining and PTM removal procedures.

In germlining procedure, antibody VH or VL sequence was firstly aligned to the closest human germline sequence by algorithms e.g. NCBI/Ig-BLAST, and then positions in the framework regions with residues different from the germline sequence were reversed to the counterpart residues in germline sequence. The antibodies composed of the sequence variants after germlining were then recombinantly produced by well-established molecular biology techniques.

Post Translational Modification (PTM) is widely observed in proteins expressed in mammalian cells. Except for conserved PTM sites in antibody, e.g. conserved N-glycosylation site on IgG1 antibody CH2 domain, other PTM sites occurred within antigen binding sites of antibody (i.e. CDR regions) may reduce antigen binding activity or reduce chemical stability. For example, deamidation or isomerization may make the molecules unstable and heterogenous. To reduce the sequence liability, the PTM motifs could be removed by mutations. The VH or VL sequences were scanned by the presence of PTM motifs, e.g., isomerization motifs (e.g. DG). Then the "hotspot" residue (e.g., D or G in DG motif) was mutated to either the counterpart residue in germline sequence or other residue with similar biophysical properties. The antibodies composed of the sequence variants after PTM removal were then recombinantly produced by well-established molecular biology techniques.

The sequence analysis for PR000506, PR000497 and PR001408 was shown in table 2. Designed variants from PR000506 by germlining and PTM removal were shown in table 3. The amino acid sequences of anti-CD73 antibodies were shown in table 4, wherein PR000815-PR000820, PR000822, PR000824, PR000825, and PR003832-PR003836 were PTM removed antibodies derivatized from PR000497. PR002078 is Tab1, PR000752 is Tab 2 and PR000690 is Tab3.

TABLE 2

Anti-CD73 antibody germline analyses

| Clone name | Antibody | VH germline | VL germline | PTM sites |
|---|---|---|---|---|
| 38H6E5 | PR000506 | VH3-30*01 | VK3-11*01 | DG (HCDR2), DG (HCDR3) |
| | PR000497 | IGHV3-33 | IGKV1-5 | DG (HCDR2) NxS/T (LCDR3) |
| | PR001408 | IGHV3-33 | IGKV1-9 | DG (HCDR2) |

TABLE 3

PR000506-derived variants designed

| Parental Antibody | Variant Antibody | Strategy | Mutations | PTM sites |
|---|---|---|---|---|
| PR000506 | PR000851 | germlining | Light chain: K01E, M04L | DG (HCDR2), DG (HCDR3) |
| PR000506 | PR000843 | PTM removal | Heavy chain: D54E, D99E | none |
| PR000506 | PR000844 | PTM removal | Heavy chain: D54E, G100A | none |
| PR000506 | PR000845 | PTM removal | Heavy chain: G55A, D99E | none |
| PR000506 | PR000846 | PTM removal | Heavy chain: G55A, G100A | none |
| PR000851 | PR000847 | PTM removal | Heavy chain: D54E, D99E | none |
| PR000851 | PR000848 | PTM removal | Heavy chain: D54E, G100A | none |
| PR000851 | PR000849 | PTM removal | Heavy chain: G55A, D99E | none |
| PR000851 | PR000850 | PTM removal | Heavy chain: G55A, G100A | none |

TABLE 4 the SEQ ID NO of Anti-CD73 antibodies in the present disclosure

| SEQ ID NO: | LC | HC | VL | VH | LCDR1 | LCDR2 | LCDR3 | HCDR1 | HCDR2 | HCDR3 |
|---|---|---|---|---|---|---|---|---|---|---|
| PR000506 | 139 | 124 | 111 | 96 | 55 | 66 | 78 | 7 | 18 | 35 |
| PR000843 | 139 | 132 | 111 | 104 | 55 | 66 | 78 | 7 | 23 | 38 |
| PR000844 | 139 | 133 | 111 | 105 | 55 | 66 | 78 | 7 | 23 | 39 |
| PR000845 | 139 | 134 | 111 | 106 | 55 | 66 | 78 | 7 | 24 | 38 |
| PR000846 | 139 | 135 | 111 | 107 | 55 | 66 | 78 | 7 | 24 | 39 |
| PR000847 | 143 | 132 | 115 | 104 | 55 | 66 | 78 | 7 | 23 | 38 |
| PR000848 | 143 | 133 | 115 | 105 | 55 | 66 | 78 | 7 | 23 | 39 |

TABLE 4-continued

| | | | | the SEQ ID NO of Anti-CD73 antibodies in the present disclosure | | | | | |
|---|---|---|---|---|---|---|---|---|---|
| SEQ ID NO: | LC | HC | VL | VH | LCDR1 | LCDR2 | LCDR3 | HCDR1 | HCDR2 | HCDR3 |
| PR000849 | 143 | 134 | 115 | 106 | 55 | 66 | 78 | 7 | 24 | 38 |
| PR000850 | 143 | 135 | 115 | 107 | 55 | 66 | 78 | 7 | 24 | 39 |
| PR000851 | 143 | 124 | 115 | 96 | 55 | 66 | 78 | 7 | 18 | 35 |
| PR000497 | 138 | 123 | 110 | 95 | 54 | 65 | 77 | 6 | 17 | 34 |
| PR000815 | 138 | 127 | 110 | 99 | 54 | 65 | 77 | 6 | 21 | 34 |
| PR000816 | 138 | 128 | 110 | 100 | 54 | 65 | 77 | 6 | 22 | 34 |
| PR000817 | 138 | 129 | 110 | 101 | 54 | 65 | 77 | 6 | 21 | 34 |
| PR000818 | 138 | 130 | 110 | 102 | 54 | 65 | 77 | 6 | 22 | 34 |
| PR000819 | 138 | 131 | 110 | 103 | 54 | 65 | 77 | 6 | 17 | 34 |
| PR000820 | 142 | 123 | 114 | 95 | 54 | 65 | 81 | 6 | 17 | 34 |
| PR000822 | 142 | 128 | 114 | 100 | 54 | 65 | 81 | 6 | 22 | 34 |
| PR000824 | 142 | 130 | 114 | 102 | 54 | 65 | 81 | 6 | 22 | 34 |
| PR000825 | 142 | 131 | 114 | 103 | 54 | 65 | 81 | 6 | 17 | 34 |
| PR003832 | 146 | 130 | 118 | 102 | 54 | 65 | 84 | 6 | 22 | 34 |
| PR003833 | 147 | 130 | 119 | 102 | 54 | 65 | 85 | 6 | 22 | 34 |
| PR003834 | 148 | 130 | 120 | 102 | 54 | 65 | 86 | 6 | 22 | 34 |
| PR003835 | 149 | 130 | 121 | 102 | 54 | 65 | 87 | 6 | 22 | 34 |
| PR003836 | 150 | 130 | 122 | 102 | 54 | 65 | 88 | 6 | 22 | 34 |
| PR001408 | 144 | 136 | 116 | 108 | 58 | 69 | 82 | 10 | 25 | 40 |
| PR002078 | 145 | 137 | 117 | 109 | 59 | 70 | 83 | 6 | 26 | 41 |
| PR000752 | 141 | 126 | 113 | 98 | 57 | 68 | 80 | 9 | 20 | 37 |
| PR000690 | 140 | 125 | 112 | 97 | 56 | 67 | 79 | 8 | 19 | 36 |

Example 4 Binding of Anti-CD73 Antibodies to CD73

Binding of antibodies to hCD73 and cynoCD73 expression in stable cell line was characterized by Flow cytometry. The cells were incubated with various concentration antibodies (the top concentration was 50 nM, 8 points, dilution factor 3), then incubate for 1 h at 4° C. Wash two times by PBS, then add the secondary antibody Goat anti-human(H+ L) (Thermo fisher, A11013), incubate for 30 min at 4° C. And the fluorescence intensity was read by FACS Machine (BD FACS CantoII). A plot of median fluorescence intensity and the binding EC50 were fitted and calculated by Graph-Pad Prism 5. The results were shown in FIGS. 1-5 and tables 5-8.

Figure 1B:
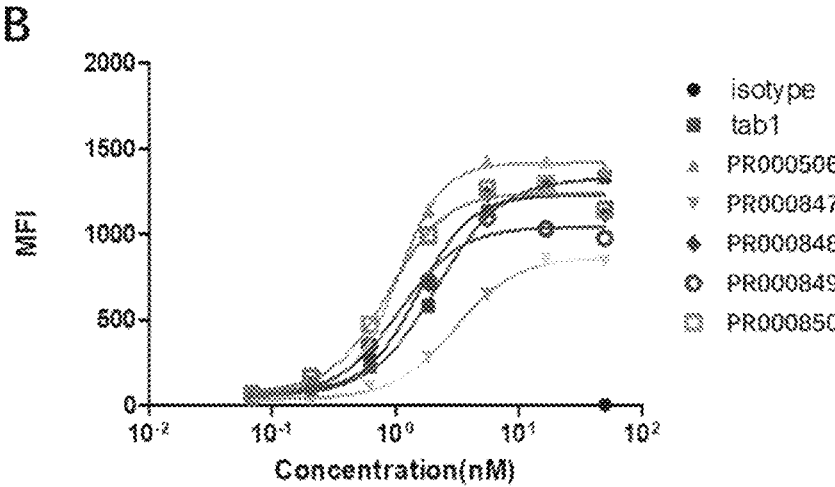
Figure 2:
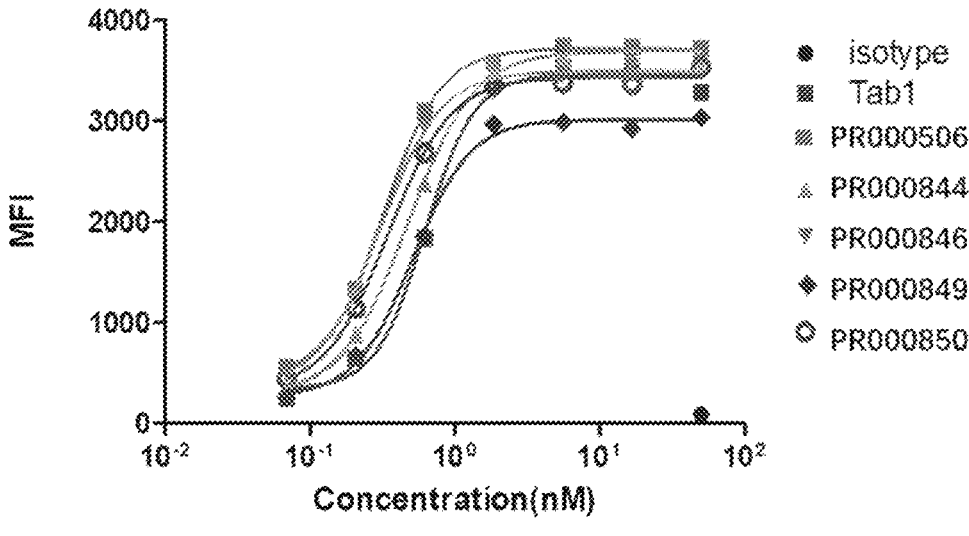
FIG. 2 illustrates the antibodies binding to HEK293-cynoCD73 cell line by FACS.
Figure 3:
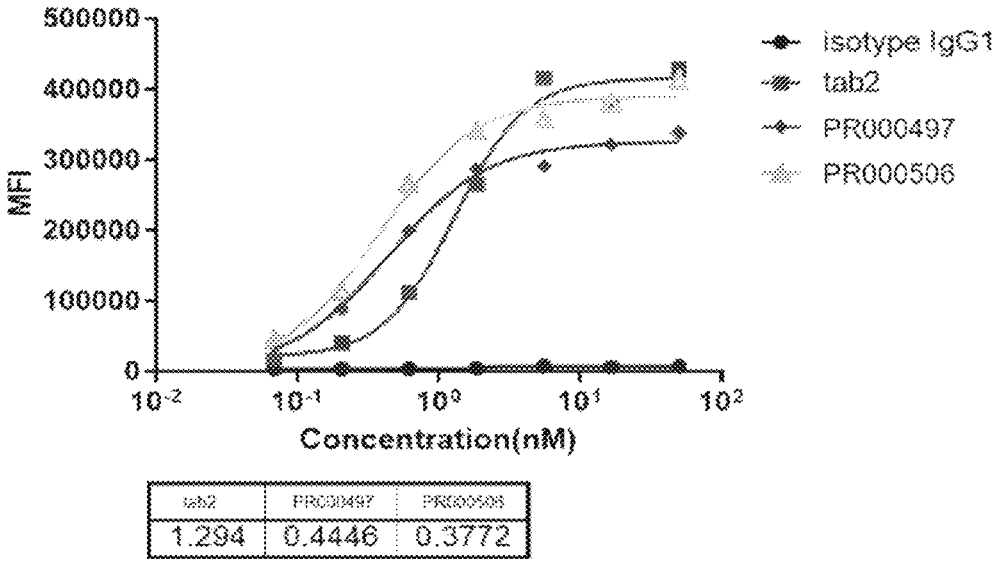
FIG. 3 illustrates the antibodies binding to CHO-K1-hCD73 cell line by FACS.
Figure 4:
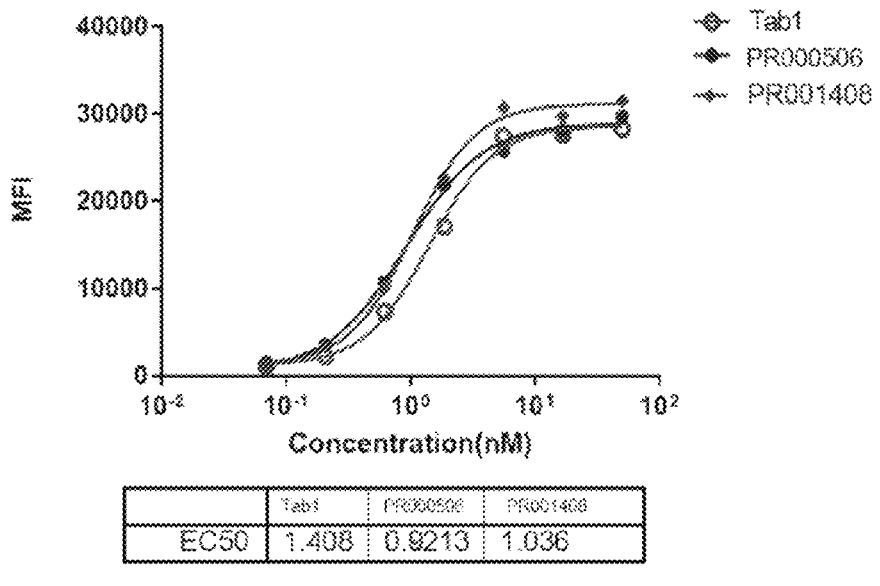
FIG. 4 illustrates the antibodies binding to CHO-K1-hCD73 cell analyzed by FACS.
Figure 5A:
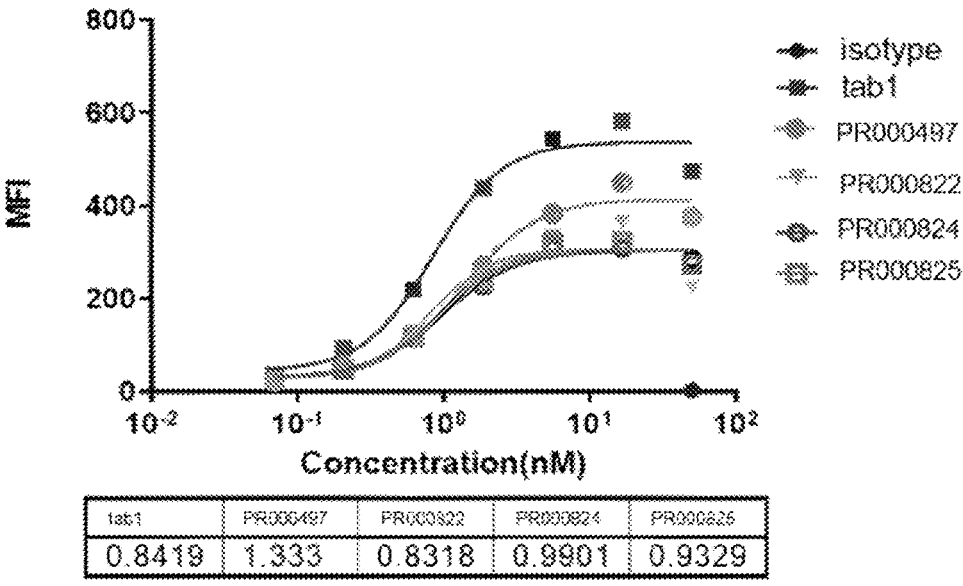
FIGS. 5A and 5B illustrate the antibodies binding to CHO-K1-hCD73 cell line by FACS.
Figure 5B:
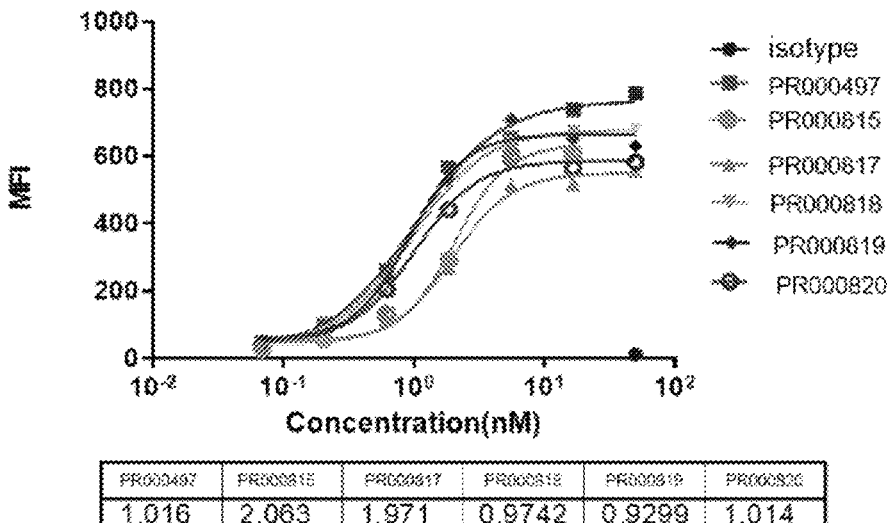

FIG. 1 and FIG. 3 shows the binding activities of anti-CD73 antibodies to CHO-K1-humanCD73 stable cell line. The table 5 and table 6 show PTM removal antibodies EC50 to CHO-K1-hCD73 stable cell line. The table 7 shows the ratio of PTM removal antibodies EC50 to PR000506 EC50. FIG. 2 shows the binding activities of anti-CD73 antibodies to HEK293-cynoCD73 stable cell line. The table 8 shows PTM removal antibodies EC50 to HEK293-cynoCD73 stable cell line. FIG. 4 and FIG. 5 shows the binding activities of anti-CD73 antibodies to CHO-K1-humanCD73 stable cell line. The results indicate that all the antibodies had comparative affinity with cell based CD73.

TABLE 5

| | PTM removal antibodies EC50 to CHO-K1-hCD73 stable cell line | | | | | |
|---|---|---|---|---|---|---|
| | PR000506 | PR000843 | PR000844 | PR000845 | PR000846 | PR000851 |
| EC 50(nM) | 0.7342 | 1.855 | 0.8358 | 0.8527 | 0.7499 | 0.7997 |

TABLE 6

| | PTM removal antibodies EC50 to CHO-K1-hCD73 stable cell line | | | | | |
|---|---|---|---|---|---|---|
| | Tab1 | PR000506 | PR000847 | PR000848 | PR000849 | PR000850 |
| EC 50(nM) | 2.172 | 1.047 | 3.026 | 1.528 | 1.079 | 0.8790 |

TABLE 7

| the ratio to PR000506 EC50 | |
|---|---|
| Antibody Name | Antibody EC50/PR000506 EC50 |
| Tab1 | 2.074 |
| PR000843 | 2.527 |
| PR000844 | 1.138 |

TABLE 7-continued

| the ratio to PR000506 EC50 | |
| --- | --- |
| Antibody Name | Antibody EC50/PR000506 EC50 |
| PR000845 | 1.161 |
| PR000846 | 1.021 |
| PR000847 | 2.890 |
| PR000848 | 1.459 |
| PR000849 | 1.031 |
| PR000850 | 0.840 |
| PR000851 | 1.089 |

TABLE 8

| PTM removal antibodies EC50 to HEK293-cynoCD73 stable cell line | | | | | |
| --- | --- | --- | --- | --- | --- |
| | Tab1 | PR000506 | PR000844 | PR000846 | PR000849 | PR000850 |
| EC 50(nM) | 0.6229 | 0.3225 | 0.4750 | 0.3071 | 0.5146 | 0.3467 |

Example 5 Inhibition of 5'Ectonucleotidase by Anti-CD73 Antibodies 5.1 Inhibition of Cell Based CD73 Enzyme Activity by Anti-CD73 Antibody The functional activity of the anti-CD73 antibodies were determined in vitro assay that measured by inhibition CD73 catalyzed AMP hydrolysis to adenosine in CHO-K1-hCD73 stable cell line. The cells were digested by trypsin-EDTA, then centrifuge at 1000 rpm 5 min, resuspend the cells in serum-free F12K medium, Count the cells using cell counter (Thermofisher, Countess™ II Automated Cell Counter), then seed 5000 cells per 100 ul to 96-well flat plate (corning, 3599), and add 4× diluted antibody (8 points, ⅓ diluted by serum-free medium) to the plate, incubate 30 min at 37° C. then 500 4×AMP (200 μM) were added to plate, and then incubate 1 hour at 37° C. Centrifuge the plate at 1500 rpm 3 min, then transfer 50 μL culture supernatant well-to well to black 96-well plate (PerkinElmer,6005225), 2×ATP (65 μM) was then added. The Cell Titer-Glo (PROMEGA, G7573) was added 100 μL/well as the manufacture's instruction. And the luminescence was recorded by PE Enspire workstation. The blocking activity was calculated with the Formula below:

Blocking %=[(Max luminescence–sample luminescence)/(Max luminescence–Min luminescence)]×100.Note:Max luminescence wells were added AMP,ATP with cells. Min luminescence wells were added AMP,ATP without cells.

Figure 6A:
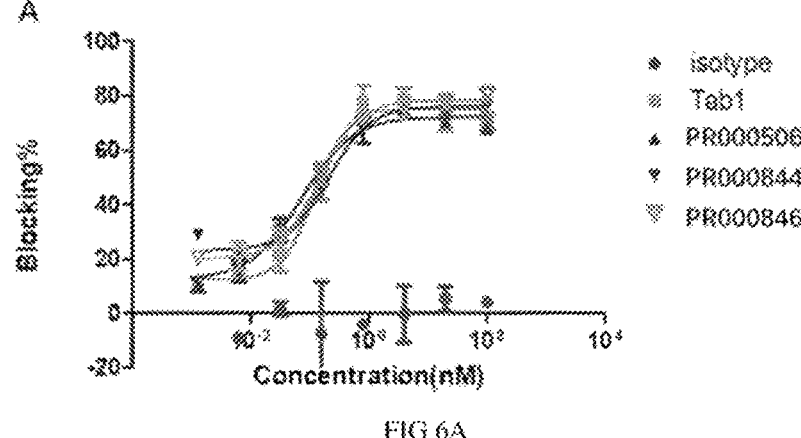
FIGS. 6A and 6B illustrate inhibition of cell based CD73 enzyme activity of the antibodies.
Figure 6B:
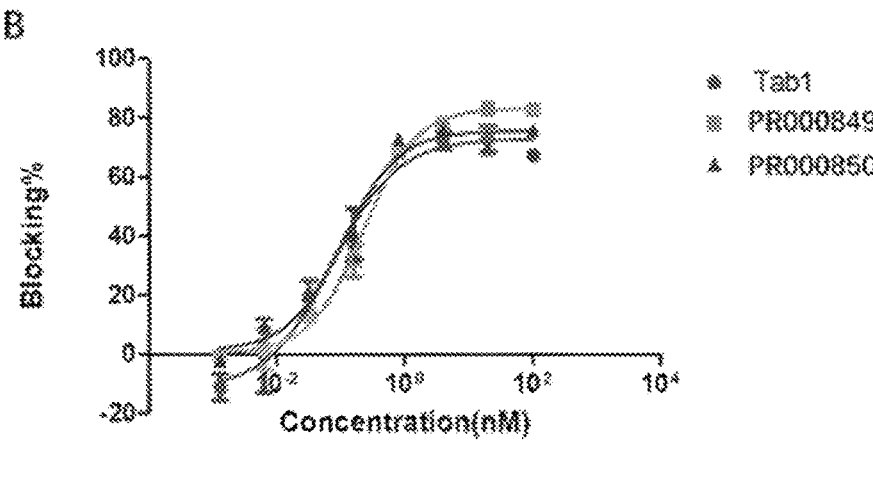

The graph and the EC50 were analyzed by GraphPad Prism. The results were shown in FIG. 6. FIG. 6A-6B shows inhibition of CD73 Enzyme activity on CHO-K1 by anti-CD73 antibody. The table 9 and table 10 show anti-CD73 antibodies EC50 to CHO-K1 stable cell line. It can be seen that all antibodies have ability to block enzymatic activity of cell based CD73. And the blocking activity of PR000506 is better than Tab1.

TABLE 9

| anti-CD73 antibodies EC50 to CHO-K1 | | | |
| --- | --- | --- | --- |
| | Tab1 | PR000506 | PR000844 | PR000846 |
| EC50(nM) | 0.1218 | 0.07376 | 0.2073 | 0.1514 |

TABLE 10

| anti-CD73 antibodies EC50 to CHO-K1 | | | |
| --- | --- | --- | --- |
| | Tab1 | PR000849 | PR000850 |
| EC50(nM) | 0.07330 | 0.2243 | 0.1091 |

5.2 Inhibition of sCD73 Enzyme Activity by Anti-CD73 Antibody

Figures 7A, 7B:
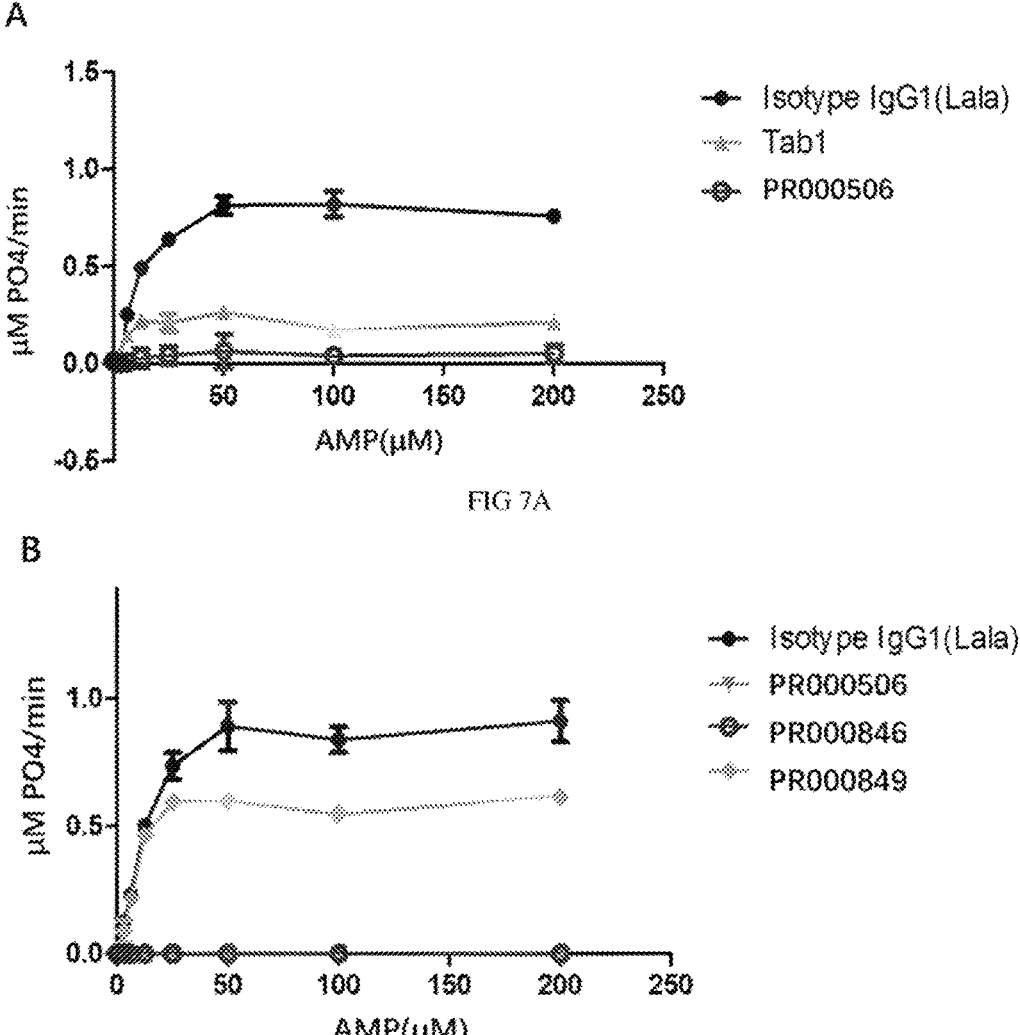
FIGS. 7A, 7B, 8A and 8B illustrate inhibition of soluble CD73 enzyme activity of the antibodies treated with different time.
Figure 8A:
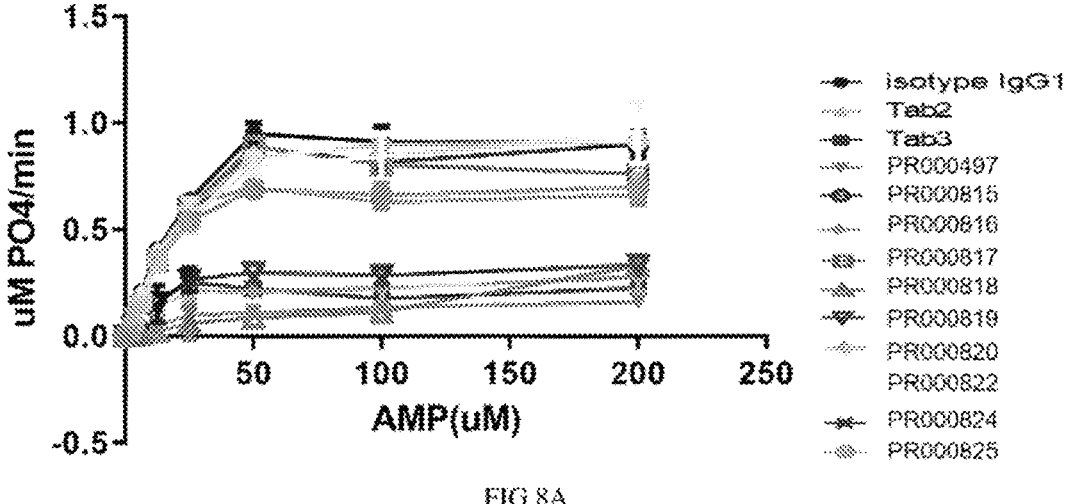
Figure 8B:
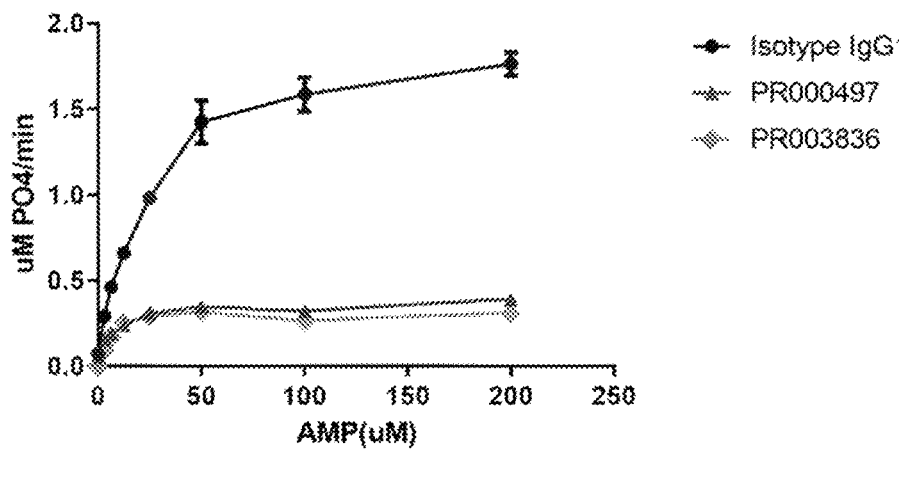

For measurements of soluble recombinant CD73 activity using the Malachite Green assay, 12.5 μL nM recombinant CD73 and either 12.5 μl nM antibody were added in 384-well plate (Corning, 3799) and incubated in assay buffer (25 mM Tris pH 7.5, 5 mM MgCl2, 0.005% Tween-20) for 1 hour at room temperature. An 250 of AMP (top concentration 20004, ½ diluted 8 points in assay buffer) was added and samples were incubated for 15 minutes at room temperature. The concentration of inorganic phosphate was determined using the Malachite Green assay following the manufacturer's instructions. And the Optical density value was recorded by PE Envision workstation in 620 nm. The graph was analyzed by GraphPad Prism. The results were shown in FIG. 7 and FIG. 8. It can be seen that all antibodies have ability to block enzymatic activity of soluble CD73 and inhibit CD73 dephosphorylating AMP to adenosine.

Example 6 Internalization CD73 by Anti-CD73 Antibodies 6.1 Antibody-Mediated CD73 Internalization Assay by Flow Cytometry NCI-H292 cells were incubated in presence of 50 nM antibodies or negative control isotype IgG1 at 37° C. 4 hours or 30 min. Wash the plate two times by PBS, then added the antibodies 50 nM 100 μL to the isotype control wells, incubate the plate at 4° C. 1 hour, wash the plate two times by PBS. Aspirate the wash buffer and add 100 μL of FACS buffer with Secondary antibody Goat anti-Human IgG (H+L) (Thermofisher, A-21445) per well. Incubate for 30 min at 4° C. Wash the plate two times by PBS and suspended the cells by 100 μL PBS. And the median fluorescence intensity was read by FACS Machine (BD FACS CantoII), The surface remaining % was calculated by the below formula:

Surface remaining %=[antibody 4h/(isotype 4h+antibody)]×100

Figures 9A, 9B:
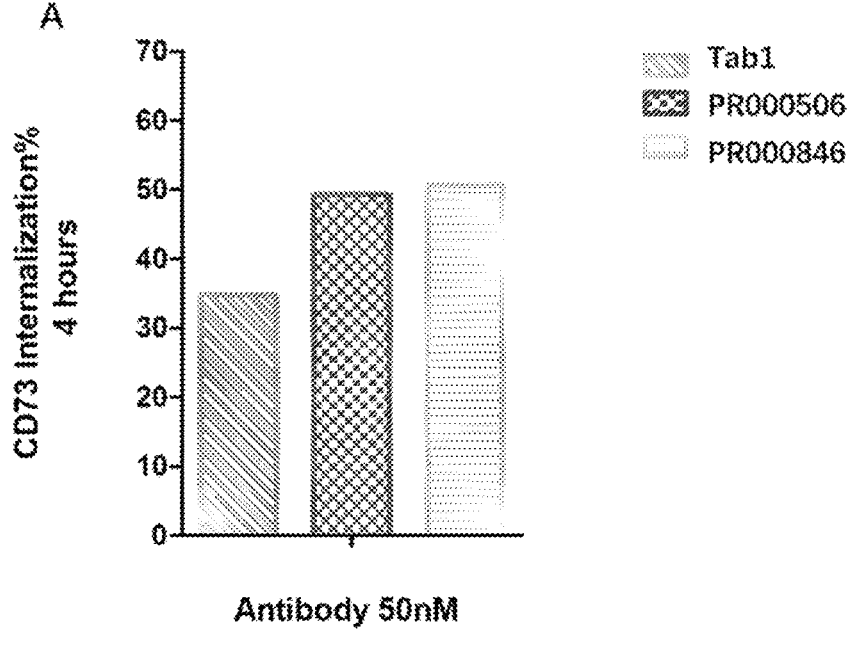
FIGS. 9A, 9B, 10 and 11 illustrate internalization activities of the antibodies.
Figure 11:
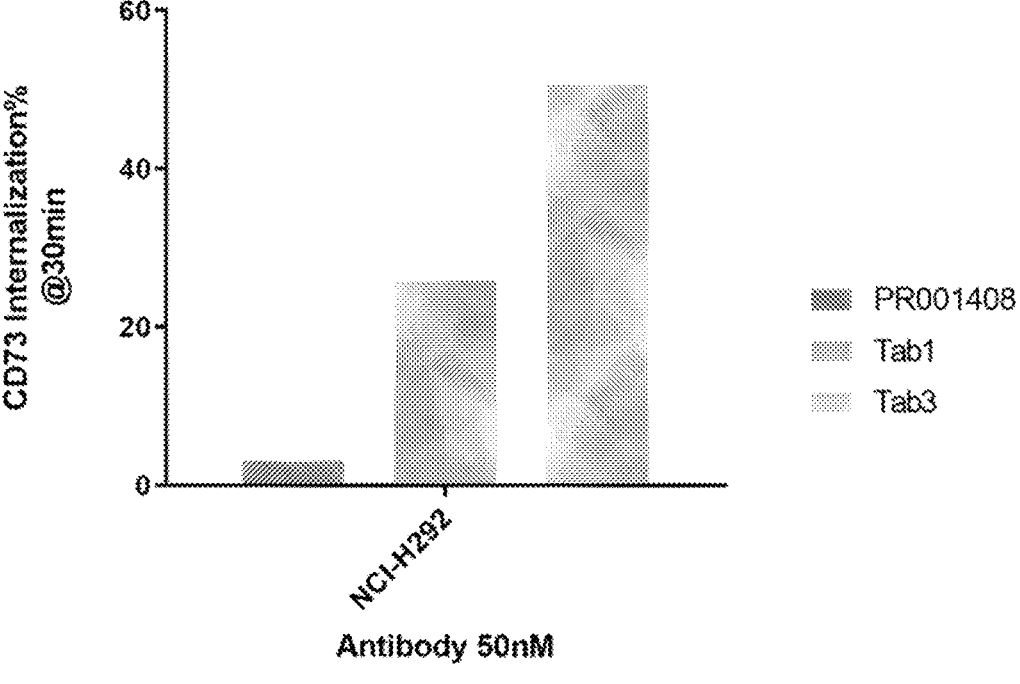

The results were shown in FIG. 9A and FIG. 11. The antibodies of the present disclosure can mediate CD73 internalization after 4 hours.

6.2 Antibody-Mediated CD73 Internalization Assay by Internalization Kit

The cell CHO-K1-hCD73 was digested by trypsin-EDTA, then centrifuge at 1000 rpm 5 min, resuspend the cells in F12K medium with 10% FBS. Count the cells using cell counter (Thermofisher, Countess™ II Automated Cell Counter), then seed 5000 cells per 90 μL to 96-well flat black view TC plate (PerkinElmer,6005225). Incubate overnight at 37°

C., 5% $CO_2$ incubator. Add 10× diluted antibody (top concentration 10 nM, 6 points, ⅕ diluted by complete F12K medium) to the plate, prepare Hu-zap buffer at conc 50 μg/ml (50×). Add 2 μL to the wells, the final conc is 1 μg/ml. incubate 3 days at 37° C., 5% $CO_2$ incubator. The Cell Titer-Glo (PROMEGA, G7573) was added 100 ul/well as the manufacture's instruction. And the luminescence was recorded by PE Enspire workstation. The result was calculated by CD73 Internalization %. Note: control well was only seeded cells. The graph was analyzed by GraphPad Prism.

Figure 10:
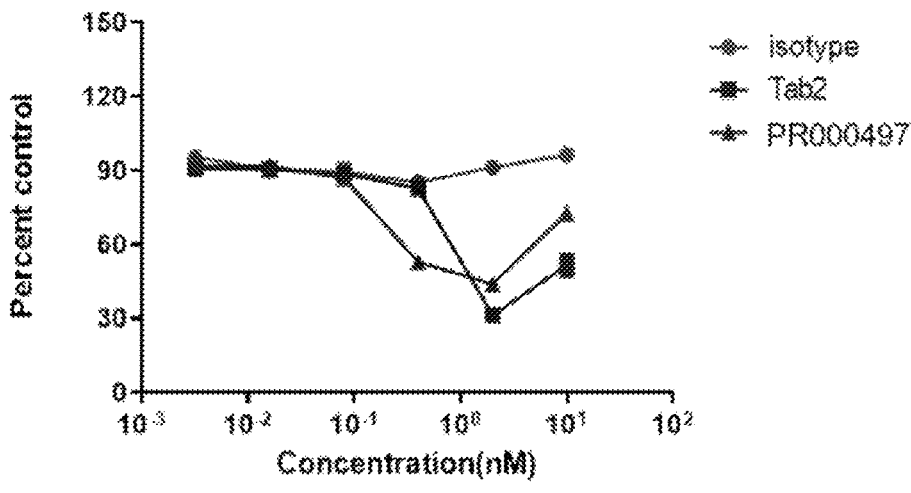

The results were shown in FIG. 9B and FIG. 10. The antibodies of the present disclosure can mediate CD73 internalization after 3 days.

Example 7 Antibodies Inhibited AMP-Mediated Suppression of CD4+ T Cell Proliferation Assay 7.1 CD4+ T Cells Isolated from Fresh Human PBMC PBMC were washed with pre-cold PBS twice by centrifugation at 300×g for 10 minutes at 4° C. Supernatant was discarded and cells were suspended in 20 ml pre-cold PBS. Viable cells were determined, then pelleted at 300×g for 7 minutes. Aspirate the supernatant completely. Isolated CD4+ T cells using the manufacture's protocol (Miltenyi, 130-045-101).

7.2 CFSE Labeling

Prepare CellTrace™ stock solution(Invitrogen, C34554) immediately prior to use by adding the appropriate volume of DMSO (Component B) to one vial of CellTrace™ reagent (Component A) and mixing well, Dilute the CellTrace™ DMSO stock solution (5 mM) in pre-warmed (37° C.) phosphate-buffered saline (PBS) or other protein-free buffer to 1 μM (5000 fold), and labelled the cells as the manufacture's instruction.

7.3 T Cell Activation and Expansion

Cells from each donor were washed twice with warm complete culture media and suspended at 2×10$^6$ cells per mL Dynabeads Human T-Activator CD3/CD28(life, 11131D) was suspended at 1×10$^6$/ml, 1:1 Mix the cell suspension and the Dynabeads. Add 100 μL/well the cell and beads mixture to 96 well flat-bottom plate.

7.4 Add 4× antibody

Add 4× antibody 50 μL, antibody concentration: 6 points (the top concentration was 20 nM, ⅟10 diluted 6 points by RPMI1640 complete medium). Incubate the plate 30 min at 37° C., 5% $CO_2$ 7.5 Add 4×AMP Add 4×AMP (Sigma) 504, (final concentration is 650 μM or 800 μM), incubate the plate 96 h at 37° C., 5% $CO_2$.

7.6 FACS Analysis

Cells were pelleted by centrifugation at 350 g for 5 min, washed once with 200 μl PBS and finally suspended in 200 μl PBS for flow cytometry analysis on BD FACS Canto II. CFSE CD4+ T cells with no AMP (Beads only) wells were used to identify cells that have undergone cellular division.

Figure 12A:
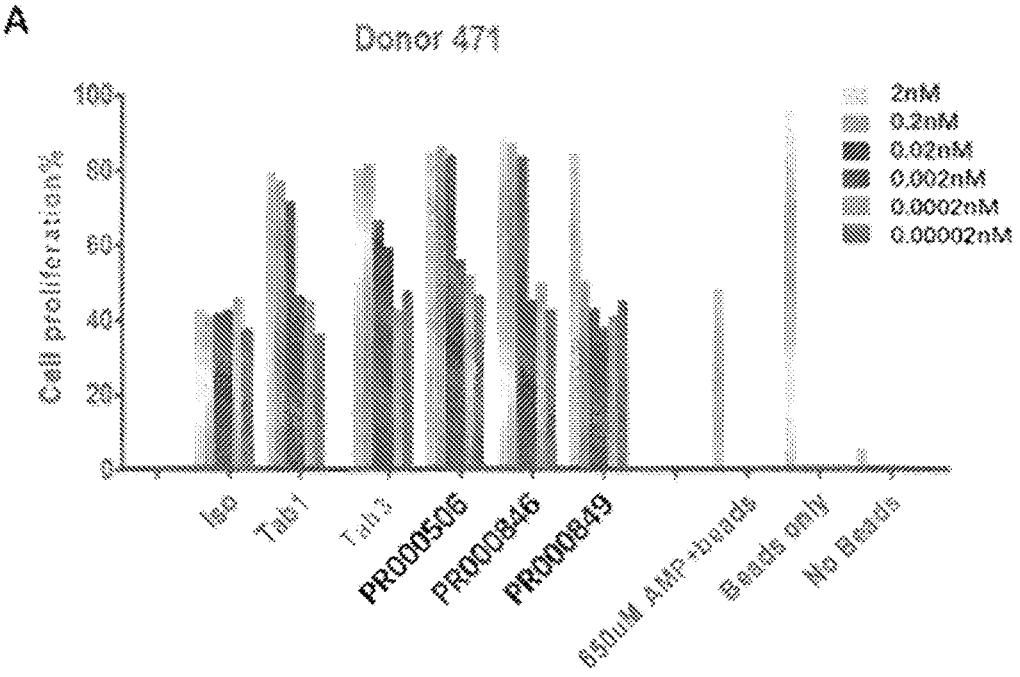
FIGS. 12A, 12B, 13A and 13B illustrate the cell proliferation in primary T cell assay of the antibodies.
Figure 12B:
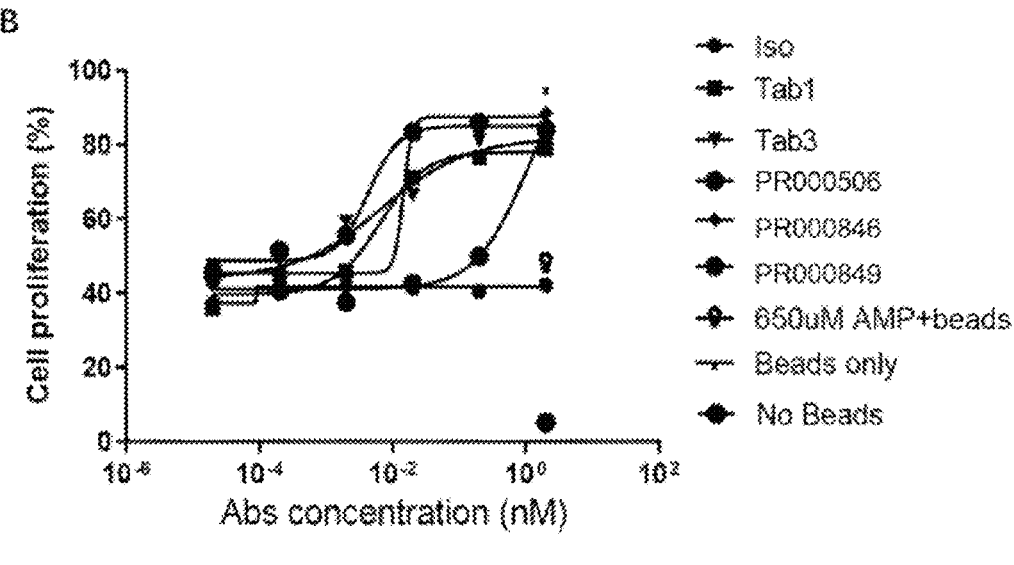
Figure 13A:
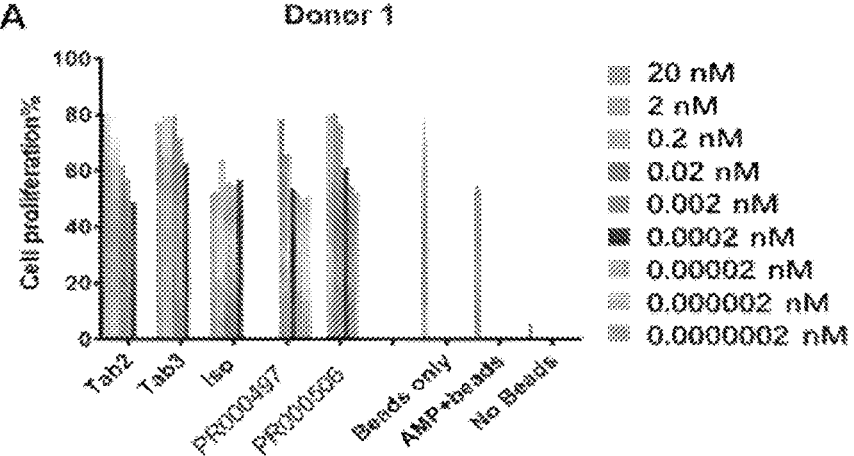
Figure 13B:
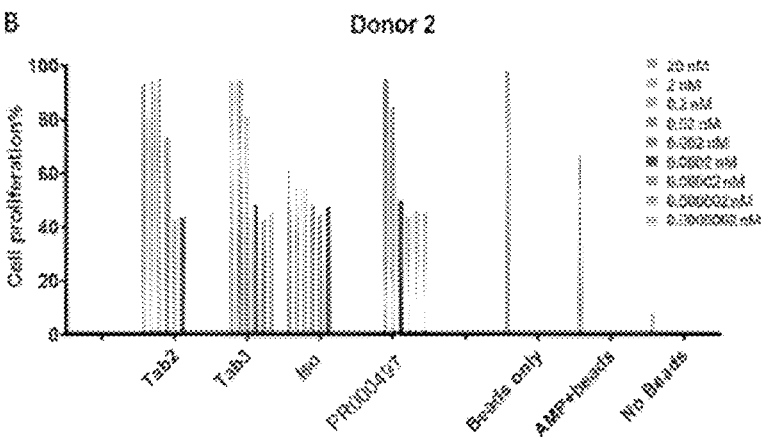

The results were shown in FIG. 12 and FIG. 13. The antibodies can inhibit AMP-mediated suppression of CD$^{4+}$ T cell proliferation. And the effect is dosage depended.

Example 8 PK Analysis 8.1 Plate Coating

Dilute antigen CD73 into 5 μg/mL in PBS. Add 50 μL/well into the ELISA plate. Seal the plate and incubate overnight in 4° C. Wash the plate 3 times with 300 μl of washing buffer. Add 200 μl/well of assay diluent, and incubate at room temperature for 1-3 hour. Wash the plate 3 times with 300 μl of washing buffer.

8.2 Preparation of Standard, QC, Test Sample, and Sample Incubation

Standard: 2-fold serial dilution was made in 5% pooled mouse serum. Eight standards ranged from 50 to 0.391 ng/mL. 0.391 ng/mL standard was anchor point. QC preparation: two sets of QCs were prepared in 5% pooled mouse serum. HQC (40 ng/mL), MQC (10 ng/mL) and LQC (2 ng/mL). Sample preparation: all serum samples were diluted at 20 folds in Assay Diluent first. Additional dilution was made in 5% pooled mouse serum. 50 μL of standards, QCs and samples were added into the ELISA plate. The plate was sealed and incubated at 37° C. for about 1 hour.

8.3 Detection Reagent Reaction

Wash the plate 3 times with 300 μl of washing buffer. Prepare HRP-conjugated detection antibody working solution: the antibody solution was diluted in Assay Diluent at 1:5000. Add 100 μl/well of the detection antibody working solution into the assay plate. The plate was sealed and incubated at 37° C. for 30 minutes.

8.4 Substrate Reaction and Plate Reading

Wash the plate 3 times with 300 μl of washing buffer. Prepare TMB working solution: bring the substrate to room temperature 30 min before use. Mix equal volume of substrate A and substrate B. Add 100 μl/well of premixed TMB substrate and incubate at room temperature for about 6 min. Add 100 μL/well of ELISA stopping solution. Mix the plate and read at 450/630 nm wavelength using SpectraMax M2. Data processing using Soft Max Pro GxP. Fit the standard curve using 4-PL model, wih a weighting factor of 1/y.

Figure 14A:
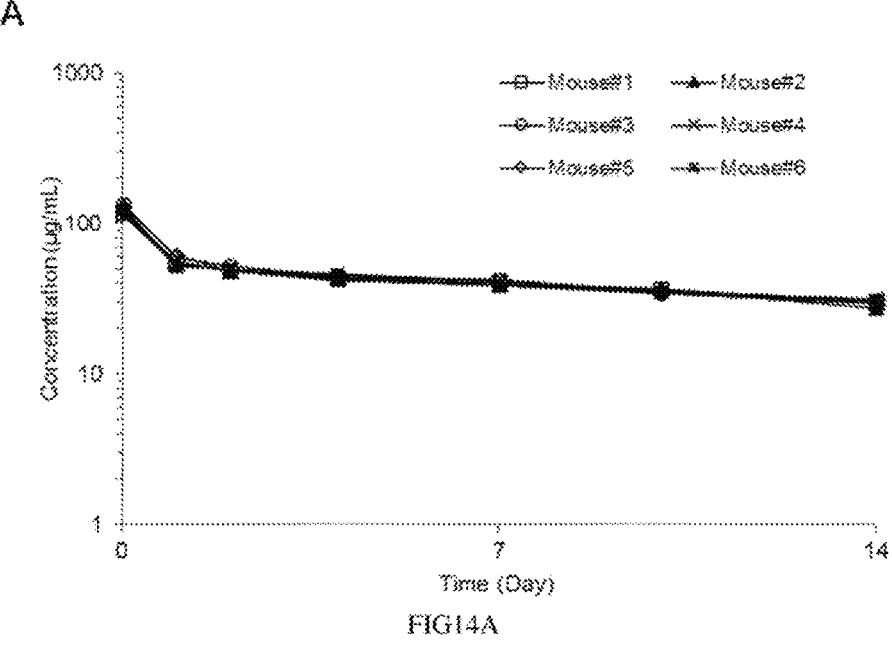
FIGS. 14A, 14B and 14C illustrate individual serum concentration-time profiles of the antibodies, A: PR000506, B: PR000846 and C: PR000497.
Figure 14B:
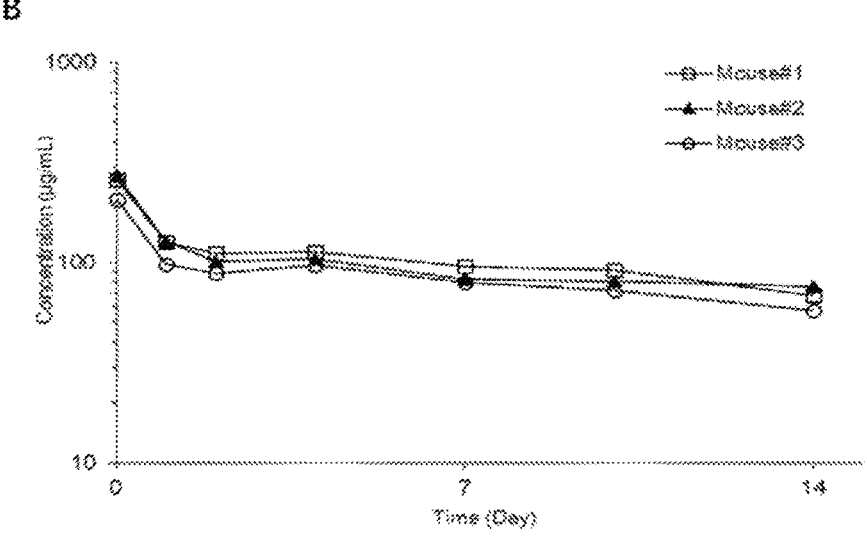
Figure 14C:
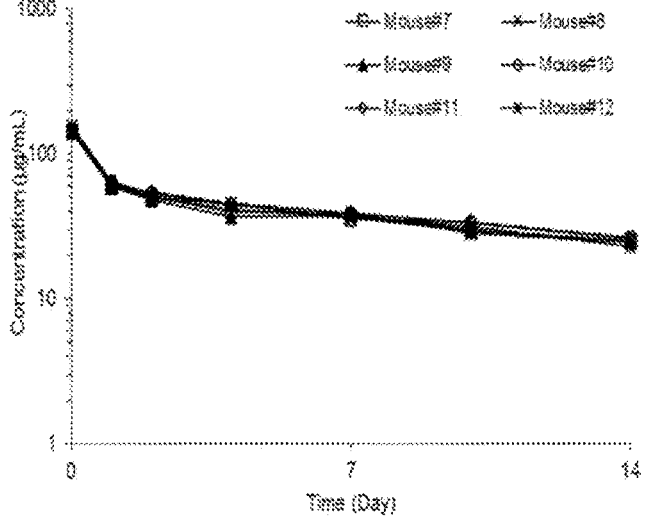

FIG. 14A and Table 11 shows the individual concentration-time profile of PR000506 after an IV dose of 5 mg/kg in female C57BL/6 mice (N=6/time point). FIG. 14B and Table 12 shows the individual concentration-time profile of PR000846 after an IV dose of 10 mg/kg in female C57BL/6 mice (N=3/time point). The t½ of PR000506 in serum is 17.4 days and PR000846 is 18.1 days. FIG. 14C and Table 13 shows the individual serum concentration-time profile of PR000497 after an IV dose of 5 mg/kg in female C57BL/6 mice (N=6/time point).

TABLE 11

| dose of 5 mg/kg in female C57BL/6 mice (N = 6/time point) PR000506 | | | | |
|---|---|---|---|---|
| PK parameters | Unit | Mean | SD | CV (%) |
| CL | ml/day/kg | 3.73 | 0.359 | 9.63 |
| Vss | ml/kg | 89.1 | 5.16 | 5.79 |
| Terminal $t_{1/2}$ | day | 17.4 | 2.76 | 15.9 |
| AUC$_{last}$ | day*μg/ml | 606 | 11.0 | 1.82 |
| AUC$_{INF}$ | day*μg/ml | 1353 | 139 | 10.3 |

TABLE 12

| dose of 10 mg/kg in female C57BL/6 mice (N = 3/time point) PR000846 | | | | |
|---|---|---|---|---|
| PK parameters | Unit | Mean | SD | CV (%) |
| CL | ml/day/kg | 3.23 | 0.454 | 14.4 |
| Vss | ml/kg | 81.7 | 9.37 | 9.04 |
| Terminal $t_{1/2}$ | day | 18.1 | 1.54 | 12.9 |
| AUC$_{last}$ | day*μg/ml | 1329 | 137 | 14.3 |
| AUC$_{INF}$ | day*μg/ml | 3098 | 430 | 15.5 |

TABLE 13

| dose of 5 mg/kg in female C57BL/6 mice (N = 6/time point) PR000497 | | | | |
|---|---|---|---|---|
| PK parameters | Unit | Mean | SD | CV (%) |
| CL | ml/day/kg | 4.83 | 0.283 | 5.87 |
| Vss | ml/kg | 80.7 | 4.59 | 5.70 |
| Terminal $t_{1/2}$ | day | 12.3 | 1.09 | 8.89 |
| $AUC_{last}$ | day*μg/ml | 591 | 21.0 | 3.55 |
| $AUC_{INF}$ | day*μg/ml | 1039 | 60.2 | 5.79 |

Example 9 Tumor Inhibition In Vivo

The NCG mice were inoculated s.c. with NCI-H292 cell and PBMCs on day 0 to obtain tumor model. The mice bearing the tumors were divided into several groups: group isotype control, group tab1; group PR000506, group Tab3, group PR000846 and group PR000497. In each group the mice were treated with corresponding compounds with a dosage of 10 mpk, twice a week, 3 weeks. Tumor volume and body weight were measured at selected time.

Figure 15A:
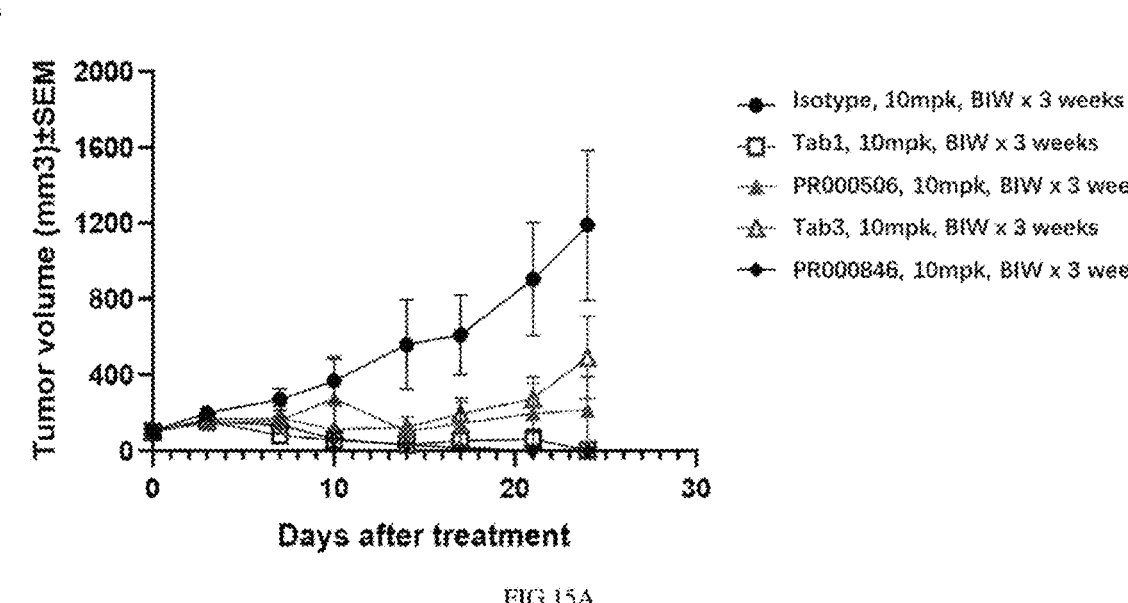
FIGS. 15A, 15B, 16A and 16B illustrate inhibiting tumor growth activities of the antibodies in vivo, wherein, A: tumor volume, B: body weight.
Figure 15B:
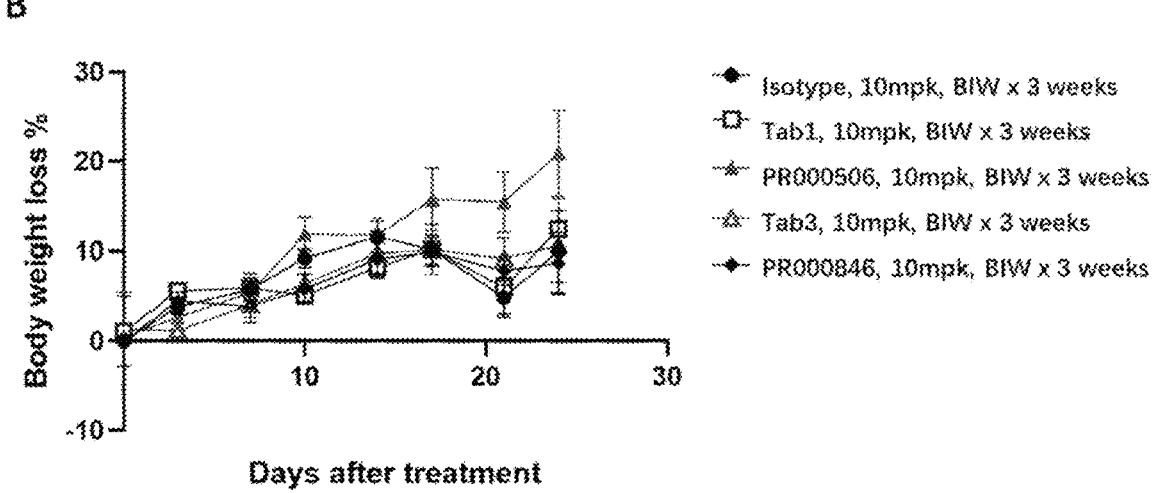
Figure 16A:
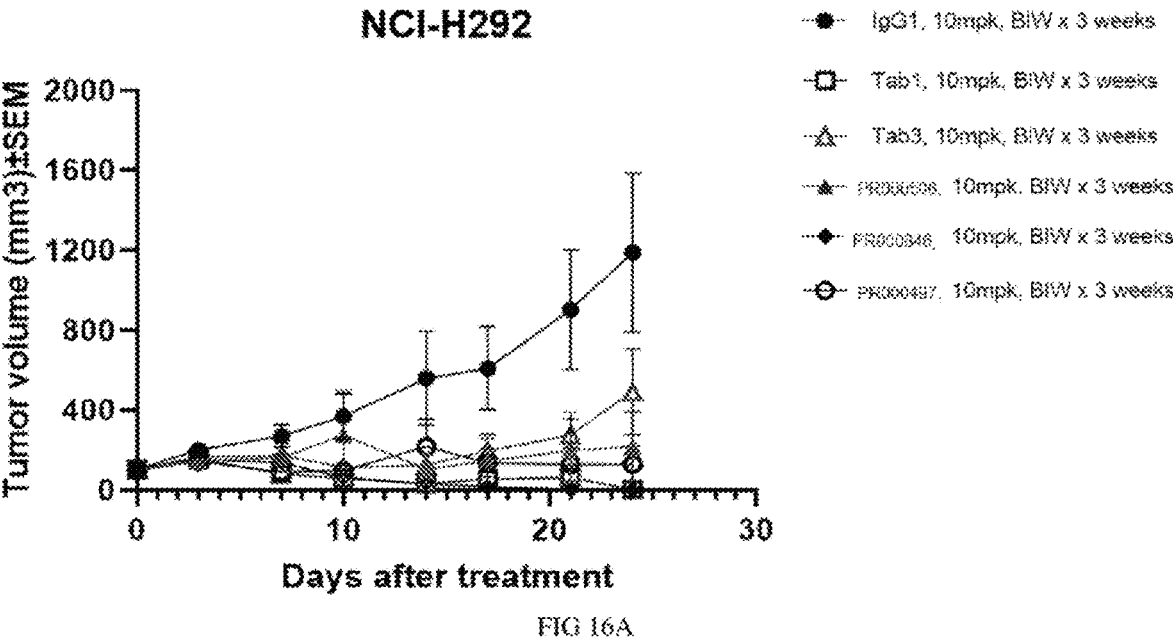
Figure 16B:
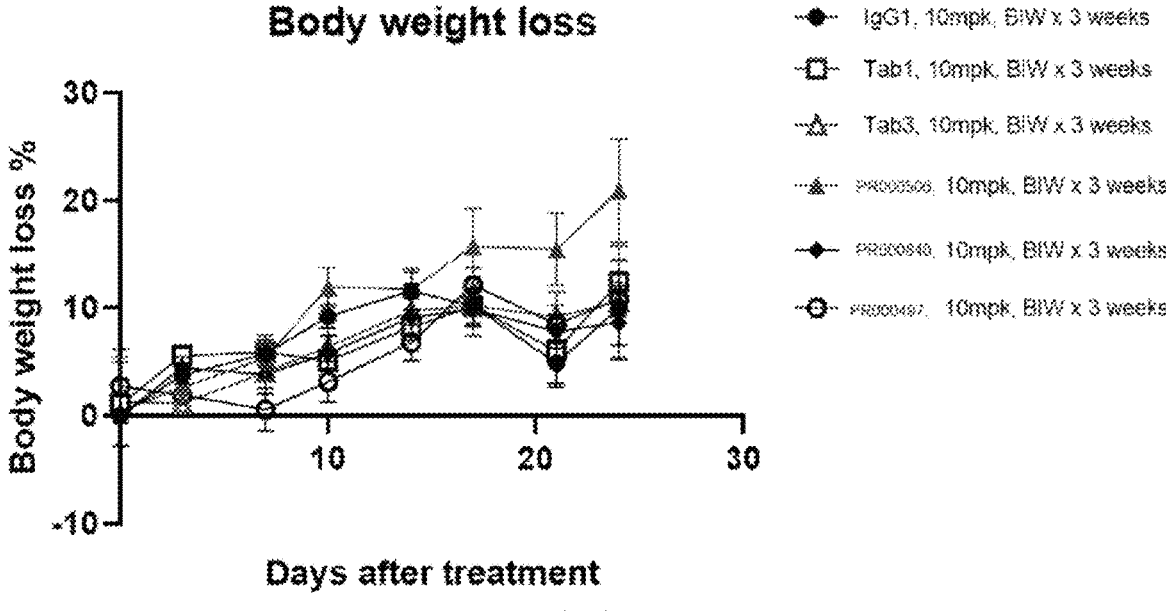

The results were shown in FIGS. 15 and 16. It could be seen that the anti-CD73 antibodies had an inhibiting effect in tumor growth.

Example 10 Determination of the Epitope of CD73 with PR000846

In this example, the epitope of CD73 binding with anti-CD73 antibody PR000846 was determined by Hydrogen Deuterium-Exchange Mass Spectrometry (HDX-MS), and the critical amin acid of the epitope were confirmed by alanine mutation of CD73 protein.
Hydrogen Deuterium-Exchange Mass Spectrometry (HDX-MS)

HDX-MS experiments were performed by Genechem as previously described (Park I H, et al., J. Chem. Inf.Model.; 55(9): 1914-1925 (2015); Chalmers M J, et al., Anal. Chem.; 78(4): 1005-14 (2006)). Antibody antigen complexes were prepared and used in a 1:1 molar ratio by overnight incubation at 4° C.

Room temperature on-exchange experiments were performed by manual addition of 2 μl of 0.5 mg/ml rhCD73 protein (Novoprotein, C446) or 2 μl of a molar equivalent amount of CD73-mAb complex into 36 μl of D2O buffer. Samples were quenched after 30 s, 120 s, 600 s, 1800 s, 7200 s of in-exchange at room temperature by addition of 40 μl ice cold storage quench buffer (4M guanidinium hydrochloride (Sangon Biotech, A510243-0500), 0.5 M TECP (Aladdin, T107252, 0.2M phosphate, pH 2.5, 0° C.). Loading of samples onto the pre-column of the chromatographic system and online pepsin digestion. Mass spectra were acquired, and peptides were identified. Peptide identification was performed by converting raw data to .mgf format using ProteomeDiscoverer2.1 and the results imported into HDExaminer for quantitation of deuteration.

FIGS. 17-20 depict the results of hydrogen deuterium exchange MS (HDX-MS) analysis indicating regions of CD73 and PR000846 that undergo differential hydrogen exchange in free versus bound states.

Figure 17:
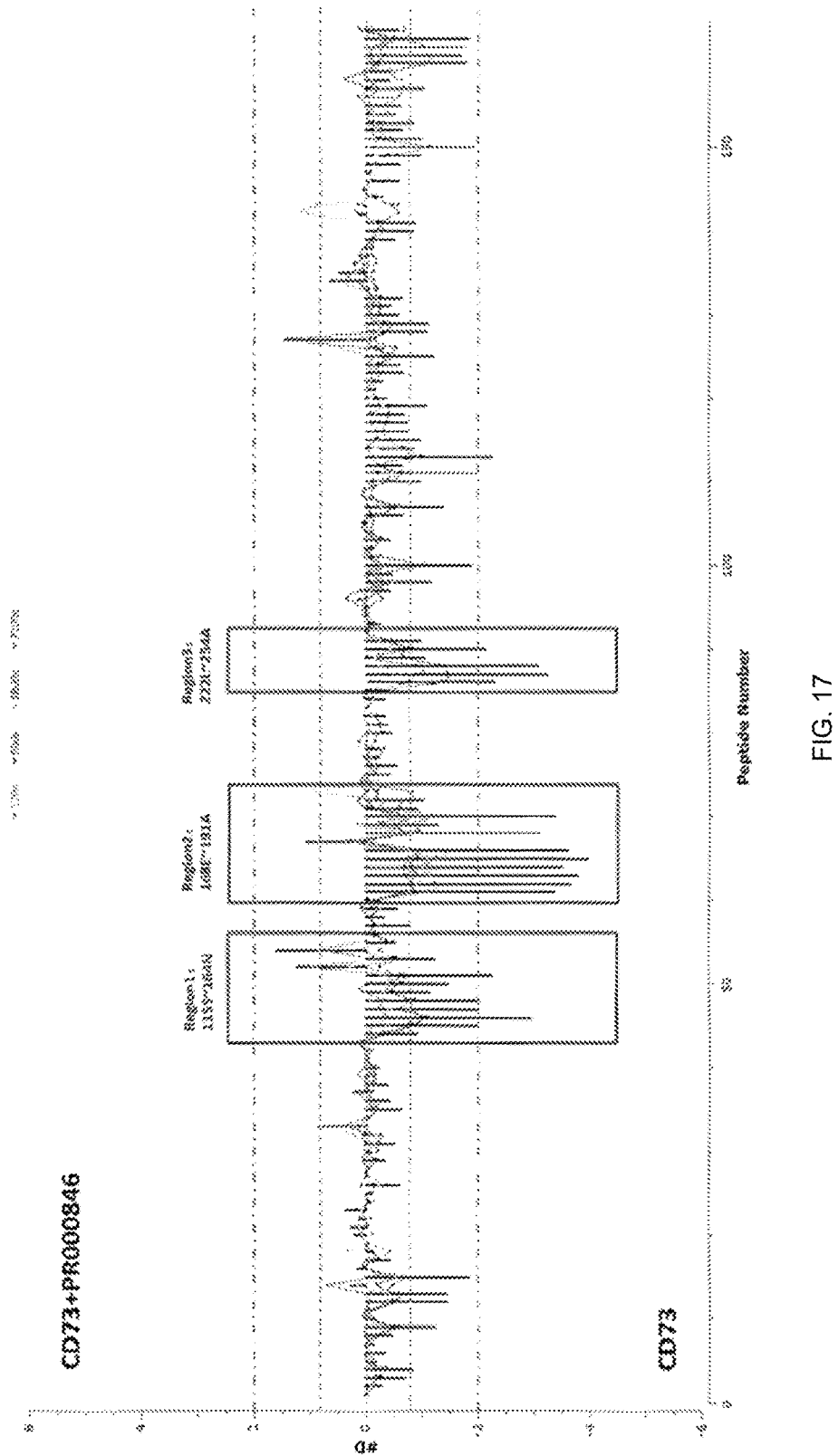
FIG. 17 illustrates the difference in deuterium uptake between the CD73+PR000846 complex (positive values on y-axis) and CD73 alone (negative values on y-axis)

FIG. 17: each data point indicates the difference in deuterium uptake between the CD73+PR000846 complex (positive values on y-axis) and CD73 alone (negative values on y-axis). The vertical bar represents the sum of the uptake differences across the exposure time-points. The horizontal axis corresponds to the analyzed peptides from the N- to C-terminus (left to right). Comparing the kinetics of exchange between free and complexed CD73 revealed 3 regions located within the N-terminal domain of sCD73 (Region 1: aa115-164; Region 2: aa168-191; Region 3: aa222-254) that exhibit decreased deuterium uptake when bound to PR000846.

Figure 18:
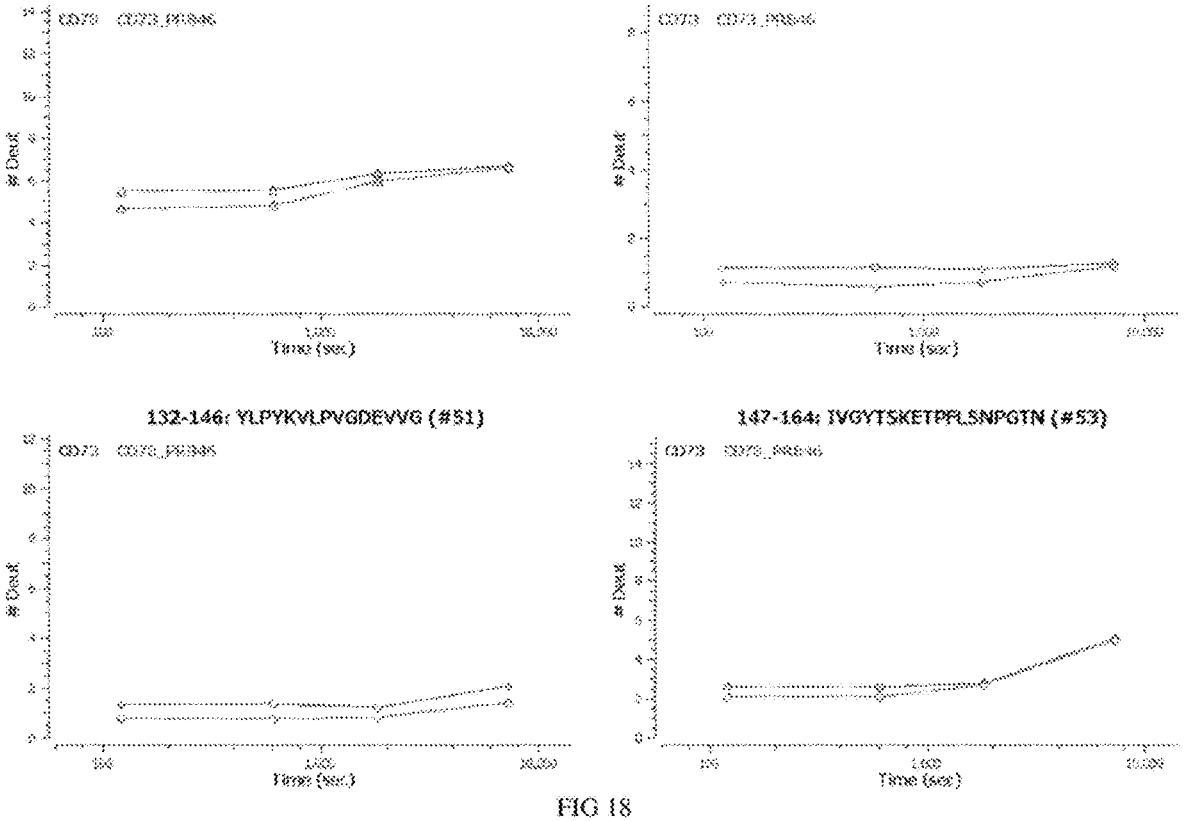
FIGS. 18, 19 and 20 illustrate relative deuterium uptake (mass change in Daltons) as a function of deuterium exposure time within peptides encompassing the region 1, 2, 3.
Figure 19:
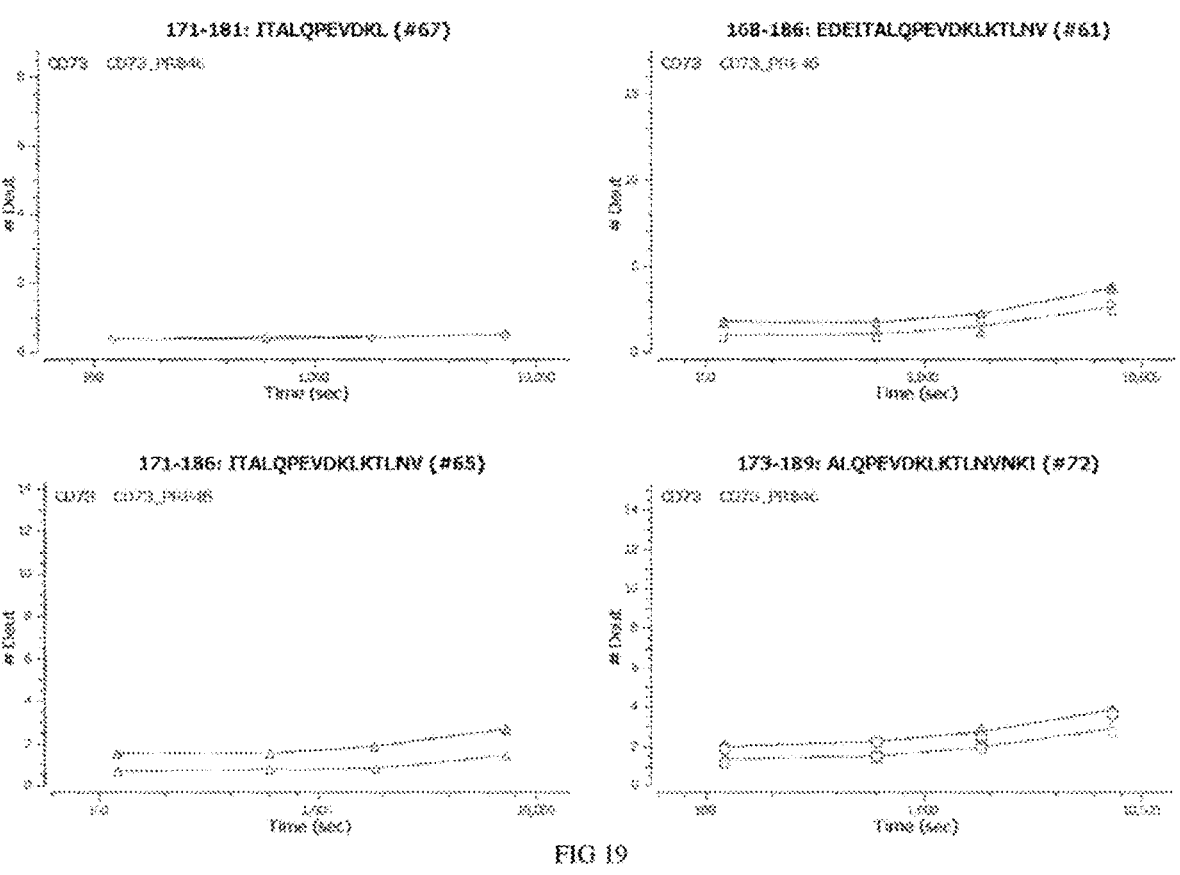
Figure 20:
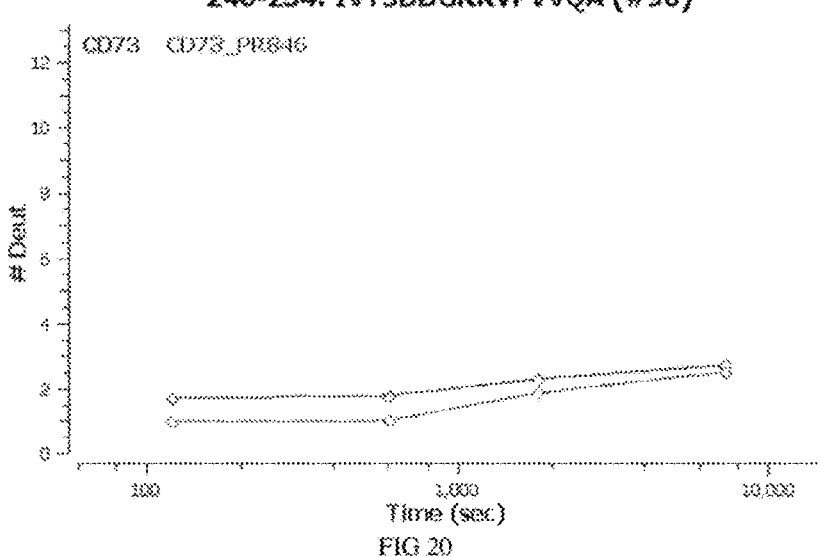

FIG. 18-20 depicts plots representing relative deuterium uptake (mass change in Daltons) as a function of deuterium exposure time within peptides encompassing the region 1, 2, 3. The peptide sequence, position, and mass are indicted in the plot box. To narrow the region that contains the sequence displaying a change in hydrogen exchange and would be predicted to form the epitope, relative mass change in overlapping peptides was compared. For example, in the Region 2 the peptide spanning positions 168-186 displayed differential exchange while there was no difference in the peptide spanning 168-181. Thus, it was inferred that residues upstream of 182 are not differentially labeled. Then these 3 regions could narrow to (amino acids (aa) 132-146 (YLPYKVGDEVVG) and 182-189 (KTLNVNKI) and 240-254 (IVTSDDGRKVPVVQA)) that exhibit decreased deuterium uptake when bound to PR000846.

Example 11 Alanine Mutant of CD73

To obtain a finer, residue-level mapping of the epitope, alanine scanning was applied these 3 regions of CD73. Plasmids encoding alanine mutant CD73 on these 3 regions were constructed, these plasmids transfected and expressed by HEK293 cell. Then using ELISA to identify the critical amin acids of the epitope as follow. Coating 0.5 ug/ml anti-his antibody(TransGen, HT501-02) and block with 3% milk PBS for 2 hours in 37° C., add 100 ul supernatant of CD73 mutants and incubate for 30 min at 37° C., to saturate the binding of CD73 mutants supernatants by repeated 3 times; Then add serial diluted PR000846 (start concentration is 100 nM) 37° C. for 1 h; Add anti-CD73 antibody 1:5000 by 0.5% blocking buffer and then incubate at 37° C. for 1 h; Wash three times with PBST (0.05% Tween 20), add 100 ul TMB (KPL), incubate about 5 min at room, then add 50 ul stop solution. Read the absorbance (optical density at 450 nm) of each well with a plate reader.

Figure 21:
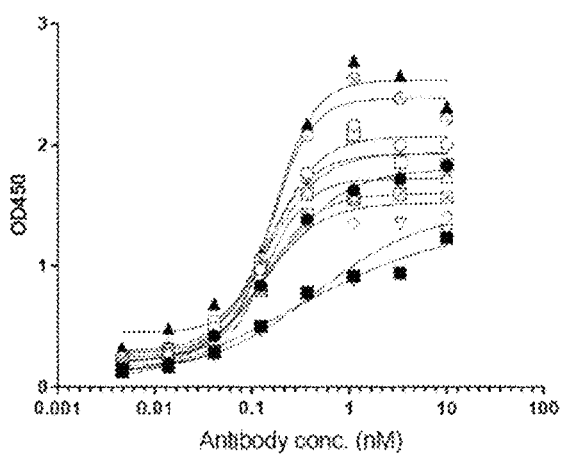
FIGS. 21 and 22 illustrates results of epitope analysis for CD73 binding to PR000846.
Figure 22:
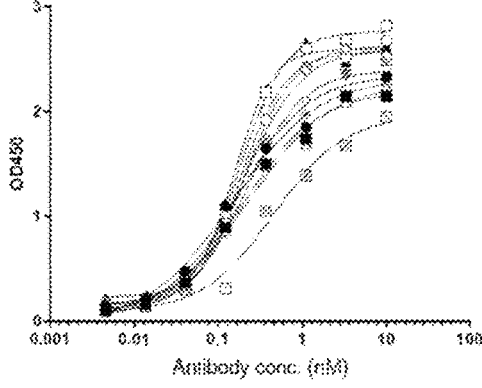

FIGS. 21 and 22: ELISA binding data revealed that K136, V137, L138, D142, E143, V144 in the region 1, and K180, V186, N187, K188 in region 2 and Y223, P238, I240 in or near region 3 are the primary epitope residues for CD73 binding to PR000846. And V137, D142 in region 1 are the critical epitope residues. While N185 which is critical epitope acid for CD73 binding to MEDI9447(TAB1), it is not the epitope residue for CD73 binding to PR000846.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. An isolated antigen binding protein that binds to CD73, the antigen binding protein comprising a heavy chain variable region (VH) and a light chain variable region (VL), wherein the VH comprises a heavy chain complementarity determining region 1 (HCDR1), a heavy chain complementarity determining region 2 (HCDR2), and a heavy chain complementarity determining region 3 (HCDR3), and the VL comprises a light chain complementarity determining region 1 (LCDR1), a light chain complementarity determining region 2 (LCDR2), and a light chain complementarity determining region 3 (LCDR3); and wherein (1) the HCDR1, HCDR2 and HCDR3 regions comprise amino acid sequences as set forth in SEQ ID NOs: 7, 24 and 39, respectively; and the LCDR1, LCDR2 and LCDR3 regions comprise amino acid sequences as set forth in SEQ ID NOs: 55, 66 and 78, respectively;

(2) the HCDR1, HCDR2 and HCDR3 regions comprise amino acid sequences as set forth in SEQ ID NOs: 7, 18 and 35, respectively; and the LCDR1, LCDR2 and LCDR3 regions comprise amino acid sequences as set forth in SEQ ID NOs: 55, 66 and 78, respectively;

(3) the HCDR1, HCDR2 and HCDR3 regions comprise amino acid sequences as set forth in SEQ ID NOs: 7, 23 and 38, respectively; and the LCDR1, LCDR2 and LCDR3 regions comprise amino acid sequences as set forth in SEQ ID NOs: 55, 66 and 78, respectively;

(4) the HCDR1, HCDR2 and HCDR3 regions comprise amino acid sequences as set forth in SEQ ID NOs: 7, 23 and 39, respectively; and the LCDR1, LCDR2 and LCDR3 regions comprise amino acid sequences as set forth in SEQ ID NOs: 55, 66 and 78, respectively;

(5) the HCDR1, HCDR2 and HCDR3 regions comprise amino acid sequences as set forth in SEQ ID NOs: 7, 24 and 38, respectively; and the LCDR1, LCDR2 and LCDR3 regions comprise amino acid sequences as set forth in SEQ ID NOs: 55, 66 and 78, respectively;

(6) the HCDR1, HCDR2 and HCDR3 regions comprise amino acid sequences as set forth in SEQ ID NOs: 6, 17 and 34, respectively; and the LCDR1, LCDR2 and LCDR3 regions comprise amino acid sequences as set forth in SEQ ID NOs: 54, 65 and 77, respectively;

(7) the HCDR1, HCDR2 and HCDR3 regions comprise amino acid sequences as set forth in SEQ ID NOs: 6, 21 and 34, respectively; and the LCDR1, LCDR2 and LCDR3 regions comprise amino acid sequences as set forth in SEQ ID NOs: 54, 65 and 77, respectively;

(8) the HCDR1, HCDR2 and HCDR3 regions comprise amino acid sequences as set forth in SEQ ID NOs: 6, 22 and 34 respectively; and the LCDR1, LCDR2 and LCDR3 regions comprise amino acid sequences as set forth in SEQ ID NOs: 54, 65 and 77, respectively;

(9) the HCDR1, HCDR2 and HCDR3 regions comprise amino acid sequences as set forth in SEQ ID NOs: 6, 17 and 34, respectively; and the LCDR1, LCDR2 and LCDR3 regions comprise amino acid sequences as set forth in SEQ ID NOs: 54, 65 and 81, respectively;

(10) the HCDR1, HCDR2 and HCDR3 regions comprise amino acid sequences as set forth in SEQ ID NOs: 6, 22 and 34, respectively; and the LCDR1, LCDR2 and LCDR3 regions comprise amino acid sequences as set forth in SEQ ID NOs: 54, 65 and 81, respectively;

(11) the HCDR1, HCDR2 and HCDR3 regions comprise amino acid sequences as set forth in SEQ ID NOs: 6, 22 and 34, respectively; and the LCDR1, LCDR2 and LCDR3 regions comprise amino acid sequences as set forth in SEQ ID NOs: 54, 65 and 84, respectively;

(12) the HCDR1, HCDR2 and HCDR3 regions comprise amino acid sequences as set forth in SEQ ID NOs: 6, 22 and 34, respectively; and the LCDR1, LCDR2 and LCDR3 regions comprise amino acid sequences as set forth in SEQ ID NOs: 54, 65 and 85, respectively;

(13) the HCDR1, HCDR2 and HCDR3 regions comprise amino acid sequences as set forth in SEQ ID NOs: 6, 22 and 34, respectively; and the LCDR1, LCDR2 and LCDR3 regions comprise amino acid sequences as set forth in SEQ ID NOs: 54, 65 and 86, respectively;

(14) the HCDR1, HCDR2 and HCDR3 regions comprise amino acid sequences as set forth in SEQ ID NOs: 6, 22 and 34, respectively; and the LCDR1, LCDR2 and LCDR3 regions comprise amino acid sequences as set forth in SEQ ID NOs: 54, 65 and 87, respectively;

(15) the HCDR1, HCDR2 and HCDR3 regions comprise amino acid sequences as set forth in SEQ ID NOs: 6, 22 and 34, respectively; and the LCDR1, LCDR2 and LCDR3 regions comprise amino acid sequences as set forth in SEQ ID NOs: 54, 65 and 88, respectively; or

(16) the HCDR1, HCDR2 and HCDR3 regions comprise amino acid sequences as set forth in SEQ ID NOs: 10, 25 and 40, respectively; and the LCDR1, LCDR2 and LCDR3 regions comprise amino acid sequences as set forth in SEQ ID NOs: 58, 69 and 82, respectively.

2. The isolated antigen binding protein of claim 1, wherein (1) said VH comprises an amino acid sequence as set forth in SEQ ID NO: 107, and said VL comprises an amino acid sequence as set forth in SEQ ID NO: 111;

(2) said VH comprises an amino acid sequence as set forth in SEQ ID NO: 96, and said VL comprises an amino acid sequence as set forth in SEQ ID NO: 111;

(3) said VH comprises an amino acid sequence as set forth in SEQ ID NO: 104, and said VL comprises an amino acid sequence as set forth in SEQ ID NO: 111;

(4) said VH comprises an amino acid sequence as set forth in SEQ ID NO: 105, and said VL comprises an amino acid sequence as set forth in SEQ ID NO: 111;

(5) said VH comprises an amino acid sequence as set forth in SEQ ID NO: 106, and said VL comprises an amino acid sequence as set forth in SEQ ID NO: 111;

(6) said VH comprises an amino acid sequence as set forth in SEQ ID NO: 104, and said VL comprises an amino acid sequence as set forth in SEQ ID NO: 115;

(7) said VH comprises an amino acid sequence as set forth in SEQ ID NO: 105, and said VL comprises an amino acid sequence as set forth in SEQ ID NO: 115;

(8) said VH comprises an amino acid sequence as set forth in SEQ ID NO: 106, and said VL comprises an amino acid sequence as set forth in SEQ ID NO: 115;

(9) said VH comprises an amino acid sequence as set forth in SEQ ID NO: 107, and said VL comprises an amino acid sequence as set forth in SEQ ID NO: 115;

(10) said VH comprises an amino acid sequence as set forth in SEQ ID NO: 96, and said VL comprises an amino acid sequence as set forth in SEQ ID NO: 115;

(11) said VH comprises an amino acid sequence as set forth in SEQ ID NO: 95, and said VL comprises an amino acid sequence as set forth in SEQ ID NO: 110;

(12) said VH comprises an amino acid sequence as set forth in SEQ ID NO: 99, and said VL comprises an amino acid sequence as set forth in SEQ ID NO: 110;

(13) said VH comprises an amino acid sequence as set forth in SEQ ID NO: 100, and said VL comprises an amino acid sequence as set forth in SEQ ID NO: 110;

(14) said VH comprises an amino acid sequence as set forth in SEQ ID NO: 101, and said VL comprises an amino acid sequence as set forth in SEQ ID NO: 110;

(15) said VH comprises an amino acid sequence as set forth in SEQ ID NO: 102, and said VL comprises an amino acid sequence as set forth in SEQ ID NO: 110;

(16) said VH comprises an amino acid sequence as set forth in SEQ ID NO: 103, and said VL comprises an amino acid sequence as set forth in SEQ ID NO: 110;

(17) said VH comprises an amino acid sequence as set forth in SEQ ID NO: 95, and said VL comprises an amino acid sequence as set forth in SEQ ID NO: 114;

(18) said VH comprises an amino acid sequence as set forth in SEQ ID NO: 100, and said VL comprises an amino acid sequence as set forth in SEQ ID NO: 114;

(19) said VH comprises an amino acid sequence as set forth in SEQ ID NO: 102, and said VL comprises an amino acid sequence as set forth in SEQ ID NO: 114;

(20) said VH comprises an amino acid sequence as set forth in SEQ ID NO: 103, and said VL comprises an amino acid sequence as set forth in SEQ ID NO: 114;

(21) said VH comprises an amino acid sequence as set forth in SEQ ID NO: 102, and said VL comprises an amino acid sequence as set forth in SEQ ID NO: 118;

(22) said VH comprises an amino acid sequence as set forth in SEQ ID NO: 102, and said VL comprises an amino acid sequence as set forth in SEQ ID NO: 119;

(23) said VH comprises an amino acid sequence as set forth in SEQ ID NO: 102, and said VL comprises an amino acid sequence as set forth in SEQ ID NO: 120;

(24) said VH comprises an amino acid sequence as set forth in SEQ ID NO: 102, and said VL comprises an amino acid sequence as set forth in SEQ ID NO: 121;

(25) said VH comprises an amino acid sequence as set forth in SEQ ID NO: 102, and said VL comprises an amino acid sequence as set forth in SEQ ID NO: 122; or

(26) said VH comprises an amino acid sequence as set forth in SEQ ID NO: 108, and said VL comprises an amino acid sequence as set forth in SEQ ID NO: 116.

3. The isolated antigen binding protein of claim 1, having one or more of the following properties:
a. capable of binding to both human CD73 and Cynomolgus monkey CD73, with comparable binding affinity;
b. capable of inhibiting 5'ectonucleotidase activity of CD73;
c. capable of mediating CD73 internalization;
d. capable of promoting T cell proliferation;
e. with a relatively stable concentration in serum for at least 15 days; and
f. capable of inhibiting tumor growth and/or tumor cell proliferation.

4. The isolated antigen binding protein of claim 1, wherein said antigen binding protein comprises an antibody or an antigen binding fragment thereof.

5. The isolated antigen binding protein of claim 4, wherein said antigen binding fragment comprises Fab, Fab', F(ab)$_2$, Fv fragment, F(ab')$_2$, scFv, di-scFv and/or dAb.

6. The isolated antigen binding protein of claim 4, wherein said antibody is a monoclonal antibody, a chimeric antibody, or a fully human antibody.

7. The isolated antigen binding protein of claim 4, wherein the antibody comprises a heavy chain (HC) and a light chain (LC), and wherein (1) said HC comprises an amino acid sequence as set forth in SEQ ID NO: 135, and said LC comprises an amino acid sequence as set forth in SEQ ID NO: 139;

(2) said HC comprises an amino acid sequence as set forth in SEQ ID NO: 124, and said LC comprises an amino acid sequence as set forth in SEQ ID NO: 139;

(3) said HC comprises an amino acid sequence as set forth in SEQ ID NO: 132, and said LC comprises an amino acid sequence as set forth in SEQ ID NO: 139;

(4) said HC comprises an amino acid sequence as set forth in SEQ ID NO: 133, and said LC comprises an amino acid sequence as set forth in SEQ ID NO: 139;

(5) said HC comprises an amino acid sequence as set forth in SEQ ID NO: 134, and said LC comprises an amino acid sequence as set forth in SEQ ID NO: 139;

(6) said HC comprises an amino acid sequence as set forth in SEQ ID NO: 132, and said LC comprises an amino acid sequence as set forth in SEQ ID NO: 143;

(7) said HC comprises an amino acid sequence as set forth in SEQ ID NO: 133, and said LC comprises an amino acid sequence as set forth in SEQ ID NO: 143;

(8) said HC comprises an amino acid sequence as set forth in SEQ ID NO: 134, and said LC comprises an amino acid sequence as set forth in SEQ ID NO: 143;

(9) said HC comprises an amino acid sequence as set forth in SEQ ID NO: 135, and said LC comprises an amino acid sequence as set forth in SEQ ID NO: 143;

(10) said HC comprises an amino acid sequence as set forth in SEQ ID NO: 124, and said LC comprises an amino acid sequence as set forth in SEQ ID NO: 143;

(11) said HC comprises an amino acid sequence as set forth in SEQ ID NO: 123, and said LC comprises an amino acid sequence as set forth in SEQ ID NO: 138;

(12) said HC comprises an amino acid sequence as set forth in SEQ ID NO: 127, and said LC comprises an amino acid sequence as set forth in SEQ ID NO: 138;

(13) said HC comprises an amino acid sequence as set forth in SEQ ID NO: 128, and said LC comprises an amino acid sequence as set forth in SEQ ID NO: 138;

(14) said HC comprises an amino acid sequence as set forth in SEQ ID NO: 129, and said LC comprises an amino acid sequence as set forth in SEQ ID NO: 138;

(15) said HC comprises an amino acid sequence as set forth in SEQ ID NO: 130, and said LC comprises an amino acid sequence as set forth in SEQ ID NO: 138;

(16) said HC comprises an amino acid sequence as set forth in SEQ ID NO: 131, and said LC comprises an amino acid sequence as set forth in SEQ ID NO: 138;

(17) said HC comprises an amino acid sequence as set forth in SEQ ID NO: 123, and said LC comprises an amino acid sequence as set forth in SEQ ID NO: 142;

(18) said HC comprises an amino acid sequence as set forth in SEQ ID NO: 128, and said LC comprises an amino acid sequence as set forth in SEQ ID NO: 142;

(19) said HC comprises an amino acid sequence as set forth in SEQ ID NO: 130, and said LC comprises an amino acid sequence as set forth in SEQ ID NO: 142;

(20) said HC comprises an amino acid sequence as set forth in SEQ ID NO: 131, and said LC comprises an amino acid sequence as set forth in SEQ ID NO: 142;

(21) said HC comprises an amino acid sequence as set forth in SEQ ID NO: 130, and said LC comprises an amino acid sequence as set forth in SEQ ID NO: 146;

(22) said HC comprises an amino acid sequence as set forth in SEQ ID NO: 130, and said LC comprises an amino acid sequence as set forth in SEQ ID NO: 147;

(23) said HC comprises an amino acid sequence as set forth in SEQ ID NO: 130, and said LC comprises an amino acid sequence as set forth in SEQ ID NO: 148;

(24) said HC comprises an amino acid sequence as set forth in SEQ ID NO: 130, and said LC comprises an amino acid sequence as set forth in SEQ ID NO: 149;

(25) said HC comprises an amino acid sequence as set forth in SEQ ID NO: 130, and said LC comprises an amino acid sequence as set forth in SEQ ID NO: 150; or

(26) said HC comprises an amino acid sequence as set forth in SEQ ID NO: 136, and said LC comprises an amino acid sequence as set forth in SEQ ID NO: 144.

8. An isolated nucleic acid molecule, encoding said isolated antigen binding protein of claim 1.

9. A vector, comprising said nucleic acid molecule of claim 8.

10. A cell, comprising said nucleic acid molecule of claim 8.

11. A cell, comprising said vector of claim 9.

12. A pharmaceutical composition, comprising the isolated antigen binding protein of claim 1, and a pharmaceutically acceptable carrier.

13. A method for preventing, alleviating and/or treating tumor, comprising administrating to a subject in need thereof the isolated antigen binding protein of claim 1 or a pharmaceutical composition comprising the antigen binding protein.

14. The method of claim 13, wherein said tumor is a solid tumor or a blood tumor.

15. A method of inhibiting 5' ectonucleotidase activity of CD73 in a subject, comprising administrating an isolated antigen binding protein of claim 1 to the subject.

16. A method of mediating CD73 internalization in a subject, comprising administrating an isolated antigen binding protein of claim 1 to the subject.

17. An anti-CD73 antibody or an antigen binding fragment thereof, comprising a heavy chain that comprises a heavy chain variable region (VH) and a light chain that comprises a light chain variable region (VL), wherein the VH comprises HCDR1, HCDR2 and HCDR3, and the VL comprises LCDR1, LCDR2 and LCDR3, and wherein the HCDR1, HCDR2 and HCDR3 regions comprise amino acid sequences as set forth in SEQ ID NOs: 7, 24 and 39 respectively; and the LCDR1, LCDR2 and LCDR3 regions comprise amino acid sequences as set forth in SEQ ID NOs: 55, 66 and 78, respectively.

18. The anti-CD73 antibody or the antigen binding fragment thereof of claim 17, wherein the heavy chain comprises the amino acid sequence as set forth in SEQ ID NO: 135 and the light chain comprises the amino acid sequence as set forth in SEQ ID NO: 139.

19. A method for treating tumor, comprising administrating to a subject in need thereof the anti-CD73 antibody or the antigen binding fragment thereof of claim 18.

20. The method of claim 19, wherein said tumor is a solid tumor.

* * * * *